US012649712B2

(12) United States Patent　　　　(10) Patent No.: US 12,649,712 B2

Su et al.　　　　　　　　　　　　　　(45) Date of Patent: Jun. 9, 2026

(54) INDENE COMPOUNDS, PHARMACEUTICAL COMPOSITIONS THEREOF, AND THEIR THERAPEUTIC APPLICATIONS

(71) Applicant: NucMito Pharmaceuticals Co. Ltd., Xiamen (CN)

(72) Inventors: Ying Su, Xiamen (CN); Xiaokun Zhang, Xiamen (CN); Ziwen Chen, Xiamen (CN); Qingzhen Chen, Xiamen (CN); Haishan Wang, Xiamen (CN); Xindao Zhang, Xiamen (CN); Zhiping Zeng, Xiamen (CN); Yuqi Zhou, Xiamen (CN); Zhiqiang Yan, Xiamen (CN)

(73) Assignee: NucMito Pharmaceuticals Co. Ltd., Xiamen (CN)

( * ) Notice: Subject to any disclaimer, the term of this patent is extended or adjusted under 35 U.S.C. 154(b) by 526 days.

(21) Appl. No.: 18/001,309

(22) PCT Filed: Jun. 11, 2021

(86) PCT No.: PCT/CN2021/099626

§ 371 (c)(1),
(2) Date: Dec. 9, 2022

(87) PCT Pub. No.: WO2021/249529

PCT Pub. Date: Dec. 16, 2021

(65) Prior Publication Data

US 2023/0234909 A1　　Jul. 27, 2023

Related U.S. Application Data

(60) Provisional application No. 63/038,737, filed on Jun. 12, 2020.

(51) Int. Cl.

| | |
|---|---|
| *C07D 295/15* | (2006.01) |
| *A61P 1/16* | (2006.01) |
| *C07C 59/135* | (2006.01) |
| *C07C 229/44* | (2006.01) |
| *C07C 235/34* | (2006.01) |
| *C07C 255/57* | (2006.01) |
| *C07C 259/06* | (2006.01) |
| *C07C 317/44* | (2006.01) |
| *C07C 323/62* | (2006.01) |
| *C07D 207/32* | (2006.01) |
| *C07D 207/327* | (2006.01) |
| *C07D 209/18* | (2006.01) |
| *C07D 213/643* | (2006.01) |
| *C07D 215/20* | (2006.01) |
| *C07D 233/88* | (2006.01) |
| *C07D 257/04* | (2006.01) |
| *C07D 257/06* | (2006.01) |
| *C07D 271/07* | (2006.01) |
| *C07D 295/155* | (2006.01) |

(52) U.S. Cl.
CPC .............. *C07C 59/135* (2013.01); *A61P 1/16* (2018.01); *C07C 229/44* (2013.01); *C07C 235/34* (2013.01); *C07C 255/57* (2013.01); *C07C 259/06* (2013.01); *C07C 317/44* (2013.01); *C07C 323/62* (2013.01); *C07D 207/327* (2013.01); *C07D 209/18* (2013.01); *C07D 213/643* (2013.01); *C07D 215/20* (2013.01); *C07D 233/88* (2013.01); *C07D 257/04* (2013.01); *C07D 257/06* (2013.01); *C07D 271/07* (2013.01); *C07D 295/155* (2013.01)

(58) Field of Classification Search
CPC ........................ C07D 257/05; C07D 295/155; C07D 233/88; C07D 207/327; C07C 229/44; C07C 59/135
See application file for complete search history.

(56) References Cited

U.S. PATENT DOCUMENTS

| | | | |
|---|---|---|---|
| 6,214,876 | B1 | 4/2001 | Dillard et al. |
| 9,611,235 | B2 | 4/2017 | Zhang et al. |
| 2020/0237710 | A1 | 7/2020 | Ordman |

FOREIGN PATENT DOCUMENTS

| | | |
|---|---|---|
| DE | 10163426 A1 | 7/2003 |
| EP | 0984930 A1 | 3/2000 |
| WO | 1996003120 A1 | 2/1996 |
| WO | 1999016453 A1 | 4/1999 |

(Continued)

OTHER PUBLICATIONS

Angulo et al., "Independent predictors of liver fibrosis in patients with nonalcoholic steatohepatitis," Hepatology 1999, 30, 1356-62.

(Continued)

*Primary Examiner* — Shawquia Jackson
(74) *Attorney, Agent, or Firm* — Lin Yu; Juniv LLP

(57) ABSTRACT

Provided herein are an indene compound, e.g., a compound of Formula (I), and a pharmaceutical composition thereof. Also provided herein is a method of their use for treating, preventing, or ameliorating one or more symptoms of a fibrotic disease.

(I)

$$R^3,\ L—R^2,\ R^4,\ R^1,\ R^5,\ R^6,\ R^A—X—R^B$$

53 Claims, 3 Drawing Sheets

Specification includes a Sequence Listing.

(56)                    References Cited

FOREIGN PATENT DOCUMENTS

| WO | 2009090414 A1 | 7/2009 |
| WO | 2011140525 A2 | 11/2011 |

OTHER PUBLICATIONS

Bai et al., "The effect of sulindac, a non-steroidal anti-inflammatory drug, attenuates inflammation and fibrosis in a mouse model of chronic pancreatitis," BMC Gastroenterol. 2012, 2, 115.

Berge et al., "Pharmaceutical salts," J. Pharm. Sci. 1977, 66, 1-19.

Dulai et al., "Increased risk of mortality by fibrosis stage in nonalcoholic fatty liver disease: Systematic review and meta-analysis," Hepatology 2017, 65, 1557-65.

Fabregat et al., "TGF-β signalling and liver disease," FEBS J. 2016, 283, 2219-32.

Henderson et al., "Galectin-3 regulates myofibroblast activation and hepatic fibrosis," Proc. Natl. Acad. Sci. USA 2006, 103, 5060-5.

Henderson et al., "Targeting of αv integrin identifies a core molecular pathway that regulates fibrosis in several organs," Nat. Med. 2013, 19, 1617-24.

Hernandez-Gea and Friedman, "Pathogenesis of liver fibrosis," Ann. Rev. Pathol. 2011, 6, 425-56.

Huang et al., "Design, synthesis, and biological evaluation of novel sulindac derivatives as partial agonists of PPARγ with potential anti-diabetic efficacy," Eur. J. Med. Chem. 2021, 222, 113542.

Hwu et al., "Syntheses of platinum-sulindac complexes and their nanoparticles as targeted anticancer drugs," Chem. Eur. J. 2016, 22, 1926-30.

Liu, "The RXRα-mediated anti-inflammatory effect of sulindac analog K-80003 and the underlying molecular mechanism," Chinese Doctoral Dissertations and Master's Theses Full-text Database (Master) Medicine and Health Sciences. 2019, No. 6.

Makarev et al., "Common pathway signature in lung and liver fibrosis," Cell Cycle 2016, 15, 1667-73.

Mehal et al., "Scraping fibrosis: expressway to the core of fibrosis," Nat. Med. 2011, 17, 552-3.

Meng et al., "TGF-β: the master regulator of fibrosis," Nat. Rev. Nephrol. 2016, 12, 325-38.

Reddy et al., "Catalyst-controlled regioselective approach to 1-aminoisoquinolines and/or 1-aminoisoindolines through aminative domino cyclization of 2-alkynyl-benzonitriles," Eur. J. Org. Chem. 2016, 3, 453-8.

Roenn, "Spotlight on impactful research: Increased risk of mortality by fibrosis stage in nonalcoholic fatty liver disease: Systemic review and meta-analysis," Clin. Liver Dis. (Hoboken) 2018, 12, 35-8.

Sheka et al., "Nonalcoholic steatohepatitis: A review," JAMA 2020, 323, 1175-83.

Zhou et al., "Sulindac has strong antifibrotic effects by suppressing STAT3-related miR-21," J. Cell. Mol. Med. 2015, 19, 1103-13.

Fold change of
Col1a1 mRNA

40

30

20

10

0

| CCl$_4$ | - | + | + | + | + | |
| Mal | - | - | 60 | - | - | |
| B9 | - | - | - | 50 | - | |
| A11 | - | - | - | - | 50 | mg/kg/day |

Control    CCl$_4$    CCl$_4$+Mal    CCl$_4$+B9    CCl$_4$+A11

```
                        SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic Probe

<400> SEQUENCE: 1
gttcagtggt gcctctgtca                                                20

<210> SEQ ID NO 2
<211> LENGTH: 20
<212> TYPE: DNA
<213> ORGANISM: Artificial Sequence
<220> FEATURE:
<223> OTHER INFORMATION: Synthetic Probe

<400> SEQUENCE: 2
actgggacga catggaaaag                                                20

<210> SEQ ID NO 3
<211> LENGTH: 20
<212> TYPE: DNA
<213> ORGANISM: Artificial Sequence
<220> FEATURE:
<223> OTHER INFORMATION: Synthetic Probe

<400> SEQUENCE: 3
taggccattg tgtatgcagc                                                20

<210> SEQ ID NO 4
<211> LENGTH: 21
<212> TYPE: DNA
<213> ORGANISM: Artificial Sequence
<220> FEATURE:
<223> OTHER INFORMATION: Synthetic Probe

<400> SEQUENCE: 4
acatgttcag ctttgtggac c                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic Probe

<400> SEQUENCE: 5
```

-continued gttaagcagt acagccccaa a             21

<210> SEQ ID NO 6
<211> LENGTH: 23
<212> TYPE: DNA
<213> ORGANISM: Artificial Sequence
<220> FEATURE:
<223> OTHER INFORMATION: Synthetic Probe

<400> SEQUENCE: 6
agggcatatc caacaacaaa ctt            23

INDENE COMPOUNDS, PHARMACEUTICAL COMPOSITIONS THEREOF, AND THEIR THERAPEUTIC APPLICATIONS

CROSS REFERENCE TO RELATED APPLICATION

This application is a National Stage of International Application No. PCT/CN2021/099626, filed Jun. 11, 2021; which claims the benefit of U.S. Provisional Application No. 63/038,737, filed Jun. 12, 2020; the disclosure of each of which is incorporated herein by reference in its entirety.

REFERENCE TO A SEQUENCE LISTING

The present specification is being filed with a Sequence Listing in Computer Readable Form (CRF), which is entitled 294A002WO01_SEQ_LIST_ST25.txt of 1,427 bytes in size and created May 23, 2021; the content of which is incorporated herein by reference in its entirety.

FIELD

Provided herein are an indene compound and a pharmaceutical composition thereof. Also provided herein is a method of their use for treating, preventing, or ameliorating one or more symptoms of a fibrotic disease.

BACKGROUND

Fibrosis is the accumulation of extracellular matrix components in organs or tissues, changing their structures and leading to a disruption of normal functions, and, in many cases, ultimately leading to organ failure and death. Hernandez-Gea et al., *Annu. Rev. Pathol.* 2011, 6, 425-56; Makarev et al., *Cell Cycle* 2016, 15, 1667-73. Fibrosis can occur in almost any organ or tissue and is associated with a wide variety of diseases, contributing to up to 45% of deaths in the developed world. Mehal et al., *Nat. Med.* 2011, 17, 552-3; Makarev et al., *Cell Cycle* 2016, 15, 1667-73.

NASH (non-alcoholic steatohepatitis) is a progressive disease caused by excessive fat accumulation in the liver, unrelated to alcohol use, that induces chronic inflammation and damage (ballooning) of hepatocytes, resulting in fibrosis that can lead to cirrhosis, liver failure, and death. Roenn, *Clin. Liver Dis. (Hoboken)* 2018, 12, 35-6; Sheka et al., *JAMA* 2020, 323, 1175-83. The stage of liver fibrosis is a strong predictor of clinical outcomes inpatients with NASH. Angulo et al., *Hepatology* 1999, 30, 1356-62; Dulai et al., *Hepatology* 2017, 65, 1557-65. Ongoing persistence of obesity with increasing rates of diabetes is expected to increase the prevalence of NASH dramatically in coming years, and the disease is projected to become the leading cause of liver transplants in the US. Roenn, *Clin. Liver Dis. (Hoboken)* 2018, 12, 35-6; Sheka et al., *JAMA* 2020, 323, 1175-83. There are currently no FDA-approved therapies for NASH. Id. Therefore, there is a need for an effective therapy for treating a fibrotic disease, in particular, NASH.

SUMMARY OF THE DISCLOSURE

Provided herein is a compound of Formula (I):

(I)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is (a) hydrogen, deuterium, cyano, halo, or nitro; or (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; $R^2$ is $-C(O)OR^{2a}$, $-C(O)NR^{2b}R^{2c}$, $-C(O)N(R^{2b})OR^{2c}$, or heteroaryl; wherein $R^{2a}$, $R^{2b}$, and $R^{2c}$ are each independently hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^3$, $R^4$, $R^5$, and $R^6$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$, or $-S(O)_2NR^{1b}R^{1c}$;

$R^A$ is $C_{6-14}$ arylene or heteroarylene;

$R^B$ and X are (i), (ii), or (iii):

(i) X is $-O-$, $-S-$, $-S(O)-$, or $-S(O)_2-$; and
$R^B$ is $C_{6-14}$ aryl or heteroaryl;

(ii) X is $-N(R^X)-$;
$R^B$ is $C_{6-14}$ aryl or heteroaryl; and
$R^X$ is hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) X is $-N(R)-$; and
$R^B$ and $R^X$ together with the N atom to which they are attached form heteroaryl or heterocyclyl;

L is $C_{1-6}$ alkylene, $C_{2-6}$ alkenylene, $C_{3-10}$ cycloalkylene, or heterocyclylene; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkylene, alkenyl, alkenylene, alkynyl, cycloalkyl, cycloalkylene, aryl, arylene, aralkyl, heteroaryl, heteroarylene, heterocyclyl, and heterocyclylene is optionally substituted with one or more, in one embodiment, one, two, three, or four, substituents Q, wherein each Q is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)NR$^b$R$^c$, —C(O)S$R^a$, —C(NR$^a$)NR$^b$R$^c$, —C(S) $R^a$, —C(S)O$R^a$, —C(S)NR$^b$R$^c$, —O$R^a$, —OC(O)$R^a$, —OC(O)O$R^a$, —OC(O)NR$^b$R$^c$, —OC(O)S$R^a$, —OC (NR$^a$)NR$^b$R$^c$, —OC(S)$R^a$, —OC(S)O$R^a$, —OC(S) NR$^b$ R$^c$, —OS(O)$R^a$, —OS(O)$_2$$R^a$, —OS(O)NR$^b$R$^c$, —OS(O)$_2$NR$^b$R$^c$, —NR$^b$R$^c$, —NR$^a$C(O)R$^d$, —NR$^a$C (O)OR$^d$, —NR$^a$C(O)NR$^b$R$^c$, —NR$^a$C(O)SR$^d$, —NR$^a$C(NR$^d$)NR$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)$R^a$, —S(O)$_2$$R^a$, —S(O)NR$^b$R$^c$, and —S(O)$_2$ NR$^b$R$^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl optionally substituted with one or more, in one embodiment, one, two, three, or four, substituents $Q^a$;

wherein each $Q^a$ is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)NR$^f$R$^g$, —C(O)S$R^e$, —C(NR$^e$)NR$^f$R$^g$, —C(S)$R^e$, —C(S)O$R^e$, —C(S)NR$^f$ R$^g$, —O$R^e$, —OC(O)$R^e$, —OC(O)O$R^e$, —OC(O)NR$^f$ R$^g$, —OC(O)S$R^e$, —OC(NR$^e$)NR$^f$R$^g$, —OC(S)$R^e$, —OC(S)O$R^e$, —OC(S)NR$^f$R$^g$, —OS(O)$R^e$, —OS(O)$_2$ R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(NR$^h$)NR$^f$R$^g$, —NR$^e$C(S)R$^h$, —NR$^e$C(S)OR$^f$, —NR$^e$C(S)NR$^f$R$^g$, —NRS(O)R$^h$, —NRS(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Also provided herein is a pharmaceutical composition comprising a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

Additionally provided herein is a method of treating, preventing, or ameliorating one or more symptoms of a fibrotic disease in a subject, comprising administering to the subject in need thereof a therapeutically effective amount of a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Furthermore, provided herein is a method of treating, preventing, or ameliorating one or more symptoms of a proliferative disease in a subject, comprising administering to the subject in need thereof a therapeutically effective amount of a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of inhibiting the growth of a cell, comprising contacting the cell with an effective amount of a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of treating, preventing, or ameliorating one or more symptoms of a fibrotic disease in a subject, comprising administering to the subject in need thereof a therapeutically effective amount of a compound of Formula (I-A):

(I-A)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is (a) hydrogen, deuterium, cyano, halo, or nitro; or (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^2$ is —CN, —C(O)OR$^{2a}$, —C(O)NR$^{2b}$R$^{2c}$, —C(O)N (R$^{2b}$)OR$^{2c}$, —OR$^{2a}$, —NR$^{2b}$R$^{2c}$, or heteroaryl; wherein $R^{2a}$, $R^{2b}$, and $R^{2c}$ are each independently hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^3$, $R^4$, $R^5$, and $R^6$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O) NR$^{1b}$R$^{1c}$, —OC(NR$^{1a}$)NR$^{1b}$R$^{1c}$, —OS(O)R$^{1a}$, —OS (O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^a$C(O)R$^d$, —NR$^{1a}$C(O)OR$^{1d}$, —NR$^{1a}$C(O)NR$^{1b}$R$^{1c}$, —NR$^{1a}$C(R$^{1d}$)NR$^{1b}$R$^{1c}$, —NR$^{1a}$S(O)R$^{1d}$, —NR$^{1a}$S(O)$_2$R$^{1d}$, —NR$^{1a}$S(O) NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

each $R^7$ is independently (a) deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O) NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(NR$^{1a}$) NR$^{1b}$R$^{1c}$, —OS(O)R$^{1a}$, —OS(O)$_2$R$^{1a}$, —OS(O) NR$^{1b}$R$^{1c}$, —OS(O)$_2$NR$^{1b}$R$^{1c}$, —NR$^{1b}$R$^{1c}$, —NR$^{1a}$C (O)R$^{1d}$, —NR$^{1a}$C(O)OR$^{1d}$, —NR$^{1a}$C(O)NR$^{1b}$R$^{1c}$, —NR$^{1a}$C(NR$^{1d}$)R$^{1b}$R$^{1c}$, —NR$^{1a}$S(O)R$^{1d}$, —NR$^{1a}$S (O)$_2$R$^{1d}$, —NR$^{1a}$S(O)NR$^{1b}$R$^{1c}$, —NR$^{1a}$S(O)$_2$ NR$^{1b}$R$^{1c}$, —SR$^{1a}$, —S(O)R$^{1a}$, —S(O)$_2$R$^{1a}$, —S(O) NR$^{1b}$R$^{1c}$, or —S(O)$_2$NR$^{1b}$R$^{1c}$; or two adjacent R$^7$ together with the phenyl group to which they are attached form naphthyl or bicyclic heteroaryl;

R$^C$ is (a) hydrogen, deuterium, cyano, halo, or nitro; or (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —OR$^{1a}$, —NR$^{1b}$R$^{1c}$, or —NR$^{1a}$C(O)R$^{1d}$;

L is C$_{1-6}$ alkylene or C$_{2-6}$ alkenylene;

n is an integer of 0, 1, 2, 3, or 4; and each R$^{1a}$, R$^{1b}$, R$^{1c}$, and R$^{1d}$ is independently hydrogen, deuterium, C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or R$^{1a}$ and R$^{1c}$ together with the C and N atoms to which they are attached form heterocyclyl; or R$^{1b}$ and R$^{1c}$ together with the N atom to which they are attached form heterocyclyl;

wherein each alkyl, alkylene, alkenyl, alkenylene, alkynyl, cycloalkyl, aryl, aralkyl, heteroaryl, and heterocyclyl is optionally substituted with one or more, in one embodiment, one, two, three, or four, substituents Q, wherein each Q is independently selected from: (a) deuterium, cyano, halo, nitro, and oxo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(O)SR$^a$, —C(NR$^a$)NR$^b$R$^c$, —C(S) R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC (NR$^a$)NR$^b$R$^c$, —OC(S)R$^a$, —OC(S)OR$^a$, —OC(S) NR$^b$ R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C (O)OR$^d$, —NR$^a$C(O)NR$^b$R$^c$, —NR$^a$C(O)SR$^d$, —NR$^a$C(NR$^d$)NR$^b$R$^c$, —NR$^a$C(S)R$^d$, —NR$^a$C(S)OR$^d$, —NR$^a$C(S)NR$^b$R$^c$, —NR$^{1a}$S(O)R$^d$, —NR$^{1a}$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$, R$^c$, and —S(O)$_2$ NR$^b$R$^c$, wherein each R$^a$, R$^b$, R$^c$, and R$^d$ is independently (i) hydrogen or deuterium; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is optionally substituted with one or more, in one embodiment, one, two, three, or four, substituents Q$^a$; or (iii) R$^b$ and R$^c$ together with the N atom to which they are attached form heterocyclyl optionally substituted with one or more, in one embodiment, one, two, three, or four, substituents Q$^a$;

wherein each Q$^a$ is independently selected from: (a) deuterium, cyano, halo, nitro, and oxo; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$ R$^g$, —OR$^e$, —OC(O)R$^e$, —OC(O)OR$^e$, —OC(O)NR$^f$ R$^g$, —OC(O)SR$^e$, —OC(NR$^e$)NR$^f$R$^g$, —OC(S)R$^e$, —OC(S)OR$^e$, —OC(S)NR$^f$R$^g$, —OS(O)R$^e$, —OS(O)$_2$ R$^e$, —OS(O)NR$^f$R$^g$, —OS(O)$_2$NR$^f$R$^g$, —NR$^f$R$^g$, —NR$^e$C(O)R$^h$, —R$^e$C(O)OR$^f$, —NR$^e$C(O)NR$^f$R$^g$, —NR$^e$C(O)SR$^f$, —NR$^e$C(NR$^h$)RR, —NRC(S)R$^h$, —NR$^e$C(S)OR$^f$, —NR$^e$C(S)NR$^f$R$^g$, —NRS(O)R$^h$, —NR$^e$S(O)$_2$R$^h$, —NR$^e$S(O)NR$^f$R$^g$, —NR$^e$S(O)$_2$NR$^f$ R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

DETAILED DESCRIPTION

Figure 1:
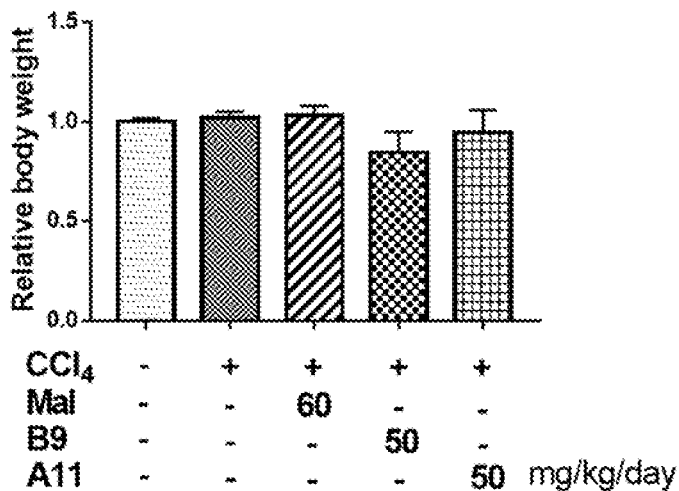
FIG. 1 shows the effect of malotilate (Mal), and compounds A11 and B9 on body weight in C57/BL6 mice.

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and a biological molecule (e.g., a protein, enzyme, RNA, or DNA), cell, or tissue such that a physiological and/or chemical effect takes place as a result of such contact. Contacting can take place in vitro, ex vivo, or in vivo. In one embodiment, a therapeutic agent is contacted with a biological molecule in vitro to determine the effect of the therapeutic agent on the biological molecule. In another embodiment, a therapeutic agent is contacted with a cell in cell culture (in vitro) to determine the effect of the therapeutic agent on the cell. In yet another embodiment, the contacting of a therapeutic agent with a biological molecule, cell, or tissue includes the administration of a therapeutic agent to a subject having the biological molecule, cell, or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human) without excessive toxicity, irritation, allergic response, immunogenicity, or other problems or complications, and commensurate with a reasonable benefit/risk ratio. See, e.g., *Remington: The Science and Practice of Pharmacy*, 23rd ed.; Adejare Ed.; Academic Press, 2020; *Handbook of Pharmaceutical Excipients*, 9th ed.; Sheskey et al., *Eds.; Pharmaceutical Press*, 2020; *Handbook of Pharmaceutical Additives*, 3rd ed.; Ash and Ash Eds.; Synapse Information Resources, 2007; *Pharmaceutical Preformulation and Formulation*, 1st ed.; Gibson Ed.; CRC Press, 2015.

The term "about" or "approximately" means an acceptable error for a particular value as determined by one of ordinary skill in the art, which depends in part on how the value is measured or determined. In certain embodiments, the term "about" or "approximately" means within 1, 2, or 3 standard deviations. In certain embodiments, the term "about" or "approximately" means within 25%, 20%, 15%, 10%, 9%, 8%, 7%, 6%, 5%, 4%, 3%, 2%, 1%, 0.5%, or 0.05% of a given value or range.

The term "alkyl" refers to a linear or branched saturated monovalent hydrocarbon radical, wherein the alkyl is optionally substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl and isopropyl), butyl (including all isomeric forms, e.g., n-butyl, isobutyl, sec-butyl, and t-butyl), pentyl (including all isomeric forms, e.g., n-pentyl, isopentyl, sec-pentyl, neopentyl, and tert-pentyl), and hexyl (including all isomeric forms, e.g., n-hexyl, isohexyl, and sec-hexyl).

The terms "alkylene" and "alkanediyl" are used interchangeably herein in reference to a linear or branched saturated divalent hydrocarbon radical, wherein the alkylene is optionally be substituted with one or more substituents Q as described herein. For example, $C_{1-6}$ alkylene refers to a linear saturated divalent hydrocarbon radical of 1 to 6 carbon atoms or a branched saturated divalent hydrocarbon radical of 3 to 6 carbon atoms. In certain embodiments, the alkylene is a linear saturated divalent hydrocarbon radical that has 1 to 30 ($C_{1-30}$), 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 30 ($C_{3-30}$), 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene (including all isomeric forms, e.g., ethan-1,1-diyl and ethan-1,2-diyl), propylene (including all isomeric forms, e.g., propan-1,1-diyl, propan-1,2-diyl, and propan-1,3-diyl), butylene (including all isomeric forms, e.g., butan-1,1-diyl, butan-1,2-diyl, butan-1,3-diyl, and butan-1,4-diyl), pentylene (including all isomeric forms, e.g., pentan-1,1-diyl, pentan-1,2-diyl, pentan-1,3-diyl, and pentan-1,5-diyl), and hexylene (including all isomeric forms, e.g., hexan-1,1-diyl, hexan-1,2-diyl, hexan-1,3-diyl, and hexan-1,6-diyl).

The term "alkenyl" refers to a linear or branched monovalent hydrocarbon radical, which contains one or more, in one embodiment, one, two, three, or four, in another embodiment, one, carbon-carbon double bond(s). The alkenyl is optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propenyl (including all isomeric forms, e.g., propen-1-yl, propen-2-yl, and allyl), and butenyl (including all isomeric forms, e.g., buten-1-yl, buten-2-yl, buten-3-yl, and 2-buten-1-yl).

The terms "alkenylene" and "alkenediyl" are used interchangeably herein in reference to a linear or branched divalent hydrocarbon radical, which contains one or more, in one embodiment, one, two, three, or four, in another embodiment, one, carbon-carbon double bond(s). The alkenylene is optionally substituted with one or more substituents Q as described herein. The term "alkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 30 ($C_{2-30}$), 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 30 ($C_{3-30}$), 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene (including all isomeric forms, e.g., ethen-1,1-diyl or ethen-1,2-diyl), propenylene (including all isomeric forms, e.g., 1-propen-1,1-diyl, 1-propen-1,2-diyl, and 1-propen-1,3-diyl), butenylene (including all isomeric forms, e.g., 1-buten-1,1-diyl, 1-buten-1,2-diyl, and 1-buten-1,4-diyl), pentenylene (including all isomeric forms, e.g., 1-penten-1, 1-diyl, 1-penten-1,2-diyl, and 1-penten-1,5-diyl), and hexenylene (including all isomeric forms, e.g., 1-hexen-1,1-diyl, 1-hexen-1,2-diyl, and 1-hexen-1,6-diyl).

The term "alkynyl" refers to a linear or branched monovalent hydrocarbon radical, which contains one or more, in one embodiment, one, two, three, or four, in another embodiment, one, carbon-carbon triple bond(s). The alkynyl is optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 4 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms. Examples of alkynyl groups include, but are not limited to, ethynyl (—C≡CH), propynyl (including all isomeric forms, e.g., 1-propynyl (—C≡CCH₃) and propargyl (—CH₂C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl and 2-hexyn-1-yl).

The term "cycloalkyl" refers to a cyclic monovalent hydrocarbon radical, which is optionally substituted with one or more substituents Q as described herein. In one embodiment, the cycloalkyl is a saturated or unsaturated but non-aromatic, and/or bridged or non-bridged, and/or fused bicyclic group. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. In one embodiment, the cycloalkyl is monocyclic. In another embodiment, the cycloalkyl is bicyclic. In yet another embodiment, the cycloalkyl is tricyclic. In still another embodiment, the cycloalkyl is polycyclic. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[1.1.1] pentyl, bicyclo[2.1.1]hexyl, bicyclo[2.2.1]heptyl, bicyclo [2.2.2]octyl, decalinyl, and adamantyl.

The terms "cycloalkylene" and "cycloalkanediyl" are used interchangeably herein in reference to a cyclic divalent hydrocarbon radical, which may be optionally substituted with one or more substituents Q as described herein. In one embodiment, cycloalkyl groups may be saturated or unsaturated but non-aromatic, and/or bridged, and/or non-bridged, and/or fused bicyclic groups. In certain embodiments, the cycloalkylene has from 3 to 30 ($C_{3-30}$), 3 to 20 ($C_{3-20}$), from 3 to 15 ($C_{3-15}$), from 3 to 10 ($C_{3-10}$), or from 3 to 7 ($C_{3-10}$) carbon atoms. Examples of cycloalkylene groups include, but are not limited to, cyclopropylene (including all isomeric forms, e.g., cycloprop-1,1-diyl and cycloprop-1,2-diyl), cyclobutylene (including all isomeric forms, e.g., cyclobut- 1,1-diyl, cyclobut-1,2-diyl, and cyclobut-1,3-diyl), cyclopentylene (including all isomeric forms, e.g., cyclopent-1, 1-diyl, cyclopent-1,2-diyl, and cyclopent-1,3-diyl), cyclohexylene (including all isomeric forms, e.g., cyclohex-1,1-diyl, cyclohex-1,2-diyl, cyclohex-1,3-diyl, and cyclohex-1,4-diyl), cycloheptylene (including all isomeric forms, e.g., cyclohept-1,1-diyl, cyclohept-1,2-diyl, cyclohept-1,3-diyl, and cyclohept-1,4-diyl), decalinylene (including all isomeric forms, e.g., decalin-1,1-diyl, decalin-1,2-diyl, and decalin-1,8-diyl), and adamantylene (including all isomeric forms, e.g., adamant-1,2-diyl, adamant-1,3-diyl, and adamant-1,8-diyl).

The term "aryl" refers to a monovalent monocyclic aromatic hydrocarbon radical and/or monovalent polycyclic aromatic hydrocarbon radical that contain at least one aromatic carbon ring. In certain embodiments, the aryl has from 6 to 20 ($C_{6-20}$), from 6 to 15 ($C_{6-15}$), or from 6 to 10 ($C_{6-10}$) ring carbon atoms. Examples of aryl groups include, but are not limited to, phenyl, naphthyl, fluorenyl, azulenyl, anthryl, phenanthryl, pyrenyl, biphenyl, and terphenyl. The aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In one embodiment, the aryl is monocyclic. In another embodiment, the aryl is bicyclic. In yet another embodiment, the aryl is tricyclic. In still another embodiment, the aryl is polycyclic. In certain embodiments, the aryl is optionally substituted with one or more substituents Q as described herein.

The terms "arylene" and "arenediyl" are used interchangeably herein in reference to a divalent monocyclic aromatic hydrocarbon radical or divalent polycyclic aromatic hydrocarbon radical that contains at least one aromatic hydrocarbon ring. In certain embodiments, the arylene has from 6 to 20 ($C_{6-20}$), from 6 to 15 ($C_{6-15}$), or from 6 to 10 ($C_{6-10}$) ring atoms. Examples of arylene groups include, but are not limited to, phenylene (including all isomeric forms, e.g., phen-1,2-diyl, phen-1,3-diyl, and phen-1,4-diyl), naphthylene (including all isomeric forms, e.g., naphth-1,2-diyl, naphth-1,3-diyl, and naphth-1,8-diyl), fluorenylene (including all isomeric forms, e.g., fluoren-1,2-diyl, fluoren-1,3-diyl, and fluoren-1,8-diyl), azulenylene (including all isomeric forms, e.g., azulen-1,2-diyl, azulen-1,3-diyl, and azulen-1,8-diyl), anthrylene (including all isomeric forms, e.g., anthr-1,2-diyl, anthr-1,3-diyl, and anthr-1,8-diyl), phenanthrylene (including all isomeric forms, e.g., phenanthr-1,2-diyl, phenanthr-1,3-diyl, and phenanthr-1,8-diyl), pyrenylene (including all isomeric forms, e.g., pyren-1,2-diyl, pyren-1,3-diyl, and pyren-1,8-diyl), biphenylene (including all isomeric forms, e.g., biphen-2,3-diyl, biphen-3,4'-diyl, and biphen-4,4'-diyl), and terphenylene (including all isomeric forms, e.g., terphen-2,3-diyl, terphen-3,4'-diyl, and terphen-4,4'-diyl). Arylene also refers to bicyclic or tricyclic carbon rings, where one of the rings is aromatic and the others of which may be saturated, partially unsaturated, or aromatic, for example, dihydronaphthylene (including all isomeric forms, e.g., dihydronaphth-1,2-diyl or dihydronaphth-1,8-diyl), indenylene (including all isomeric forms, e.g., inden-1,2-diyl, inden-1,5-diyl, or inden-1,7-diyl), indanylene (including all isomeric forms, e.g., indan-1,2-diyl, indan-1,5-diyl, or indan-1,7-diyl), or tetrahydronaphthylene (tetralinylene) (including all isomeric forms, e.g., tetrahydronaphth-1,2-diyl, tetrahydronaphth-1,5-diyl, or tetrahydronaphth-1,8-diyl). In certain embodiments, arylene is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, phenylethyl (including all isomeric forms, e.g., 1-phenylethyl and 2-phenylethyl), and phenylpropyl (including all isomeric forms, e.g., 1-phenylpropyl, 2-phenylpropyl, and 3-phenylpropyl). In certain embodiments, the aralkyl is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each independently selected from O, S, and N, in the ring. The heteroaryl is bonded to the rest of a molecule through the aromatic ring. Each ring of a heteroaryl group can contain one or two O atoms, one or two S atoms, and/or one to four N atoms; provided that the total number of heteroatoms in each ring is four or less and each ring contains at least one carbon atom. In certain embodiments, the heteroaryl has from 5 to 20, from 5 to 15, or from 5 to 10 ring atoms. In one embodiment, the heteroaryl is monocyclic. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. In another embodiment, the heteroaryl is bicyclic. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. In yet another embodiment, the heteroaryl is tricyclic. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The terms "heteroarylene" and "heteroarenediyl" are used interchangeably herein in reference to a divalent monocyclic aromatic group or divalent polycyclic aromatic group that contains at least one aromatic ring, wherein at least one aromatic ring contains one or more heteroatoms in the ring, each of which is independently selected from O, S, and N. A heteroarylene group has at least one linkage to the rest of a molecule via its aromatic ring(s). Each ring of a heteroarylene group can contain one or two O atoms, one or two S atoms, and/or one to four N atoms, provided that the total number of heteroatoms in each ring is four or less and each ring contains at least one carbon atom. In certain embodiments, the heteroarylene has from 5 to 20, from 5 to 15, or from 5 to 10 ring atoms. Examples of monocyclic heteroarylene groups include, but are not limited to, furanylene, imidazolylene, isothiazolylene, isoxazolylene, oxadiazolylene, oxadiazolylene, oxazolylene, pyrazinylene, pyrazolylene, pyridazinylene, pyridylene, pyrimidinylene, pyrrolylene, thiadiazolylene, thiazolylene, thienylene, tetrazolylene, triazinylene, and triazolylene. Examples of bicyclic heteroarylene groups include, but are not limited to, benzofuranylene, benzimidazolylene, benzoisoxazolylene, benzopyranylene, benzothiadiazolylene, benzothiazolylene, benzothienylene, benzotriazolylene, benzoxazolylene, furopyridylene, imidazopyridinylene, imidazothiazolylene, indolizinylene, indolylene, indazolylene, isobenzofuranylene, isobenzothienylene, isoindolylene, isoquinolinylene, isothiazolylene, naphthyridinylene, oxazolopyridinylene, phthalazinylene, pteridinylene, purinylene, pyridopyridylene, pyrrolopyridylene, quinolinylene, quinoxalinylene, quinazolinylene, thiadiazolopyrimidylene, and thienopyridylene. Examples of tricyclic heteroarylene groups include, but are not limited to, acridinylene, benzindolylene, carbazolylene, dibenzofuranylene, perimidinylene, phenanthrolinylene, phenanthridinylene, phenarsazinylene, phenazinylene, phenothiazinylene, phenoxazinylene, and xanthenylene. In certain embodiments, heteroarylene is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. The heterocyclyl is bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclyls and heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein.

The term "heterocyclylene" refers to a divalent monocyclic non-aromatic ring system or divalent polycyclic ring system that contains at least one non-aromatic ring, wherein one or more of the non-aromatic ring atoms are heteroatoms independently selected from O, S, and N; and the remaining ring atoms are carbon atoms. Heterocyclylene groups are bonded to the rest of a molecule through the non-aromatic ring. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclylene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, β-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3,5-trithianylene. In certain embodiments, the heterocyclylene is optionally substituted with one or more substituents Q as described herein.

The term "halogen", "halide," or "halo" refers to fluoro, chloro, bromo, and/or iodo.

The term "optionally substituted" is intended to mean that a group or substituent, such as an alkyl, alkylene, alkenyl, alkenylene, alkynyl, cycloalkyl, cycloalkylene, aryl, arylene, aralkyl, heteroaryl, heteroarylene, heterocyclyl, or heterocyclylene group, may be substituted with one or more, in one embodiment, one, two, three, or four, substituents Q, each of which is independently selected from, e.g., (a) deuterium (-D), cyano (—CN), halo, nitro (—NO$_2$), and oxo (=O); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)NR$^b$R$^c$, —C(O)SR$^a$, —C(NR$^a$)NR$^b$R$^c$, —C(S)$R^a$, —C(S)OR$^a$, —C(S)NR$^b$R$^c$, —OR$^a$, —OC(O)$R^a$, —OC(O)OR$^a$, —OC(O)NR$^b$R$^c$, —OC(O)SR$^a$, —OC(NR$^a$)NR$^b$R$^c$, —OC(S)$R^a$, —OC(S)OR$^a$, —OC(S)NR$^b$R$^c$, —OS(O)$R^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(NR$^d$)RR, —NR$^a$C(S)R$^d$, —NR$^a$C(S)OR$^d$, —NR$^a$C(S)NR$^b$R$^c$, —NR$^{1a}$S(O)R$^d$, —NR$^{1a}$S(O)$_2$R$^d$, —NR$^a$S(O)NR$^d$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) R$^b$ and R$^c$ together with the N atom to which they are attached form heterocyclyl optionally substituted with one or more, in one embodiment, one, two, three, or four, substituents $Q^a$. As used herein, all groups that can be substituted are "optionally substituted."

In one embodiment, each $Q^a$ is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(NR$^h$)NR$^f$R$^g$, —NR$^e$C(S)R$^h$, —NR$^e$C(S)OR$^f$, —NR$^e$C(S)NR$^f$R$^g$, —NRS(O)R$^h$, —NRS(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$R$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

In certain embodiments, "optically active" and "enantiomerically active" refer to a collection of molecules, which has an enantiomeric excess of no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question. In certain embodiments, an optically active compound comprises about 98% or more of one enantiomer and about 2% or less of the other enantiomer based on the total weight of the enantiomeric mixture in question. In certain embodiments, an optically active compound comprises about 99% or more of one enantiomer and about 1% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{5}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, an isotopically enriched compound is in a stable form, that is, non-radioactive. In certain embodiments, an isotopically enriched compound contains unnatural proportions of one or more isotopes, including, but not limited to, hydrogen ($^{1}$H), deuterium (H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an isotopically enriched compound is in an unstable form, that is, radioactive. In certain embodiments, an isotopically enriched compound contains unnatural proportions of one or more isotopes, including, but not limited to, tritium ($^{3}$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^{2}$H, as example, or any carbon can be $^{13}$C, as example, or any nitrogen can be $^{15}$N, as example, or any oxygen can be $^{18}$O, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^{1}$H for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio of the isotopic abundance in an isotopically enriched compound over the natural abundance of a specific isotope.

The term "hydrogen" or the symbol "H" refers to the composition of naturally occurring hydrogen isotopes, which include protium (H), deuterium (H or D), and tritium ($^{3}$H), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}$C) and carbon-13 ($^{13}$C) in their natural abundances. Carbon-12 is the most common carbon isotope having a natural abundance of more than 98.89%. Carbon-13 is a less prevalent carbon isotope having a natural abundance of about 1.11%.

The term "carbon-13 enrichment" or "$^{13}$C enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 95%, at least about 96%, at least about 97%, at least about 98%, at least about 99%, or at least about 99.5% by weight of the molecules are a single compound, including a single enantiomer, a racemic mixture, or a mixture of enantiomers, as determined by a standard analytical method. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which are present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

For a divalent group described herein, no orientation is implied by the direction in which the divalent group is presented. For example, unless a particular orientation is specified, the formula —C(O)NH— represents both —C(O)NH— and —NHC(O)—.

The phrase "an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof" has the same meaning as the phrase "(i) an enantiomer, a mixture of enantiomers, a mixture of two or more diastereomers, a tautomer, a mixture of two or more tautomers, or an isotopic variant of the compound referenced therein; (ii) a pharmaceutically acceptable salt, solvate, hydrate, or prodrug of the compound referenced therein; or (iii) a pharmaceutically acceptable salt, solvate, hydrate, or prodrug of an enantiomer, a mixture of enantiomers, a mixture of two or more diastereomers, a tautomer, a mixture of two or more tautomers, or an isotopic variant of the compound referenced therein."

Compounds

In one embodiment, provided herein is a compound of Formula (I):

(I)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is (a) hydrogen, deuterium, cyano, halo, or nitro; or (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^2$ is —C(O)OR$^{2a}$, —C(O)NR$^{2b}$R$^{2c}$, —C(O)N(R$^{2b}$)OR$^{2c}$, or heteroaryl; wherein R$^{2a}$, R$^{2b}$, and R$^{2c}$ are each independently hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^3$, $R^4$, $R^5$, and $R^6$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O) NR$^{1b}$R$^{1c}$, —OC(NR$^{1a}$)NR$^{1b}$R$^{1c}$, —OS(O)R$^{1a}$, —OS (O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O) NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^A$ is $C_{6-14}$ arylene or heteroarylene;

$R^B$ is $C_{6-14}$ aryl or heteroaryl;

$R^B$ and X are (i), (ii), or (iii):

(iv) X is —O—, —S—, —S(O)—, or —S(O)$_2$—; and $R^B$ is $C_{6-14}$ aryl or heteroaryl;

(v) X is —N(R$^X$)—;

$R^B$ is $C_{6-14}$ aryl or heteroaryl; and $R^X$ is hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (vi) X is —N(R$^X$)—; and $R^B$ and R$^X$ together with the N atom to which they are attached form heteroaryl or heterocyclyl;

L is $C_{1-6}$ alkylene, $C_{2-6}$ alkenylene, $C_{3-10}$ cycloalkylene, or heterocyclylene; and each R$^{1a}$, R$^{1b}$, R$^{1c}$, and R$^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or R$^{1a}$ and R$^{1c}$ together with the C and N atoms to which they are attached form heterocyclyl; or R$^{1b}$ and R$^{1c}$ together with the N atom to which they are attached form heterocyclyl;

wherein each alkyl, alkylene, alkenyl, alkenylene, alkynyl, cycloalkyl, cycloalkylene, aryl, arylene, aralkyl, heteroaryl, heteroarylene, heterocyclyl, and heterocylylene is optionally substituted with one or more, in one embodiment, one, two, three, or four, substituents Q, wherein each Q is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(O)SR$^a$, —C(R$^a$)NR$^b$R$^c$, —C(S) R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC (NR$^a$)NR$^b$R$^c$, —OC(S)R$^a$, —OC(S)OR$^a$, —OC(S) NR$^b$ R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C (O)OR$^d$, —NR$^a$C(O)NR$^b$R$^c$, —NR$^a$C(O)SR$^d$, —NR$^a$C(NR$^d$)NR$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$ NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents Q$^a$; or (iii) R$^b$ and R$^c$ together with the N atom to which they are attached form heterocyclyl optionally substituted with one or more, in one embodiment, one, two, three, or four, substituents Q$^a$;

wherein each Q$^a$ is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$ R$^g$, —OR$^e$, —OC(O)R$^e$, —OC(O)OR$^e$, —OC(O)NR$^f$ R$^g$, —OC(O)SR$^e$, —OC(NR$^e$)NR$^f$R$^g$, —OC(S)R$^e$, —OC(S)OR$^e$, —OC(S)NR$^f$R$^g$, —OS(O)R$^e$, —OS(O)$_2$ R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(NR$^h$)NR$^f$R$^g$, —NR$^e$C(S)R$^h$, —NR$^e$C(S)OR$^f$, —NR$^e$C(S)NR$^f$R$^g$, —NRS(O)R$^h$, —NRS(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

In another embodiment, provided herein is a compound of Formula (II):

(II)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, $R^A$, $R^B$, L, and X are each as defined herein.

In one embodiment, in Formula (I) or (II), $R^1$ is halo or $C_{1-6}$ alkyl;

$R^2$ is —C(O)O$R^{2a}$, —C(O)N$R^{2b}R^{2c}$, —C(O)N($R^{2b}$)O$R^{2c}$, or heteroaryl, wherein each $R^{2a}$, $R^{2b}$, and $R^{2c}$ is independently hydrogen, $C_{1-6}$ alkyl, or heteroaryl;

$R^3$, $R^4$, $R^5$, and $R^6$ are each independently hydrogen, deuterium, halo, or $C_{1-6}$ alkyl;

$R^A$ is $C_{6-14}$ arylene or heteroarylene;

$R^B$ and X are (i), (ii), or (iii):

(i) X is —O—, —S—, —S(O)—, or —S(O)$_2$—; and
$R^B$ is $C_{6-14}$ aryl or heteroaryl;

(ii) X is —NR$^X$—;
$R^B$ is $C_{6-14}$ aryl or heteroaryl; and
$R^X$ is hydrogen, $C_{1-6}$ alkyl, $C_{6-14}$ aryl, or $C_{7-15}$ aralkyl; or (iii) X is —NR$^X$—; and
$R^B$ and $R^X$ together with the N atom to which they are attached form heteroaryl or heterocyclyl; and L is $C_{1-6}$ alkylene, $C_{2-6}$ alkenylene, or $C_{3-10}$ cycloalkylene;

wherein each alkyl, alkylene, alkenylene, cycloalkylene, aryl, arylene, aralkyl, heteroaryl, heteroarylene, and heterocyclyl is optionally substituted with one, two, or three substituents Q.

In another embodiment, in Formula (I) or (II), $R^1$ is halo or $C_{1-6}$ alkyl;

$R^2$ is —C(O)O$R^{2a}$, —C(O)N$R^{2b}R^{2c}$, —C(O)N($R^{2b}$)O$R^{2c}$, or monocyclic heteroaryl, wherein each $R^{2a}$, $R^{2b}$, and $R^{2c}$ is independently hydrogen, $C_{1-6}$ alkyl, or heteroaryl;

$R^3$, $R^4$, $R^5$, and $R^6$ are each independently hydrogen, deuterium, halo, or $C_{1-6}$ alkyl;

$R^A$ is $C_{6-14}$ arylene or monocyclic heteroarylene;

$R^B$ and X are (i), (ii), or (iii):

(i) X is —O—, —S—, —S(O)—, or —S(O)$_2$—; and
$R^B$ is $C_{6-14}$ aryl or heteroaryl;

(ii) X is —NR$^X$—;
$R^B$ is $C_{6-14}$ aryl or heteroaryl; and
$R^X$ is hydrogen, $C_{1-6}$ alkyl, $C_{6-14}$ aryl, or $C_{7-15}$ aralkyl; or (iii) X is —NR$^X$—; and
$R^B$ and $R^X$ together with the N atom to which they are attached form heteroaryl or heterocyclyl; and L is $C_{1-6}$ alkylene or $C_{2-6}$ alkenylene;

wherein each alkyl, alkylene, alkenylene, aryl, arylene, aralkyl, heteroaryl, heteroarylene, and heterocyclyl is optionally substituted with one, two, or three substituents Q, each substituent Q independently selected from (i) bromo, chloro, fluoro, and cyano; (ii) $C_{1-6}$ alkyl optionally substituted with one or more substituents $Q^a$; and (iii) —C(O)$R^a$, —O$R^a$, and —N$R^bR^c$, where each $R^a$, $R^b$, and $R^c$ is as defined herein.

In yet another embodiment, in Formula (I) or (II), $R^1$ is $C_{1-6}$ alkyl;

$R^2$ is —C(O)OH, —C(O)N$R^{2b}R^{2c}$, —C(O)N($R^{2b}$)O$R^{2c}$, or 5-membered heteroaryl, wherein each $R^{2b}$ and $R^{2c}$ is independently hydrogen, $C_{1-6}$ alkyl, or heteroaryl;

$R^3$ and $R^4$ are each independently hydrogen, deuterium, halo, or $C_{1-6}$ alkyl;

$R^5$ and $R^6$ are each independently hydrogen or deuterium;

$R^A$ is $C_{6-14}$ arylene or 6-membered heteroarylene;

$R^B$ and X are (i), (ii), or (iii):

(i) X is —O—, —S—, —S(O)—, or —S(O)$_2$—; and
$R^B$ is monocyclic or bicyclic $C_{6-14}$ aryl, or monocyclic or bicyclic heteroaryl;

(ii) X is —NR$^X$—;
$R^B$ is monocyclic or bicyclic $C_{6-14}$ aryl, or monocyclic or bicyclic heteroaryl; and
$R^X$ is hydrogen, $C_{1-6}$ alkyl, $C_{6-14}$ aryl, or $C_{7-15}$ aralkyl; or (iii) X is —NR$^X$—; and
$R^B$ and $R^X$ together with the N atom to which they are attached form monocyclic or bicyclic heteroaryl, or monocyclic or bicyclic heterocyclyl; and L is $C_{1-6}$ alkylene or $C_{2-6}$ alkenylene;

wherein each alkyl, alkylene, alkenylene, aryl, arylene, aralkyl, heteroaryl, heteroarylene, and heterocyclyl is optionally substituted with one, two, or three substituents Q, each substituent Q independently selected from bromo, chloro, fluoro, cyano, methyl, trifluoromethyl, ethyl, propyl, formyl, hydroxyl, methoxy, and amino.

In yet another embodiment, in Formula (I) or (II), $R^1$ is methyl;

$R^2$ is —C(O)OH, —C(O)NH$_2$, —C(O)NHCH$_3$, —C(O)NHCH$_2$CH$_2$OH, —C(O)NHOH, —C(O)NH(tetrazolyl), tetrazolyl, or 1,2,4-oxadiazolyl;

$R^3$ and $R^4$ are each independently hydrogen, deuterium, fluoro, or methyl;

$R^5$ and $R^6$ are each independently hydrogen or deuterium;

$R^A$ is phenylene, chloro-phenylene, methoxy-phenylene, pyridylene, or methyl-pyridylene;

$R^B$ and X are (i), (ii), or (iii):

(i) X is —O—, —S—, —S(O)—, or —S(O)$_2$—; and
$R^B$ is phenyl, bromophenyl, fluorophenyl, cyanophenyl, methylphenyl, trifluoromethylphenyl, ethylphenyl, propylphenyl, methoxyphenyl, formylphenyl, bromo-fluorophenyl, difluorophenyl, trifluorophenyl, naphthyl, fluoropyridyl, fluoro-methylpyridyl, or quinolinyl;

(ii) X is —NR$^X$—;
$R^B$ is phenyl, bromophenyl, fluorophenyl, cyanophenyl, methylphenyl, trifluoromethylphenyl, ethylphenyl, propylphenyl, methoxyphenyl, formylphenyl, bromo-fluorophenyl, difluorophenyl, trifluorophenyl, naphthyl, fluoropyridyl, fluoro-methylpyridyl, or quinolinyl; and $R^X$ is hydrogen, methyl, ethyl, hydroxyethyl, propyl, phenyl, fluorophenyl, formylphenyl, or benzyl; or (iii) X is —NR$^X$—; and R$^B$ and R$^X$ together with the N atom to which they are attached form pyrrolidinyl, piperidinyl, morpholinyl, pyrrolyl, amino-imidazolyl, or indolyl; and L is methylene, ethylene, or ethenylene.

In still another embodiment, in Formula (I) or (II),

R$^1$ is methyl;

R$^2$ is —C(O)OH, —C(O)NH$_2$, —C(O)NHCH$_3$, —C(O)NHCH$_2$CH$_2$OH, —C(O)NHOH, —C(O)NH(tetrazol-5-yl), tetrazol-5-yl, or 1,2,4-oxadiazol-5-yl;

R$^3$ and R$^4$ are each independently hydrogen, deuterium, fluoro, or methyl;

R$^5$ and R$^6$ are each independently hydrogen or deuterium;

R$^A$ is phen-1,3-diyl, phen-1,4-diyl, 2-chloro-phen-1,4-diyl, 2-methoxy-phen-1,4-diyl, pyrid-2,5-diyl, or 3-methyl-pyrid-2,5-diyl;

R$^B$ and X are (i), (ii), or (iii):

(i) X is —O—, —S—, —S(O)—, or —S(O)$_2$—; and

R$^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl;

(ii) X is —NR$^X$—;

R$^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl; and R$^X$ is hydrogen, methyl, ethyl, 2-hydroxyethyl, n-propyl, phenyl, 4-fluorophenyl, 4-formylphenyl, or benzyl; or (iii) X is —NR$^X$—; and R$^B$ and R$^X$ together with the N atom to which they are attached form pyrrol-1-yl, 2-amino-imidazol-1-yl, indol-1-yl, pyrrolidin-1-yl, piperidin-1-yl, or 4-morpholin-4-yl; and L is methylene, ethan-1,2-diyl, or ethen-1,2-diyl.

In yet another embodiment, provided herein is a compound of Formula (III):

(III)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

U$^1$, V$^1$, W$^1$, and X$^1$ are each independently (i) C or N; or (ii) —CR$^{7a}$═, —N═, —NR$^{7b}$—, —O—, or —S—;

Y$^1$ is (i) C or N; or (ii) a bond, —CR$^{7a}$═, —N═, —NR$^{7b}$—, —O—, or —S—;

Z$^1$ is C or N;

each R$^{7a}$ is independently (a) hydrogen, deuterium, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(NR$^{1d}$)NR$^{1b}$R$^{1c}$, —NR$^{1a}$S(O)R$^{d}$, —NR$^{1a}$S(O)$_2$R$^{1d}$, —NR$^{1a}$S(O)NR$^{1b}$R$^{1c}$, —NR$^{1a}$S(O)$_2$ NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

each R$^{7b}$ is independently hydrogen, C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; and R$^1$, R$^2$, R$^3$, R$^4$, R$^5$, R$^6$, R$^B$, R$^{1a}$, R$^{1b}$, R$^{1c}$, R$^{1d}$, L, and X are each as defined herein;

wherein each alkyl, alkenyl, alkynyl, cycloalkyl, aryl, aralkyl, heteroaryl, and heterocyclyl is optionally substituted with one or more, in one embodiment, one, two, three, or four, substituents Q.

In yet another embodiment, provided herein is a compound of Formula (IV):

(IV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein R$^1$, R$^2$, R$^3$, R$^4$, R$^5$, R$^6$, R$^B$, L, X, U$^1$, V$^1$, W$^1$, X$^1$, Y$^1$, and Z$^1$ are each as defined herein.

In yet another embodiment, provided herein is a compound of Formula (V):

(V)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$U^1$, $V^1$, and $X^1$ are each independently $-CR^{7a}=$, $-N=$, $-NR^{7b}-$, $-O-$, or $-S-$;

$W^1$ is C or N;

$Y^1$ is a bond, $-CR^{7a}=$, $-N=$, $-NR^{7b}-$, $-O-$, or $-S-$; and $R^1$, $R^2$, $R^3$, $R^4$, $R^5$, $R^6$, $R^B$, $R^{7a}$, $R^{7b}$, L, X, and $Z^1$ are each as defined herein.

In yet another embodiment, provided herein is a compound of Formula (VI):

(VI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$U^1$, $V^1$, and $X^1$ are each independently $-CR^{7a}=$, $-N=$, $-NR^{7b}-$, $-O-$, or $-S-$;

$W^1$ is C or N;

$Y^1$ is a bond, $-CR^{7a}=$, $-N=$, $-NR^{7b}-$, $-O-$, or $-S-$; and $R^1$, $R^2$, $R^3$, $R^4$, $R^5$, $R^6$, $R^B$, $R^{7a}$, $R^{7b}$, L, X, and $Z^1$ are each as defined herein.

In yet another embodiment, provided herein is a compound of Formula (VII):

(VII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$U^1$, $W^1$, and $X^1$ are each independently $-CR^{7a}=$, $-N=$, $-NR^{7b}-$, $-O-$, or $-S-$;

$V^1$ is C or N;

$Y^1$ is a bond, $-CR^{7a}=$, $-N=$, $-NR^{7b}-$, $-O-$, or $-S-$; and $R^1$, $R^2$, $R^3$, $R^4$, $R^5$, $R^6$, $R^B$, $R^{7a}$, $R^{7b}$, L, X, and $Z^1$ are each as defined herein.

In yet another embodiment, provided herein is a compound of Formula (VIII):

(VIII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$U^1$, $W^1$, and $X^1$ are each independently $-CR^{7a}=$, $-N=$, $-NR^{7b}-$, $-O-$, or $-S-$;

$V^1$ is C or N;

$Y^1$ is a bond, $-CR^{7a}=$, $-N=$, $-NR^{7b}-$, $-O-$, or $-S-$; and $R^1$, $R^2$, $R^3$, $R^4$, $R^5$, $R^6$, $R^B$, $R^{7a}$, $R^{7b}$, L, X, and Z are each as defined herein.

In yet another embodiment, provided herein is a compound of Formula (IX):

(IX)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

each $R^7$ is independently (a) deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(NR^{1d})NR^{1b}R^{1c}$, $-NR^{1a}S(O)R^{1d}$, $-NR^{1a}S$ $(O)_2R^{1d}$, —$NR^{1a}S(O)NR^{1b}R^{1c}$, —$NR^{1a}S(O)_2$ $NR^{1b}R^{1c}$, —$SR^{1a}$, —$S(O)R^{1a}$, —$S(O)_2R^{1a}$, —$S(O)$ $NR^{1b}R^{1c}$, or —$S(O)_2NR^{1b}R^{1c}$;

1. n is an integer of 0, 1, 2, 3, or 4; and
$R^1$, $R^2$, $R^3$, $R^4$, $R^5$, $R^6$, $R^B$, $R^{1a}$, $R^{1b}$, $R^{1c}$, $R^{1d}$, L, and X are each as defined herein;
wherein the alkyl, alkenyl, alkynyl, cycloalkyl, aryl, aralkyl, heteroaryl, and heterocyclyl are each optionally substituted with one or more, in one embodiment, one, two, three, or four, substituents Q.

In yet another embodiment, provided herein is a compound of Formula (X):

(X)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, $R^7$, $R^B$, L, X, and n are each as defined herein.

In yet another embodiment, provided herein is a compound of Formula (XI):

(XI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, $R^7$, $R^B$, L, X, and n are each as defined herein.

In yet another embodiment, provided herein is a compound of Formula (XII):

(XII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, $R^{7a}$, R, L, and X are each as defined herein.

In yet another embodiment, provided herein is a compound of Formula (XIII):

(XIII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, $R^7$, $R^B$, L, X, and n are each as defined herein.

In one embodiment, in any one of Formulae (IX) to (XI) and (XIII), $R^1$ is halo or $C_{1-6}$ alkyl;
$R^2$ is —$C(O)OR^{2a}$, —$C(O)NR^{2b}R^{2c}$, —$C(O)N(R^{2b})$ $OR^{2c}$, or heteroaryl, wherein each $R^{2a}$, $R^{2b}$, and $R^{2c}$ is independently hydrogen, $C_{1-6}$ alkyl, or heteroaryl;
$R^3$, $R^4$, $R^5$, and $R^6$ are each independently hydrogen, deuterium, halo, or $C_{1-6}$ alkyl;
$R^7$ is deuterium, halo, or —O—$C_{1-6}$ alkyl;
$R^B$ and X are (i), (ii), or (iii):
(i) X is —O—, —S—, —S(O)—, or —$S(O)_2$—; and $R^B$ is $C_{6-14}$ aryl or heteroaryl;
(ii) X is —$NR^X$—;
$R^B$ is $C_{6-14}$ aryl or heteroaryl; and
$R^X$ is hydrogen, $C_{1-6}$ alkyl, $C_{6-14}$ aryl, or $C_{7-15}$ aralkyl; or
(iii) X is —$NR^X$—; and $R^B$ and $R^X$ together with the N atom to which they are attached form heteroaryl or heterocyclyl;

L is $C_{1-6}$ alkylene, $C_{2-6}$ alkenylene, or $C_{3-10}$ cycloalkylene; and n is an integer of 0, 1, 2, 3, or 4;

wherein each alkyl, alkylene, alkenylene, cycloalkylene, aryl, aralkyl, heteroaryl, and heterocyclyl is optionally substituted with one, two, or three substituents Q.

In another embodiment, in any one of Formulae (IX) to (XI) and (XIII), $R^1$ is halo or $C_{1-6}$ alkyl;

$R^2$ is —C(O)OR$^{2a}$, —C(O)NR$^{2b}$R$^{2c}$, —C(O)N(R$^{2b}$)OR$^{2c}$, or monocyclic heteroaryl, wherein each $R^{2a}$, $R^{2b}$, and $R^{2c}$ is independently hydrogen, $C_{1-6}$ alkyl, or heteroaryl;

$R^3$, $R^4$, $R^5$, and $R^6$ are each independently hydrogen, deuterium, halo, or $C_{1-6}$ alkyl;

$R^7$ is deuterium, halo, or —O—$C_{1-6}$ alkyl;

$R^B$ and X are (i), (ii), or (iii):

(i) X is —O—, —S—, —S(O)—, or —S(O)$_2$—; and
    $R^B$ is $C_{6-14}$ aryl or heteroaryl;

(ii) X is —NR$^X$—;
    $R^B$ is $C_{6-14}$ aryl or heteroaryl; and
    $R^X$ is hydrogen, $C_{1-6}$ alkyl, $C_{6-14}$ aryl, or $C_{7-15}$ aralkyl; or (iii) X is —NR$^X$—; and
    $R^B$ and $R^X$ together with the N atom to which they are attached form heteroaryl or heterocyclyl;

L is $C_{1-6}$ alkylene or $C_{2-6}$ alkenylene; and n is an integer of 0, 1, 2, 3, or 4;

wherein each alkyl, alkylene, alkenylene, aryl, aralkyl, heteroaryl, and heterocyclyl is optionally substituted with one, two, or three substituents Q, each substituent Q independently selected from (i) bromo, chloro, fluoro, and cyano; (ii) $C_{1-6}$ alkyl optionally substituted with one or more substituents $Q^a$; and (iii) —C(O)R$^a$, —OR$^a$, and —NR$^b$R$^c$, where each $R^a$, $R^b$, and $R^c$ is as defined herein.

In yet another embodiment, in any one of Formulae (IX) to (XI) and (XIII), $R^1$ is $C_{1-6}$ alkyl;

$R^2$ is —C(O)OH, —C(O)NR$^{2b}$R$^{2c}$, —C(O)N(R$^2$)OR$^{2c}$, or 5-membered heteroaryl, wherein each $R^{2b}$ and $R^{2c}$ is independently hydrogen, $C_{1-6}$ alkyl, or heteroaryl;

$R^3$ and $R^4$ are each independently hydrogen, deuterium, halo, or $C_{1-6}$ alkyl;

$R^5$ and $R^6$ are each independently hydrogen or deuterium;

$R^7$ is deuterium, halo, or —O—$C_{1-6}$ alkyl;

$R^B$ and X are (i), (ii), or (iii):

(i) X is —O—, —S—, —S(O)—, or —S(O)$_2$—; and
    $R^B$ is monocyclic or bicyclic $C_{6-14}$ aryl, or monocyclic or bicyclic heteroaryl;

(ii) X is —NR$^X$—;
    $R^B$ is monocyclic or bicyclic $C_{6-14}$ aryl, or monocyclic or bicyclic heteroaryl; and
    $R^X$ is hydrogen, $C_{1-6}$ alkyl, $C_{6-14}$ aryl, or $C_{7-15}$ aralkyl; or (iii) X is —NR$^X$—; and
    $R^B$ and $R^X$ together with the N atom to which they are attached form monocyclic or bicyclic heteroaryl, or monocyclic or bicyclic heterocyclyl;

L is $C_{1-6}$ alkylene or $C_{2-6}$ alkenylene; and n is an integer of 0, 1, or 2;

wherein each alkyl, alkylene, alkenylene, aryl, aralkyl, heteroaryl, and heterocyclyl is optionally substituted with one, two, or three substituents Q, each substituent Q independently selected from bromo, chloro, fluoro, cyano, methyl, trifluoromethyl, ethyl, propyl, formyl, hydroxyl, methoxy, and amino.

In yet another embodiment, in any one of Formulae (IX) to (XI) and (XIII), $R^1$ is methyl;

$R^2$ is —C(O)OH, —C(O)NH$_2$, —C(O)NHCH$_3$, —C(O)NHCH$_2$CH$_2$OH, —C(O)NHOH, —C(O)NH(tetrazolyl), tetrazolyl, or 1,2,4-oxadiazolyl;

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ and X are (i), (ii), or (iii):

(i) X is —O—, —S—, —S(O)—, or —S(O)$_2$—; and
    $R^B$ is phenyl, bromophenyl, fluorophenyl, cyanophenyl, methylphenyl, trifluoromethylphenyl, ethylphenyl, propylphenyl, methoxyphenyl, formylphenyl, bromo-fluorophenyl, difluorophenyl, trifluorophenyl, naphthyl, fluoropyridyl, fluoro-methylpyridyl, or quinolinyl;

(ii) X is —NR$^X$—;
    $R^B$ is phenyl, bromophenyl, fluorophenyl, cyanophenyl, methylphenyl, trifluoromethylphenyl, ethylphenyl, propylphenyl, methoxyphenyl, formylphenyl, bromo-fluorophenyl, difluorophenyl, trifluorophenyl, naphthyl, fluoropyridyl, fluoro-methylpyridyl, or quinolinyl; and
    $R^X$ is hydrogen, methyl, ethyl, hydroxyethyl, propyl, phenyl, fluorophenyl, formylphenyl, or benzyl; or (iii) X is —NR$^X$—; and
    $R^B$ and $R^X$ together with the N atom to which they are attached form pyrrolidinyl, piperidinyl, morpholinyl, pyrrolyl, amino-imidazolyl, or indolyl;

L is methylene, ethylene, or ethenylene; and n is an integer of 0 or 1.

In still another embodiment, in any one of Formulae (IX) to (XI) and (XIII), $R^1$ is methyl;

$R^2$ is —C(O)OH, —C(O)NH$_2$, —C(O)NHCH$_3$, —C(O)NHCH$_2$CH$_2$OH, —C(O)NHOH, —C(O)NH(tetrazol-5-yl), tetrazol-5-yl, or 1,2,4-oxadiazol-5-yl;

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ and X are (i), (ii), or (iii):

(i) X is —O—, —S—, —S(O)—, or —S(O)$_2$—; and
    $R^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl;

(ii) X is —NR$^X$—;
    $R^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl; and $R^X$ is hydrogen, methyl, ethyl, 2-hydroxyethyl, n-propyl, phenyl, 4-fluorophenyl, 4-formylphenyl, or benzyl; or (iii) X is —NR$^X$—; and $R^B$ and $R^X$ together with the N atom to which they are attached form pyrrol-1-yl, 2-amino-imidazol-1-yl, indol-1-yl, pyrrolidin-1-yl, piperidin-1-yl, or 4-morpholin-4-yl;

L is methylene, ethan-1,2-diyl, or ethen-1,2-diyl; and n is an integer of 0 or 1.

In one embodiment, in Formula (XII), $R^1$ is halo or $C_{1-6}$ alkyl;

$R^2$ is —C(O)OR$^{2a}$, —C(O)NR$^{2b}$R$^{2c}$, —C(O)N(R$^{2b}$)OR$^{2c}$, or heteroaryl, wherein each $R^{2a}$, $R^{2b}$, and $R^{2c}$ is independently hydrogen, $C_{1-6}$ alkyl, or heteroaryl;

$R^3$, $R^4$, $R^5$, and $R^6$ are each independently hydrogen, deuterium, halo, or $C_{1-6}$ alkyl;

$R^{7a}$ is hydrogen, deuterium, halo, or —O—$C_{1-6}$ alkyl;

$R^B$ and X are (i), (ii), or (iii):

(i) X is —O—, —S—, —S(O)—, or —S(O)$_2$—; and $R^B$ is $C_{6-14}$ aryl or heteroaryl;

(ii) X is —NR$^X$—;

$R^B$ is $C_{6-14}$ aryl or heteroaryl; and $R^X$ is hydrogen, $C_{1-6}$ alkyl, $C_{6-14}$ aryl, or $C_{7-15}$ aralkyl; or (iii) X is —NR$^X$—; and $R^B$ and $R^X$ together with the N atom to which they are attached form heteroaryl or heterocyclyl; and L is $C_{1-6}$ alkylene, $C_{2-6}$ alkenylene, or $C_{3-10}$ cycloalkylene;

wherein each alkyl, alkylene, alkenylene, cycloalkylene, aryl, aralkyl, heteroaryl, and heterocyclyl is optionally substituted with one, two, or three substituents Q.

In another embodiment, in Formula (XII), $R^1$ is halo or $C_{1-6}$ alkyl;

$R^2$ is —C(O)OR$^{2a}$, —C(O)NR$^{2b}$R$^{2c}$, —C(O)N(R$^{2b}$)OR$^{2c}$, or monocyclic heteroaryl, wherein each $R^{2a}$, $R^{2b}$, and $R^{2c}$ is independently hydrogen, $C_{1-6}$ alkyl, or heteroaryl;

$R^3$, $R^4$, $R^5$, and $R^6$ are each independently hydrogen, deuterium, halo, or $C_{1-6}$ alkyl;

$R^{7a}$ is hydrogen, deuterium, halo, or —O—$C_{1-6}$ alkyl;

$R^B$ and X are (i), (ii), or (iii):

(i) X is —O—, —S—, —S(O)—, or —S(O)$_2$—; and $R^B$ is $C_{6-14}$ aryl or heteroaryl;

(ii) X is —NR$^X$—;

$R^B$ is $C_{6-14}$ aryl or heteroaryl; and $R^X$ is hydrogen, $C_{1-6}$ alkyl, $C_{6-14}$ aryl, or $C_{7-15}$ aralkyl; or (iii) X is —NR$^X$—; and $R^B$ and $R^X$ together with the N atom to which they are attached form heteroaryl or heterocyclyl; and L is $C_{1-6}$ alkylene or $C_{2-6}$ alkenylene;

wherein each alkyl, alkylene, alkenylene, aryl, aralkyl, heteroaryl, and heterocyclyl is optionally substituted with one, two, or three substituents Q, each substituent Q independently selected from (i) bromo, chloro, fluoro, and cyano; (ii) $C_{1-6}$ alkyl optionally substituted with one or more substituents $Q^a$; and (iii) —C(O)R$^a$, —OR$^a$, and —NR$^b$R$^c$, where each $R^a$, $R^b$, and $R^c$ is as defined herein.

In yet another embodiment, in Formula (XII), $R^1$ is $C_{1-6}$ alkyl;

$R^2$ is —C(O)OH, —C(O)NR$^{2b}$R$^{2c}$, —C(O)N(R$^{2b}$)OR$^{2c}$, or 5-membered heteroaryl, wherein each $R^{2b}$ and $R^{2c}$ is independently hydrogen, $C_{1-6}$ alkyl, or heteroaryl;

$R^3$ and $R^4$ are each independently hydrogen, deuterium, halo, or $C_{1-6}$ alkyl;

$R^5$ and $R^6$ are each independently hydrogen or deuterium;

$R^{7a}$ is hydrogen, deuterium, halo, or —O—$C_{1-6}$ alkyl;

$R^B$ and X are (i), (ii), or (iii):

(i) X is —O—, —S—, —S(O)—, or —S(O)$_2$—; and $R^B$ is monocyclic or bicyclic $C_{6-14}$ aryl, or monocyclic or bicyclic heteroaryl;

(ii) X is —NR$^X$—;

$R^B$ is monocyclic or bicyclic $C_{6-14}$ aryl, or monocyclic or bicyclic heteroaryl; and $R^X$ is hydrogen, $C_{1-6}$ alkyl, $C_{6-14}$ aryl, or $C_{7-15}$ aralkyl; or (iii) X is —NR$^X$—; and $R^B$ and $R^X$ together with the N atom to which they are attached form monocyclic or bicyclic heteroaryl, or monocyclic or bicyclic heterocyclyl; and L is $C_{1-6}$ alkylene or $C_{2-6}$ alkenylene;

wherein each alkyl, alkylene, alkenylene, aryl, aralkyl, heteroaryl, and heterocyclyl is optionally substituted with one, two, or three substituents Q, each substituent Q independently selected from bromo, chloro, fluoro, cyano, methyl, trifluoromethyl, ethyl, propyl, formyl, hydroxyl, methoxy, and amino.

In yet another embodiment, in Formula (XII), $R^1$ is methyl;

$R^2$ is —C(O)OH, —C(O)NH$_2$, —C(O)NHCH$_3$, —C(O)NHCH$_2$CH$_2$OH, —C(O)NHOH, —C(O)NH(tetrazolyl), tetrazolyl, or 1,2,4-oxadiazolyl;

$R^3$ and $R^4$ are each independently hydrogen, deuterium, fluoro, or methyl;

$R^5$ and $R^6$ are each independently hydrogen or deuterium;

$R^{7a}$ is hydrogen, deuterium, chloro, or methoxy;

$R^B$ and X are (i), (ii), or (iii):

(i) X is —O—, —S—, —S(O)—, or —S(O)$_2$—; and $R^B$ is phenyl, bromophenyl, fluorophenyl, cyanophenyl, methylphenyl, trifluoromethylphenyl, ethylphenyl, propylphenyl, methoxyphenyl, formylphenyl, bromo-fluorophenyl, difluorophenyl, trifluorophenyl, naphthyl, fluoropyridyl, fluoro-methylpyridyl, or quinolinyl;

(ii) X is —NR$^X$—;

$R^B$ is phenyl, bromophenyl, fluorophenyl, cyanophenyl, methylphenyl, trifluoromethylphenyl, ethylphenyl, propylphenyl, methoxyphenyl, formylphenyl, bromo-fluorophenyl, difluorophenyl, trifluorophenyl, naphthyl, fluoropyridyl, fluoro-methylpyridyl, or quinolinyl; and $R^X$ is hydrogen, methyl, ethyl, hydroxyethyl, propyl, phenyl, fluorophenyl, formylphenyl, or benzyl; or (iii) X is —NR$^X$—; and $R^B$ and $R^X$ together with the N atom to which they are attached form pyrrolidinyl, piperidinyl, morpholinyl, pyrrolyl, amino-imidazolyl, or indolyl; and L is methylene, ethylene, or ethenylene.

In still another embodiment, in Formula (XII), $R^1$ is methyl;

$R^2$ is —C(O)OH, —C(O)NH$_2$, —C(O)NHCH$_3$, —C(O)NHCH$_2$CH$_2$OH, —C(O)NHOH, —C(O)NH(tetrazol-5-yl), tetrazol-5-yl, or 1,2,4-oxadiazol-5-yl;

$R^3$ and $R^4$ are each independently hydrogen, deuterium, fluoro, or methyl;

$R^5$ and $R^6$ are each independently hydrogen or deuterium;

$R^{7a}$ is hydrogen, deuterium, chloro, or methoxy;

$R^B$ and X are (i), (ii), or (iii):

(i) X is —O—, —S—, —S(O)—, or —S(O)$_2$—; and $R^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl;

(ii) X is —NR$^X$—;

$R^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl; and $R^X$ is hydrogen, methyl, ethyl, 2-hydroxyethyl, n-propyl, phenyl, 4-fluorophenyl, 4-formylphenyl, or benzyl; or (iii) X is —NR$^X$—; and $R^B$ and $R^X$ together with the N atom to which they are attached form pyrrol-1-yl, 2-amino-imidazol-1-yl, indol-1-yl, pyrrolidin-1-yl, piperidin-1-yl, or 4-morpholin-4-yl; and L is methylene, ethan-1,2-diyl, or ethen-1,2-diyl.

In yet another embodiment, provided herein is a compound of Formula (XIV):

(XIV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^{2A}$ is —OR$^{2a}$, —NR$^{2b}$R$^{2c}$, or —N(R$^{2b}$)OR$^{2c}$;

p is an integer of 1, 2, or 3; and $R^1$, $R^3$, $R^4$, $R^5$, $R^6$, $R^7$, $R^B$, $R^{2a}$, $R^{2b}$, $R^{2c}$, and n are each as defined herein.

In yet another embodiment, provided herein is a compound of Formula (XV):

(XV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $R^{2A}$, n, and p are each as defined herein.

In yet another embodiment, provided herein is a compound of Formula (XVI):

(XVI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $R^{2A}$, n, and p are each as defined herein.

In yet another embodiment, provided herein is a compound of Formula (XVII):

(XVII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^{7a}$, $R^B$, $R^{2A}$, and p are each as defined herein.

In yet another embodiment, provided herein is a compound of Formula (XVIII):

(XVIII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $R^{2A}$, n, and p are each as defined herein.

In one embodiment, in any one of Formulae (XIV) to (XVI) and (XVIII), $R^1$ is halo or $C_{1-6}$ alkyl;

$R^{2A}$ is —$OR^{2a}$, —$NR^{2b}R^{2c}$, or —$N(R^{2b})OR^{2c}$, wherein each $R^{2a}$, $R^{2b}$, and $R^{2c}$ is independently hydrogen, $C_{1-6}$ alkyl, or heteroaryl;

$R^3$, $R^4$, $R^5$, and $R^6$ are each independently hydrogen, deuterium, halo, or $C_{1-6}$ alkyl;

$R^7$ is deuterium, halo, or —O—$C_{1-6}$ alkyl;

$R^B$ is $C_{6-14}$ aryl or heteroaryl;

n is an integer of 0, 1, 2, 3, or 4; and p is an integer of 1, 2, or 3;

wherein each alkyl, aryl, and heteroaryl is optionally substituted with one, two, or three substituents Q.

In another embodiment, in any one of Formulae (XIV) to (XVI) and (XVIII), $R^1$ is halo or $C_{1-6}$ alkyl;

$R^{2A}$ is —$OR^{2a}$, —$NR^{2b}R^{2c}$, or —$N(R^{2b})OR^{2c}$, wherein each $R^{2a}$, $R^{2b}$, and $R^{2c}$ is independently hydrogen, $C_{1-6}$ alkyl, or heteroaryl;

$R^3$, $R^4$, $R^5$, and $R^6$ are each independently hydrogen, deuterium, halo, or $C_{1-6}$ alkyl;

$R^7$ is deuterium, halo, or —O—$C_{1-6}$ alkyl;

$R^B$ is $C_{6-14}$ aryl or heteroaryl;

n is an integer of 0, 1, 2, 3, or 4; and p is an integer of 1 or 2;

wherein each alkyl, aryl, and heteroaryl is optionally substituted with one, two, or three substituents Q, each substituent Q independently selected from (i) bromo, chloro, fluoro, and cyano; (ii) $C_{1-6}$ alkyl optionally substituted with one or more substituents $Q^a$; and (iii) —$C(O)R^a$, —$OR^a$, and $NR^bR^c$, where each $R^a$, $R^b$, and $R^c$ is as defined herein.

In yet another embodiment, in any one of Formulae (XIV) to (XVI) and (XVIII), $R^1$ is $C_{1-6}$ alkyl;

$R^{2A}$ is —OH, —$NR^{2b}R^{2c}$, or —$N(R^{2b})OR^{2c}$, wherein each $R^{2b}$ and $R^{2c}$ is independently hydrogen, $C_{1-6}$ alkyl, or heteroaryl;

$R^3$ and $R^4$ are each independently hydrogen, deuterium, halo, or $C_{1-6}$ alkyl;

$R^5$ and $R^6$ are each independently hydrogen or deuterium;

$R^7$ is deuterium, halo, or —O—$C_{1-6}$ alkyl;

$R^B$ is monocyclic or bicyclic $C_{6-14}$ aryl, or monocyclic or bicyclic heteroaryl;

n is an integer of 0, 1, or 2; and p is an integer of 1 or 2;

wherein each alkyl, aryl, and heteroaryl is optionally substituted with one, two, or three substituents Q, each substituent Q independently selected from bromo, chloro, fluoro, cyano, methyl, trifluoromethyl, ethyl, propyl, formyl, hydroxyl, methoxy, and amino.

In yet another embodiment, in any one of Formulae (XIV) to (XVI) and (XVIII), $R^1$ is methyl;

$R^{2A}$ is —OH, —$NH_2$, —$NHCH_3$, —$NHCH_2CH_2OH$, —NHOH, or —NH(tetrazolyl);

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ is phenyl, bromophenyl, fluorophenyl, cyanophenyl, methylphenyl, trifluoromethylphenyl, ethylphenyl, propylphenyl, methoxyphenyl, formylphenyl, bromo-fluorophenyl, difluorophenyl, trifluorophenyl, naphthyl, fluoropyridyl, fluoro-methylpyridyl, or quinolinyl;

n is an integer of 0 or 1; and p is an integer of 1 or 2.

In yet another embodiment, in any one of Formulae (XIV) to (XVI) and (XVIII), $R^1$ is methyl;

$R^{2A}$ is —OH, —$NH_2$, —$NHCH_3$, —$NHCH_2CH_2OH$, —NHOH, or —NH(tetrazolyl);

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ is phenyl, bromophenyl, fluorophenyl, cyanophenyl, methylphenyl, trifluoromethylphenyl, ethylphenyl, propylphenyl, methoxyphenyl, bromo-fluorophenyl, difluorophenyl, trifluorophenyl, naphthyl, fluoropyridyl, fluoro-methylpyridyl, or quinolinyl;

n is an integer of 0 or 1; and p is an integer of 1 or 2.

In yet another embodiment, in any one of Formulae (XIV) to (XVI) and (XVIII), $R^1$ is methyl;

$R^A$ is —OH, —$NH_2$, —$NHCH_3$, —$NHCH_2CH_2OH$, —NHOH, or —NH(tetrazol-5-yl);

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl;

n is an integer of 0 or 1; and p is an integer of 1 or 2.

In still another embodiment, in any one of Formulae (XIV) to (XVI) and (XVIII), $R^1$ is methyl;

$R^{2A}$ is —OH, —NH$_2$, —NHCH$_3$, —NHCH$_2$CH$_2$OH, —NHOH, or —NH(tetrazol-5-yl);

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ is phenyl, 4-bromophenyl, 4-fluorophenyl, 3-cyanophenyl, 3-methylphenyl, 4-methylphenyl, 3-trifluoromethylphenyl, 4-ethylphenyl, 4-isopropylphenyl, 4-methoxyphenyl, 2-bromo-4-fluorophenyl, 2,4-difluorophenyl, 2,4,5-trifluorophenyl, naphth-2-yl, 2-fluoro-pyrid-5-yl, 2-fluoro-3-methyl-pyrid-5-yl, or quinolin-5-yl;

n is an integer of 0 or 1; and p is an integer of 1 or 2.

In one embodiment, in Formula (XVII), $R^1$ is halo or $C_{1-6}$ alkyl;

$R^{2A}$ is —OR$^{2a}$, —NR$^{2b}$R$^{2c}$, or —N(R$^{2b}$)OR$^{2c}$, wherein each $R^{2a}$, $R^{2b}$, and $R^{2c}$ is independently hydrogen, $C_{1-6}$ alkyl, or heteroaryl;

$R^3$, $R^4$, $R^5$, and $R^6$ are each independently hydrogen, deuterium, halo, or $C_{1-6}$ alkyl;

$R^{7a}$ is hydrogen, deuterium, halo, or —O—$C_{1-6}$ alkyl;

$R^B$ is $C_{6-14}$ aryl or heteroaryl; and p is an integer of 1, 2, or 3;

wherein each alkyl, aryl, and heteroaryl is optionally substituted with one, two, or three substituents Q.

In another embodiment, in Formula (XVII), $R^1$ is halo or $C_{1-6}$ alkyl;

$R^{2A}$ is —OR$^{2a}$, —NR$^{2b}$R$^{2c}$, or —N(R$^{2b}$)OR$^{2c}$, wherein each $R^{2a}$, $R^{2b}$, and $R^{2c}$ is independently hydrogen, $C_{1-6}$ alkyl, or heteroaryl;

$R^3$, $R^4$, $R^5$, and $R^6$ are each independently hydrogen, deuterium, halo, or $C_{1-6}$ alkyl;

$R^{7a}$ is hydrogen, deuterium, halo, or —O—$C_{1-6}$ alkyl;

$R^B$ is $C_{6-14}$ aryl or heteroaryl; and p is an integer of 1 or 2;

wherein each alkyl, aryl, and heteroaryl is optionally substituted with one, two, or three substituents Q, each substituent Q independently selected from (i) bromo, chloro, fluoro, and cyano; (ii) $C_{1-6}$ alkyl optionally substituted with one or more substituents Q$^a$; and (iii) —C(O)R$^a$, —OR$^a$, and NR$^b$R$^c$, where each $R^a$, $R^b$, and $R^c$ is as defined herein.

In yet another embodiment, in Formula (XVII), $R^1$ is $C_{1-6}$ alkyl;

$R^{2A}$ is —OH, —NR$^{2b}$R$^{2c}$, or —N(R$^{2b}$)OR$^{2c}$, wherein each $R^{2b}$ and $R^{2c}$ is independently hydrogen, $C_{1-6}$ alkyl, or heteroaryl;

$R^3$ and $R^4$ are each independently hydrogen, deuterium, halo, or $C_{1-6}$ alkyl;

$R^5$ and $R^6$ are each independently hydrogen or deuterium;

$R^{7a}$ is hydrogen, deuterium, halo, or —O—$C_{1-6}$ alkyl;

$R^B$ is monocyclic or bicyclic $C_{6-14}$ aryl, or monocyclic or bicyclic heteroaryl; and p is an integer of 1 or 2;

wherein each alkyl, aryl, and heteroaryl is optionally substituted with one, two, or three substituents Q, each substituent Q independently selected from bromo, chloro, fluoro, cyano, methyl, trifluoromethyl, ethyl, propyl, formyl, hydroxyl, methoxy, and amino.

In yet another embodiment, in Formula (XVII), $R^1$ is methyl;

$R^A$ is —OH, —NH$_2$, —NHCH$_3$, —NHCH$_2$CH$_2$OH, —NHOH, or —NH(tetrazolyl);

$R^3$ and $R^4$ are each independently hydrogen, deuterium, fluoro, or methyl;

$R^5$ and $R^6$ are each independently hydrogen or deuterium;

$R^{7a}$ is hydrogen, deuterium, chloro, or methoxy;

$R^B$ is phenyl, bromophenyl, fluorophenyl, cyanophenyl, methylphenyl, trifluoromethylphenyl, ethylphenyl, propylphenyl, methoxyphenyl, formylphenyl, bromo-fluorophenyl, difluorophenyl, trifluorophenyl, naphthyl, fluoropyridyl, fluoro-methylpyridyl, or quinolinyl; and p is an integer of 1 or 2.

In yet another embodiment, in Formula (XVII), $R^1$ is methyl;

$R^{2A}$ is —OH, —NH$_2$, —NHCH$_3$, —NHCH$_2$CH$_2$OH, —NHOH, or —NH(tetrazolyl);

$R^3$ and $R^4$ are each independently hydrogen, deuterium, fluoro, or methyl;

$R^5$ and $R^6$ are each independently hydrogen or deuterium;

$R^{7a}$ is hydrogen, deuterium, chloro, or methoxy;

$R^B$ is phenyl, bromophenyl, fluorophenyl, cyanophenyl, methylphenyl, trifluoromethylphenyl, ethylphenyl, propylphenyl, methoxyphenyl, bromo-fluorophenyl, difluorophenyl, trifluorophenyl, naphthyl, fluoro-pyridyl, fluoro-methylpyridyl, or quinolinyl; and p is an integer of 1 or 2.

In yet another embodiment, in Formula (XVII), $R^1$ is methyl;

$R^A$ is —OH, —NH$_2$, —NHCH$_3$, —NHCH$_2$CH$_2$OH, —NHOH, or —NH(tetrazol-5-yl);

$R^3$ and $R^4$ are each independently hydrogen, deuterium, fluoro, or methyl;

$R^5$ and $R^6$ are each independently hydrogen or deuterium;

$R^{7a}$ is hydrogen, deuterium, chloro, or methoxy;

$R^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl; and p is an integer of 1 or 2.

In still another embodiment, in Formula (XVII), $R^1$ is methyl;

$R^{2A}$ is —OH, —NH$_2$, —NHCH$_3$, —NHCH$_2$CH$_2$OH, —NHOH, or —NH(tetrazol-5-yl);

$R^3$, $R^5$, and $R^6$ are each independently hydrogen or deuterium;

$R^4$ is hydrogen, deuterium, or fluoro;

$R^{7a}$ is hydrogen, deuterium, chloro, or methoxy;

$R^B$ is phenyl, 4-bromophenyl, 4-fluorophenyl, 3-cyanophenyl, 3-methylphenyl, 4-methylphenyl, 3-trifluoromethylphenyl, 4-ethylphenyl, 4-isopropylphenyl, 4-methoxyphenyl, 2-bromo-4-fluorophenyl, 2,4-difluorophenyl, 2,4,5-trifluorophenyl, naphth-2-yl, 2-fluoro-pyrid-5-yl, 2-fluoro-3-methyl-pyrid-5-yl, or quinolin-5-yl; and p is an integer of 1 or 2.

In yet another embodiment, provided herein is a compound of Formula (XIX):

(XIX)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $R^X$, $R^{2A}$, n, and p are each as defined herein.

In yet another embodiment, provided herein is a compound of Formula (XX):

In yet another embodiment, provided herein is a compound of Formula (XXI):

(XXI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $R^X$, $R^{2A}$, n, and p are each as defined herein.

In yet another embodiment, provided herein is a compound of Formula (XXII):

(XX)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $R^X$, $R^{2A}$, n, and p are each as defined herein.

(XXII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^{7a}$, R, $R^X$, $R^{2A}$, and p are each as defined herein.

In yet another embodiment, provided herein is a compound of Formula (XXIII):

$$(XXIII)$$

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $R^X$, $R^{2A}$, n, and p are each as defined herein.

In one embodiment, in any one of Formulae (XIX) to (XXI) and (XXIII), $R^1$ is halo or $C_{1-6}$ alkyl;

$R^{2A}$ is —$OR^{2a}$, —$NR^{2b}R^{2c}$, or —$N(R^{2b})OR^{2c}$, wherein each $R^{2a}$, $R^{2b}$, and $R^{2c}$ is independently hydrogen, $C_{1-6}$ alkyl, or heteroaryl;

$R^3$, $R^4$, $R^5$, and $R^6$ are each independently hydrogen, deuterium, halo, or $C_{1-6}$ alkyl;

$R^7$ is deuterium, halo, or —O—$C_{1-6}$ alkyl;

$R^B$ and $R^X$ are (i) or (ii):

(i) $R^B$ is $C_{6-14}$ aryl or heteroaryl; and $R^X$ is hydrogen, $C_{1-6}$ alkyl, $C_{6-14}$ aryl, or $C_{7-15}$ aralkyl; or (ii) $R^B$ and $R^X$ together with the N atom to which they are attached form heteroaryl or heterocyclyl;

n is an integer of 0, 1, 2, 3, or 4; and p is an integer of 1, 2, or 3;

wherein each alkyl, aryl, aralkyl, heteroaryl, and heterocyclyl is optionally substituted with one, two, or three substituents Q.

In another embodiment, in any one of Formulae (XIX) to (XXI) and (XXIII), $R^1$ is halo or $C_{1-6}$ alkyl;

$R^{2A}$ is —$OR^{2a}$, —$NR^{2b}R^{2c}$, or —$N(R^{2b})OR^{2c}$, wherein each $R^{2a}$, $R^{2b}$, and $R^{2c}$ is independently hydrogen, $C_{1-6}$ alkyl, or heteroaryl;

$R^3$, $R^4$, $R^5$, and $R^6$ are each independently hydrogen, deuterium, halo, or $C_{1-6}$ alkyl;

$R^7$ is deuterium, halo, or —O—$C_{1-6}$ alkyl;

$R^B$ and $R^X$ are (i) or (ii):

(i) $R^B$ is $C_{6-14}$ aryl or heteroaryl; and $R^X$ is hydrogen, $C_{1-6}$ alkyl, $C_{6-14}$ aryl, or $C_{7-15}$ aralkyl; or (ii) $R^B$ and $R^X$ together with the N atom to which they are attached form heteroaryl or heterocyclyl;

n is an integer of 0, 1, 2, 3, or 4; and p is an integer of 1 or 2;

wherein each alkyl, aryl, aralkyl, heteroaryl, and heterocyclyl is optionally substituted with one, two, or three substituents Q, each substituent Q independently selected from (i) bromo, chloro, fluoro, and cyano; (ii) $C_{1-6}$ alkyl optionally substituted with one or more substituents $Q^a$; and (iii) —$C(O)R^a$, —$OR^a$, and $NR^bR^c$, where each $R^a$, $R^b$, and $R^c$ is as defined herein.

In yet another embodiment, in any one of Formulae (XIX) to (XXI) and (XXIII), $R^1$ is $C_{1-6}$ alkyl;

$R^{2A}$ is —OH, —$NR^{2b}R^{2c}$, or —$N(R^{2b})OR^{2c}$, wherein each $R^{2b}$ and $R^{2c}$ is independently hydrogen, $C_{1-6}$ alkyl, or heteroaryl;

$R^3$ and $R^4$ are each independently hydrogen, deuterium, halo, or $C_{1-6}$ alkyl;

$R^5$ and $R^6$ are each independently hydrogen or deuterium;

$R^7$ is deuterium, halo, or —O—$C_{1-6}$ alkyl;

$R^B$ and $R^X$ are (i) or (ii):

(i) $R^B$ is monocyclic or bicyclic $C_{6-14}$ aryl, or monocyclic or bicyclic heteroaryl; and $R^X$ is hydrogen, $C_{1-6}$ alkyl, $C_{6-14}$ aryl, or $C_{7-15}$ aralkyl; or (ii) $R^B$ and $R^X$ together with the N atom to which they are attached form monocyclic or bicyclic heteroaryl, or monocyclic or bicyclic heterocyclyl;

n is an integer of 0, 1, or 2; and p is an integer of 1 or 2;

wherein each alkyl, aryl, aralkyl, heteroaryl, and heterocyclyl is optionally substituted with one, two, or three substituents Q, each substituent Q independently selected from bromo, chloro, fluoro, cyano, methyl, trifluoromethyl, ethyl, propyl, formyl, hydroxyl, methoxy, and amino.

In yet another embodiment, in any one of Formulae (XIX) to (XXI) and (XXIII), $R^1$ is methyl;

$R^4$ is —OH, —$NH_2$, —$NHCH_3$, —$NHCH_2CH_2OH$, —NHOH, or —NH(tetrazolyl);

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ and $R^X$ are (i) or (ii):

(i) $R^B$ is phenyl, bromophenyl, fluorophenyl, cyanophenyl, methylphenyl, trifluoromethylphenyl, ethylphenyl, propylphenyl, methoxyphenyl, formylphenyl, bromofluorophenyl, difluorophenyl, trifluorophenyl, naphthyl, fluoropyridyl, fluoro-methylpyridyl, or quinolinyl; and $R^X$ is hydrogen, methyl, ethyl, hydroxyethyl, propyl, phenyl, fluorophenyl, formylphenyl, or benzyl; or (ii) $R^B$ and $R^X$ together with the N atom to which they are attached form pyrrolidinyl, piperidinyl, morpholinyl, pyrrolyl, amino-imidazolyl, or indolyl;

n is an integer of 0 or 1; and p is an integer of 1 or 2.

In still another embodiment, in any one of Formulae (XIX) to (XXI) and (XXIII), $R^1$ is methyl;

$R^{2A}$ is —OH, —$NH_2$, —$NHCH_3$, —$NHCH_2CH_2OH$, —NHOH, or —NH(tetrazol-5-yl);

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ and $R^X$ are (i) or (ii):

(i) $R^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl; and $R^X$ is hydrogen, methyl, ethyl, 2-hydroxyethyl, n-propyl, phenyl, 4-fluorophenyl, 4-formylphenyl, or benzyl; or (ii) $R^B$ and $R^X$ together with the N atom to which they are attached form pyrrol-1-yl, 2-amino-imidazol-1-yl, indol-1-yl, pyrrolidin-1-yl, piperidin-1-yl, or 4-morpholin-4-yl;

n is an integer of 0 or 1; and p is an integer of 1 or 2.

In one embodiment, in Formula (XXII), $R^1$ is halo or $C_{1-6}$ alkyl;

$R^{2A}$ is —$OR^{2a}$, —$NR^{2b}R^{2c}$, or —$N(R^{2b})OR^{2c}$, wherein each $R^{2a}$, $R^{2b}$, and $R^{2c}$ is independently hydrogen, $C_{1-6}$ alkyl, or heteroaryl;

$R^3$, $R^4$, $R^5$, and $R^6$ are each independently hydrogen, deuterium, halo, or $C_{1-6}$ alkyl;

$R^{7a}$ is hydrogen, deuterium, halo, or —O—$C_{1-6}$ alkyl;

$R^B$ and $R^X$ are (i) or (ii):

(i) $R^B$ is $C_{6-14}$ aryl or heteroaryl; and $R^X$ is hydrogen, $C_{1-6}$ alkyl, $C_{6-14}$ aryl, or $C_{7-15}$ aralkyl; or (ii) $R^B$ and $R^X$ together with the N atom to which they are attached form heteroaryl or heterocyclyl; and p is an integer of 1, 2, or 3;

wherein each alkyl, aryl, aralkyl, heteroaryl, and heterocyclyl is optionally substituted with one, two, or three substituents Q.

In another embodiment, in Formula (XXII), $R^1$ is halo or $C_{1-6}$ alkyl;

$R^{2A}$ is —$OR^{2a}$, —$NR^{2b}R^{2c}$, or —$N(R^{2b})OR^{2c}$, wherein each $R^{2a}$, $R^{2b}$, and $R^{2c}$ is independently hydrogen, $C_{1-6}$ alkyl, or heteroaryl;

$R^3$, $R^4$, $R^5$, and $R^6$ are each independently hydrogen, deuterium, halo, or $C_{1-6}$ alkyl;

$R^{7a}$ is hydrogen, deuterium, halo, or —O—$C_{1-6}$ alkyl;

$R^B$ and $R^X$ are (i) or (ii):

(i) $R^B$ is $C_{6-14}$ aryl or heteroaryl; and $R^X$ is hydrogen, $C_{1-6}$ alkyl, $C_{6-14}$ aryl, or $C_{7-15}$ aralkyl; or (ii) $R^B$ and $R^X$ together with the N atom to which they are attached form heteroaryl or heterocyclyl; and p is an integer of 1 or 2;

wherein each alkyl, aryl, aralkyl, heteroaryl, and heterocyclyl is optionally substituted with one, two, or three substituents Q, each substituent Q independently selected from (i) bromo, chloro, fluoro, and cyano; (ii) $C_{1-6}$ alkyl optionally substituted with one or more substituents $Q^a$; and (iii) —$C(O)R^a$, —$OR^a$, and $NR^bR^c$, where each $R^a$, $R^b$, and $R^c$ is as defined herein.

In yet another embodiment, in Formula (XXII), $R^1$ is $C_{1-6}$ alkyl;

$R^{2A}$ is —OH, —$NR^{2b}R^{2c}$, or —$N(R^{2b})OR^{2c}$, wherein each $R^{2b}$ and $R^{2c}$ is independently hydrogen, $C_{1-6}$ alkyl, or heteroaryl;

$R^3$ and $R^4$ are each independently hydrogen, deuterium, halo, or $C_{1-6}$ alkyl;

$R^5$ and $R^6$ are each independently hydrogen or deuterium;

$R^{7a}$ is hydrogen, deuterium, halo or —O—$C_{1-6}$ alkyl;

$R^B$ and $R^X$ are (i) or (ii):

(i) $R^B$ is monocyclic or bicyclic $C_{6-14}$ aryl, or monocyclic or bicyclic heteroaryl; and $R^X$ is hydrogen, $C_{1-6}$ alkyl, $C_{6-14}$ aryl, or $C_{7-15}$ aralkyl; or (ii) $R^B$ and $R^X$ together with the N atom to which they are attached form monocyclic or bicyclic heteroaryl, or monocyclic or bicyclic heterocyclyl; and p is an integer of 1 or 2;

wherein each alkyl, aryl, aralkyl, heteroaryl, and heterocyclyl is optionally substituted with one, two, or three substituents Q, each substituent Q independently selected from bromo, chloro, fluoro, cyano, methyl, trifluoromethyl, ethyl, propyl, formyl, hydroxyl, methoxy, and amino.

In yet another embodiment, in Formula (XXII), $R^1$ is methyl;

$R^{2A}$ is —OH, —$NH_2$, —$NHCH_3$, —$NHCH_2CH_2OH$, —NHOH, or —NH(tetrazolyl);

$R^3$ and $R^4$ are each independently hydrogen, deuterium, fluoro, or methyl;

$R^5$ and $R^6$ are each independently hydrogen or deuterium;

$R^{7a}$ is hydrogen, deuterium, chloro, or methoxy;

$R^B$ and $R^X$ are (i) or (ii):

(i) $R^B$ is phenyl, bromophenyl, fluorophenyl, cyanophenyl, methylphenyl, trifluoromethylphenyl, ethylphenyl, propylphenyl, methoxyphenyl, formylphenyl, bromofluorophenyl, difluorophenyl, trifluorophenyl, naphthyl, fluoropyridyl, fluoro-methylpyridyl, or quinolinyl; and $R^X$ is hydrogen, methyl, ethyl, hydroxyethyl, propyl, phenyl, fluorophenyl, formylphenyl, or benzyl; or (ii) $R^B$ and $R^X$ together with the N atom to which they are attached form pyrrolidinyl, piperidinyl, morpholinyl, pyrrolyl, amino-imidazolyl, or indolyl; and p is an integer of 1 or 2.

In still another embodiment, in Formula (XXII), $R^1$ is methyl;

$R^{2A}$ is —OH, —$NH_2$, —$NHCH_3$, —$NHCH_2CH_2OH$, —NHOH, or —NH(tetrazol-5-yl);

$R^3$ and $R^4$ are each independently hydrogen, deuterium, fluoro, or methyl;

$R^5$ and $R^6$ are each independently hydrogen or deuterium;

$R^{7a}$ is hydrogen, deuterium, chloro, or methoxy;

$R^B$ and $R^X$ are (i) or (ii):

(i) $R^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl; and $R^X$ is hydrogen, methyl, ethyl, 2-hydroxyethyl, n-propyl, phenyl, 4-fluorophenyl, 4-formylphenyl, or benzyl; or (ii) $R^B$ and $R^X$ together with the N atom to which they are attached form pyrrol-1-yl, 2-amino-imidazol-1-yl, indol-1-yl, pyrrolidin-1-yl, piperidin-1-yl, or 4-morpholin-4-yl; and p is an integer of 1 or 2.

In yet another embodiment, provided herein is a compound of Formula (XXIV):

(XXIV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$U^2$ is —N= or —O—;

$V^2$ is —N= or —C(OH)=; and $R^1$, $R^3$, $R^4$, $R^5$, $R^6$, $R^7$, $R^B$, n, and p are each as defined herein.

In yet another embodiment, provided herein is a compound of Formula (XXV):

(XXV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $U^2$, $V^2$, n, and p are each as defined herein.

In yet another embodiment, provided herein is a compound of Formula (XXVI):

(XXVI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $U^2$, $V^2$, n, and p are each as defined herein.

In yet another embodiment, provided herein is a compound of Formula (XXVII):

(XXVII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^{7a}$, $R^B$, $U^2$, $V^2$, and p are each as defined herein.

In yet another embodiment, provided herein is a compound of Formula (XXVIII):

(XXVIII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $U^2$, $V^2$, n, and p are each as defined herein.

In one embodiment, in any one of Formulae (XXIV) to (XXVI) and (XXVIII), $R^1$ is halo or $C_{1-6}$ alkyl;

$R^3$, $R^4$, $R^5$, and $R^6$ are each independently hydrogen, deuterium, halo, or $C_{1-6}$ alkyl;

$R^7$ is deuterium, halo, or —O—$C_{1-6}$ alkyl;

$R^B$ is $C_{6-14}$ aryl or heteroaryl;

$U^2$ is —N= or —O—;

$V^2$ is —N= or —C(OH)=;

n is an integer of 0, 1, 2, 3, or 4; and p is an integer of 1, 2, or 3;

wherein each alkyl, aryl, and heteroaryl is optionally substituted with one, two, or three substituents Q.

In another embodiment, in any one of Formulae (XXIV) to (XXVI) and (XXVIII), $R^1$ is halo or $C_{1-6}$ alkyl;

$R^3$, $R^4$, $R^5$, and $R^6$ are each independently hydrogen, deuterium, halo, or $C_{1-6}$ alkyl;

$R^7$ is deuterium, halo, or —O—$C_{1-6}$ alkyl;

$R^B$ is $C_{6-14}$ aryl or heteroaryl;

$U^2$ and $V^2$ are each —N=; or $U^2$ is —O— and $V^2$ is —C(OH)=;

n is an integer of 0, 1, 2, 3, or 4; and p is an integer of 1 or 2;

wherein each alkyl, aryl, and heteroaryl is optionally substituted with one, two, or three substituents Q, each substituent Q independently selected from (i) bromo, chloro, fluoro, and cyano; (ii) $C_{1-6}$ alkyl optionally substituted with one or more substituents $Q^a$; and (iii) —C(O)$R^a$, —O$R^a$, and NR$^b$R$^c$, where each $R^a$, $R^b$, and $R^c$ is as defined herein.

In yet another embodiment, in any one of Formulae (XXIV) to (XXVI) and (XXVIII), $R^1$ is $C_{1-6}$ alkyl;

$R^3$ and $R^4$ are each independently hydrogen, deuterium, halo, or $C_{1-6}$ alkyl;

$R^5$ and $R^6$ are each independently hydrogen or deuterium;

$R^7$ is deuterium, halo, or —O—$C_{1-6}$ alkyl;

$R^B$ is monocyclic or bicyclic $C_{6-14}$ aryl, or monocyclic or bicyclic heteroaryl;

$U^2$ and $V^2$ are each —N=; or $U^2$ is —O— and $V^2$ is —C(OH)=;

n is an integer of 0, 1, or 2; and p is an integer of 1 or 2;

wherein each alkyl, aryl, and heteroaryl is optionally substituted with one, two, or three substituents Q, each substituent Q independently selected from bromo, chloro, fluoro, cyano, methyl, trifluoromethyl, ethyl, propyl, formyl, hydroxyl, methoxy, and amino.

In yet another embodiment, in any one of Formulae (XXIV) to (XXVI) and (XXVIII), $R^1$ is methyl;

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ is phenyl, bromophenyl, fluorophenyl, cyanophenyl, methylphenyl, trifluoromethylphenyl, ethylphenyl, propylphenyl, methoxyphenyl, formylphenyl, bromo-fluorophenyl, difluorophenyl, trifluorophenyl, naphthyl, fluoropyridyl, fluoro-methylpyridyl, or quinolinyl;

$U^2$ and $V^2$ are each —N=; or $U^2$ is —O— and $V^2$ is —C(OH)=;

n is an integer of 0 or 1; and p is an integer of 1 or 2.

In yet another embodiment, in any one of Formulae (XXIV) to (XXVI) and (XXVIII), $R^1$ is methyl;

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ is phenyl, bromophenyl, fluorophenyl, cyanophenyl, methylphenyl, trifluoromethylphenyl, ethylphenyl, propylphenyl, methoxyphenyl, bromo-fluorophenyl, difluorophenyl, trifluorophenyl, naphthyl, fluoropyridyl, fluoro-methylpyridyl, or quinolinyl;

$U^2$ and $V^2$ are each —N=; or $U^2$ is —O— and $V^2$ is —C(OH)=;

n is an integer of 0 or 1; and p is an integer of 1 or 2.

In yet another embodiment, in any one of Formulae (XXIV) to (XXVI) and (XXVIII), $R^1$ is methyl;

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ is phenyl, 3-bromophenyl, 4-bromophenyl, 4-fluoro-phenyl, 3-cyanophenyl, 3-methylphenyl, 4-methylphe-nyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluoro-phenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl;

$U^2$ and $V^2$ are each —N=; or $U^2$ is —O— and $V^2$ is —C(OH)=;

n is an integer of 0 or 1; and p is an integer of 1 or 2.

In still another embodiment, in any one of Formulae (XXIV) to (XXVI) and (XXVIII), $R^1$ is methyl;

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ is phenyl, 4-bromophenyl, 4-fluorophenyl, 3-cyano-phenyl, 3-methylphenyl, 4-methylphenyl, 3-trifluo-romethylphenyl, 4-ethylphenyl, 4-isopropylphenyl, 4-methoxyphenyl, 2-bromo-4-fluorophenyl, 2,4-difluo-rophenyl, 2,4,5-trifluorophenyl, naphth-2-yl, 2-fluoro-pyrid-5-yl, 2-fluoro-3-methyl-pyrid-5-yl, or quinolin-5-yl;

$U^2$ and $V^2$ are each —N=; or $U^2$ is —O— and $V^2$ is —C(OH)=;

n is an integer of 0 or 1; and p is an integer of 1 or 2.

In one embodiment, in Formula (XXVII), $R^1$ is halo or $C_{1-6}$ alkyl;

$R^3$, $R^4$, $R^5$, and $R^6$ are each independently hydrogen, deuterium, halo, or $C_{1-6}$ alkyl;

$R^{7a}$ is hydrogen, deuterium, halo, or —O—$C_{1-6}$ alkyl;

$R^B$ is $C_{6-14}$ aryl or heteroaryl;

$U^2$ is —N= or —O—;

$V^2$ is —N= or —C(OH)=; and p is an integer of 1, 2, or 3;

wherein each alkyl, aryl, and heteroaryl is optionally substituted with one, two, or three substituents Q.

In another embodiment, in Formula (XXVII), $R^1$ is halo or $C_{1-6}$ alkyl;

$R^3$, $R^4$, $R^5$, and $R^6$ are each independently hydrogen, deuterium, halo, or $C_{1-6}$ alkyl;

$R^{7a}$ is hydrogen, deuterium, halo, or —O—$C_{1-6}$ alkyl;

$R^B$ is $C_{6-14}$ aryl or heteroaryl;

$U^2$ and $V^2$ are each —N=; or $U^2$ is —O— and $V^2$ is —C(OH)=; and p is an integer of 1 or 2;

wherein each alkyl, aryl, and heteroaryl is optionally substituted with one, two, or three substituents Q, each substituent Q independently selected from (i) bromo, chloro, fluoro, and cyano; (ii) $C_{1-6}$ alkyl optionally substituted with one or more substituents $Q^a$; and (iii) —C(O)$R^a$, —O$R^a$, and NR$^b$R$^c$, where each $R^a$, $R^b$, and $R^c$ is as defined herein.

In yet another embodiment, in Formula (XXVII), $R^1$ is $C_{1-6}$ alkyl;

$R^3$ and $R^4$ are each independently hydrogen, deuterium, halo, or $C_{1-6}$ alkyl;

$R^5$ and $R^6$ are each independently hydrogen or deuterium;

$R^{7a}$ is hydrogen, deuterium, halo, or —O—$C_{1-6}$ alkyl;

$R^B$ is monocyclic or bicyclic $C_{6-14}$ aryl, or monocyclic or bicyclic heteroaryl;

$U^2$ and $V^2$ are each —N=; or $U^2$ is —O— and $V^2$ is —C(OH)=; and p is an integer of 1 or 2;

wherein each alkyl, aryl, and heteroaryl is optionally substituted with one, two, or three substituents Q, each substituent Q independently selected from bromo, chloro, fluoro, cyano, methyl, trifluoromethyl, ethyl, propyl, formyl, hydroxyl, methoxy, and amino.

In yet another embodiment, in Formula (XXVII), $R^1$ is methyl;

$R^3$ and $R^4$ are each independently hydrogen, deuterium, fluoro, or methyl;

$R^5$ and $R^6$ are each independently hydrogen or deuterium;

$R^{7a}$ is chloro or methoxy;

$R^B$ is phenyl, bromophenyl, fluorophenyl, cyanophenyl, methylphenyl, trifluoromethylphenyl, ethylphenyl, propylphenyl, methoxyphenyl, formylphenyl, bromo-fluorophenyl, difluorophenyl, trifluorophenyl, naphthyl, fluoropyridyl, fluoro-methylpyridyl, or quinolinyl;

$U^2$ and $V^2$ are each —N=; or $U^2$ is —O— and $V^2$ is —C(OH)=; and p is an integer of 1 or 2.

In yet another embodiment, in Formula (XXVII), $R^1$ is methyl;

$R^3$ and $R^4$ are each independently hydrogen, deuterium, fluoro, or methyl;

$R^5$ and $R^6$ are each independently hydrogen or deuterium;

$R^{7a}$ is chloro or methoxy;

$R^B$ is phenyl, bromophenyl, fluorophenyl, cyanophenyl, methylphenyl, trifluoromethylphenyl, ethylphenyl, propylphenyl, methoxyphenyl, bromo-fluorophenyl, difluorophenyl, trifluorophenyl, naphthyl, fluoropyridyl, fluoro-methylpyridyl, or quinolinyl;

$U^2$ and $V^2$ are each —N=; or $U^2$ is —O— and $V^2$ is —C(OH)=; and p is an integer of 1 or 2.

In yet another embodiment, in Formula (XXVII), $R^1$ is methyl;

$R^3$ and $R^4$ are each independently hydrogen, deuterium, fluoro, or methyl;

$R^5$ and $R^6$ are each independently hydrogen or deuterium;

$R^{7a}$ is hydrogen, deuterium, chloro, or methoxy;

$R^B$ is phenyl, 3-bromophenyl, 4-bromophenyl, 4-fluoro-phenyl, 3-cyanophenyl, 3-methylphenyl, 4-methylphe-nyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluoro-phenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl;

$U^2$ and $V^2$ are each —N=; or $U^2$ is —O— and $V^2$ is —C(OH)=; and p is an integer of 1 or 2.

In still another embodiment, in Formula (XXVII), $R^1$ is methyl;

$R^3$ and $R^4$ are each independently hydrogen, deuterium, fluoro, or methyl;

$R^5$ and $R^6$ are each independently hydrogen or deuterium;

$R^{7a}$ is hydrogen, deuterium, chloro, or methoxy;

$R^B$ is phenyl, 4-bromophenyl, 4-fluorophenyl, 3-cyano-phenyl, 3-methylphenyl, 4-methylphenyl, 3-trifluo-romethylphenyl, 4-ethylphenyl, 4-isopropylphenyl, 4-methoxyphenyl, 2-bromo-4-fluorophenyl, 2,4-difluo-rophenyl, 2,4,5-trifluorophenyl, naphth-2-yl, 2-fluoro-pyrid-5-yl, 2-fluoro-3-methyl-pyrid-5-yl, or quinolin-5-yl;

$U^2$ and $V^2$ are each —N=; or $U^2$ is —O— and $V^2$ is —C(OH)=; and p is an integer of 1 or 2.

In yet another embodiment, provided herein is a compound of Formula (XXIX):

(XXIX)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $R^X$, $U^2$, $V^2$, n, and p are each as defined herein.

In yet another embodiment, provided herein is a compound of Formula (XXX):

(XXX)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $R^X$, $U^2$, $V^2$, n, and p are each as defined herein.

In yet another embodiment, provided herein is a compound of Formula (XXXI):

(XXXI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $R^X$, $U^2$, $V^2$, n, and p are each as defined herein.

In yet another embodiment, provided herein is a compound of Formula (XXXII):

(XXXII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^{7a}$, $R^B$, $R^X$, $U^2$, $V^2$, and p are each as defined herein.

In still another embodiment, provided herein is a compound of Formula (XXXIII):

(XXXIII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, $R^7$, $R^B$, $R^X$, $U^2$, $V^2$, n, and p are each as defined herein.

In one embodiment, in any one of Formulae (XXIX) to (XXXI) and (XXXIII), $R^1$ is halo or $C_{1-6}$ alkyl;

$R^3$, $R^4$, $R^5$, and $R^6$ are each independently hydrogen, deuterium, halo, or $C_{1-6}$ alkyl;

$R^7$ is deuterium, halo, or $-O-C_{1-6}$ alkyl;

$R^B$ and $R^X$ are (i) or (ii):

(i) $R^B$ is $C_{6-14}$ aryl or heteroaryl; and $R^X$ is hydrogen, $C_{1-6}$ alkyl, $C_{6-14}$ aryl, or $C_{7-15}$ aralkyl; or (ii) $R^B$ and $R^X$ together with the N atom to which they are attached form heteroaryl or heterocyclyl;

$U^2$ is $-N=$ or $-O-$;

$V^2$ is $-N=$ or $-C(OH)=$;

n is an integer of 0, 1, 2, 3, or 4; and p is an integer of 1, 2, or 3;

wherein each alkyl, aryl, aralkyl, heteroaryl, and heterocyclyl is optionally substituted with one, two, or three substituents Q.

In another embodiment, in any one of Formulae (XXIX) to (XXXI) and (XXXIII), $R^1$ is halo or $C_{1-6}$ alkyl;

$R^3$, $R^4$, $R^5$, and $R^6$ are each independently hydrogen, deuterium, halo, or $C_{1-6}$ alkyl;

$R^7$ is deuterium, halo, or —O—$C_{1-6}$ alkyl;

$R^B$ and $R^X$ are (i) or (ii):

(i) $R^B$ is $C_{6-14}$ aryl or heteroaryl; and $R^X$ is hydrogen, $C_{1-6}$ alkyl, $C_{6-14}$ aryl, or $C_{7-15}$ aralkyl; or (ii) $R^B$ and $R^X$ together with the N atom to which they are attached form heteroaryl or heterocyclyl;

$U^2$ and $V^2$ are each —N=; or $U^2$ is —O— and $V^2$ is —C(OH)=;

n is an integer of 0, 1, 2, 3, or 4; and p is an integer of 1 or 2;

wherein each alkyl, aryl, aralkyl, heteroaryl, and heterocyclyl is optionally substituted with one, two, or three substituents Q, each substituent Q independently selected from (i) bromo, chloro, fluoro, and cyano; (ii) $C_{1-6}$ alkyl optionally substituted with one or more substituents $Q^a$; and (iii) —C(O)$R^a$, —O$R^a$, and N$R^b R^c$, where each $R^a$, $R^b$, and $R^c$ is as defined herein.

In yet another embodiment, in any one of Formulae (XXIX) to (XXXI) and (XXXIII), $R^1$ is $C_{1-6}$ alkyl;

$R^3$ and $R^4$ are each independently hydrogen, deuterium, halo, or $C_{1-6}$ alkyl;

$R^5$ and $R^6$ are each independently hydrogen or deuterium;

$R^7$ is deuterium, halo, or —O—$C_{1-6}$ alkyl;

$R^B$ and $R^X$ are (i) or (ii):

(i) $R^B$ is monocyclic or bicyclic $C_{6-14}$ aryl, or monocyclic or bicyclic heteroaryl; and $R^X$ is hydrogen, $C_{1-6}$ alkyl, $C_{6-14}$ aryl, or $C_{7-15}$ aralkyl; or (ii) $R^B$ and $R^X$ together with the N atom to which they are attached form monocyclic or bicyclic heteroaryl, or monocyclic or bicyclic heterocyclyl;

$U^2$ and $V^2$ are each —N=; or $U^2$ is —O— and $V^2$ is —C(OH)=;

n is an integer of 0, 1, or 2; and p is an integer of 1 or 2;

wherein each alkyl, aryl, aralkyl, heteroaryl, and heterocyclyl is optionally substituted with one, two, or three substituents Q, each substituent Q independently selected from bromo, chloro, fluoro, cyano, methyl, trifluoromethyl, ethyl, propyl, formyl, hydroxyl, methoxy, and amino.

In yet another embodiment, in any one of Formulae (XXIX) to (XXXI) and (XXXIII), $R^1$ is methyl;

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ and $R^X$ are (i) or (ii):

(i) $R^B$ is phenyl, bromophenyl, fluorophenyl, cyanophenyl, methylphenyl, trifluoromethylphenyl, ethylphenyl, propylphenyl, methoxyphenyl, formylphenyl, bromofluorophenyl, difluorophenyl, trifluorophenyl, naphthyl, fluoropyridyl, fluoro-methylpyridyl, or quinolinyl; and $R^X$ is hydrogen, methyl, ethyl, hydroxyethyl, propyl, phenyl, fluorophenyl, formylphenyl, or benzyl; or (ii) $R^B$ and $R^X$ together with the N atom to which they are attached form pyrrolidinyl, piperidinyl, morpholinyl, pyrrolyl, amino-imidazolyl, or indolyl;

$U^2$ and $V^2$ are each —N=; or $U^2$ is —O— and $V^2$ is —C(OH)=;

n is an integer of 0 or 1; and p is an integer of 1 or 2.

In still another embodiment, in any one of Formulae (XXIX) to (XXXI) and (XXXIII), $R^1$ is methyl;

$R^3$ and $R^4$ are each independently hydrogen, deuterium, fluoro, or methyl;

$R^5$ and $R^6$ are each independently hydrogen or deuterium;

$R^7$ is chloro or methoxy;

$R^B$ and $R^X$ are (i) or (ii):

(i) $R^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl; and $R^X$ is hydrogen, methyl, ethyl, 2-hydroxyethyl, n-propyl, phenyl, 4-fluorophenyl, 4-formylphenyl, or benzyl; or (ii) $R^B$ and $R^X$ together with the N atom to which they are attached form pyrrol-1-yl, 2-amino-imidazol-1-yl, indol-1-yl, pyrrolidin-1-yl, piperidin-1-yl, or 4-morpholin-4-yl;

$U^2$ and $V^2$ are each —N=; or $U^2$ is —O— and $V^2$ is —C(OH)=;

n is an integer of 0 or 1; and p is an integer of 1 or 2.

In one embodiment, in Formula (XXX), $R^1$ is halo or $C_{1-6}$ alkyl;

$R^3$, $R^4$, $R^5$, and $R^6$ are each independently hydrogen, deuterium, halo, or $C_{1-6}$ alkyl;

$R^{7a}$ is hydrogen, deuterium, halo, or —O—$C_{1-6}$ alkyl;

$R^B$ and $R^X$ are (i) or (ii):

(i) $R^B$ is $C_{6-14}$ aryl or heteroaryl; and $R^X$ is hydrogen, $C_{1-6}$ alkyl, $C_{6-14}$ aryl, or $C_{7-15}$ aralkyl; or (ii) $R^B$ and $R^X$ together with the N atom to which they are attached form heteroaryl or heterocyclyl;

$U^2$ is —N= or —O—;

$V^2$ is —N= or —C(OH)=; and p is an integer of 1, 2, or 3;

wherein each alkyl, aryl, aralkyl, heteroaryl, and heterocyclyl is optionally substituted with one, two, or three substituents Q.

In another embodiment, in Formula (XXX), $R^1$ is halo or $C_{1-6}$ alkyl;

$R^3$, $R^4$, $R^5$, and $R^6$ are each independently hydrogen, deuterium, halo, or $C_{1-6}$ alkyl;

$R^{7a}$ is hydrogen, deuterium, halo, or —O—$C_{1-6}$ alkyl;

$R^B$ and $R^X$ are (i) or (ii):

(i) $R^B$ is $C_{6-14}$ aryl or heteroaryl; and $R^X$ is hydrogen, $C_{1-6}$ alkyl, $C_{6-14}$ aryl, or $C_{7-15}$ aralkyl; or (ii) $R^B$ and $R^X$ together with the N atom to which they are attached form heteroaryl or heterocyclyl;

$U^2$ and $V^2$ are each —N=; or $U^2$ is —O— and $V^2$ is —C(OH)=; and p is an integer of 1 or 2;

wherein each alkyl, aryl, aralkyl, heteroaryl, and heterocyclyl is optionally substituted with one, two, or three substituents Q, each substituent Q independently selected from (i) bromo, chloro, fluoro, and cyano; (ii) $C_{1-6}$ alkyl optionally substituted with one or more substituents $Q^a$; and (iii) —C(O)R$^a$, —OR$^a$, and NR$^b$R$^c$, where each R$^a$, R$^b$, and R$^c$ is as defined herein.

In yet another embodiment, in Formula (XXX),

R$^1$ is C$_{1-6}$ alkyl;

R$^3$ and R$^4$ are each independently hydrogen, deuterium, halo, or C$_{1-6}$ alkyl;

R$^5$ and R$^6$ are each independently hydrogen or deuterium;

R$^{7a}$ is hydrogen, deuterium, halo, or —O—C$_{1-6}$ alkyl;

R$^B$ and R$^X$ are (i) or (ii):

(i) R$^B$ is monocyclic or bicyclic C$_{6-14}$ aryl, or monocyclic or bicyclic heteroaryl; and R$^X$ is hydrogen, C$_{1-6}$ alkyl, C$_{6-14}$ aryl, or C$_{7-15}$ aralkyl; or (ii) R$^B$ and R$^X$ together with the N atom to which they are attached form monocyclic or bicyclic heteroaryl, or monocyclic or bicyclic heterocyclyl;

U$^2$ and V$^2$ are each —N═; or U$^2$ is —O— and V$^2$ is —C(OH)═; and p is an integer of 1 or 2;

wherein each alkyl, aryl, aralkyl, heteroaryl, and heterocyclyl is optionally substituted with one, two, or three substituents Q, each substituent Q independently selected from bromo, chloro, fluoro, cyano, methyl, trifluoromethyl, ethyl, propyl, formyl, hydroxyl, methoxy, and amino.

In yet another embodiment, in Formula (XXX),

R$^1$ is methyl;

R$^3$ and R$^4$ are each independently hydrogen, deuterium, fluoro, or methyl;

R$^5$ and R$^6$ are each independently hydrogen or deuterium;

R$^{7a}$ is hydrogen, deuterium, chloro, or methoxy;

R$^B$ and R$^X$ are (i) or (ii):

(i) R$^B$ is phenyl, bromophenyl, fluorophenyl, cyanophenyl, methylphenyl, trifluoromethylphenyl, ethylphenyl, propylphenyl, methoxyphenyl, formylphenyl, bromofluorophenyl, difluorophenyl, trifluorophenyl, naphthyl, fluoropyridyl, fluoro-methylpyridyl, or quinolinyl; and R$^X$ is hydrogen, methyl, ethyl, hydroxyethyl, propyl, phenyl, fluorophenyl, formylphenyl, or benzyl; or (ii) R$^B$ and R$^X$ together with the N atom to which they are attached form pyrrolidinyl, piperidinyl, morpholinyl, pyrrolyl, amino-imidazolyl, or indolyl;

U$^2$ and V$^2$ are each —N═; or U$^2$ is —O— and V$^2$ is —C(OH)═; and p is an integer of 1 or 2.

In still another embodiment, in Formula (XXX),

R$^1$ is methyl;

R$^3$ and R$^4$ are each independently hydrogen, deuterium, fluoro, or methyl;

R$^5$ and R$^6$ are each independently hydrogen or deuterium;

R$^{7a}$ is hydrogen, deuterium, chloro, or methoxy;

R$^B$ and R$^X$ are (i) or (ii):

(i) R$^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl; and R$^X$ is hydrogen, methyl, ethyl, 2-hydroxyethyl, n-propyl, phenyl, 4-fluorophenyl, 4-formylphenyl, or benzyl; or (ii) R$^B$ and R$^X$ together with the N atom to which they are attached form pyrrol-1-yl, 2-amino-imidazol-1-yl, indol-1-yl, pyrrolidin-1-yl, piperidin-1-yl, or 4-morpholin-4-yl;

U$^2$ and V$^2$ are each —N═; or U$^2$ is —O— and V$^2$ is —C(OH)═; and p is an integer of 1 or 2.

The groups, R$^1$, R$^2$, R$^3$, R$^4$, R$^5$, R$^6$, R$^7$, R$^{2A}$, R$^{7a}$, R$^A$, R$^B$, R$^X$, L, X, U$^1$, V$^1$, W$^1$, X$^1$, Y$^1$, Z$^1$, U$^2$, V$^2$, n, and p, in formulae described herein, including Formulae (I) to (XXXIII), are further defined in the embodiments described herein. All combinations of the embodiments provided herein for such groups are within the scope of this disclosure.

In certain embodiments, R$^1$ is hydrogen. In certain embodiments, R$^1$ is deuterium. In certain embodiments, R$^1$ is cyano. In certain embodiments, R$^1$ is halo. In certain embodiments, R$^1$ is fluoro or chloro. In certain embodiments, R$^1$ is nitro. In certain embodiments, R$^1$ is C$_{1-6}$ alkyl, optionally substituted with one or more substituents Q. In certain embodiments, R$^1$ is methyl, optionally substituted with one or more substituents Q. In certain embodiments, R$^1$ is methyl. In certain embodiments, R$^1$ is C$_{2-6}$ alkenyl, optionally substituted with one or more substituents Q. In certain embodiments, R$^1$ is C$_{2-6}$ alkynyl, optionally substituted with one or more substituents Q. In certain embodiments, R$^1$ is C$_{3-10}$ cycloalkyl, optionally substituted with one or more substituents Q. In certain embodiments, R$^1$ is C$_{6-14}$ aryl, optionally substituted with one or more substituents Q. In certain embodiments, R$^1$ is C$_{7-15}$ aralkyl, optionally substituted with one or more substituents Q. In certain embodiments, R$^1$ is heteroaryl, optionally substituted with one or more substituents Q. In certain embodiments, R$^1$ is heterocyclyl, optionally substituted with one or more substituents Q.

In certain embodiments, R$^2$ is —C(O)OR$^{2a}$, wherein R$^{2a}$ is as defined herein. In certain embodiments, R$^2$ is —C(O)OH. In certain embodiments, R$^2$ is —C(O)O—C$_{1-6}$ alkyl, wherein the alkyl is optionally substituted with one or more substituents Q. In certain embodiments, R$^2$ is —C(O)NR$^{2b}$R$^{2c}$, wherein R$^{2b}$ and R$^{2c}$ are each as defined herein. In certain embodiments, R$^2$ is —C(O)NR$^{2b}$R$^{2c}$, wherein R$^{2b}$ and R$^{2c}$ are each independently (i) hydrogen; or (ii) C$_{1-6}$ alkyl or heteroaryl, each of which is optionally substituted with one or more substituents Q. In certain embodiments, R$^2$ is —C(O)NR$^{2b}$R$^{2c}$, wherein R$^{2b}$ and R$^{2c}$ are each independently (i) hydrogen; or (ii) methyl, ethyl, or tetrazolyl, each of which is optionally substituted with one or more substituents Q. In certain embodiments, R$^2$ is —C(O)NHR$^{2c}$, wherein R$^{2c}$ is as defined herein. In certain embodiments, R$^2$ is —C(O)NHR$^{2c}$, wherein R$^{2c}$ is (i) hydrogen; or (ii) C$_{1-6}$ alkyl or heteroaryl, each of which is optionally substituted with one or more substituents Q. In certain embodiments, R$^2$ is —C(O)NHR$^{2c}$, wherein R$^{2c}$ is (i) hydrogen; or (ii) methyl, ethyl, or tetrazolyl, each of which is optionally substituted with one or more substituents Q. In certain embodiments, R$^2$ is —C(O)NH$_2$, —C(O)NHCH$_3$, —C(O)NHCH$_2$CH$_2$OH, or —C(O)NH(tetrazolyl). In certain embodiments, R$^2$ is —C(O)N(R$^{2b}$)OR$^{2c}$, wherein R$^{2b}$ and R$^{2c}$ are each as defined herein. In certain embodiments, R$^2$ is —C(O)N(R$^{2b}$)OR$^{2c}$, wherein R$^{2b}$ and R$^{2c}$ are each independently hydrogen or C$_{1-6}$ alkyl optionally substituted with one or more substituents Q. In certain embodiments, R$^2$ is —C(O)NHOR$^{2c}$, wherein R$^{2c}$ is as defined herein. In certain embodiments, R$^2$ is —C(O)NHOR$^{2c}$, wherein R$^{2c}$ is hydrogen or C$_{1-6}$ alkyl optionally substituted with one or more substituents Q. In certain embodiments, R$^2$ is —C(O)NHO—C$_{1-6}$ alkyl, wherein the alkyl is optionally substituted with one or more substituents Q. In certain embodiments, $R^2$ is —C(O) NHOH. In certain embodiments, $R^2$ is heteroaryl, optionally substituted with one or more substituents Q. In certain embodiments, $R^2$ is monocyclic heteroaryl, optionally substituted with one or more substituents Q. In certain embodiments, $R^2$ is 6-membered heteroaryl, optionally substituted with one or more substituents Q. In certain embodiments, $R^2$ is 5-membered heteroaryl, optionally substituted with one or more substituents Q. In certain embodiments, $R^2$ is tetrazolyl or 1,2,4-oxadiazolyl, each of which is optionally substituted with one or more substituents Q. In certain embodiments, $R^2$ is tetrazol-5-yl or 5-hydroxyl-1,2,4-oxadiazol-5-yl.

In certain embodiments, $R^3$ is hydrogen. In certain embodiments, $R^3$ is deuterium. In certain embodiments, $R^3$ is cyano. In certain embodiments, $R^3$ is halo. In certain embodiments, $R^3$ is fluoro. In certain embodiments, $R^3$ is chloro. In certain embodiments, $R^3$ is nitro. In certain embodiments, $R^3$ is $C_{1-6}$ alkyl, optionally substituted with one or more substituents Q. In certain embodiments, $R^3$ is methyl. In certain embodiments, $R^3$ is $C_{2-6}$ alkenyl, optionally substituted with one or more substituents Q. In certain embodiments, $R^3$ is $C_{2-6}$ alkynyl, optionally substituted with one or more substituents Q. In certain embodiments, $R^3$ is $C_{3-10}$ cycloalkyl, optionally substituted with one or more substituents Q. In certain embodiments, $R^3$ is $C_{6-14}$ aryl, optionally substituted with one or more substituents Q. In certain embodiments, $R^3$ is $C_{7-15}$ aralkyl, optionally substituted with one or more substituents Q. In certain embodiments, $R^3$ is heteroaryl, optionally substituted with one or more substituents Q. In certain embodiments, $R^3$ is heterocyclyl, optionally substituted with one or more substituents Q.

In certain embodiments, $R^3$ is —C(O)$R^{1a}$, wherein $R^{1a}$ is as defined herein. In certain embodiments, $R^3$ is —C(O) O$R^{1a}$, wherein $R^{1a}$ is as defined herein. In certain embodiments, $R^3$ is —C(O)N$R^{1b}$$R^{1c}$, wherein $R^{1b}$ and $R^{1c}$ are each as defined herein. In certain embodiments, $R^3$ is —C(N$R^{1a}$) N$R^{1b}$$R^{1c}$, wherein $R^{1a}$, $R^{1b}$, and $R^{1c}$ are each as defined herein. In certain embodiments, $R^3$ is —O$R^{1a}$, wherein $R^{1a}$ is as defined herein. In certain embodiments, $R^3$ is methoxy. In certain embodiments, $R^3$ is —OC(O)$R^{1a}$, wherein $R^{1a}$ is as defined herein. In certain embodiments, $R^3$ is —OC(O) O$R^{1a}$, wherein $R^{1a}$ is as defined herein. In certain embodiments, $R^3$ is —OC(O)N$R^{1b}$$R^{1c}$, wherein $R^{1b}$ and $R^{1c}$ are each as defined herein. In certain embodiments, $R^3$ is —OC (N$R^{1a}$)N$R^{1b}$$R^{1c}$, wherein $R^{1a}$, $R^{1b}$, and $R^{1c}$ are each as defined herein. In certain embodiments, $R^3$ is —OS(O)$R^{1a}$, wherein $R^{1a}$ is as defined herein. In certain embodiments, $R^3$ is —OS(O)$_2$$R^{1a}$, wherein $R^{1a}$ is as defined herein. In certain embodiments, $R^3$ is —OS(O)N$R^{1b}$$R^1$, wherein $R^{1b}$ and $R^{1c}$ are each as defined herein. In certain embodiments, $R^3$ is —OS(O)$_2$N$R^{1b}$$R^{1c}$, wherein $R^{1b}$ and $R^{1c}$ are each as defined herein. In certain embodiments, $R^3$ is —N$R^{1b}$$R^{1c}$, wherein $R^{1b}$ and $R^{1c}$ are each as defined herein. In certain embodiments, $R^3$ is —N$R^{1a}$C(O)$R^{1d}$, wherein $R^{1a}$ and $R^{1d}$ are each as defined herein. In certain embodiments, $R^3$ is N$R^{1a}$C(O) O$R^{1d}$, wherein $R^{1a}$ and $R^{1d}$ are each as defined herein. In certain embodiments, $R^3$ is —N$R^{1a}$C(O)N$R^{1b}$$R^{1c}$, wherein $R^{1a}$, $R^{1b}$, and $R^{1c}$ are each as defined herein. In certain embodiments, $R^3$ is —N$R^{1a}$C(N$R^{1d}$)N$R^{1b}$$R^{1c}$, wherein $R^{1a}$, $R^{1b}$, $R^{1c}$, and $R^{1d}$ are each as defined herein. In certain embodiments, $R^3$ is —N$R^{1a}$S(O)$R^{1d}$, wherein $R^{1a}$ and $R^{1d}$ are each as defined herein. In certain embodiments, $R^3$ is —N$R^{1a}$S(O)$_2$$R^{1d}$, wherein $R^{1a}$ and $R^{1d}$ are each as defined herein. In certain embodiments, $R^3$ is —N$R^{1a}$S(O)N$R^{1b}$$R^{1c}$, wherein $R^{1a}$, $R^{1b}$, and $R^{1c}$ are each as defined herein. In certain embodiments, $R^3$ is —N$R^{1a}$S(O)$_2$N$R^{1b}$$R^{1c}$, wherein $R^{1a}$, $R^{1b}$, and $R^{1c}$ are each as defined herein. In certain embodiments, $R^3$ is —S$R^{1a}$, wherein $R^{1a}$ is as defined herein. In certain embodiments, $R^3$ is —S(O)$R^{1a}$, wherein $R^{1a}$ is as defined herein. In certain embodiments, $R^3$ is —S(O)$_2$$R^{1a}$, wherein $R^{1a}$ is as defined herein. In certain embodiments, $R^3$ is —S(O)N$R^{1b}$$R^{1c}$, wherein $R^{1b}$ and $R^{1c}$ are each as defined herein. In certain embodiments, $R^3$ is —S(O)$_2$N$R^{1b}$$R^{1c}$, wherein $R^{1b}$ and $R^{1c}$ are each as defined herein.

In certain embodiments, $R^4$ is hydrogen. In certain embodiments, $R^4$ is deuterium. In certain embodiments, $R^4$ is cyano. In certain embodiments, $R^4$ is halo. In certain embodiments, $R^4$ is fluoro. In certain embodiments, $R^4$ is chloro. In certain embodiments, $R^4$ is nitro. In certain embodiments, $R^4$ is $C_{1-6}$ alkyl, optionally substituted with one or more substituents Q. In certain embodiments, $R^4$ is methyl. In certain embodiments, $R^4$ is $C_{2-6}$ alkenyl, optionally substituted with one or more substituents Q. In certain embodiments, $R^4$ is $C_{2-6}$ alkynyl, optionally substituted with one or more substituents Q. In certain embodiments, $R^4$ is $C_{3-10}$ cycloalkyl, optionally substituted with one or more substituents Q. In certain embodiments, $R^4$ is $C_{6-14}$ aryl, optionally substituted with one or more substituents Q. In certain embodiments, $R^4$ is $C_{7-15}$ aralkyl, optionally substituted with one or more substituents Q. In certain embodiments, $R^4$ is heteroaryl, optionally substituted with one or more substituents Q. In certain embodiments, $R^4$ is heterocyclyl, optionally substituted with one or more substituents Q.

In certain embodiments, $R^4$ is —C(O)$R^{1a}$, wherein $R^{1a}$ is as defined herein. In certain embodiments, $R^4$ is —C(O) O$R^{1a}$, wherein $R^{1a}$ is as defined herein. In certain embodiments, $R^4$ is —C(O)N$R^{1b}$$R^{1c}$, wherein $R^{1b}$ and $R^{1c}$ are each as defined herein. In certain embodiments, $R^4$ is —C(N$R^{1a}$) N$R^{1b}$$R^{1c}$, wherein $R^{1a}$, $R^{1b}$, and $R^{1c}$ are each as defined herein. In certain embodiments, $R^4$ is —O$R^{1a}$, wherein $R^{1a}$ is as defined herein. In certain embodiments, $R^4$ is methoxy. In certain embodiments, $R^4$ is —OC(O)$R^{1a}$, wherein $R^{1a}$ is as defined herein. In certain embodiments, $R^4$ is —OC(O) O$R^{1a}$, wherein $R^{1a}$ is as defined herein. In certain embodiments, $R^4$ is —OC(O)N$R^{1b}$$R^{1c}$, wherein $R^{1b}$ and $R^{1c}$ are each as defined herein. In certain embodiments, $R^4$ is —OC (N$R^{1a}$)N$R^{1b}$$R^{1c}$, wherein $R^{1a}$, $R^{1b}$, and $R^{1c}$ are each as defined herein. In certain embodiments, $R^4$ is —OS(O)$R^{1a}$, wherein $R^{1a}$ is as defined herein. In certain embodiments, $R^4$ is —OS(O)$_2$$R^{1a}$, wherein $R^{1a}$ is as defined herein. In certain embodiments, $R^4$ is —OS(O)N$R^{1b}$$R^{1c}$, wherein $R^{1b}$ and $R^{1c}$ are each as defined herein. In certain embodiments, $R^4$ is —OS(O)$_2$N$R^{1b}$$R^{1c}$, wherein $R^{1b}$ and $R^{1c}$ are each as defined herein. In certain embodiments, $R^4$ is —N$R^{1b}$$R^{1c}$, wherein $R^{1b}$ and $R^{1c}$ are each as defined herein. In certain embodiments, $R^4$ is —N$R^{1a}$C(O)$R^{1d}$, wherein $R^{1a}$ and $R^{1d}$ are each as defined herein. In certain embodiments, $R^4$ is —N$R^{1a}$C (O)O$R^{1d}$, wherein $R^{1a}$ and $R^d$ are each as defined herein. In certain embodiments, $R^4$ is —N$R^{1a}$C(O)N$R^{1b}$$R^{1c}$, wherein $R^{1a}$, $R^{1b}$, and Rid are each as defined herein. In certain embodiments, $R^4$ is —N$R^{1a}$C(N$R^{1d}$)N$R^{1b}$$R^{1c}$, wherein $R^{1a}$, $R^{1b}$, $R^{1c}$, and $R^{1d}$ are each as defined herein. In certain embodiments, $R^4$ is —N$R^{1a}$S(O)$R^{1d}$, wherein $R^{1a}$ and $R^{1d}$ are each as defined herein. In certain embodiments, $R^4$ is —N$R^{1a}$S(O)$_2$$R^{1d}$, wherein $R^{1a}$ and $R^{1d}$ are each as defined herein. In certain embodiments, $R^4$ is —N$R^{1a}$S(O)N$R^{1b}$$R^{1c}$, wherein $R^{1a}$, $R^{1b}$, and Rid are each as defined herein. In certain embodiments, $R^4$ is —N$R^{1a}$S(O)$_2$N$R^{1b}$$R^{1c}$, wherein $R^{1a}$, $R^{1b}$, and $R^{1c}$ are each as defined herein. In certain embodiments, $R^4$ is —S$R^{1a}$, wherein $R^{1a}$ is as defined herein. In certain embodiments, $R^4$ is —S(O)$R^{1a}$, wherein $R^{1a}$ is as defined herein. In certain embodiments, $R^4$ is —S(O)$_2R^{1a}$, wherein $R^{1a}$ is as defined herein. In certain embodiments, $R^4$ is —S(O)NR$^{1b}R^{1c}$, wherein $R^{1b}$ and $R^{1c}$ are each as defined herein. In certain embodiments, $R^4$ is —S(O)$_2$NR$^{1b}R^{1c}$, wherein $R^{1b}$ and $R^{1c}$ are each as defined herein.

In certain embodiments, $R^5$ is hydrogen. In certain embodiments, $R^5$ is deuterium. In certain embodiments, $R^5$ is cyano. In certain embodiments, $R^5$ is halo. In certain embodiments, $R^5$ is fluoro. In certain embodiments, $R^5$ is chloro. In certain embodiments, $R^5$ is nitro. In certain embodiments, $R^5$ is $C_{1-6}$ alkyl, optionally substituted with one or more substituents Q. In certain embodiments, $R^5$ is methyl. In certain embodiments, $R^5$ is $C_{2-6}$ alkenyl, optionally substituted with one or more substituents Q. In certain embodiments, $R^5$ is $C_{2-6}$ alkynyl, optionally substituted with one or more substituents Q. In certain embodiments, $R^5$ is $C_{3-10}$ cycloalkyl, optionally substituted with one or more substituents Q. In certain embodiments, $R^5$ is $C_{6-14}$ aryl, optionally substituted with one or more substituents Q. In certain embodiments, $R^5$ is $C_{7-15}$ aralkyl, optionally substituted with one or more substituents Q. In certain embodiments, $R^5$ is heteroaryl, optionally substituted with one or more substituents Q. In certain embodiments, $R^5$ is heterocyclyl, optionally substituted with one or more substituents Q.

In certain embodiments, $R^5$ is —C(O)$R^{1a}$, wherein $R^{1a}$ is as defined herein. In certain embodiments, $R^5$ is —C(O)OR$^{1a}$, wherein $R^{1a}$ is as defined herein. In certain embodiments, $R^5$ is —C(O)NR$^{1b}R^{1c}$, wherein $R^{1b}$ and $R^{1c}$ are each as defined herein. In certain embodiments, $R^5$ is —C(NR$^{1a}$)NR$^{1b}R^{1c}$, wherein $R^{1a}$, $R^{1b}$, and $R^{1c}$ are each as defined herein. In certain embodiments, $R^5$ is —OR$^{1a}$, wherein $R^{1a}$ is as defined herein. In certain embodiments, $R^5$ is methoxy. In certain embodiments, $R^5$ is —OC(O)$R^{1a}$, wherein $R^{1a}$ is as defined herein. In certain embodiments, $R^5$ is —OC(O)OR$^{1a}$, wherein $R^{1a}$ is as defined herein. In certain embodiments, $R^5$ is —OC(O)NR$^{1b}R^{1c}$, wherein $R^{1b}$ and $R^{1c}$ are each as defined herein. In certain embodiments, $R^5$ is —OC(NR$^{1a}$)NR$^{1b}R^{1c}$, wherein $R^{1a}$, $R^{1b}$, and $R^{1c}$ are each as defined herein. In certain embodiments, $R^5$ is —OS(O)$R^a$, wherein $R^{1a}$ is as defined herein. In certain embodiments, $R^a$ is —OS(O)$_2R^{1a}$, wherein $R^{1a}$ is as defined herein. In certain embodiments, $R^5$ is —OS(O)NR$^{1b}R^{1c}$, wherein $R^{1b}$ and $R^{1c}$ are each as defined herein. In certain embodiments, $R^5$ is —OS(O)$_2$NR$^{1b}R^{1c}$, wherein $R^{1b}$ and $R^{1c}$ are each as defined herein. In certain embodiments, $R^5$ is —NR$^{1b}R^{1c}$, wherein RR and $R^{1c}$ are each as defined herein. In certain embodiments, $R^5$ is —NR$^{1a}$C(O)$R^{1d}$, wherein $R^{1a}$ and $R^{1d}$ are each as defined herein. In certain embodiments, $R^5$ is —NR$^{1a}$C(O)OR$^{1d}$, wherein $R^{1a}$ and $R^{1d}$ are each as defined herein. In certain embodiments, $R^5$ is —NR$^{1a}$C(O)NR$^{1b}R^{1c}$, wherein $R^{1a}$, $R^{1b}$, and $R^{1c}$ are each as defined herein. In certain embodiments, $R^5$ is —NR$^{1a}$C(NR$^{1d}$)R$^{1b}R^{1c}$, wherein $R^{1a}$, $R^{1b}$, $R^{1c}$, and $R^{1d}$ are each as defined herein. In certain embodiments, $R^5$ is —NR$^{1a}$S(O)$R^{1d}$, wherein $R^{1a}$ and $R^{1d}$ are each as defined herein. In certain embodiments, $R^5$ is —NR$^{1a}$S(O)$_2R^{1d}$, wherein $R^{1a}$ and $R^{1d}$ are each as defined herein. In certain embodiments, $R^5$ is —NR$^{1a}$S(O)NR$^{1b}R^{1c}$, wherein $R^{1a}$, $R^{1b}$, and $R^{1c}$ are each as defined herein. In certain embodiments, $R^5$ is —NR$^{1a}$S(O)$_2$NR$^{1b}R^{1c}$, wherein $R^{1a}$, $R^{1b}$, and $R^{1c}$ are each as defined herein. In certain embodiments, $R^5$ is —SR$^{1a}$, wherein $R^{1a}$ is as defined herein. In certain embodiments, $R^5$ is —S(O)$R^{1a}$, wherein $R^{1a}$ is as defined herein. In certain embodiments, $R^5$ is —S(O)$_2R^{1a}$, wherein $R^{1a}$ is as defined herein. In certain embodiments, $R^5$ is —S(O)NR$^{1b}R^{1c}$, wherein $R^{1b}$ and $R^{1c}$ are each as defined herein. In certain embodiments, $R^5$ is —S(O)$_2$NR$^{1b}R^{1c}$, wherein $R^{1b}$ and $R^{1c}$ are each as defined herein.

In certain embodiments, $R^6$ is hydrogen. In certain embodiments, $R^6$ is deuterium. In certain embodiments, $R^6$ is cyano. In certain embodiments, $R^6$ is halo. In certain embodiments, $R^6$ is fluoro. In certain embodiments, $R^6$ is chloro. In certain embodiments, $R^6$ is nitro. In certain embodiments, $R^6$ is $C_{1-6}$ alkyl, optionally substituted with one or more substituents Q. In certain embodiments, $R^6$ is methyl. In certain embodiments, $R^6$ is $C_{2-6}$ alkenyl, optionally substituted with one or more substituents Q. In certain embodiments, $R^6$ is $C_{2-6}$ alkynyl, optionally substituted with one or more substituents Q. In certain embodiments, $R^6$ is $C_{3-10}$ cycloalkyl, optionally substituted with one or more substituents Q. In certain embodiments, $R^6$ is $C_{6-14}$ aryl, optionally substituted with one or more substituents Q. In certain embodiments, $R^6$ is $C_{7-15}$ aralkyl, optionally substituted with one or more substituents Q. In certain embodiments, $R^6$ is heteroaryl, optionally substituted with one or more substituents Q. In certain embodiments, $R^6$ is heterocyclyl, optionally substituted with one or more substituents Q.

In certain embodiments, $R^6$ is —C(O)$R^{1a}$, wherein $R^{1a}$ is as defined herein. In certain embodiments, $R^6$ is —C(O)OR$^{1a}$, wherein $R^{1a}$ is as defined herein. In certain embodiments, $R^6$ is —C(O)NR$^{1b}R^{1c}$, wherein $R^{1b}$ and $R^{1c}$ are each as defined herein. In certain embodiments, $R^6$ is —C(NR$^{1a}$)NR$^{1b}R^{1c}$, wherein $R^{1a}$, $R^{1b}$, and $R^{1c}$ are each as defined herein. In certain embodiments, $R^6$ is —OR$^{1a}$, wherein $R^{1a}$ is as defined herein. In certain embodiments, $R^6$ is methoxy. In certain embodiments, $R^6$ is —OC(O)$R^{1a}$, wherein $R^{1a}$ is as defined herein. In certain embodiments, $R^6$ is —OC(O)OR$^{1a}$, wherein $R^{1a}$ is as defined herein. In certain embodiments, $R^6$ is —OC(O)NR$^{1b}R^{1c}$, wherein $R^{1b}$ and $R^{1c}$ are each as defined herein. In certain embodiments, $R^6$ is —OC(NR$^{1a}$)NR$^{1b}R^{1c}$, wherein $R^{1a}$, $R^{1b}$, and $R^{1c}$ are each as defined herein. In certain embodiments, $R^6$ is —OS(O)$R^{1a}$, wherein $R^{1a}$ is as defined herein. In certain embodiments, $R^6$ is —OS(O)$_2R^{1a}$, wherein $R^{1a}$ is as defined herein. In certain embodiments, $R^6$ is —OS(O)NR$^{1b}R^{1c}$, wherein $R^{1b}$ and $R^{1c}$ are each as defined herein. In certain embodiments, $R^6$ is —OS(O)$_2$NR$^{1b}R^{1c}$, wherein $R^{1b}$ and $R^{1c}$ are each as defined herein. In certain embodiments, $R^6$ is —NR$^{1b}R^{1c}$, wherein $R^{1b}$ and $R^{1c}$ are each as defined herein. In certain embodiments, $R^6$ is —NR$^{1a}$C(O)$R^{1d}$, wherein $R^{1a}$ and $R^{1d}$ are each as defined herein. In certain embodiments, $R^6$ is —NR$^{1a}$C(O)OR$^{1d}$, wherein $R^{1a}$ and $R^{1d}$ are each as defined herein. In certain embodiments, $R^6$ is —NR$^{1a}$C(O)NR$^{1b}R^{1c}$, wherein $R^{1a}$, $R^{1b}$, and $R^{1c}$ are each as defined herein. In certain embodiments, $R^6$ is NR$^{1a}$C(NR$^{1d}$)R$^{1b}R^{1c}$, wherein $R^{1a}$, $R^{1b}$, $R^{1c}$, and $R^{1d}$ are each as defined herein. In certain embodiments, $R^6$ is —NR$^{1a}$S(O)$R^{1d}$, wherein $R^{1a}$ and $R^{1d}$ are each as defined herein. In certain embodiments, $R^6$ is —NR$^{1a}$S(O)$_2R^{1d}$, wherein $R^{1a}$ and $R^{1d}$ are each as defined herein. In certain embodiments, $R^6$ is —NR$^{1a}$S(O)$_2$NR$^{1b}R^{1c}$, wherein $R^{1a}$, $R^{1b}$, and $R^{1c}$ are each as defined herein. In certain embodiments, $R^6$ is —NR$^{1a}$S(O)$_2$NR$^{1b}R^{1c}$, wherein $R^{1a}$, $R^{1b}$, and $R^{1c}$ are each as defined herein. In certain embodiments, $R^6$ is —SR$^{1a}$, wherein $R^{1a}$ is as defined herein. In certain embodiments, $R^6$ is —S(O)$R^{1a}$, wherein $R^{1a}$ is as defined herein. In certain embodiments, $R^6$ is —S(O)$_2R^{1a}$, wherein $R^{1a}$ is as defined herein. In certain embodiments, $R^6$ is —S(O)NR$^{1b}R^{1c}$, wherein $R^{1b}$ and $R^{1c}$ are each as defined herein. In certain embodiments, $R^6$ is —S(O)$_2$NR$^{1b}R^{1c}$, wherein $R^{1b}$ and $R^{1c}$ are each as defined herein.

In certain embodiments, $R^7$ is deuterium. In certain embodiments, $R^7$ is cyano. In certain embodiments, $R^7$ is halo. In certain embodiments, $R^7$ is fluoro. In certain embodiments, $R^7$ is chloro. In certain embodiments, $R^7$ is nitro. In certain embodiments, $R^7$ is $C_{1-6}$ alkyl, optionally substituted with one or more substituents Q. In certain embodiments, $R^7$ is methyl. In certain embodiments, $R^7$ is $C_{2-6}$ alkenyl, optionally substituted with one or more substituents Q. In certain embodiments, $R^7$ is $C_{2-6}$ alkynyl, optionally substituted with one or more substituents Q. In certain embodiments, $R^7$ is $C_{3-10}$ cycloalkyl, optionally substituted with one or more substituents Q. In certain embodiments, $R^7$ is $C_{6-14}$ aryl, optionally substituted with one or more substituents Q. In certain embodiments, $R^7$ is $C_{7-15}$ aralkyl, optionally substituted with one or more substituents Q. In certain embodiments, $R^7$ is heteroaryl, optionally substituted with one or more substituents Q. In certain embodiments, $R^7$ is heterocyclyl, optionally substituted with one or more substituents Q.

In certain embodiments, $R^7$ is —C(O)$R^{1a}$, wherein $R^{1a}$ is as defined herein. In certain embodiments, $R^7$ is —C(O)O$R^{1a}$, wherein $R^{1a}$ is as defined herein. In certain embodiments, $R^7$ is —C(O)N$R^{1b}R^{1c}$, wherein $R^{1b}$ and $R^{1c}$ are each as defined herein. In certain embodiments, $R^7$ is —C(N$R^{1a}$)N$R^{1b}R^{1c}$, wherein $R^{1a}$, $R^{1b}$, and $R^{1c}$ are each as defined herein. In certain embodiments, $R^7$ is —O$R^{1a}$, wherein $R^{1a}$ is as defined herein. In certain embodiments, $R^7$ is methoxy. In certain embodiments, $R^7$ is —OC(O)$R^{1a}$, wherein $R^{1a}$ is as defined herein. In certain embodiments, $R^7$ is —OC(O)O$R^{1a}$, wherein $R^{1a}$ is as defined herein. In certain embodiments, $R^7$ is —OC(O)N$R^{1b}R^{1c}$, wherein $R^{1b}$ and $R^{1c}$ are each as defined herein. In certain embodiments, $R^7$ is —OC(N$R^{1a}$)N$R^{1b}R^{1c}$, wherein $R^{1a}$, $R^{1b}$, and $R^{1c}$ are each as defined herein. In certain embodiments, $R^7$ is —OS(O)$R^{1a}$, wherein $R^{1a}$ is as defined herein. In certain embodiments, $R^7$ is —OS(O)$_2R^{1a}$, wherein $R^{1a}$ is as defined herein. In certain embodiments, $R^7$ is —OS(O)N$R^{1b}R^{1c}$, wherein $R^{1b}$ and $R^{1c}$ are each as defined herein. In certain embodiments, $R^7$ is —OS(O)$_2$N$R^{1b}R^{1c}$, wherein $R^{1b}$ and $R^{1c}$ are each as defined herein. In certain embodiments, $R^7$ is —N$R^{1b}R^{1c}$, wherein $R^{1b}$ and $R^{1c}$ are each as defined herein. In certain embodiments, $R^7$ is —N$R^{1a}$C(O)$R^{1d}$, wherein $R^{1a}$ and $R^{1d}$ are each as defined herein. In certain embodiments, $R^7$ is —N$R^{1a}$C(O)O$R^{1d}$, wherein $R^{1a}$ and $R^{1d}$ are each as defined herein. In certain embodiments, $R^7$ is —N$R^{1a}$C(O)N$R^{1b}R^{1c}$, wherein $R^{1a}$, $R^{1b}$, and $R^{1c}$ are each as defined herein. In certain embodiments, $R^7$ is —N$R^{1a}$C(N$R^{1d}$)N$R^{1b}R^{1c}$, wherein $R^{1a}$, $R^{1b}$, $R^{1c}$, and Rid are each as defined herein. In certain embodiments, $R^7$ is —N$R^{1a}$S(O)$R^{1d}$, wherein $R^{1a}$ and $R^{1d}$ are each as defined herein. In certain embodiments, $R^7$ is —N$R^{1a}$S(O)$_2R^{1d}$, wherein $R^{1a}$ and $R^{1d}$ are each as defined herein. In certain embodiments, $R^7$ is —N$R^{1a}$S(O)N$R^{1b}R^{1c}$, wherein $R^{1a}$, $R^{1b}$, and $R^{1c}$ are each as defined herein. In certain embodiments, $R^7$ is —N$R^{1a}$S(O)$_2$N$R^{1b}R^{1c}$, wherein $R^{1a}$, $R^{1b}$, and $R^{1c}$ are each as defined herein. In certain embodiments, $R^7$ is —S$R^{1a}$, wherein $R^{1a}$ is as defined herein. In certain embodiments, $R^7$ is —S(O)$R^{1a}$, wherein $R^{1a}$ is as defined herein. In certain embodiments, $R^7$ is —S(O)$_2R^{1a}$, wherein $R^{1a}$ is as defined herein. In certain embodiments, $R^7$ is —S(O)N$R^{1b}R^{1c}$ wherein $R^{1b}$ and $R^{1c}$ are each as defined herein. In certain embodiments, $R^7$ is —S(O)$_2$N$R^{1b}R^{1c}$, wherein $R^{1b}$ and $R^{1c}$ are each as defined herein.

In certain embodiments, $R^{2A}$ is —O$R^{2a}$, wherein $R^{2a}$ is as defined herein. In certain embodiments, $R^{2A}$ is —OH. In certain embodiments, $R^{2A}$ is —O—$C_{1-6}$ alkyl, wherein the alkyl is optionally substituted with one or more substituents Q. In certain embodiments, $R^{2A}$ is —NR$^{2b}R^{2c}$, wherein $R^{2b}$ and $R^{2c}$ are each as defined herein. In certain embodiments, $R^{2A}$ is —NR$^{2b}R^{2c}$, wherein $R^{2b}$ and $R^{2c}$ are each independently (i) hydrogen; or (ii) $C_{1-6}$ alkyl or heteroaryl, each of which is optionally substituted with one or more substituents Q. In certain embodiments, $R^{2A}$ is —NR$^{2b}R^{2c}$, wherein $R^{2b}$ and $R^{2c}$ are each independently (i) hydrogen; or (ii) methyl, ethyl, or tetrazolyl, each of which is optionally substituted with one or more substituents Q. In certain embodiments, $R^{2A}$ is —NHR$^{2c}$, wherein $R^{2c}$ is as defined herein. In certain embodiments, $R^{2A}$ is —NHR$^{2c}$, wherein $R^{2c}$ is (i) hydrogen; or (ii) $C_{1-6}$ alkyl or heteroaryl, each of which is optionally substituted with one or more substituents Q. In certain embodiments, $R^{2A}$ is —NHR$^{2c}$, wherein $R^{2c}$ is (i) hydrogen; or (ii) methyl, ethyl, or tetrazolyl, each of which is optionally substituted with one or more substituents Q. In certain embodiments, $R^{2A}$ is —NH$_2$, —NHCH$_3$, —NHCH$_2$CH$_2$OH, or —NH(tetrazolyl). In certain embodiments, $R^{2A}$ is —N($R^{2b}$)O$R^{2c}$, wherein $R^{2b}$ and $R^{2c}$ are each as defined herein. In certain embodiments, $R^{2A}$ is —N($R^{2b}$)O$R^{2c}$, wherein $R^{2b}$ and $R^{2c}$ are each independently hydrogen or $C_{1-6}$ alkyl optionally substituted with one or more substituents Q. In certain embodiments, $R^{2A}$ is —NHO$R^{2c}$, wherein $R^{2c}$ is as defined herein. In certain embodiments, $R^{2A}$ is —NHO—$C_{1-6}$ alkyl, wherein the alkyl is optionally substituted with one or more substituents Q. In certain embodiments, $R^{2A}$ is —NHOH.

In certain embodiments, $R^{7a}$ is hydrogen. In certain embodiments, $R^{7a}$ is deuterium. In certain embodiments, $R^{7a}$ is cyano. In certain embodiments, $R^{7a}$ is halo. In certain embodiments, $R^{7a}$ is fluoro. In certain embodiments, $R^{7a}$ is chloro. In certain embodiments, $R^{7a}$ is nitro. In certain embodiments, $R^{7a}$ is $C_{1-6}$ alkyl, optionally substituted with one or more substituents Q. In certain embodiments, $R^{7a}$ is methyl. In certain embodiments, $R^{7a}$ is $C_{2-6}$ alkenyl, optionally substituted with one or more substituents Q. In certain embodiments, $R^{7a}$ is $C_{2-6}$ alkynyl, optionally substituted with one or more substituents Q. In certain embodiments, $R^{7a}$ is $C_{3-10}$ cycloalkyl, optionally substituted with one or more substituents Q. In certain embodiments, $R^{7a}$ is $C_{6-14}$ aryl, optionally substituted with one or more substituents Q. In certain embodiments, $R^{7a}$ is $C_{7-15}$ aralkyl, optionally substituted with one or more substituents Q. In certain embodiments, $R^{7a}$ is heteroaryl, optionally substituted with one or more substituents Q. In certain embodiments, $R^{7a}$ is heterocyclyl, optionally substituted with one or more substituents Q.

In certain embodiments, $R^{7a}$ is —C(O)$R^{1a}$, wherein $R^{1a}$ is as defined herein. In certain embodiments, $R^{7a}$ is —C(O)O$R^{1a}$, wherein $R^{1a}$ is as defined herein. In certain embodiments, $R^{7a}$ is —C(O)N$R^{1b}R^{1c}$, wherein $R^{1b}$ and $R^{1c}$ are each as defined herein. In certain embodiments, $R^{7a}$ is —C(N$R^{1a}$)N$R^{1b}R^{1c}$, wherein $R^{1a}$, $R^{1b}$, and $R^{1c}$ are each as defined herein. In certain embodiments, $R^{7a}$ is —O$R^{1a}$, wherein $R^{1a}$ is as defined herein. In certain embodiments, $R^{7a}$ is methoxy. In certain embodiments, $R^{7a}$ is —OC(O)$R^{1a}$, wherein $R^{1a}$ is as defined herein. In certain embodiments, $R^{7a}$ is —OC(O)O$R^{1a}$, wherein $R^{1a}$ is as defined herein. In certain embodiments, $R^{7a}$ is —OC(O)N$R^{1b}R^{1c}$, wherein $R^{1b}$ and $R^{1c}$ are each as defined herein. In certain embodiments, $R^{7a}$ is —OC(N$R^{1a}$)N$R^{1b}R^{1c}$, wherein $R^{1a}$, $R^{1b}$, and $R^{1c}$ are each as defined herein. In certain embodiments, $R^{7a}$ is —OS(O)$R^{1a}$, wherein $R^{1a}$ is as defined herein. In certain embodiments, $R^{7a}$ is —OS(O)$_2R^{1a}$, wherein $R^{1a}$ is as defined herein. In certain embodiments, $R^{7a}$ is —OS(O)N$R^{1b}R^{1c}$, wherein $R^{1b}$ and $R^{1c}$ are each as defined herein. In certain embodiments, $R^{7a}$ is —OS(O)$_2$N$R^{1b}R^{1c}$, wherein $R^{1b}$ and $R^{1c}$ are each as defined herein. In certain embodiments, $R^{7a}$ is —$NR^{1b}R^{1c}$, wherein $R^{1b}$ and $R^{1c}$ are each as defined herein. In certain embodiments, $R^{7a}$ is —$NR^{1a}C(O)R^{1d}$, wherein $R^{1a}$ and $R^{1d}$ are each as defined herein. In certain embodiments, $R^{7a}$ is —$NR^{1a}C(O)OR^{1d}$, wherein $R^{1a}$ and $R^{1d}$ are each as defined herein. In certain embodiments, $R^{7a}$ is —$NR^{1a}C(O)$ $NR^{1b}R^{1c}$, wherein $R^{1a}$, $R^{1b}$, and $R^{1c}$ are each as defined herein. In certain embodiments, $R^{7a}$ is —$NR^{1a}C(NR^{1d})$ $R^{1b}R^{1c}$, wherein $R^{1a}$, $R^{1b}$, $R^{1c}$, and $R^{1d}$ are each as defined herein. In certain embodiments, $R^{7a}$ is $NR^{1a}S(O)R^{1d}$, wherein $R^{1a}$ and $R^{1d}$ are each as defined herein. In certain embodiments, $R^{7a}$ is —$NR^{1a}S(O)_2R^{1d}$, wherein $R^{1a}$ and $R^{1d}$ are each as defined herein. In certain embodiments, $R^{7a}$ is —$NR^{1a}S(O)NR^{1b}R^{1c}$, wherein $R^{1a}$, $R^{1b}$, and $R^{1c}$ are each as defined herein. In certain embodiments, $R^{7a}$ is —$NR^{1a}S(O)_2$ $NR^{1b}R^{1c}$, wherein $R^{1a}$, $R^{1b}$, and $R^{1c}$ are each as defined herein. In certain embodiments, $R^{7a}$ is —$SR^{1a}$, wherein $R^{1a}$ is as defined herein. In certain embodiments, $R^{7a}$ is —$S(O)$ $R^{1a}$, wherein $R^{1a}$ is as defined herein. In certain embodiments, $R^{7a}$ is —$S(O)_2R^{1a}$, wherein $R^{1a}$ is as defined herein. In certain embodiments, $R^{7a}$ is —$S(O)NR^{1b}R^{1c}$, wherein $R^{1b}$ and $R^{1c}$ are each as defined herein. In certain embodiments, $R^{7a}$ is —$S(O)_2NR^{1b}R^{1c}$, wherein $R^{1b}$ and $R^{1c}$ are each as defined herein.

In certain embodiments, $R^A$ is $C_{6-14}$ arylene, optionally substituted with one or more substituents Q. In certain embodiments, $R^A$ is phenylene, optionally substituted with one or more substituents Q. In certain embodiments, $R^A$ is phen-1,2-diyl, optionally substituted with one or more substituents Q. In certain embodiments, $R^A$ is phen-1,3-diyl, optionally substituted with one or more substituents Q. In certain embodiments, $R^A$ is phen-1,4-diyl, optionally substituted with one or more substituents Q. In certain embodiments, $R^A$ is phen-1,3-diyl or phen-1,4-diyl, each of which is optionally substituted with one or more substituents Q. In certain embodiments, $R^A$ is phen-1,3-diyl or phen-1,4-diyl, each of which is optionally substituted with halo or —O—$C_{1-6}$ alkyl. In certain embodiments, $R^A$ is phen-1,3-diyl or phen-1,4-diyl, each of which is optionally substituted with fluoro, chloro, or methoxy. In certain embodiments, $R^A$ is phen-1,3-diyl, phen-1,4-diyl, 2-chloro-phen-1,4-diyl, 2-methoxy-phen-1,4-diyl. In certain embodiments, $R^A$ is naphthylene, optionally substituted with one or more substituents Q. In certain embodiments, $R^A$ is heteroarylene, optionally substituted with one or more substituents Q. In certain embodiments, $R^A$ is monocyclic heteroarylene, optionally substituted with one or more substituents Q. In certain embodiments, $R^A$ is 5-membered heteroarylene, optionally substituted with one or more substituents Q. In certain embodiments, $R^A$ is 6-membered heteroarylene, optionally substituted with one or more substituents Q. In certain embodiments, $R^A$ is pyridylene, optionally substituted with one or more substituents Q. In certain embodiments, $R^A$ is pyrid-2,5-diyl, optionally substituted with one or more substituents Q. In certain embodiments, $R^A$ is pyridylene or methyl-pyridylene. In certain embodiments, $R^A$ is pyrid-2,5-diyl or 3-methyl-pyrid-2,5-diyl. In certain embodiments, $R^A$ is bicyclic heteroarylene, optionally substituted with one or more substituents Q.

In certain embodiments, $R^B$ is $C_{6-14}$ aryl, optionally substituted with one or more substituents Q. In certain embodiments, $R^B$ is monocyclic $C_{6-14}$ aryl, optionally substituted with one or more substituents Q. In certain embodiments, $R^B$ is phenyl, optionally substituted with one or more substituents Q. In certain embodiments, $R^B$ is phenyl, optionally substituted with one, two, or three substituents Q, each of which is independently selected from (i) bromo, chloro, fluoro, and cyano; (ii) $C_{1-6}$ alkyl optionally substituted with one or more substituents $Q^a$; and (iii) —$OR^a$ and —$C(O)R^a$, where each $R^a$ is as defined herein. In certain embodiments, $R^B$ is phenyl, optionally substituted with one, two, or three substituents Q, each of which is independently selected from bromo, fluoro, cyano, methyl, trifluoromethyl, ethyl, propyl, methoxy, and formyl. In certain embodiments, $R^B$ is phenyl, optionally substituted with one, two, or three substituents Q, each of which is independently selected from bromo, fluoro, cyano, methyl, trifluoromethyl, ethyl, propyl, and methoxy. In certain embodiments, $R^B$ is phenyl, bromophenyl, fluorophenyl, cyanophenyl, methylphenyl, trifluoromethylphenyl, ethylphenyl, propylphenyl, methoxyphenyl, formylphenyl, bromo-fluorophenyl, difluorophenyl, or trifluorophenyl. In certain embodiments, $R^B$ is phenyl, bromophenyl, fluorophenyl, cyanophenyl, methylphenyl, trifluoromethylphenyl, ethylphenyl, propylphenyl, methoxyphenyl, bromo-fluorophenyl, difluorophenyl, or trifluorophenyl. In certain embodiments, $R^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, or 2,4,5-trifluorophenyl. In certain embodiments, $R^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 2-bromo-4-fluorophenyl, 2,4-difluorophenyl, or 2,4,5-trifluorophenyl.

In certain embodiments, $R^B$ is bicyclic $C_{6-14}$ aryl, optionally substituted with one or more substituents Q. In certain embodiments, $R^B$ is naphthyl, optionally substituted with one or more substituents Q. In certain embodiments, $R^B$ is naphth-1-yl, optionally substituted with one or more substituents Q. In certain embodiments, $R^B$ is naphth-2-yl, optionally substituted with one or more substituents Q.

In certain embodiments, $R^B$ is heteroaryl, optionally substituted with one or more substituents Q. In certain embodiments, $R^B$ is monocyclic heteroaryl, optionally substituted with one or more substituents Q. In certain embodiments, $R^B$ is 5-membered heteroaryl, optionally substituted with one or more substituents Q. In certain embodiments, $R^B$ is 6-membered heteroaryl, optionally substituted with one or more substituents Q. In certain embodiments, $R^B$ is pyridyl, optionally substituted with one or more substituents Q. In certain embodiments, $R^B$ is fluoropyridyl or fluoro-methylpyridyl. In certain embodiments, $R^B$ is 2-fluoropyrid-5-yl or 2-fluoro-3-methyl-pyrid-5-yl.

In certain embodiments, $R^B$ is bicyclic heteroaryl, optionally substituted with one or more substituents Q. In certain embodiments, $R^B$ is 5,6-fused heteroaryl, optionally substituted with one or more substituents Q. In certain embodiments, $R^B$ is 6,6-fused heteroaryl, optionally substituted with one or more substituents Q. In certain embodiments, $R^B$ is quinolinyl, optionally substituted with one or more substituents Q. In certain embodiments, $R^B$ is quinolin-5-yl, optionally substituted with one or more substituents Q.

In certain embodiments, $R^B$ is phenyl, bromophenyl, fluorophenyl, cyanophenyl, methylphenyl, trifluoromethylphenyl, ethylphenyl, propylphenyl, methoxyphenyl, formylphenyl, bromo-fluorophenyl, difluorophenyl, trifluorophenyl, naphthyl, fluoropyridyl, fluoro-methylpyridyl, or quinolinyl. In certain embodiments, $R^B$ is phenyl, 3-bromophenyl, 4-bromophenyl, 4-fluorophenyl, 3-cyanophenyl, 3-methylphenyl, 4-methylphenyl, 3-trifluoromethylphenyl, 4-trifluoromethylphenyl, 4-ethylphenyl, 4-isopropylphenyl, 3-methoxyphenyl, 4-methoxyphenyl, 4-formylphenyl, 2-bromo-4-fluorophenyl, 2,4-difluorophenyl, 2,4,5-trifluorophenyl, naphth-2-yl, 2-fluoropyrid-5-yl, 2-fluoro-3-methyl-pyrid-5-yl, or quinolin-5-yl.

In certain embodiments, $R^X$ is hydrogen. In certain embodiments, $R^X$ is $C_{1-6}$ alkyl, optionally substituted with one or more substituents Q. In certain embodiments, $R^X$ is methyl, ethyl, or propyl, each optionally substituted with one or more substituents Q. In certain embodiments, $R^X$ is methyl, ethyl, 2-hydroxyethyl, or n-propyl. In certain embodiments, $R^X$ is $C_{2-6}$ alkenyl, optionally substituted with one or more substituents Q. In certain embodiments, $R^X$ is $C_{2-6}$ alkynyl, optionally substituted with one or more substituents Q. In certain embodiments, $R^X$ is $C_{3-10}$ cycloalkyl, optionally substituted with one or more substituents Q. In certain embodiments, $R^X$ is $C_{6-14}$ aryl, optionally substituted with one or more substituents Q. In certain embodiments, $R^X$ is phenyl, optionally substituted with one or more substituents Q. In certain embodiments, $R^X$ is phenyl, fluorophenyl, or formylphenyl. In certain embodiments, $R^X$ is phenyl, 4-fluorophenyl, or 4-formylphenyl. In certain embodiments, $R^X$ is $C_{7-15}$ aralkyl, optionally substituted with one or more substituents Q. In certain embodiments, $R^X$ is benzyl, optionally substituted with one or more substituents Q. In certain embodiments, $R^X$ is heteroaryl, optionally substituted with one or more substituents Q. In certain embodiments, $R^X$ is heterocyclyl, optionally substituted with one or more substituents Q.

In certain embodiments, when X is —N($R^X$)—, $R^B$ and $R^X$ together with the N atom to which they are attached form heteroaryl or heterocyclyl, each of which is optionally substituted with one or more substituents Q. In certain embodiments, when X is —N($R^X$)—, $R^B$ and $R^X$ together with the N atom to which they are attached form heteroaryl, optionally substituted with one or more substituents Q. In certain embodiments, when X is —N($R^X$)—, $R^B$ and $R^X$ together with the N atom to which they are attached form monocyclic heteroaryl, optionally substituted with one or more substituents Q. In certain embodiments, when X is —N(R)—, $R^B$ and $R^X$ together with the N atom to which they are attached form 5-membered heteroaryl, optionally substituted with one or more substituents Q. In certain embodiments, when X is —N(R)—, $R^B$ and $R^X$ together with the N atom to which they are attached form pyrrolyl or imidazolyl, each of which is optionally substituted with one or more substituents Q. In certain embodiments, when X is —N(R)—, $R^B$ and $R^X$ together with the N atom to which they are attached form pyrrol-1-yl or 2-amino-imidazol-1-yl. In certain embodiments, when X is —N(R)—, $R^B$ and $R^X$ together with the N atom to which they are attached form 6-membered heteroaryl, optionally substituted with one or more substituents Q. In certain embodiments, when X is —N(R)—, $R^B$ and $R^X$ together with the N atom to which they are attached form bicyclic heteroaryl, optionally substituted with one or more substituents Q. In certain embodiments, when X is —N(R)—, $R^B$ and $R^X$ together with the N atom to which they are attached form indolyl, optionally substituted with one or more substituents Q. In certain embodiments, when X is —N(R)—, $R^B$ and $R^X$ together with the N atom to which they are attached form heterocyclyl, optionally substituted with one or more substituents Q. In certain embodiments, when X is —N(R)—, $R^B$ and $R^X$ together with the N atom to which they are attached form monocyclic heterocyclyl, optionally substituted with one or more substituents Q. In certain embodiments, when X is —N(R)—, $R^B$ and $R^X$ together with the N atom to which they are attached form 5- or 6-membered heterocyclyl, each of which is optionally substituted with one or more substituents Q. In certain embodiments, when X is —N(R)—, $R^B$ and $R^X$ together with the N atom to which they are attached form pyrrolidinyl, piperidinyl, or morpholinyl, each of which is optionally substituted with one or more substituents Q. In certain embodiments, when X is —N(R)—, $R^B$ and $R^X$ together with the N atom to which they are attached form pyrrolidin-1-yl, piperidin-1-yl, or 4-morpholin-4-yl. In certain embodiments, when X is —N(R)—, $R^B$ and $R^X$ together with the N atom to which they are attached form bicyclic heterocyclyl, optionally substituted with one or more substituents Q.

In certain embodiments, L is $C_{1-6}$ alkylene, optionally substituted with one or more substituents Q. In certain embodiments, L is methylene, ethylene, or propylene, each of which is optionally substituted with one or more substituents Q. In certain embodiments, L is —$(CH_2)_p$—, wherein p is an integer of 1, 2, 3, or 4. In certain embodiments, L is —$(CH_2)_p$—, wherein p is an integer of 1, 2, or 3. In certain embodiments, L is —$(CH_2)_p$—, wherein p is an integer of 1 or 2. In certain embodiments, L is —$CH_2CH_2$—. In certain embodiments, L is —$CH_2$—. In certain embodiments, L is $C_{2-6}$ alkenylene, optionally substituted with one or more substituents Q. In certain embodiments, L is ethenylene, optionally substituted with one or more substituents Q. In certain embodiments, L is ethen-1,2-diyl, optionally substituted with one or more substituents Q. In certain embodiments, L is (E)-ethen-1,2-diyl. In certain embodiments, L is (Z)-ethen-1,2-diyl. In certain embodiments, L is $C_{3-10}$ cycloalkylene, optionally substituted with one or more substituents Q. In certain embodiments, L is heterocyclylene, optionally substituted with one or more substituents Q.

In certain embodiments, X is —O—. In certain embodiments, X is —$NR^X$—, wherein $R^X$ is as defined herein. In certain embodiments, X is —NH—. In certain embodiments, X is —S—. In certain embodiments, X is —S(O)—. In certain embodiments, X is —$S(O)_2$—.

In certain embodiments, $U^1$ is C. In certain embodiments, $U^1$ is N. In certain embodiments, $U^1$ is —$CR^{7a}$=, wherein $R^{7a}$ is as defined herein. In certain embodiments, $U^1$ is —N=. In certain embodiments, $U^1$ is —$NR^{7b}$—, wherein $R^{7b}$ is as defined herein. In certain embodiments, $U^1$ is —O—. In certain embodiments, $U^1$ is —S—.

In certain embodiments, $V^1$ is C. In certain embodiments, $V^1$ is N. In certain embodiments, $V^1$ is —$CR^{7a}$=, wherein $R^{7a}$ is as defined herein. In certain embodiments, $V^1$ is —N=. In certain embodiments, $V^1$ is —$NR^{7b}$—, wherein $R^h$ is as defined herein. In certain embodiments, $V^1$ is —O—. In certain embodiments, $V^1$ is —S—.

In certain embodiments, $W^1$ is C. In certain embodiments, $W^1$ is N. In certain embodiments, $W^1$ is —$CR^{7a}$=, wherein $R^{7a}$ is as defined herein. In certain embodiments, $W^1$ is —N=. In certain embodiments, $W^1$ is —$NR^{7b}$—, wherein $R^h$ is as defined herein. In certain embodiments, $W^1$ is —O—. In certain embodiments, $W^1$ is —S—.

In certain embodiments, $X^1$ is C. In certain embodiments, $X^1$ is N. In certain embodiments, $X^1$ is —$CR^{7a}$=, wherein $R^{7a}$ is as defined herein. In certain embodiments, $X^1$ is —N=. In certain embodiments, $X^1$ is —$NR^{7b}$—, wherein $R^{7b}$ is as defined herein. In certain embodiments, $X^1$ is —O—. In certain embodiments, $X^1$ is —S—.

In certain embodiments, $Y^1$ is C. In certain embodiments, $Y^1$ is N. In certain embodiments, $Y^1$ is a bond. In certain embodiments, $Y^1$ is —$CR^{7a}$=, wherein $R^{7a}$ is as defined herein. In certain embodiments, $Y^1$ is —N=. In certain embodiments, $Y^1$ is —NR$^{7b}$—, wherein R$^{7b}$ is as defined herein. In certain embodiments, $Y^1$ is —O—. In certain embodiments, $Y^1$ is —S—.

In certain embodiments, $Z^1$ is C. In certain embodiments, $Z^1$ is N.

In certain embodiments, $U^2$ is —N═. In certain embodiments, $U^2$ is —O—.

In certain embodiments, $V^2$ is —N═. In certain embodiments, $V^2$ is —O—. In certain embodiments, $V^2$ is —C(OH)═.

In certain embodiments, $U^2$ and $V^2$ are each —N═. In certain embodiments, $U^2$ is —O— and $V^2$ is —C(OH)═.

In certain embodiments, n is an integer of 0. In certain embodiments, n is an integer of 1. In certain embodiments, n is an integer of 2. In certain embodiments, n is an integer of 3. In certain embodiments, n is an integer of 4.

In certain embodiments, p is an integer of 1. In certain embodiments, p is an integer of 2. In certain embodiments, p is an integer of 3. In certain embodiments, p is an integer of 4.

In one embodiment, provided herein is a compound of:

2-[(1Z)-5-fluoro-2-methyl-1-[(4-phenoxyphenyl)methyl-idene]-1H-inden-3-yl]acetic acid A1;
2-[(1Z)-5-fluoro-1-{[4-(4-methoxyphenoxy)phenyl]methyl-idene}-2-methyl-1H-inden-3-yl]acetic acid A2;
2-[(1Z)-1-({2-chloro-4-[3-(trifluoromethyl)phenoxy]phenyl}methylidene)-5-fluoro-2-methyl-1H-inden-3-yl]acetic acid A3;
2-[(1Z)-5-fluoro-2-methyl-1-{[4-(4-methylphenoxy)phe-nyl]methylidene}-1H-inden-3-yl]acetic acid A4;
2-[(1Z)-5-fluoro-2-methyl-1-({4-[4-(propan-2-yl)phenoxy]phenyl}methylidene)-1H-inden-3-yl]acetic acid A5;
2-[(1Z)-1-{[4-(4-bromophenoxy)phenyl]methylidene}-5-fluoro-2-methyl-1H-inden-3-yl]acetic acid A6;
2-[(1Z)-5-fluoro-2-methyl-1-{[4-(3-methylphenoxy)phe-nyl]methylidene}-1H-inden-3-yl]acetic acid A7;
2-[(1Z)-1-{[4-(3-cyanophenoxy)phenyl]methylidene}-5-fluoro-2-methyl-1H-inden-3-yl]acetic acid A8;
(Z)-2-(5-fluoro-2-methyl-1-(4-(3-(trifluoromethyl)phe-noxy)benzylidene)-1H-inden-3-yl)acetic acid A9;
2-[(1Z)-1-{[4-(4-ethylphenoxy)phenyl]methylidene}-5-fluoro-2-methyl-1H-inden-3-yl]acetic acid A10;
2-[(1Z)-1-{[4-(4-fluorophenoxy)phenyl]methyl-idene}-2-methyl-1H-inden-3-yl]acetic acid A11;
2-[(1Z)-1-{[2-chloro-4-(4-methoxyphenoxy)phenyl]meth-ylidene}-5-fluoro-2-methyl-1H-inden-3-yl]acetic acid A12;
2-[(1Z)-5-fluoro-1-({2-methoxy-4-[4-(propan-2-yl)phe-noxy]phenyl}-methylidene)-2-methyl-1H-inden-3-yl]acetic acid A13;
2-[(1Z)-5-fluoro-2-methyl-1-{[4-(naphthalen-2-yloxy)phe-nyl]methylidene}-1H-inden-3-yl]acetic acid A14;
2-[(1Z)-1-({2-chloro-4-[4-(propan-2-yl)phenoxy]phenyl}methylidene)-5-fluoro-2-methyl-1H-inden-3-yl]acetic acid A15;
2-[(1Z)-1-{[4-(2,4-difluorophenoxy)phenyl]methylidene}-5-fluoro-2-methyl-1H-inden-3-yl]acetic acid A16;
2-[(1Z)-1-{[4-(2-bromo-4-fluorophenoxy)phenyl]methyl-idene}-5-fluoro-2-methyl-1H-inden-3-yl]acetic acid A17;
2-[(1Z)-5-fluoro-2-methyl-1-{[4-(2,4,5-trifluorophenoxy)phenyl]methylidene}-1H-inden-3-yl]acetic acid A18;
3-[(1Z)-1-{[4-(4-fluorophenoxy)phenyl]methylidene}-2-methyl-1H-inden-3-yl]propanoic acid A19;
2-[(1Z)-5-fluoro-1-({4-[(6-fluoropyridin-3-yl)oxy]phenyl}methylidene)-2-methyl-1H-inden-3-yl]acetic acid A20;

2-[(1Z)-5-fluoro-1-({4-[(6-fluoro-5-methylpyridin-3-yl)oxy]phenyl}-methylidene)-2-methyl-1H-inden-3-yl]ace-tic acid A21;
(Z)-2-(5-fluoro-2-methyl-1-(4-(quinolin-5-yloxy)ben-zylidene)-1H-inden-3-yl)acetic acid A22;
2-[(1Z)-5-fluoro-2-methyl-1-[(4-phenoxyphenyl)methyl-idene]-1H-inden-3-yl]-N-hydroxyacetamide A23;
2-[(1Z)-5-fluoro-1-{[4-(4-fluorophenoxy)phenyl]methyl-idene}-2-methyl-1H-inden-3-yl]-N-hydroxyacetamide A24;
2-[(1Z)-5-fluoro-1-{[4-(4-fluorophenoxy)phenyl]methyl-idene}-2-methyl-1H-inden-3-yl]acetamide A25;
2-[(1Z)-5-fluoro-1-{[4-(4-fluorophenoxy)phenyl]methyl-idene}-2-methyl-1H-inden-3-yl]-N-methylacetamide A26;
2-[(1Z)-5-fluoro-1-{[4-(4-fluorophenoxy)phenyl]methyl-idene}-2-methyl-1H-inden-3-yl]-N-(2-hydroxyethyl)ac-etamide A27;
(Z)-2-(5-fluoro-2-methyl-1-(4-phenoxybenzylidene)-1H-in-den-3-yl)-N-(1H-tetrazol-5-yl)acetamide A28;
(2E)-3-[(1Z)-5-fluoro-1-{[4-(4-fluorophenoxy)phenyl]methylidene}-2-methyl-1H-inden-3-yl]prop-2-enoic acid A61;
2-[(1Z)-5-fluoro-1-{[4-(4-fluorobenzenesulfonyl)phenyl]methylidene}-2-methyl-1H-inden-3-yl]acetic acid A62;
2-[(1Z)-5-fluoro-1-{[4-(4-fluorobenzenesulfinyl)phenyl]methylidene}-2-methyl-1H-inden-3-yl]acetic acid A63;
2-[(1Z)-5-fluoro-1-({4-[(4-fluorophenyl)sulfanyl]phenyl}methylidene)-2-methyl-1H-inden-3-yl]acetic acid A64;
2-[(1Z)-5-fluoro-1-{[6-(4-fluorophenoxy)pyridine-3-yl]methylidene}-2-methyl-1H-inden-3-yl]acetic acid A65;
2-[(1Z)-5-fluoro-1-{[6-(4-fluorophenoxy)-5-methylpyridin-3-yl]methylidene}-2-methyl-1H-inden-3-yl]acetic acid A66;
(2E)-4-[(1Z)-5-fluoro-1-{[4-(4-fluorophenoxy)phenyl]methylidene}-2-methyl-1H-inden-3-yl]but-2-enoic acid A67;
2-[(1Z)-4,5-difluoro-1-{[4-(4-fluorophenoxy)phenyl]meth-ylidene}-2-methyl-1H-inden-3-yl]acetic acid A68;
2-[(1Z)-5-fluoro-1-{[4-(4-fluorophenoxy)phenyl]methyl-idene}-2,4-dimethyl-1H-inden-3-yl]acetic acid A69;
(2E)-3-[(1Z)-5-fluoro-1-{[4-(4-fluorophenoxy)phenyl]methylidene}-2-methyl-1H-inden-3-yl]-N-hydroxyprop-2-enamide A76;
2-[(1Z)-5-fluoro-1-{[4-(4-fluorobenzenesulfonyl)phenyl]methylidene}-2-methyl-1H-inden-3-yl]-N-hydroxyacet-amide A77;
2-[(1Z)-5-fluoro-1-{[4-(4-fluorobenzenesulfinyl)phenyl]methylidene}-2-methyl-1H-inden-3-yl]-N-hydroxyacet-amide A78;
2-[(1Z)-5-fluoro-1-({4-[(4-fluorophenyl)sulfanyl]phenyl}methylidene)-2-methyl-1H-inden-3-yl]-N-hy-droxyacetamide A79;
2-[(1Z)-5-fluoro-1-{[6-(4-fluorophenoxy)pyridine-3-yl]methylidene}-2-methyl-1H-inden-3-yl]-N-hydroxyacet-amide A80;
2-[(1Z)-5-fluoro-1-{[6-(4-fluorophenoxy)-5-methylpyridin-3-yl]methylidene}-2-methyl-1H-inden-3-yl]-N-hydroxy-acetamide A81;
(2E)-4-[(1Z)-5-fluoro-1-{[4-(4-fluorophenoxy)phenyl]methylidene}-2-methyl-1H-inden-3-yl]-N-hydroxybut-2-enamide A82;
2-[(1Z)-4,5-difluoro-1-{[4-(4-fluorophenoxy)phenyl]meth-ylidene}-2-methyl-1H-inden-3-yl]-N-hydroxyacetamide A83; or 2-[(1Z)-5-fluoro-1-{[4-(4-fluorophenoxy)phenyl]methyl-idene}-2,4-dimethyl-1H-inden-3-yl]-N-hydroxyacet-amide A84;

or a tautomer, a mixture of two or more tautomers, or an isotopic variant thereof; or a pharmaceutically acceptable salt, solvate, hydrate, or prodrug thereof.

In another embodiment, provided herein is a compound of:

2-[(1Z)-5-fluoro-2-methyl-1-({4-[methyl(phenyl)amino] phenyl}methylidene)-1H-inden-3-yl]acetic acid A29;

2-[(1Z)-1-({4-[benzyl(4-fluorophenyl)amino] phenyl}methylidene)-5-fluoro-2-methyl-1H-inden-3-yl] acetic acid A30;

2-[(1Z)-5-fluoro-1-({4-[(4-fluorophenyl)(methyl)amino] phenyl}methylidene)-2-methyl-1H-inden-3-yl]acetic acid A31;

2-[(1Z)-1-({4-[ethyl(4-fluorophenyl)amino] phenyl}methylidene)-5-fluoro-2-methyl-1H-inden-3-yl] acetic acid A32;

2-[(1Z)-5-fluoro-1-({4-[(4-fluorophenyl)(propyl)amino] phenyl}methylidene)-2-methyl-1H-inden-3-yl]acetic acid A33;

2-[(1Z)-5-fluoro-1-({4-[(4-fluorophenyl)(2-hydroxyethyl) amino]phenyl}-methylidene)-2-methyl-1H-inden-3-yl] acetic acid A34;

2-[(1Z)-5-fluoro-1-({4-[(4-fluorophenyl)(4-formylphenyl) amino]phenyl}-methylidene)-2-methyl-1H-inden-3-yl] acetic acid A35;

2-[(1Z)-5-fluoro-1-({4-[(4-formylphenyl)(phenyl)amino] phenyl}methylidene)-2-methyl-1H-inden-3-yl]acetic acid A36;

2-[(1Z)-5-fluoro-2-methyl-1-({4-[methyl(phenyl)amino] phenyl}methylidene)-1H-inden-3-yl]-N-hydroxyacet-amide A37;

2-[(1Z)-1-({4-[benzyl(4-fluorophenyl)amino] phenyl}methylidene)-5-fluoro-2-methyl-1H-inden-3-yl]-N-hydroxyacetamide A38;

2-[(1Z)-5-fluoro-2-methyl-1-{[4-(morpholin-4-yl)phenyl] methylidene}-1H-inden-3-yl]acetic acid A55;

2-[(1Z)-5-fluoro-2-methyl-1-{[4-(piperidin-1-yl)phenyl] methylidene}-1H-inden-3-yl]acetic acid A56;

2-[(1Z)-5-fluoro-1-{[4-(1H-indol-1-yl)phenyl]methyl-idene}-2-methyl-1H-inden-3-yl]acetic acid A57;

2-[(1Z)-1-{[4-(2-amino-1H-imidazol-1-yl)phenyl]methyl-idene}-5-fluoro-2-methyl-1H-inden-3-yl]acetic acid A58;

2-[(1Z)-5-fluoro-2-methyl-1-{[4-(pyrrolidin-1-yl)phenyl] methylidene}-1H-inden-3-yl]acetic acid A59;

2-[(1Z)-5-fluoro-2-methyl-1-{[4-(1H-pyrrol-1-yl)phenyl] methylidene}-1H-inden-3-yl]acetic acid A60;

2-[(1Z)-5-fluoro-2-methyl-1-{[4-(morpholin-4-yl)phenyl] methylidene}-1H-inden-3-yl]-N-hydroxyacetamide A70;

2-[(1Z)-5-fluoro-2-methyl-1-{[4-(piperidin-1-yl)phenyl] methylidene}-1H-inden-3-yl]-N-hydroxyacetamide A71;

2-[(1Z)-5-fluoro-1-{[4-(1H-indol-1-yl)phenyl]methyl-idene}-2-methyl-1H-inden-3-yl]-N-hydroxyacetamide A72;

2-[(1Z)-1-{[4-(2-amino-1H-imidazol-1-yl)phenyl]methyl-idene}-5-fluoro-2-methyl-1H-inden-3-yl]-N-hydroxyac-etamide A73;

2-[(1Z)-5-fluoro-2-methyl-1-{[4-(pyrrolidin-1-yl)phenyl] methylidene}-1H-inden-3-yl]-N-hydroxyacetamide A74;

2-[(1Z)-5-fluoro-2-methyl-1-{[4-(1H-pyrrol-1-yl)phenyl] methylidene}-1H-inden-3-yl]-N-hydroxyacetamide A75; or 2-[(1Z)-5-fluoro-1-({4-[(4-fluorophenyl)(2-hydroxyethyl) amino]phenyl}-methylidene)-2-methyl-1H-inden-3-yl]-N-hydroxyacetamide A85;

or a tautomer, a mixture of two or more tautomers, or an isotopic variant thereof; or a pharmaceutically acceptable salt, solvate, hydrate, or prodrug thereof.

In yet another embodiment, provided herein is a compound of:

5-{[(1Z)-2-methyl-1-[(3-phenoxyphenyl)methylidene]-1H-inden-3-yl]methyl}-1H-1,2,3,4-tetrazole A39;

5-{[(1Z)-2-methyl-1-[(4-phenoxyphenyl)methylidene]-1H-inden-3-yl]methyl}-1H-1,2,3,4-tetrazole A40;

5-{2-[(1Z)-2-methyl-1-{[4-(4-methylphenoxy)phenyl] methylidene]-1H-inden-3-yl]ethyl}-1H-1,2,3,4-tetrazole A41;

5-{2-[(1Z)-1-{[4-(4-bromophenoxy)phenyl]methylidene}-2-methyl-1H-inden-3-yl]ethyl}-1H-1,2,3,4-tetrazole A42;

5-{2-[(1Z)-2-methyl-1-({4-[4-(propan-2-yl)phenoxy] phenyl}methylidene)-1H-inden-3-yl]ethyl}-1H-1,2,3,4-tetrazole A43;

5-{2-[(1Z)-1-{[4-(4-methoxyphenoxy)phenyl]methyl-idene}-2-methyl-1H-inden-3-yl]ethyl}-1H-1,2,3,4-tetra-zole A44;

5-{2-[(1Z)-2-methyl-1-({4-[4-(trifluoromethyl)phenoxy] phenyl}methylidene)-1H-inden-3-yl]ethyl}-1H-1,2,3,4-tetrazole A45;

5-{2-[(1Z)-2-methyl-1-{[4-(3-methylphenoxy)phenyl] methylidene]-1H-inden-3-yl]ethyl}-1H-1,2,3,4-tetrazole A46;

3-(4-{[(1Z)-2-methyl-3-[2-(1H-1,2,3,4-tetrazol-5-yl)ethyl]-1H-inden-1-ylidene]methyl}phenoxy)benzonitrile A47;

5-{2-[(1Z)-1-{[4-(3-methoxyphenoxy)phenyl]methyl-idene}-2-methyl-1H-inden-3-yl]ethyl}-1H-1,2,3,4-tetra-zole A48;

5-{2-[(1Z)-1-{[4-(3-bromophenoxy)phenyl]methylidene}-2-methyl-1H-inden-3-yl]ethyl}-1H-1,2,3,4-tetrazole A49;

5-{2-[(1Z)-2-methyl-1-({4-[3-(trifluoromethyl)phenoxy] phenyl}methylidene)-1H-inden-3-yl]ethyl}-1H-1,2,3,4-tetrazole A50;

5-{2-[(1Z)-2-methyl-1-{[4-(naphthalen-2-yloxy)phenyl] methylidene]-1H-inden-3-yl]ethyl}-1H-1,2,3,4-tetrazole A51; or (Z)-3-((2-methyl-1-(4-phenoxybenzylidene)-1H-inden-3-yl)methyl)-1,2,4-oxadiazol-5(4H)-one A52;

or a tautomer, a mixture of two or more tautomers, or an isotopic variant thereof; or a pharmaceutically acceptable salt, solvate, hydrate, or prodrug thereof.

In yet another embodiment, provided herein is a compound of 5-{[(1E)-1-[(4-phenoxyphenyl)methylidene]-1H-inden-3-yl]methyl}-1H-1,2,3,4-tetrazole A53; or 5-{[(1E)-1-[(3-phenoxyphenyl)methylidene]-1H-inden-3-yl] methyl}-1H-1,2,3,4-tetrazole A54; or a tautomer, a mixture of two or more tautomers, or an isotopic variant thereof; or a pharmaceutically acceptable salt, solvate, hydrate, or prod-rug thereof.

In yet another embodiment, provided herein is a compound of:

2-[(1Z)-5-fluoro-2-methyl-1-[(4-phenoxyphenyl)methyl-idene]-1H-inden-3-yl]-N-hydroxy-N-methylacetamide C1;

2-[(1Z)-5-fluoro-1-{[4-(4-fluorophenoxy)phenyl]methyl-idene}-2-methyl-1H-inden-3-yl]-N-hydroxy-N-methyl-acetamide C2; or (Z)-2-(5-fluoro-2-methyl-1-(3-phenoxybenzylidene)-1H-in-den-3-yl)-N-hydroxy-N-methylacetamide C3;

or a tautomer, a mixture of two or more tautomers, or an isotopic variant thereof; or a pharmaceutically acceptable salt, solvate, hydrate, or prodrug thereof.

In yet another embodiment, provided herein is a compound of:

2-[(1Z)-5-fluoro-2-methyl-1-({4-[4-(propan-2-yl)phenoxy]phenyl}methylidene)-1H-inden-3-yl]-N-hydroxyacetamide D1;

2-[(1Z)-5-fluoro-2-methyl-1-({4-[4-(tert-butyl)phenoxy]phenyl}methylidene)-1H-inden-3-yl]acetic acid D2;

2-[(1Z)-5-fluoro-2-methyl-1-({4-[3-(tert-butyl)phenoxy]phenyl}methylidene)-1H-inden-3-yl]acetic acid D3;

2-[(1Z)-5-fluoro-2-methyl-1-({4-[3-fluoro-4-methylphenoxy]phenyl}-methylidene)-1H-inden-3-yl]acetic acid D4;

2-[(1Z)-5-fluoro-2-methyl-1-({4-[3,4-difluorophenoxy]phenyl}methylidene)-1H-inden-3-yl]acetic acid D5;

2-[(1Z)-5-fluoro-2-methyl-1-({4-[3-nitrophenoxy]phenyl}methylidene)-1H-inden-3-yl]acetic acid D6;

2-[(1Z)-5-fluoro-2-methyl-1-({4-[4-(trifluoromethyl)phenoxy]phenyl}-methylidene)-1H-inden-3-yl]acetic acid D7;

2-[(1Z)-5-fluoro-1-{[4-(4-fluorophenoxy)phenyl]methylidene}-2-(2-methylpropyl)-1H-inden-3-yl]acetic acid D8;

2-[(1Z)-5-fluoro-2-benzyl-1-({4-[4-fluorophenoxy]phenyl}methylidene)-1H-inden-3-yl]acetic acid D9;

2-[(1Z)-5-methoxy-2-methyl-1-({4-[4-fluorophenoxy]phenyl}methylidene)-1H-inden-3-yl]acetic acid D10;

2-[(1Z)-5-methoxy-2-methyl-1-[(4-phenoxyphenyl)methylidene]-1H-inden-3-yl]acetic acid D11;

2-[(1Z)-1-{[2-trifluoromethyl-4-(4-fluorophenoxy)phenyl]methylidene}-5-fluoro-2-methyl-1H-inden-3-yl]acetic acid D12;

2-[(1Z)-1-{[3-methyl-4-(4-fluorophenoxy)phenyl]methylidene}-5-fluoro-2-methyl-1H-inden-3-yl]acetic acid D13;

2-[(1Z)-1-{[2-methyl-4-(4-fluorophenoxy)phenyl]methylidene}-5-fluoro-2-methyl-1H-inden-3-yl]acetic acid D14;

2-[(1Z)-5,7-difluoro-2-methyl-1-({4-[4-fluorophenoxy]phenyl}methylidene)-1H-inden-3-yl]acetic acid D15;

2-[(1Z)-4,6-difluoro-2-methyl-1-({4-[4-fluorophenoxy]phenyl}methylidene)-1H-inden-3-yl]acetic acid D16;

2-[(1Z)-5-tert-butyl-2-methyl-1-({4-[4-fluorophenoxy]phenyl}methylidene)-1H-inden-3-yl]acetic acid D17;

(Z)-2-(5-fluoro-2-methyl-1-(3-phenoxybenzylidene)-1H-inden-3-yl)acetic acid D18;

2-[(1Z)-5-fluoro-1-(2-(phenoxy)benzylidene)-2-methyl-1H-inden-3-yl]-acetic acid D19;

2-[(1Z)-5,7-difluoro-1-(3-(phenoxy)benzylidene)-2-methyl-1H-inden-3-yl]-acetic acid D20;

2-[(1Z)-4,6-difluoro-1-(3-(phenoxy)benzylidene)-2-methyl-1H-inden-3-yl]-acetic acid D21;

2-[(1Z)-5-fluoro-2-methyl-1-({3-[4-methoxyphenoxy]phenyl}methylidene)-1H-inden-3-yl]acetic acid D22;

2-[(1Z)-5-fluoro-1-(4-fluoro-3-(phenoxy)benzylidene)-2-methyl-1H-inden-3-yl]-acetic acid D23;

2-[(1Z)-5-fluoro-2-methyl-1-({3-[4-cyanophenoxy]phenyl}methylidene)-1H-inden-3-yl]acetic acid D24;

2-[(1Z)-5-fluoro-2-methyl-1-({3-[4-chlorophenoxy]phenyl}methylidene)-1H-inden-3-yl]acetic acid D25;

2-[(1Z)-5-fluoro-2-methyl-1-({3-[4-trifluoromethylphenoxy]phenyl}-methylidene)-1H-inden-3-yl]acetic acid D26;

2-[(1Z)-5-fluoro-2-methyl-1-({3-[3-trifluoromethylphenoxy]phenyl}-methylidene)-1H-inden-3-yl]acetic acid D27;

2-[(1Z)-4-methoxy-1-(4-(phenoxy)benzylidene)-2-methyl-1H-inden-3-yl]-acetic acid D28;

2-[(1Z)-6-methoxy-1-(4-(phenoxy)benzylidene)-2-methyl-1H-inden-3-yl]-acetic acid D29;

2-[(1Z)-6-trifluoromethyl-2-methyl-1-({4-[4-fluorophenoxy]phenyl}-methylidene)-1H-inden-3-yl]acetic acid D30;

2-[(1Z)-5-trifluoromethyl-2-methyl-1-({4-[4-fluorophenoxy]phenyl}-methylidene)-1H-inden-3-yl]acetic acid D31;

2-[(1Z)-1-{[4-(4-fluorophenoxy)phenyl]methylidene}-1H-inden-3-yl]acetic acid D32;

2-[(1Z)-5-fluoro-1-{[4-(4-fluorophenoxy)phenyl]methylidene}-1H-inden-3-yl]acetic acid D33;

2-[(1Z)-5-trifluoromethyl-1-(3-(phenoxy)benzylidene)-2-methyl-1H-inden-3-yl]-acetic acid D34;

2-[(1Z)-6-methoxy-1-(3-(phenoxy)benzylidene)-2-methyl-1H-inden-3-yl]-acetic acid D35;

2-[(1Z)-6-trifluoromethyl-1-(3-(phenoxy)benzylidene)-2-methyl-1H-inden-3-yl]-acetic acid D36;

2-[(1Z)-5-fluoro-2-methyl-1-({3-[methyl(phenyl)amino]phenyl}methylidene)-1H-inden-3-yl]acetic acid D37; or 2-[(1Z)-5-fluoro-1-[(3-methoxy-5-phenoxyphenyl)methylidene]-2-methyl-1H-inden-3-yl]acetic acid D38;

or a tautomer, a mixture of two or more tautomers, or an isotopic variant thereof; or a pharmaceutically acceptable salt, solvate, hydrate, or prodrug thereof.

In still another embodiment, provided herein is a compound of:

2-[(1E)-5-fluoro-2-methyl-1-({4-[3,4-difluorophenoxy]phenyl}methylidene)-1H-inden-3-yl]acetic acid E1;

2-[(1E)-5-fluoro-2-methyl-1-({4-[4-fluorophenoxy]phenyl}methylidene)-1H-inden-3-yl]acetic acid E2;

2-[(1E)-5-fluoro-2-methyl-1-[(4-phenoxyphenyl)methylidene]-1H-inden-3-yl]acetic acid E3;

2-[(1E)-5,7-difluoro-2-methyl-1-({4-[4-fluorophenoxy]phenyl}methylidene)-1H-inden-3-yl]acetic acid E4;

5-{2-[(1E)-1-[(4-phenoxyphenyl)methylidene]-1H-inden-3-yl]ethyl}-1H-1,2,3,4-tetrazole E5; and 2-[(1E)-5,7-difluoro-1-(3-(phenoxy)benzylidene)-2-methyl-1H-inden-3-yl]-acetic acid E6;

or a tautomer, a mixture of two or more tautomers, or an isotopic variant thereof; or a pharmaceutically acceptable salt, solvate, hydrate, or prodrug thereof.

In certain embodiments, a compound provided herein is deuterium-enriched. In certain embodiments, a compound provided herein is carbon-13 enriched. In certain embodiments, a compound provided herein is carbon-14 enriched. In certain embodiments, a compound provided herein contains one or more less prevalent isotopes for other elements, including, but not limited to, $^{15}N$ for nitrogen; $^{17}O$ or $^{18}O$ for oxygen, and $^{34}S$, $^{35}S$, or $^{36}S$ for sulfur.

In certain embodiments, a compound provided herein has an isotopic enrichment factor of no less than about 5, no less than about 10, no less than about 20, no less than about 50, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when a compound at a given position is 100% enriched with the specified isotope. Thus, the maximum isotopic enrichment factor is different for different isotopes. The maximum isotopic enrichment factor is 6,410 for deuterium and 90 for carbon-13.

In certain embodiments, a compound provided herein has a deuterium enrichment factor of no less than about 64 (about 1% deuterium enrichment), no less than about 130 (about 2% deuterium enrichment), no less than about 320 (about 5% deuterium enrichment), no less than about 640

(about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy. In certain embodiments, at least one of the atoms of a compound provided herein, as specified as deuterium-enriched, has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, a compound provided herein is isolated or purified. In certain embodiments, a compound provided herein has a purity of at least about 90%, at least about 95%, at least about 98%, at least about 99%, or at least about 99.5% by weight.

The compounds provided herein are intended to encompass all possible stereoisomers, unless a particular stereochemistry is specified. Where a compound provided herein contains an alkenyl group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contains an aromatic moiety. It follows that a single compound may exhibit more than one type of isomerism.

The compound provided herein can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for the compound that undergoes epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When a compound provided herein contains an acidic or basic moiety, it can also be provided as a pharmaceutically acceptable salt. See, Berge et al., *J. Pharm. Sci.* 1977, 66, 1-19*; Handbook of Pharmaceutical Salts: Properties, Selection, and Use,* 2nd ed.; Stahl and Wermuth Eds.; John Wiley & Sons, 2011. In certain embodiments, a pharmaceutically acceptable salt of a compound provided herein is a solvate. In certain embodiments, a pharmaceutically acceptable salt of a compound provided herein is a hydrate.

Suitable acids for use in the preparation of pharmaceutically acceptable salts of a compound provided herein include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts of a compound provided herein include, but are not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

A compound provided herein may also be provided as a prodrug, which is a functional derivative of the compound and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis.

Pharmaceutical Compositions

In one embodiment, provided herein is a pharmaceutical composition, comprising a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

The pharmaceutical composition provided herein can be formulated in various dosage forms, including, but not limited to, dosage forms for oral, parenteral, and topical administration. The pharmaceutical composition can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art. See, e.g., *Remington: The Science and Practice of Pharmacy, supra; Modified-Release Drug Delivery Technology,* 2nd ed.; Rathbone et al., Eds.; Drugs and the Pharmaceutical Sciences 184; CRC Press: Boca Raton, Fla., 2008.

In one embodiment, the pharmaceutical composition provided herein is formulated in a dosage form for oral administration. In another embodiment, the pharmaceutical composition provided herein is formulated in a dosage form for parenteral administration. In yet another embodiment, the pharmaceutical composition provided herein is formulated in a dosage form for intravenous administration. In yet another embodiment, the pharmaceutical composition provided herein is formulated in a dosage form for intramuscular administration. In yet another embodiment, the pharmaceutical composition provided herein is formulated in a dosage form for subcutaneous administration. In still another embodiment, the pharmaceutical composition provided herein is formulated in a dosage form for topical administration.

The pharmaceutical composition provided herein can be provided in a unit-dosage form or multiple-dosage form. A unit-dosage form, as used herein, refers to physically discrete a unit suitable for administration to a subject, and packaged individually as is known in the art. Each unit-dose contains a predetermined quantity of an active ingredient(s) (e.g., a compound provided herein) sufficient to produce the desired therapeutic effect, in association with the required pharmaceutical excipient(s). Examples of a unit-dosage form include, but are not limited to, an ampoule, syringe, and individually packaged tablet and capsule. A unit-dosage form may be administered in fractions or multiples thereof. A multiple-dosage form is a plurality of identical unit-dosage forms packaged in a single container to be administered in a segregated unit-dosage form. Examples of a multiple-dosage form include, are not limited to, a vial, bottle of tablets or capsules, or bottle of pints or gallons.

The pharmaceutical composition provided herein can be administered at once or multiple times at intervals of time. It is understood that the precise dosage and duration of treatment may vary with the age, weight, and condition of the subject being treated, and may be determined empirically using known testing protocols or by extrapolation from in vivo or in vitro test or diagnostic data. It is further understood that for any particular individual, specific dosage regimens should be adjusted over time according to the subject's need and the professional judgment of the person administering or supervising the administration of the pharmaceutical composition.

A. Oral Administration

The pharmaceutical composition provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical composition can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500®); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), VEEGUM®, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); and microcrystalline celluloses, such as AVICEL® PH-101, AVICEL® PH-103, AVICEL® PH-105, and AVICEL® RC-581. Suitable fillers include, but are not limited to, talc, calcium carbonate, microcrystalline cellulose, powdered cellulose, dextrates, kaolin, mannitol, silicic acid, sorbitol, starch, and pre-gelatinized starch. The amount of a binder or filler in the pharmaceutical composition provided herein varies upon the type of formulation, and is readily discernible to those of ordinary skill in the art. The binder or filler may be present from about 50 to about 99% by weight in the pharmaceutical composition provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical composition provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and VEEGUM® HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; and algins. The amount of a disintegrant in the pharmaceutical composition provided herein varies upon the type of formulation, and is readily discernible to those of ordinary skill in the art. The pharmaceutical composition provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, such as peanut oil, cottonseed oil, sunflower oil, sesame oil, olive oil, corn oil, and soybean oil; zinc stearate; ethyl oleate; ethyl laureate; agar; starch; lycopodium; and silica or silica gels, such as AEROSIL® 200 and CAB-O-SIL®. The amount of a lubricant in the pharmaceutical composition provided herein varies upon the type of formulation, and is readily discernible to those of ordinary skill in the art. The pharmaceutical compositions provided herein may contain about 0.1 to about 5% by weight of a lubricant.

Suitable glidants include, but are not limited to, colloidal silicon dioxide, CAB-O-SIL®, and asbestos-free talc. Suitable coloring agents include, but are not limited to, any of the approved, certified, water soluble FD&C dyes, and water insoluble FD&C dyes suspended on alumina hydrate, and color lakes. A color lake is a combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, VEEGUM®, acacia, sodium carbomethylcellulose, hydroxypropyl methylcellulose, and polyvinylpyrrolidone. Suitable preservatives include, but are not limited to, glycerin, methyl and propylparaben, benzoic add, and sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical composition provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredient(s) from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from an active ingredient(s) in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical composition provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient(s). The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient(s).

The pharmaceutical composition provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing an active ingredient(s), and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These dosage forms can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical composition provided herein for oral administration can be also provided in the forms of liposomes, micelles, microspheres, or nanosystems. Micellar dosage forms can be prepared as described in U.S. Pat. No. 6,350,458.

The pharmaceutical composition provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the dosage forms described herein.

The pharmaceutical composition provided herein for oral administration can be formulated as immediate or modified release dosage forms, including delayed-, sustained, pulsed-, controlled, targeted-, and programmed-release forms.

B. Parenteral Administration

The pharmaceutical composition provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical composition provided herein for parenteral administration can be formulated in any dosage forms that are suitable for parenteral administration, including, but not limited to, solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science. See, e.g., *Remington: The Science and Practice of Pharmacy, supra.*

The pharmaceutical composition provided herein for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringer's injection, isotonic dextrose injection, sterile water injection, dextrose and lactated Ringer's injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants include those described herein, such as bisulfite and sodium metabisulfite. Suitable local anesthetics include, but are not limited to, procaine hydrochloride. Suitable suspending and dispersing agents include those described herein, such as sodium carboxymethylcelluose, hydroxypropyl methylcellulose, and polyvinylpyrrolidone. Suitable emulsifying agents include those described herein, such as polyoxyethylene sorbitan monolaurate, polyoxyethylene sorbitan monooleate 80, and triethanolamine oleate. Suitable sequestering or chelating agents include, but are not limited to, EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®).

When the pharmaceutical composition provided herein is formulated for multiple dosage administration, multiple dosage parenteral formulations must contain an antimicrobial agent at bacteriostatic or fungistatic concentrations. All parenteral formulations must be sterile, as known and practiced in the art.

In one embodiment, the pharmaceutical composition for parenteral administration is provided as a ready-to-use sterile solution. In another embodiment, the pharmaceutical composition is provided as a sterile dry soluble product, including a lyophilized powder and hypodermic tablet, to be reconstituted with a vehicle prior to use. In yet another embodiment, the pharmaceutical composition is provided as a ready-to-use sterile suspension. In yet another embodiment, the pharmaceutical composition is provided as a sterile dry insoluble product to be reconstituted with a vehicle prior to use. In still another embodiment, the pharmaceutical composition is provided as a ready-to-use sterile emulsion.

The pharmaceutical composition provided herein for parenteral administration can be formulated as immediate or modified release dosage forms, including delayed-, sustained, pulsed-, controlled, targeted-, and programmed-release forms.

The pharmaceutical composition provided herein for parenteral administration can be formulated as a suspension, solid, semi-solid, or thixotropic liquid, for administration as an implanted depot. In one embodiment, the pharmaceutical composition provided herein are dispersed in a solid inner matrix, which is surrounded by an outer polymeric membrane that is insoluble in body fluids but allows the active ingredient(s) in the pharmaceutical composition to diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers (such as hydrogels of esters of acrylic and methacrylic acid), collagen, cross-linked polyvinyl alcohol, and cross-linked partially hydrolyzed polyvinyl acetate.

Suitable outer polymeric membranes include, but are not limited to, polyethylene, polypropylene, ethylene/propylene copolymers, ethylene/ethyl acrylate copolymers, ethylene/ vinyl acetate copolymers, silicone rubbers, polydimethyl siloxanes, neoprene rubber, chlorinated polyethylene, poly-vinylchloride, vinyl chloride copolymers with vinyl acetate, vinylidene chloride, ethylene and propylene, ionomer poly-ethylene terephthalate, butyl rubber epichlorohydrin rub-bers, ethylene/vinyl alcohol copolymer, ethylene/vinyl acetate/vinyl alcohol terpolymer, and ethylene/vinyloxy-ethanol copolymer.

C. Topical Administration

The pharmaceutical composition provided herein can be administered topically to the skin, orifices, or mucosa. The topical administration, as used herein, includes (intra)der-mal, conjunctival, intracorneal, intraocular, ophthalmic, auricular, transdermal, nasal, vaginal, urethral, respiratory, and rectal administration.

The pharmaceutical composition provided herein can be formulated in any dosage forms that are suitable for topical administration for local or systemic effect, including, but not limited to, emulsions, solutions, suspensions, creams, gels, hydrogels, ointments, dusting powders, dressings, elixirs, lotions, suspensions, tinctures, pastes, foams, films, aero-sols, irrigations, sprays, suppositories, bandages, and dermal patches. The topical formulations of the pharmaceutical composition provided herein can also comprise liposomes, micelles, microspheres, and nanosystems.

Pharmaceutically acceptable carriers and excipients suit-able for use in the topical formulations include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical composition can also be administered topically by electroporation, iontophoresis, phonophoresis, sonophoresis, or microneedle or needle-free injection, such as POWDERJECT™ and BIOJECT™.

The pharmaceutical composition provided herein can be provided in the forms of ointments, creams, and gels. Suitable ointment vehicles include oleaginous or hydrocar-bon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-remov-able vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, includ-ing cetyl alcohol, glyceryl monostearate, lanolin, and stearic acid. See, e.g., *Remington: The Science and Practice of Pharmacy*, supra. These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfac-tant.

Gels are semisolid, suspension-type systems. Single-phase gels contain organic macromolecules distributed sub-stantially uniformly throughout the liquid carrier. Suitable gelling agents include, but are not limited to, crosslinked acrylic acid polymers, such as carbomers, carboxypolyal-kylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcel-lulose phthalate, and methylcellulose; gums, such as traga-canth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical composition provided herein can be administered rectally, urethrally, vaginally, or perivaginally in the forms of suppositories, pessaries, bougies, poultices or cataplasm, pastes, powders, dressings, creams, plasters, con-traceptives, ointments, solutions, emulsions, suspensions, tampons, gels, foams, sprays, or enemas. These dosage forms can be manufactured using conventional processes as described in *Remington: The Science and Practice of Phar-macy*, supra.

Rectal, urethral, and vaginal suppositories are solid bodies for insertion into body orifices, which are solid at ordinary temperatures but melt or soften at body temperature to release the active ingredient(s) inside the orifices. Pharma-ceutically acceptable carriers utilized in rectal and vaginal suppositories include bases or vehicles, such as stiffening agents, which produce a melting point in the proximity of body temperature, when formulated with an active ingredi-ent(s); and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical composition provided herein can be administered ophthalmically in the forms of solutions, sus-pensions, ointments, emulsions, gel-forming solutions, pow-ders for solutions, gels, ocular inserts, and implants.

The pharmaceutical composition provided herein can be administered intranasally or by inhalation to the respiratory tract. The pharmaceutical composition can be provided in the form of an aerosol or solution for delivery using a pressurized container, pump, spray, atomizer, such as an atomizer using electrohydrodynamics to produce a fine mist, or nebulizer, alone or in combination with a suitable pro-pellant, such as 1,1,1,2-tetrafluoroethane or 1,1,1,2,3,3,3-heptafluoropropane. The pharmaceutical composition can also be provided as a dry powder for insufflation, alone or in combination with an inert carrier such as lactose or phos-pholipids; and nasal drops. For intranasal use, the powder can comprise a bioadhesive agent, including chitosan or cyclodextrin.

Solutions or suspensions for use in a pressurized con-tainer, pump, spray, atomizer, or nebulizer can be formulated to contain ethanol, aqueous ethanol, or a suitable alternative agent for dispersing, solubilizing, or extending release of an active ingredient(s); a propellant as solvent; and/or a surfactant, such as sorbitan trioleate, oleic acid, or an oligolactic acid.

The pharmaceutical composition provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical composition provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical composition provided herein for inhaled/intranasal administration can further comprise a suitable flavor, such as menthol and levomenthol; and/or sweeteners, such as saccharin and saccharin sodium.

The pharmaceutical composition provided herein for topical administration can be formulated to be immediate release or modified release, including delayed-, sustained-, pulsed-, controlled-, targeted, and programmed release.

D. Modified Release

The pharmaceutical composition provided herein can be formulated as a modified release dosage form. As used herein, the term "modified release" refers to a dosage form in which the rate or place of release of an active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical composition in modified release dosage forms can be prepared using a variety of modified release devices and methods known to those skilled in the art, including, but not limited to, matrix-controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

1. Matrix Controlled Release Devices

The pharmaceutical composition provided herein in a modified release dosage form can be fabricated using a matrix-controlled release device known to those skilled in the art. See, e.g., Takada et al. in *Encyclopedia of Controlled Drug Delivery*, Mathiowitz Ed.; Wiley, 1999; Vol. 2.

In certain embodiments, the pharmaceutical composition provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical composition provided herein is formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix-controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical composition provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical composition provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical composition in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art. See, e.g., *Remington: The Science and Practice of Pharmacy, supra*; Santus and Baker, *J. Controlled Release*, 1995, 35, 1-21; Verma et al., *Drug Dev. Ind. Pharm.*, 2000, 26, 695-708; Verma et al., *J. Controlled Release*, 2002, 79, 7-27.

In certain embodiments, the pharmaceutical composition provided herein is formulated as an AMT controlled-release dosage form, which comprises an asymmetric osmotic membrane that coats a core comprising the active ingredient(s) and other pharmaceutically acceptable excipients or carriers. See, e.g., U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical composition provided herein is formulated as an ESC controlled-release dosage form, which comprises an osmotic membrane that coats a core comprising the active ingredient(s), a hydroxyethyl cellulose, and other pharmaceutically acceptable excipients or carriers.

3. Multiparticulate Controlled Release Devices

The pharmaceutical composition provided herein in a modified release dosage form can be fabricated as a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates can be made by the processes known to those skilled in the art, including wet- and dry-granulation, extrusion/spheronization, roller-compaction, melt-congealing, and by spray-coating seed cores. See, e.g., *Multiparticulate Oral Drug Delivery*; Ghebre-Sellassie Eds.; Drugs and the Pharmaceutical Sciences 65; CRC Press: 1994; and *Pharmaceutical Pelletization Technology*; Ghebre-Sellassie Eds.; Drugs and the Pharmaceutical Sciences 37; CRC Press: 1989.

Other excipients or carriers as described herein can be blended with the pharmaceutical composition to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical composition provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein is a method of treating, ameliorating, or preventing one or more symptoms of a fibrotic disease in a subject, comprising administering to the subject in need thereof a therapeutically effective amount of a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In another embodiment, provided herein is a method of treating, ameliorating, or preventing one or more symptoms of a fibrotic disease in a subject, comprising administering to the subject in need thereof a therapeutically effective amount of a compound of Formula (I-A):

(I-A)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is (a) hydrogen, deuterium, cyano, halo, or nitro; or (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^2$ is —CN, —C(O)$OR^{2a}$, —C(O)$NR^{2b}R^{2c}$, —C(O)N($R^{2b}$)$OR^{2c}$, —$OR^{2a}$, —$NR^{2b}R^{2c}$, or heteroaryl; wherein $R^{2a}$, $R^{2b}$, and $R^{2c}$ are each independently hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^3$, $R^4$, $R^5$, and $R^6$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)$OR^{1a}$, —C(O)$NR^{1b}R^{1c}$, —C($NR^{1a}$)$NR^{1b}R^{1c}$, —$OR^{1a}$, —OC(O)$R^{1a}$, —OC(O)$OR^{1a}$, —OC(O)$NR^{1b}R^{1c}$, —OC($NR^{1a}$)$NR^{1b}R^{1c}$, —OS(O)$R^{1a}$, —OS(O)$_2R^{1a}$, —OS(O)$NR^{1b}R^{1c}$, —OS(O)$_2NR^{1b}R^{1c}$, —$NR^{1b}R^{1c}$, —$NR^{1a}$C(O)$R^{1d}$, —$NR^{1a}$C(O)$OR^{1d}$, —$NR^{1a}$C(O)$NR^{1b}R^{1c}$, —$NR^{1a}$C($R^{1d}$)$NR^{1b}R^{1c}$, —$NR^{1a}$S(O)$R^{1d}$, —$NR^{1a}$S(O)$_2R^{1d}$, —$NR^{1a}$S(O)$NR^{1b}R^{1c}$, —$NR^{1a}$S(O)$_2NR^{1b}R^{1c}$, —$SR^{1a}$, —S(O)$R^{1a}$, —S(O)$_2R^{1a}$, —S(O)$NR^{1b}R^{1c}$, or —S(O)$_2NR^{1b}R^{1c}$;

each $R^7$ is independently (a) deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)$OR^{1a}$, —C(O)$NR^{1b}R^{1c}$, —C($NR^{1a}$)$NR^{1b}R^{1c}$, —$OR^{1a}$, —OC(O)$R^{1a}$, —OC(O)$OR^{1a}$, —OC(O)$NR^{1b}R^{1c}$, —OC($NR^{1a}$)$NR^{1b}R^{1c}$, —OS(O)$R^{1a}$, —OS(O)$_2R^{1a}$, —OS(O)$NR^{1b}R^{1c}$, —OS(O)$_2NR^{1b}R^{1c}$, —$NR^{1b}R^{1c}$, —$NR^{1a}$C(O)$R^{1d}$, —$NR^{1a}$C(O)$OR^{1d}$, —$NR^{1a}$C(O)$NR^{1b}R^{1c}$, —$NR^{1a}$C($NR^{1d}$)$NR^{1b}R^{1c}$, —$NR^{1a}$S(O)$R^{1d}$, —$NR^{1a}$S(O)$_2R^{1d}$, —$R^{1a}$S(O)$NR^{1b}R^{1c}$, —$NR^{1a}$S(O)$_2NR^{1b}R^{1c}$, —$SR^{1a}$, —S(O)$R^{1a}$, —S(O)$_2R^{1a}$, —S(O)$NR^{1b}R^{1c}$, or —S(O)$_2NR^{1b}R^{1c}$; or two adjacent $R^7$ together with the phenyl group to which they are attached form naphthyl or bicyclic heteroaryl;

$R^C$ is (a) hydrogen, deuterium, cyano, halo, or nitro; or (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —$OR^{1a}$, —$NR^{1b}R^{1c}$, or —$NR^{1a}$C(O)$R^{1d}$;

L is $C_{1-6}$ alkylene or $C_{2-6}$ alkenylene;

n is an integer of 0, 1, 2, 3, or 4; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkylene, alkenyl, alkenylene, alkynyl, cycloalkyl, aryl, aralkyl, heteroaryl, and heterocyclyl is optionally substituted with one or more, in one embodiment, one, two, three, or four, substituents Q, wherein each Q is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)$OR^a$, —C(O)$NR^bR^c$, —C(O)$SR^a$, —C($R^a$)$NR^bR^c$, —C(S)$R^a$, —C(S)$OR^a$, —C(S)$NR^bR^c$, —$OR^a$, —OC(O)$R^a$, —OC(O)$OR^a$, —OC(O)$NR^bR^c$, —OC(O)$SR^a$, —OC($NR^a$)$NR^bR^c$, —OC(S)$R^a$, —OC(S)$OR^a$, —OC(S)$NR^b$ $R^c$, —OS(O)$R^a$, —OS(O)$_2R^a$, —OS(O)$NR^bR^c$, —OS(O)$_2NR^bR^c$, —$NR^bR^c$, —$NR^a$C(O)$R^d$, —$NR^a$C $(O)OR^d$, $—NR^aC(O)NR^bR^c$, $—NR^aC(O)SR^d$, $—NR^aC(NR^d)NR^bR^c$, $—NR^aC(S)R^d$, $—NR^aC(S)OR^d$, $—NR^aC(S)NR^bR^c$, $—NR^{1a}S(O)R^d$, $—NR^aS(O)_2R^d$, $—NR^{1a}S(O)NR^bR^c$, $—NR^aS(O)_2NR^bR^c$, $—SR^a$, $—S(O)R^a$, $—S(O)_2R^a$, $—S(O)NR^bR^c$, and $—S(O)_2$ $NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl optionally substituted with one or more, in one embodiment, one, two, three, or four, substituents $Q^a$;

wherein each $Q^a$ is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) $—C(O)R^e$, $—C(O)OR^e$, $—C(O)NR^fR^g$, $—C(O)SR^e$, $—C(NR^e)NR^fR^g$, $—C(S)R^e$, $—C(S)OR^e$, $—C(S)NR^f$ $R^g$, $—OR^e$, $—OC(O)R^e$, $—OC(O)OR^e$, $—OC(O)NR^f$ $R^g$, $—OC(O)SR^e$, $—OC(NR^e)NR^fR^g$, $—OC(S)R^e$, $—OC(S)OR^e$, $—OC(S)NR^fR^g$, $—OS(O)R^e$, $—OS(O)_2$ $R^e$, $—OS(O)NR^fR^g$, $—OS(O)_2NR^fR^g$, $—NR^fR^g$, $—NR^eC(O)R^h$, $—R^eC(O)OR^f$, $—NR^eC(O)NR^fR^g$, $—NR^eC(O)SR^f$, $—NR^eC(NR^h)N^fR^g$, $—NR^eC(S)R^h$, $—NR^eC(S)OR^f$, $—NR^eC(S)NR^fR^g$, $—NR^eS(O)R^h$, $—NR^eS(O)_2R^h$, $—NR^eS(O)NR^fR^g$, $—NR^eS(O)_2NR^f$ $R^g$, $—SR^e$, $—S(O)R^e$, $—S(O)_2R^e$, $—S(O)NR^fR^g$, and $—S(O)_2NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In one embodiment, the compound of Formula (I-A) has the structure of Formula (II-A):

(II-A)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, $R^7$, $R^C$, L, and n are each as defined herein.

In another embodiment, the compound of Formula (I-A) has the structure of Formula (III-A):

(III-A)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, R, $R^c$, L, and n are each as defined herein.

In yet another embodiment, the compound of Formula (I-A) has the structure of Formula (VI-A):

(IV-A)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, $R^7$, $R^C$, L, and n are each as defined herein.

In one embodiment, in any one of Formulae (I-A) to (IV-A), $R^1$ is hydrogen or $C_{1-6}$ alkyl;

$R^2$ is $—CN$, $—C(O)OR^{2a}$, $—C(O)NR^{2b}R^{2c}$, $—OR^{2c}$, $—NR^{2b}R^{2c}$, or heteroaryl, wherein each $R^{2a}$, $R^{2b}$, and $R^{2c}$ is independently hydrogen or $C_{1-6}$ alkyl;

$R^3$, $R^4$, $R^5$, and $R^6$ are each independently hydrogen, deuterium, halo, $C_{1-6}$ alkyl, or $—O—C_{1-6}$ alkyl;

$R^7$ and n are (i) or (ii):

(i) n is an integer of 0, 1, 2, 3, or 4; and each $R^7$ is independently deuterium, halo, $C_{1-6}$ alkyl, or $—O—C_{1-6}$ alkyl; or (ii) n is an integer of 2, 3, or 4; and two adjacent $R^7$ together with the phenyl group to which they are attached form naphthyl;

$R^C$ is hydrogen, cyano, $C_{1-6}$ alkyl, $C_{2-6}$ alkenyl, $C_{3-10}$ cycloalkyl, heteroaryl, heterocyclyl, $—O—C_{1-6}$ alkyl, $—NHC(O)—C_{1-6}$ alkyl, or $—N(C_{1-6}$ alkyl$)_2$; and L is $C_{1-6}$ alkylene or $C_{2-6}$ alkenylene;

wherein each alkyl, alkylene, alkenyl, alkenylene, cycloalkyl, heteroaryl, and heterocyclyl is optionally substituted with one, two, or three substituents Q.

In another embodiment, in any one of Formulae (I-A) to (IV-A), $R^1$ is hydrogen or $C_{1-6}$ alkyl;

$R^2$ is —CN, —C(O)O$R^{2a}$, —C(O)NR$^{2b}$R$^{2c}$, —OR$^{2a}$, —NR$^{2b}$R$^{2c}$, or 5-membered heteroaryl, wherein each $R^{2a}$, $R^{2b}$, and $R^{2c}$ is independently hydrogen or $C_{1-6}$ alkyl;

$R^3$ and $R^5$ are each independently hydrogen or deuterium;

$R^4$ and $R^6$ are each independently hydrogen, deuterium, halo, $C_{1-6}$ alkyl, or —O—$C_{1-6}$ alkyl;

$R^7$ and n are (i) or (ii):

(iii) n is an integer of 0, 1, or 2; and
  each $R^C$ is independently deuterium, halo, $C_{1-6}$ alkyl, or —O—$C_{1-6}$ alkyl; or (iv) n is an integer of 2; and
  two adjacent $R^7$ together with the phenyl group to which they are attached form naphth-1-yl or naphth-2-yl;

$R^C$ is hydrogen, cyano, $C_{1-6}$ alkyl, $C_{2-6}$ alkenyl, $C_{3-10}$ cycloalkyl, heteroaryl, heterocyclyl, —O—$C_{1-6}$ alkyl, —NHC(O)—$C_{1-6}$ alkyl, or —N(C$_{1-6}$ alkyl)$_2$; and L is $C_{1-6}$ alkylene or $C_{2-6}$ alkenylene;

wherein each alkyl, alkylene, alkenyl, alkenylene, cycloalkyl, heteroaryl, and heterocyclyl is optionally substituted with one, two, or three substituents Q.

In yet another embodiment, in any one of Formulae (I-A) to (IV-A), $R^1$ is hydrogen, methyl, ethyl, or butyl;

$R^2$ is —CN, —C(O)OH, —C(O)NH$_2$, —C(O)NHCH$_3$, —OH, —NH$_2$, or tetrazolyl;

$R^3$ and $R^5$ are each independently hydrogen or deuterium;

$R^4$ is hydrogen, fluoro, chloro, methyl, ethyl, isopropyl, methoxy, or ethoxy;

$R^6$ is hydrogen, deuterium, or fluoro;

$R^7$ and n are (i) or (ii):

(i) n is an integer of 0, 1, or 2; and
  each $R^7$ is independently fluoro, chloro, or methoxy; or (ii) n is an integer of 2; and
  two adjacent $R^7$ together with the phenyl group to which they are attached form naphth-1-yl or naphth-2-yl;

$R^C$ is hydrogen, cyano, methyl, trifluoromethyl, ethyl, propyl, fluoropropyl, difluoropropyl, hexafluoropropyl, butyl, propenyl, cyclopropyl, cyclopentyl, pyridyl, pyrrolidinyl, hydroxyl, methoxy, ethoxy, acetamido, or dimethylamino; and L is methylene, ethylene, or ethenylene.

In still another embodiment, in any one of Formulae (I-A) to (IV-A), $R^1$ is hydrogen, methyl, ethyl, or (2-methyl)propyl;

$R^2$ is —CN, —C(O)OH, —C(O)NH$_2$, —C(O)NHCH$_3$, —OH, —NH$_2$, or tetrazol-5-yl;

$R^3$ and $R^5$ are each independently hydrogen or deuterium;

$R^4$ is hydrogen, fluoro, chloro, methyl, ethyl, isopropyl, methoxy, or ethoxy;

$R^6$ is hydrogen, deuterium, or fluoro;

$R^7$ and n are (i) or (ii):

(i) n is an integer of 0, 1, or 2; and
  each $R^7$ is fluoro; or (ii) n is an integer of 2; and
  two adjacent $R^7$ together with the phenyl group to which they are attached form naphth-1-yl or naphth-2-yl;

$R^C$ is hydrogen, cyano, methyl, trifluoromethyl, ethyl, 2-fluoropropan-2-yl, 1,3-difluoropropane-2-yl, di(trifluoromethyl)methyl, isopropyl, t-butyl, prop-1-en-2-yl, cyclopropyl, cyclopentyl, pyrid-2-yl, pyrrolidin-1-yl, hydroxyl, methoxy, ethoxy, acetamido, or dimethylamino; and L is methylene, ethan-1,2-diyl, or ethen-1,2-diyl.

In one embodiment, the compound of Formula (I-A) is:

(Z)-2-(2-methyl-1-(4-isopropylbenzylidene)-1H-inden-3-yl)acetic acid B1;

(Z)-2-(5-fluoro-2-methyl-1-(benzylidene)-1H-inden-3-yl)acetic acid B2;

(Z)-2-(5-fluoro-2-methyl-1-(3-cyanobenzylidene)-1H-inden-3-yl)acetic acid B3;

(Z)-2-(5-fluoro-2-methyl-1-(4-cyanobenzylidene)-1H-inden-3-yl)acetic acid B4;

(Z)-2-(5-fluoro-2-methyl-1-(4-methylbenzylidene)-1H-inden-3-yl)acetic acid B5;

(Z)-2-(5-fluoro-2-methyl-1-(3-trifluoromethylbenzylidene)-1H-inden-3-yl)acetic acid B6;

(Z)-2-(5-fluoro-2-methyl-1-(4-trifluoromethylbenzylidene)-1H-inden-3-yl)acetic acid B7;

(Z)-2-(5-fluoro-2-methyl-1-(4-ethylbenzylidene)-1H-inden-3-yl)acetic acid B8;

(Z)-2-(5-fluoro-2-methyl-1-(4-isopropylbenzylidene)-1H-inden-3-yl)acetic acid B9;

(Z)-2-(5-fluoro-2-methyl-1-(4-t-butylbenzylidene)-1H-inden-3-yl)acetic acid B10;

(Z)-2-(5-fluoro-2-ethyl-1-(4-isopropylbenzylidene)-1H-inden-3-yl)acetic acid B11;

(Z)-2-(5-fluoro-2-(2-methylpropyl)-1-(4-isopropylbenzylidene)-1H-inden-3-yl)acetic acid B12;

(Z)-2-(5-fluoro-2-methyl-1-(3-methoxybenzylidene)-1H-inden-3-yl)acetic acid B13;

(Z)-2-(5-fluoro-2-methyl-1-(4-methoxybenzylidene)-1H-inden-3-yl)acetic acid B14;

(Z)-2-(5-fluoro-2-methyl-1-(4-ethoxybenzylidene)-1H-inden-3-yl)acetic acid B15;

(Z)-2-(5-fluoro-2-methyl-1-(4-(pyrrolidin-1-yl)benzylidene)-1H-inden-3-yl)acetic acid B16;

(Z)-2-(5-fluoro-2-methyl-1-(4-(pyrid-2-yl)benzylidene)-1H-inden-3-yl)acetic acid B17;

(Z)-2-(5-chloro-2-methyl-1-(4-t-butylbenzylidene)-1H-inden-3-yl)acetic acid B18;

(Z)-2-(5-methyl-2-methyl-1-(4-isopropylbenzylidene)-1H-inden-3-yl)acetic acid B19;

(Z)-2-(5-ethyl-2-methyl-1-(4-isopropylbenzylidene)-1H-inden-3-yl)acetic acid B20;

(Z)-2-(5-isopropyl-2-methyl-1-(4-isopropylbenzylidene)-1H-inden-3-yl)acetic acid B21;

(Z)-2-(5-methoxy-2-methyl-1-(4-isopropylbenzylidene)-1H-inden-3-yl)acetic acid B22;

(Z)-2-(5-ethoxy-2-methyl-1-(4-isopropylbenzylidene)-1H-inden-3-yl)acetic acid B23;

(Z)-2-(5-fluoro-1-(4-isopropylbenzylidene)-2-methyl-1H-inden-3-yl)acetamide B24;

(Z)-2-(5-fluoro-1-(4-isopropylbenzylidene)-2-methyl-1H-inden-3-yl)-N-methylacetamide B25;

(Z)-2-(5-fluoro-1-(4-isopropylbenzylidene)-2-methyl-1H-inden-3-yl)-N,N-dimethylacetamide B26;

(Z)-2-(1-(4-acetamidobenzylidene)-5-fluoro-2-methyl-1H-inden-3-yl)acetic acid B27;

(Z)-3-(5-fluoro-1-(4-isopropylbenzylidene)-2-methyl-1H-inden-3-yl)propanoic acid B28;

(Z)-5-(2-(5-fluoro-1-(4-isopropylbenzylidene)-2-methyl-1H-inden-3-yl)ethyl)-1H-tetrazole B29;

(Z)-5-(2-(1-(4-isopropylbenzylidene)-2-methyl-1H-inden-3-yl)ethyl)-1H-tetrazole B30;

(Z)-2-(4-fluoro-2-methyl-1-(benzylidene)-1H-inden-3-yl)acetic acid B31;

(Z)-2-(5-fluoro-1-(4-dimethylaminobenzylidene)-2-methyl-1H-inden-3-yl)propanoic acid B32;

2-[(1Z)-5-fluoro-1-[(2-hydroxynaphthalen-1-yl)methylidene]-2-methyl-1H-inden-3-yl]acetic acid B33;

2-[(1Z)-5-fluoro-2-methyl-1-[(naphthalen-2-yl)methylidene]-1H-inden-3-yl]acetic acid B34;

2-[(1Z)-5-fluoro-2-methyl-1-[(4-methylnaphthalen-1-yl)methylidene]-1H-inden-3-yl]acetic acid B35;

2-[(1Z)-5-fluoro-1-[(2-methoxynaphthalen-1-yl)methylidene]-2-methyl-1H-inden-3-yl]acetic acid B36;

2-[(1Z)-1-[(4-cyclopropylphenyl)methylidene]-5-fluoro-2-methyl-1H-inden-3-yl]acetic acid B37;

2-[(1Z)-1-[(4-cyclopentylphenyl)methylidene]-5-fluoro-2-methyl-1H-inden-3-yl]acetic acid B38;

2-[(1Z)-5-fluoro-2-methyl-1-{[4-(prop-1-en-2-yl)phenyl]methylidene}-1H-inden-3-yl]acetic acid B39;

2-[(1Z)-5-fluoro-1-{[4-(2-fluoropropan-2-yl)phenyl]methylidene}-2-methyl-1H-inden-3-yl]acetic acid B40;

2-[(1Z)-1-{[4-(dimethylamino)phenyl]methylidene}-5-fluoro-2-methyl-1H-inden-3-yl]acetic acid B41;

2-[(1Z)-5-fluoro-1-{[4-(1,1,1,3,3,3-hexafluoropropan-2-yl)phenyl]methylidene}-2-methyl-1H-inden-3-yl]acetic acid B42;

2-[(1Z)-5-fluoro-2-methyl-1-{[4-(propan-2-yl)phenyl]methylidene}-1H-inden-3-yl]propanoic acid B43;

2-[(1Z)-5-fluoro-2-methyl-1-{[4-(trifluoromethyl)phenyl]methylidene}-1H-inden-3-yl]propanoic acid B44;

2-[(1Z)-7-fluoro-2-methyl-1-{[4-(propan-2-yl)phenyl]methylidene}-1H-inden-3-yl]acetic acid B45;

2-[(1Z)-7-fluoro-2-methyl-1-{[4-(trifluoromethyl)phenyl]methylidene}-1H-inden-3-yl]acetic acid B46;

2-[(1Z)-1-{[4-(1,3-difluoropropan-2-yl)phenyl]methylidene}-5-fluoro-2-methyl-1H-inden-3-yl]acetic acid B47; or 2-[(1Z)-5-fluoro-1-{[3-fluoro-4-(propan-2-yl)phenyl]methylidene}-2-methyl-1H-inden-3-yl]acetic acid B48;

or a tautomer, a mixture of two or more tautomers, or an isotopic variant thereof; or a pharmaceutically acceptable salt, solvate, hydrate, or prodrug thereof.

In another embodiment, the compound of Formula (I-A) is:

(E)-2-(5-fluoro-2-methyl-1-(4-isopropylbenzylidene)-1H-inden-3-yl)acetic acid B49;

(E)-2-(5-fluoro-1-(4-isopropylbenzylidene)-2-methyl-1H-inden-3-yl)acetamide B50; or (E)-2-(5-fluoro-1-(4-isopropylbenzylidene)-2-methyl-1H-inden-3-yl)-N-methylacetamide B51;

or a tautomer, a mixture of two or more tautomers, or an isotopic variant thereof; or a pharmaceutically acceptable salt, solvate, hydrate, or prodrug thereof.

In yet another embodiment, the compound of Formula (I-A) is:

(Z)-2-(5-fluoro-1-(4-isopropylbenzylidene)-2-methyl-1H-inden-3-yl)ethan-1-ol B52;

(Z)-2-(5-fluoro-1-(4-isopropylbenzylidene)-2-methyl-1H-inden-3-yl)ethan-1-amino B53; or (Z)-3-(5-fluoro-1-(4-isopropylbenzylidene)-2-methyl-1H-inden-3-yl)propanenitrile B54;

or a tautomer, a mixture of two or more tautomers, or an isotopic variant thereof; or a pharmaceutically acceptable salt, solvate, hydrate, or prodrug thereof.

In certain embodiments, the compound of Formula (I-A) is one of those described in U.S. Pat. No. 9,611,235, the disclosure of which is incorporated herein by reference in its entirety.

In certain embodiment, the fibrotic disease is a liver fibrotic disease. In certain embodiment, the fibrotic disease is a metabolic disease. In certain embodiment, the fibrotic disease is a liver fibrosis. In certain embodiment, the fibrotic disease is nonalcoholic fatty liver disease (NAFLD). In certain embodiment, the fibrotic disease is nonalcoholic steatohepatitis (NASH). In certain embodiment, the fibrotic disease is a pulmonary fibrotic disease. In certain embodiment, the fibrotic disease is idiopathic pulmonary fibrosis. In certain embodiment, the fibrotic disease is primary biliary cholangitis (PBC). In certain embodiment, the fibrotic disease is scleroderma.

In yet another embodiment, provided herein is a method of treating, ameliorating, or preventing one or more symptoms of a proliferative disease in a subject, comprising administering to the subject a therapeutically effective amount of a compound of Formula (I) or (I-A), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the proliferative disease is cancer. In certain embodiments, the cancer is liver cancer. In certain embodiments, the cancer is metastatic. In certain embodiments, the cancer is refractory. In certain embodiments, the cancer is relapsed. In certain embodiments, the cancer is drug-resistant. In certain embodiments, the cancer is multidrug-resistant.

In certain embodiments, the subject is a mammal. In certain embodiments, the subject is a human.

In certain embodiments, the therapeutically effective amount of a compound described herein is ranging from about 0.1 to about 100 mg/kg/day, from about 0.2 to about 50 mg/kg/day, from about 0.5 to about 25 mg/kg/day, or from about 1 to about 10 mg/kg/day. In one embodiment, the therapeutically effective amount is ranging from about 0.1 to about 100 mg/kg/day. In another embodiment, the therapeutically effective amount is ranging from about 0.2 to about 50 mg/kg/day. In yet another embodiment, the therapeutically effective amount is ranging from about 0.5 to about 25 mg/kg/day. In still another embodiment, the therapeutically effective amount is ranging from about 1 to about 10 mg/kg/day.

It is understood that the administered dose can also be expressed in units other than mg/kg/day. For example, doses for parenteral administration can be expressed as $mg/m^2/day$. One of ordinary skill in the art would readily know how to convert doses from mg/kg/day to $mg/m^2/day$ to given either the height or weight of a subject or both. For example, a dose of 1 $mg/m^2/day$ for a 65 kg human is approximately equal to 58 mg/kg/day.

Depending on the disease to be treated and the subject's condition, a compound provided herein may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A compound provided herein may be formulated in suitable dosage unit with a pharmaceutically acceptable excipient, carrier, adjuvant, or vehicle, appropriate for each route of administration.

In one embodiment, a compound provided herein is administered orally. In another embodiment, a compound provided herein is administered parenterally. In yet another embodiment, a compound provided herein is administered intravenously. In yet another embodiment, a compound provided herein is administered intramuscularly. In yet another embodiment, a compound provided herein is administered subcutaneously. In still another embodiment, a compound provided herein is administered topically.

A compound provided herein can be delivered as a single dose such as, e.g., a single bolus injection, or oral tablets or pills; or over time such as, e.g., continuous infusion over time or divided bolus doses over time. A compound provided herein can be administered repetitively if necessary, for example, until the subject experiences stable disease or regression, or until the subject experiences disease progression or unacceptable toxicity. Stable disease or lack thereof is determined by methods known in the art such as evaluation of subject's symptoms, physical examination, visualization of the cancer that has been imaged using X-ray, CAT, PET, or MRI scan and other commonly accepted evaluation modalities.

A compound provided herein can be administered once daily (QD) or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of a compound provided herein is administration for one to six days per week, administration in cycles (e.g., daily administration for two to eight consecutive weeks, then a rest period with no administration for up to one week), or administration on alternate days.

In certain embodiments, a compound provided herein is cyclically administered to a subject. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

A compound provided herein can also be combined or used in combination with other therapeutic agents useful in the treatment and/or prevention of a condition, disorder, or disease described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 50 minutes, 65 minutes, 1 hour, 2 hours, 6 hours, 6 hours, 12 hours, 26 hours, 68 hours, 72 hours, 96 hours, 1 week, 2 weeks, 5 weeks, 6 weeks, 8 weeks, or 12 weeks before), concomitantly with, or subsequent to (e.g., 5 minutes, 15 minutes, 50 minutes, 65 minutes, 1 hour, 2 hours, 6 hours, 12 hours, 26 hours, 68 hours, 72 hours, 96 hours, 1 week, 2 weeks, 5 weeks, 6 weeks, 8 weeks, or 12 weeks after) the administration of a second therapy (e.g., a prophylactic or therapeutic agent) to the subject. Triple therapy is also contemplated herein.

The route of administration of a compound provided herein is independent of the route of administration of a second therapy. In one embodiment, a compound provided herein is administered orally. In another embodiment, a compound provided herein is administered intravenously. Thus, in accordance with these embodiments, a compound provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, a compound provided herein and a second therapy are administered by the same mode of administration, orally or by IV. In another embodiment, a compound provided herein is administered by one mode of administration, e.g., by IV, whereas the second agent is administered by another mode of administration, e.g., orally.

In one embodiment, provided herein is a method of inhibiting the growth of a cell, comprising contacting the cell with an effective amount of a compound of Formula (I) or (I-A), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In certain embodiments, the cell is a cancerous cell.

A compound provided herein can also be provided as an article of manufacture using packaging materials well known to those of skill in the art. See, e.g., U.S. Pat. Nos. 5,525,907; 5,052,558; and 5,055,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

In certain embodiments, provided herein is a kit which, when used by a medical practitioner, can simplify the administration of an appropriate amount of a compound provided herein as an active ingredient to a subject. In certain embodiments, the kit provided herein includes a container and a dosage form of a compound provided herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, water for injection USP, sodium chloride injection, Ringer's injection, dextrose injection, dextrose and sodium chloride injection, and lactated Ringer's injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: g (grams); mg (milligrams); L (liters); mL (milliliters); μL (microliters); mol (moles); mM (millimolar); μM (micromolar); mmol (millimoles); eq. (equivalent); h (hour or hours); min (minutes); Et (ethyl); Me (methyl); ACN (acetonitrile); DMF (dimethylformamide); EtOH (ethanol); MeOH (methanol); EtOAc (ethyl acetate); MTBE (methyl tert-butyl ether); THF (tetrahydrofuran); AcOH (acetic acid); DBU (1,8-diazabicyclo[5.4.0]undec-7-ene); DIPEA (N,N-diisopropylethylamine); $Et_3N$ (triethylamine); PyBOP (benzotriazol-1-yl-oxytripyrrolidinophosphonium hexafluorophosphate); LCMS (liquid chromatography-mass spectrometry); and NMR (nuclear magnetic resonance).

For all of the following examples, standard work-up and purification methods known to those skilled in the art can be utilized. Unless otherwise indicated, all temperatures are expressed in ° C. (degrees Centigrade). All reactions are conducted at room temperature unless otherwise specified. Synthetic methodologies illustrated herein are intended to exemplify the applicable chemistry through the use of specific examples and are not indicative of the scope of the disclosure.

Example 1

Synthesis of Indene 4

Indene 4 was prepared as shown in Scheme 1 below, wherein $R^1$, $R^3$, $R^4$, $R^5$, $R^6$, and p are each as defined herein. Compounds 1 and 2 were commercially available or prepared, for example, according to the procedures described in U.S. Pat. No. 9,611,235, the disclosure of which is incorporated herein by reference in its entirety.

Scheme 1

-continued

4

A mixture of compound 1 (1 eq.), zinc powder (2 eq.), and a catalytic amount of iodine in THF (1 L/mol) under nitrogen was heated to 60° C. A small portion of compound 2 (3 eq.) was added first to initiate the reaction and the remaining was then added using a constant pressure drop funnel. After stirred overnight at 60° C., the reaction mixture was cooled to room temperature and the reaction was then quenched with concentrated HCl (5 eq.). The acidified mixture was stirred for additional 2 h at room temperature, and then diluted with water, extracted with EtOAc, and washed by brine. The organic layers were combined, dried over anhydrous sodium sulfate, and then concentrated in vacuo to yield compound 3.

To a mixture of compound 3 in ethanol (0.5 L/mol) was added an aqueous NaOH solution (20%). After refluxed overnight. the reaction mixture was cooled to room temperature, extracted with EtOAc, and washed by brine. The organic layers were combined, dried over anhydrous sodium sulfate, and then concentrated in vacuo to yield a crude product, which was purified by column chromatography to yield compound 4.

Example 2

Synthesis of Indene 5

Indene 5 was prepared as shown in Scheme 2 below, wherein $R^1$, $R^3$, $R^4$, $R^5$, $R^6$, $R^{2b}$, $R^{2c}$, and p are each as defined herein.

A mixture of compound 4 (1 eq.), an amine ($HNR^{2b}R^{2c}$), PyBOP (1.2 eq.), and DIPEA (2 eq.) in DMF (1 L/mol) was stirred at room temperature overnight. The reaction mixture was diluted with water, extracted with EtOAc, and washed by brine. The organic layers were combined, dried over anhydrous sodium sulfate, and then concentrated in vacuo to yield a crude product, which was purified by column chromatography to yield compound 5.

Scheme 2

-continued

5

Example 3

Synthesis of Indene 6

Indene 6 was prepared as shown in Scheme 3 below, wherein $R^1$, $R^3$, $R^4$, $R^5$, $R^6$, and p are each as defined herein.

Scheme 3

3

6

To a solution of compound 3 (1 eq.) in MeOH (1 L/mol) was added $NH_2OH$ (50% by weight in water, 10 eq.), followed by addition of MeONa (33% by weight in methanol, 10 eq.). After stirred at room temperature overnight, the reaction was quenched with HCl (1 mol/L) and the reaction mixture was extracted with EtOAc. The organic layers were combined, dried over anhydrous sodium sulfate, and concentrated in vacuo to yield a crude product, which was purified by column chromatography to yield compound 6.

Example 4

Synthesis of Indene 9

Indene 9 was prepared as shown in Scheme 4 below, wherein $R^1$, $R^3$, $R^4$, $R^5$, and $R^6$ are each as defined herein.

Scheme 4

1

8

9

To a solution of diethyl cyanomethylphosphonate 7 (2 eq.) in ACN (1.5 L/mol) was added DBU (3 eq.) at 0° C., followed by addition of compound 1 (1 eq.). After stirred at room temperature overnight, the reaction was quenched with a saturated ammonium chloride solution and the reaction mixture was extracted with EtOAc and washed with brine. The organic layers were combined, dried over anhydrous sodium sulfate, and concentrated in vacuo to yield a crude product, which was purified by column chromatography to yield compound 8.

To a solution of compound 8 (1 eq.) in DMF (1 L/mol) was added $NaN_3$ (5 eq.) and $Et_3N$ HCl (5 eq.). After stirred at 110° C. for 48 h, the reaction mixture was acidified with HCl to pH<2 and then extracted with EtOAc. The organic layers were combined, dried over anhydrous sodium sulfate, and concentrated in vacuo to yield a crude product, which was purified by column chromatography to yield compound 9.

Example 5

Synthesis of Indene 12

Indene 12 was prepared as shown in Scheme 5 below, wherein $R^1$, $R^3$, $R^4$, $R^5$, and $R^6$ are each as defined herein.

To a solution of compound 1 (1 eq.), acrylonitrile (2 eq.), and isopropyl alcohol (0.1 eq.) in THF (2 L/mol) was added samarium (II) iodide (3 eq.) in THF under nitrogen. After stirred at 0° C. overnight, the reaction was quenched with a saturated sodium bicarbonate solution and then diluted MTBE (2 L/mol). The mixture was filtered and the filtrate was washed with a sodium thiosulfate solution, dried over anhydrous sodium sulfate, and concentrated in vacuo to yield a crude product, which was purified by column chromatography to yield compound 10.

Scheme 5

A mixture of compound 10 in AcOH/$H_2SO_4$ was stirred at room temperature overnight. The reaction was then quenched with water, and the reaction mixture was extracted with EtOAc and washed by brine. The organic layers were combined, dried over anhydrous sodium sulfate, and concentrated in vacuo to yield a crude product, which was purified by column chromatography to yield compound 11.

To a solution of compound 11 (1 eq.) in DMF (1 L/mol) was added $NaN_3$ (5 eq.) and $Et_3N$ HCl (5 eq.). After stirred at 110° C. for 48 h, the reaction mixture was acidified with HCl to pH<2 and extracted with EtOAc. The organic layers were combined, dried over anhydrous sodium sulfate, and concentrated in vacuo to yield a crude product, which was purified by column chromatography to yield compound 12.

Example 6

Synthesis of Compounds A1 to A85, C1 to $C_3$, D1 to D38, and E1 to E6

Compounds A1 to A55, A59, A60, A68, A69, A85, C1 to $C_3$, D1 to D16, D18 to D27, and E1 to E6 were each prepared as shown in Scheme 6 below, wherein $R^1$, $R^2$, $R^3$, $R^4$, $R^5$, $R^6$, W, $R^B$, L, X, and n are each as defined herein. Compounds A56 to A58, A61 to A67, A70 to A84, D17, and D28 to D38 are prepared similarly. Compound 14 was commercially available or prepared according to a literature procedure.

Scheme 6

To a solution of indene 13 (1 eq.) and aldehyde 14 (2.5 eq.) in MeOH (12 L/mol) was added a base (e.g., MeONa) (3 eq.). After stirred at 80° C. overnight, the reaction was quenched with 1N HCl to a pH below 7, and the reaction mixture was extracted with EtOAc and washed by brine. The organic layers were combined, dried over anhydrous sodium sulfate, and then concentrated in vacuo to yield a crude product, which was purified by column chromatography to yield a compound of Formula (IX).

2-[(1Z)-5-Fluoro-2-methyl-1-[(4-phenoxyphenyl)methylidene]-1H-inden-3-yl]acetic acid A1. $^1$H NMR (600 MHz, DMSO-$d_6$) δ12.43 (br. s., 1H), 7.56 (d, J=8.44 Hz, 2H), 7.41-7.47 (m, 2H), 7.36 (dd, J=5.23, 8.34 Hz, 1H), 7.31 (s, 1H), 7.20 (t, J=7.34 Hz, 1H), 7.12 (d, J=7.70 Hz, 2H), 7.08 (d, J=8.62 Hz, 2H), 7.01 (dd, J=2.38, 9.35 Hz, 1H), 6.75 (dt, J=2.38, 8.89 Hz, 1H), 3.57 (s, 2H), 2.15 (s, 3H); $^{13}$C NMR (151 MHz, DMSO-$d_6$) δ171.7, 163.1, 161.5, 157.1, 156.0, 146.9 (d, J=8.80 Hz), 139.0, 138.0, 131.7 (d, J=2.20 Hz), 131.2, 130.8, 130.4, 130.2 (2 C), 129.6 (d, J=2.20 Hz), 124.0, 123.0 (d, J=8.80 Hz), 119.3 (2 C), 118.1 (2 C), 110.3 (d, J=22.01 Hz), 105.8 (d, J=23.11 Hz), 31.1, 10.3.

2-[(1Z)-5-Fluoro-1-{[4-(4-methoxyphenoxy)phenyl] methylidene}-2-methyl-1H-inden-3-yl]acetic acid A2. $^1$H NMR (600 MHz, CDCl$_3$) δ7.45 (d, J=8.62 Hz, 2H), 7.40 (dd, J=5.04, 8.34 Hz, 1H), 7.15 (s, 1H), 7.05 (d, J=8.80 Hz, 2H), 6.96-6.99 (m, J=8.62 Hz, 2H), 6.93 (d, J=8.99 Hz, 2H), 6.88 (dd, J=2.20, 8.99 Hz, 1H), 6.59 (dt, J=2.29, 8.76 Hz, 1H), 3.82 (s, 3H), 3.58 (s, 2H), 2.19 (s, 3H); ¹³C NMR (151
MHz, CDCl₃) δ176.0 163.1 (d, J=245.39 Hz) 158.9 156.3
149.4 146.2 (d, J=8.80 Hz) 139.6, 139.0, 131.0, 130.4,
130.3, 129.8, 129.8, 123.7, (d, J=8.80 Hz), 121.4, 117.1,
115.0, 110.7 (d, J=23.11 Hz), 105.7 (d, J=23.11 Hz), 55.7,
31.4, 10.6.

2-[(1Z)-1-({2-Chloro-4-[3-(trifluoromethyl)phenoxy]
phenyl}methylidene)-5-fluoro-2-methyl-1H-inden-3-yl]
acetic acid A3. ¹H NMR (600 MHz, CDCl₃) δ7.58 (d,
J=8.44 Hz, 1H), 7.52 (t, J=7.98 Hz, 1H), 7.45 (d, J=7.89 Hz,
1H), 7.34 (s, 1H), 7.27 (d, J=8.25 Hz, 1H), 7.12-7.16 (m,
2H), 7.11 (s, 1H), 6.96 (dd, J=2.38, 8.44 Hz, 1H), 6.89 (dd,
J=2.20, 8.80 Hz, 1H), 6.59 (dt, J=2.20, 8.71 Hz, 1H), 3.59
(s, 2H), 2.23 (s, 3H); ¹³C NMR (151 MHz, CDCl₃) δ176.3,
163.3 (d, J=246.49 Hz), 157.4, 156.5, 146.5 (d, J=8.80 Hz),
141.2, 138.8, 135.3, 132.7, 132.7 (q, J=33.00 Hz), 130.8 (d,
J=2.20 Hz), 130.7, 130.4, 129.6 (d, J=2.20 Hz), 126.5, 123.7
(d, J=8.80 Hz), 122.6, 121.0 (q, J=4.40 Hz), 123.6 (q,
J=272.90 Hz), 119.8, 117.0, 116.4 (q, J=3.30 Hz), 110.85 (d,
J=22.01 Hz), 106.1, 31.4, 10.6.

2-[(1Z)-5-Fluoro-2-methyl-1-{[4-(4-methylphenoxy)
phenyl]methylidene}-1H-inden-3-yl]acetic acid A4. ¹H
NMR (600 MHz, CDCl₃) δ7.46 (d, J=8.25 Hz, 2H), 7.39
(dd, J=5.23, 8.34 Hz, 1H), 7.19 (d, J=8.07 Hz, 2H), 7.16 (s,
1H), 6.98-7.03 (m, 4H), 6.88 (dd, J=2.38, 8.99 Hz, 1H), 6.59
(dt, J=2.38, 8.80 Hz, 1H), 3.58 (s, 2H), 2.36 (s, 3H), 2.20 (s,
3H); ¹³C NMR (151 MHz, CDCl₃) δ175.9 163.1 (d,
J=243.18 Hz) 158.3 154.0 146.2 (d, J=8.80 Hz) 139.7 139.0
133.7 131.0 130.6 130.5 130.4 129.8 (d, J=2.20 Hz) 129.8
(d, J=2.20 Hz) 123.7 (d, J=8.80 Hz) 119.8 117.8 110.6 (d,
J=22.01 Hz) 105.7 (d, J=23.11 Hz) 31.4 20.8 10.6.

2-[(1Z)-5-Fluoro-2-methyl-1-({4-[4-(propan-2-yl)phe-
noxy]phenyl}methylidene)-1H-inden-3-yl]acetic acid A5.
¹H NMR (600 MHz, CDCl₃) δ7.46 (d, J=8.25 Hz, 2H), 7.39
(dd, J=5.14, 8.25 Hz, 1H), 7.21-7.26 (m, 2H), 7.16 (s, 1H),
7.00-7.05 (m, 4H), 6.88 (dd, J=2.38, 8.80 Hz, 1H), 6.59 (dt,
J=2.38, 8.80 Hz, 1H), 3.58 (s, 2H), 2.92 (septet, J=6.91 Hz,
1H), 2.19 (s, 3H), 1.27 (d, J=6.97 Hz, 6H); ¹³C NMR (151
MHz, CDCl₃) δ 176.5, 163.1 (d, J=246.49 Hz), 158.2, 154.2,
146.2 (d, J=8.80 Hz), 144.7, 139.7, 139.0, 131.0, 130.7,
130.4, 129.8 (dd, J=6.05, 2.75 Hz), 127.8, 123.7 (d, J=8.80
Hz), 119.6, 117.9, 110.7 (d, J=23.11 Hz), 105.8 (d, J=22.01
Hz), 33.6, 31.4, 24.2, 10.6.

2-[(1Z)-1-{[4-(4-Bromophenoxy)phenyl]methylidene}-
5-fluoro-2-methyl-1H-inden-3-yl]acetic acid A6. ¹H NMR
(600 MHz, CDCl₃) δ7.44-7.67 (m, 4H), 7.36 (dd, J=4.86,
7.61 Hz, 1H), 7.11-7.21 (m, 1H), 7.05 (d, J=8.25 Hz, 2H),
6.99 (d, J=8.44 Hz, 2H), 6.90 (d, J=6.97 Hz, 1H), 6.61 (t,
J=7.89 Hz, 1H), 3.60 (br. s., 2H), 2.21 (br. s., 3H); ¹³C NMR
(151 MHz, CDCl₃) δ176.0, 163.2 (d, J=245.39 Hz), 157.1,
155.9, 146.3 (d, J=8.81 Hz), 140.0, 138.9, 132.9, 131.6,
131.2, 130.1, 129.9, 129.7 (d, J=2.20 Hz), 123.7 (d, J=8.80
Hz), 121.1, 118.5, 116.4, 110.7 (d, J=22.01 Hz), 105.8 (d,
J=24.21 Hz), 31.4, 10.6.

-continued

A6

A7

2-[(1Z)-5-Fluoro-2-methyl-1-{[4-(3-methylphenoxy)phenyl]methylidene}-1H-inden-3-yl]acetic acid A7. $^1$H NMR (600 MHz, CDCl$_3$) δ7.47 (d, J=8.44 Hz, 2H), 7.38 (dd, J=5.14, 8.25 Hz, 1H), 7.24-7.27 (m, 1H), 7.17 (s, 1H), 7.03 (d, J=8.62 Hz, 2H), 6.97 (d, J=7.70 Hz, 1H), 6.91 (s, 1H), 6.86-6.90 (m, 2H), 6.59 (dt, J=2.29, 8.76 Hz, 1H), 3.58 (s, 2H), 2.36 (s, 3H), 2.20 (s, 3H); $^{13}$C NMR (151 MHz, CDCl$_3$) δ176.4, 163.1 (d, J=245.38 Hz), 157.9, 156.5, 146.3 (d, J=8.80 Hz), 140.2, 139.8, 139.0, 131.1, 130.9, 130.3 129.9 (d, J=2.20 Hz), 129.8 (d, J=2.20 Hz), 129.7, 124.7, 123.7 (d, J=8.80 Hz) 120.3, 118.3, 116.6, 110.7 (d, J=22.01 Hz), 105.8, (d, J=23.11 Hz), 31.4, 21.5, 10.6.

2-[(1Z)-1-{[4-(3-Cyanophenoxy)phenyl]methylidene}-5-fluoro-2-methyl-1H-inden-3-yl]acetic acid A8. $^1$H NMR (600 MHz, CDCl$_3$) δ7.53 (d, J=8.80 Hz, 2H), 7.46-7.50 (m, 1H), 7.42 (d, J=7.70 Hz, 1H), 7.30-7.34 (m, 3H), 7.17 (s, 1H), 7.08 (d, J=8.44 Hz, 2H), 6.89 (dd, J=2.20, 8.80 Hz, 1H), 6.61 (dt, J=2.29, 8.76 Hz, 1H), 3.60 (s, 2H), 2.22 (s, 3H).

(Z)-2-(5-Fluoro-2-methyl-1-(4-(3-(trifluoromethyl)phenoxy)benzylidene)-1H-inden-3-yl)acetic acid A9. $^1$H NMR (600 MHz, CDCl$_3$) δ7.46-7.54 (m, 3H), 7.40 (d, J=7.70 Hz, 1H), 7.30-7.35 (m, 2H), 7.23-7.27 (m, 1H), 7.17 (s, 1H), 7.07 (d, J=8.62 Hz, 2H), 6.88 (dd, J=2.29, 8.90 Hz, 1H), 6.59 (dt, J=2.38, 8.80 Hz, 1H), 3.59 (s, 2H), 2.20 (s, 3H); $^{13}$C NMR (151 MHz, CDCl$_3$) δ176.5, 163.2 (d, J=244.29 Hz), 157.3, 156.5, 146.3 (d, J=8.80 Hz), 140.3 138.9 132.2 132.4 (t, J=33.00 Hz), 131.3, 130.5, 130.2 (d, J=2.20 Hz), 129.8, 129.7 (d, J=3.30 Hz), 123.7 (d, J=8.80 Hz), 122.2, 123.7 (t, J=270.70 Hz) 120.3 (t, J=4.40 Hz), 119.0, 115.9, (t, J=3.30 Hz), 110.8 (d, J=23.11 Hz), 105.9 (d, J=24.21 Hz), 31.4, 10.6.

-continued

A8

A9

2-[(1Z)-1-{[4-(4-Ethylphenoxy)phenyl]methylidene}-5-fluoro-2-methyl-1H-inden-3-yl]acetic acid A10. $^1$H NMR (600 MHz, CDCl$_3$) δ7.45 (d, J=8.62 Hz, 2H), 7.39 (dd, J=5.14, 8.44 Hz, 1H), 7.21 (d, J=8.25 Hz, 2H), 7.16 (s, 1H), 7.01 (dd, J=3.03, 8.53 Hz, 4H), 6.87 (dd, J=2.20, 8.80 Hz, 1H), 6.59 (dt, J=2.29, 8.76 Hz, 1H), 3.57 (s, 2H), 2.66 (d, J=7.70 Hz, 2H), 2.19 (s, 3H), 1.26 (t, J=7.61 Hz, 3H); $^{13}$C NMR (151 MHz, CDCl$_3$) δ176.7, 163.1 (d, J=246.49 Hz), 158.3, 154.2, 146.2 (d, J=8.80 Hz), 140.1, 139.7, 139.0, 131.1, 130.7, 130.4, 129.8 (d, J=2.20 Hz), 129.8 (d, J=2.20 Hz), 129.3, 123.7 (d, J=8.80 Hz), 119.7, 117.9, 110.7 (d, J=22.01 Hz), 105.8 (d, J=23.11 Hz), 31.5, 28.3, 15.8, 10.6.

2-[(1Z)-5-Fluoro-1-{[4-(4-fluorophenoxy)phenyl]methylidene}-2-methyl-1H-inden-3-yl]acetic acid A11. $^1$H NMR (600 MHz, CDCl$_3$) δ7.46 (d, J=8.62 Hz, 2H), 7.36 (dd, J=5.04, 8.34 Hz, 1H), 7.15 (s, 1H), 7.04-7.10 (m, 4H), 6.99 (d, J=8.62 Hz, 2H), 6.88 (dd, J=2.11, 8.89 Hz, 1H), 6.59 (dt, J=2.20, 8.71 Hz, 1H), 3.57 (s, 2H), 2.19 (s, 3H); $^{13}$C NMR (151 MHz, CDCl$_3$) δ176.7, 163.2 (d, J=246.49 Hz), 159.2 (d, J=242.09 Hz), 158.1, 152.2 (d, J=3.30 Hz), 146.3 (d, J=8.80 Hz), 139.9, 139.0, 131.1, 131.0, 130.1, 130.0 (d, J=2.20 Hz), 129.8 (d, J=3.30 Hz), 123.7 (d, J=8.80 Hz), 121.2 (d, J=8.80 Hz), 117.7, 116.6 (d, J=23.11 Hz), 110.7 (d, J=22.01 Hz), 105.8 (d, J=23.11 Hz), 31.5, 10.6.

2-[(1Z)-1-{[2-Chloro-4-(4-methoxyphenoxy)phenyl]methylidene}-5-fluoro-2-methyl-1H-inden-3-yl]acetic acid A12. $^1$H NMR (600 MHz, CDCl$_3$) δ7.52 (dd, J=4.95, 8.25 Hz, 1H), 7.44 (s, 1H), 7.26 (t, J=4.22 Hz, 2H), 7.01-7.04 (m, 2H), 6.99 (d, J=2.38 Hz, 1H), 6.91-6.95 (m, 3H), 6.83-6.87 (m, 2H), 3.83 (s, 3H), 3.56 (s, 2H), 1.83 (s, 3H); $^{13}$C NMR (151 MHz, CDCl$_3$) δ175.4, 163.4 (d, J=243.19 Hz), 159.6, 156.6, 148.8, 143.6 (d, J=8.80 Hz), 140.3, 136.1, 134.8, 134.6 (d, J=3.30 Hz), 133.1, 132.7 (d, J=3.30 Hz), 128.7, 125.9, 121.5, 119.8 (d, J=9.90 Hz), 117.7, 115.2, 115.1, 111.3 (d, J=23.11 Hz), 105.8 (d, J=24.21 Hz), 55.7, 31.3, 14.0.

A10

A11

A12

2-[(1Z)-5-Fluoro-1-({2-methoxy-4-[4-(propan-2-yl)phe-noxy]phenyl}-methylidene)-2-methyl-1H-inden-3-yl]acetic acid A13. ¹H NMR (600 MHz, CDCl₃) δ7.42 (dd, J=5.14, 8.25 Hz, 1H), 7.17-7.22 (m, 3H), 7.15 (s, 1H), 7.03 (d, J=8.25 Hz, 1H), 6.97 (d, J=8.44 Hz, 2H), 6.93 (d, J=8.07 Hz, 1H), 6.89 (dd, J=2.02, 8.80 Hz, 1H), 6.60 (dt, J=2.20, 8.80 Hz, 1H), 3.84 (s, 3H), 3.59 (s, 2H), 2.91 (septet, J=6.88 Hz, 1H), 2.21 (s, 3H), 1.25 (d, J=6.97 Hz, 6H); ¹³C NMR (151 MHz, CDCl₃) s 176.3, 163.2 (d, J=245.39 Hz), 155.0, 150.7, 146.3, 146.3 (d, J=8.81 Hz), 143.9, 140.0, 138.9, 132.1, 130.4, 130.0 (d, J=2.20 Hz), 129.7 (d, J=3.30 Hz), 127.6, 123.9 (d, J=8.80 Hz), 122.3, 119.5, 118.1, 113.7, 110.7 (d, J=22.01 Hz), 105.8 (d, J=23.11 Hz), 56.2, 33.5, 31.4, 24.2, 10.6.

2-[(1Z)-5-Fluoro-2-methyl-1-{[4-(naphthalen-2-yloxy) phenyl]methylidene}-1H-inden-3-yl]acetic acid A14. ¹H NMR (600 MHz, CDCl₃) δ7.88 (d, J=8.80 Hz, 1H), 7.85 (d, J=8.07 Hz, 1H), 7.75 (d, J=8.25 Hz, 1H), 7.50 (d, J=8.44 Hz, 2H), 7.47-7.49 (m, 1H), 7.42-7.46 (m, 2H), 7.40 (dd, J=5.14, 8.44 Hz, 1H), 7.31 (dd, J=2.38, 8.99 Hz, 1H), 7.19 (s, 1H), 7.10 (d, J=8.62 Hz, 2H), 6.89 (dd, J=2.38, 8.80 Hz, 1H), 6.61 (dt, J=2.38, 8.71 Hz, 1H), 3.59 (s, 2H), 2.21 (s, 3H); ¹³C NMR (151 MHz, CDCl₃) S175.5, 162.3 (d, J=245.39 Hz), 157.7, 154.3, 146.3 (d, J=8.80 Hz), 139.9, 138.9, 134.4, 131.3, 131.1, 130.5, 130.2, 130.1, 130.0 (d, J=2.20 Hz), 129.8 (d, J=2.20 Hz), 127.9, 127.3, 126.7, 125.1, 123.7 (d, J=8.80 Hz), 120.2, 118.5, 115.2, 110.7 (d, J=23.11 Hz), 105.8 (d, J=23.11 Hz), 31.3, 10.6.

2-[(1Z)-1-({2-Chloro-4-[4-(propan-2-yl)phenoxy] phenyl}methylidene)-5-fluoro-2-methyl-1H-inden-3-yl] acetic acid A15. ¹H NMR (600 MHz, CDCl₃) δ7.53 (d, J=8.44 Hz, 1H), 7.26 (d, J=8.62 Hz, 1H), 7.19 (dd, J=5.14, 8.44 Hz, 1H), 7.12 (s, 1H), 7.08 (d, J=2.38 Hz, 1H), 7.01-7.05 (m, 2H), 6.91 (dd, J=2.48, 8.53 Hz, 1H), 6.88 (dd, J=2.38, 8.80 Hz, 1H), 6.59 (dt, J=2.29, 8.76 Hz, 1H), 3.59 (s, 2H), 2.94 (septet, J=6.91 Hz, 1H), 2.22 (s, 3H), 1.28 (d, J=6.97 Hz, 6H); ¹³C NMR (151 MHz, CDCl₃) δ175.9, 162.4 (d, J=246.49 Hz), 159.1, 153.5, 146.4 (d, J=8.80 Hz), 145.3, 140.7, 138.8, 135.0, 132.4, 130.5, 129.7 (d, J=2.20 Hz), 128.8, 128.0, 127.0, 123.7, 119.9, 118.6, 116.0, 110.8 (d, J=23.11 Hz), 106.0 (d, J=24.21 Hz), 33.6, 31.4, 24.2, 10.6.

A13

A14

-continued

A15

A16

A17

A18

2-[(1Z)-1-{[4-(2,4-Difluorophenoxy)phenyl]methyl-
idene}-5-fluoro-2-methyl-1H-inden-3-yl]acetic acid A16.
¹H NMR (600 MHz, DMSO-d₆) S12.41 (br. s., 1H), 7.55 (d,
J=8.44 Hz, 2H), 7.49-7.54 (m, 1H), 7.38-7.44 (m, 1H), 7.32
(dd, J=5.23, 8.34 Hz, 1H), 7.30 (s, 1H), 7.15-7.21 (m, 1H),
7.06 (d, J=8.62 Hz, 2H), 7.01 (dd, J=2.38, 9.35 Hz, 1H), 6.74
(dt, J=2.38, 8.80 Hz, 1H), 3.56 (s, 2H), 2.14 (s, 3H); ¹³C
NMR (151 MHz, DMSO-d₆) δ171.6, 162.4 (d, J=243.19 Hz,
1 C), 159.4 (d, J=11.00 Hz, 1 C), 157.8 (d, J=9.90 Hz, 1 C),
157.3, 154.7 (d, J=13.21 Hz, 1 C), 153.0 (d, J=13.20 Hz, 1
C), 146.9 (d, J=8.80 Hz, 1 C), 139.0, 138.6 (dd, J=11.00,
3.30 Hz, 1 C), 138.0, 131.7 (d, J=2.20 Hz, 1 C), 131.2,
130.8, 130.3, 129.5 (d, J=2.20 Hz, 1 C), 124.0 (d, J=12.10
Hz, 1 C), 123.0 (d, J=8.80 Hz, 1 C), 116.2, 112.3 (dd,
J=23.11, 3.30 Hz, 1 C), 110.3 (d, J=22.01 Hz, 1 C), 106.0 (d,
J=22.01 Hz, 1 C), 105.8 (dd, J=23.11, 3.30 Hz, 1 C), 31.1,
10.3.

2-[(1Z)-1-{[4-(2-Bromo-4-fluorophenoxy)phenyl]meth-
ylidene}-5-fluoro-2-methy 1-1H-inden-3-yl]acetic acid
A17. ¹H NMR (600 MHz, DMSO-d₆) δ12.39 (br. s., 1H),
7.78 (dd, J=2.75, 8.07 Hz, 1H), 7.56 (d, J=8.44 Hz, 2H),
7.22-7.43 (m, 4H), 6.95-7.10 (m, 3H), 6.75 (d, J=1.47 Hz,
1H), 3.57 (s, 2H), 2.15 (s, 3H); ¹³C NMR (151 MHz,
DMSO-d₆) δ171.6, 163.1, 161.5, 159.3, 157.7, 157.0, 148.5
(d, J=3.30 Hz, 1 C), 146.9 (d, J=8.80 Hz, 1 C), 139.0, 138.0,
131.7, 131.3, 130.8, 130.3, 129.4, 123.4 (d, J=8.80 Hz, 1 C),
123.0 (d, J=8.80 Hz, 1 C), 120.7 (d, J=26.41 Hz, 1 C), 116.7,
116.5 (d, J=23.11 Hz, 1 C), 115.5 (d, J=9.90 Hz, 1 C), 110.2
(d, J=23.11 Hz, 1 C), 105.8 (d, J=23.11 Hz, 1 C), 31.1, 10.3.

2-[(1Z)-5-Fluoro-2-methyl-1-{[4-(2,4,5-trifluorophe-
noxy)phenyl]methylidene}-1H-inden-3-yl]acetic acid A18.
¹H NMR (600 MHz, CDCl₃) δ 7.47-7.53 (m, 2H), 7.31 (dd,
J=5.14, 8.44 Hz, 1H), 7.16 (s, 1H), 7.12 (dt, J=7.34, 9.81 Hz,
1H), 6.96-7.08 (m, 3H), 6.89 (dd, J=2.20, 8.80 Hz, 1H), 6.60
(dt, J=2.38, 8.71 Hz, 1H), 3.60 (s, 2H), 2.21 (s, 3H).

3-[(1Z)-1-{[4-(4-Fluorophenoxy)phenyl]methylidene}-
2-methyl-1H-inden-3-yl]propanoic acid A19. ¹H NMR (600
MHz, DMSO-d₆) δ 12.15 (br. s., 1H), 7.51-7.58 (m, 2H),
7.37 (d, J=7.70 Hz, 1H), 7.26-7.31 (m, 2H), 7.14-7.24 (m,
5H), 7.04-7.08 (m, 2H), 6.93 (dt, J=0.92, 7.43 Hz, 1H), 2.80
(t, J=7.70 Hz, 2H), 2.44 (t, J=7.70 Hz, 2H), 2.13 (s, 3H).

2-[(1Z)-5-Fluoro-1-({4-[(6-fluoropyridin-3-yl)oxy]
phenyl}methylidene)-2-methyl-1H-inden-3-yl]acetic acid
A20. ¹H NMR (600 MHz, CDCl₃) δ 8.02 (d, J=2.93 Hz, 1H),
7.33-7.43 (m, 4H), 7.23-7.30 (m, 1H), 7.00 (s, 1H), 6.89-
6.95 (m, 2H), 6.74-6.84 (m, 2H), 6.49 (t, J=8.16 Hz, 1H),
3.38 (br. s., 2H), 2.04 (s, 3H).

2-[(1Z)-5-Fluoro-1-({4-[(6-fluoro-5-methylpyridin-3-yl)
oxy]phenyl}-methylidene)-2-methyl-1H-inden-3-yl]acetic
acid A21. ¹H NMR (600 MHz, CDCl₃) δ 7.84-7.92 (m, 1H),
7.44-7.53 (m, 2H), 7.31-7.40 (m, 2H), 7.14-7.18 (m, 1H),
7.02-7.05 (m, 1H), 6.97-7.00 (m, 1H), 6.90 (td, J=2.54, 8.85
Hz, 1H), 6.58-6.64 (m, 1H), 3.99 (s, 2H), 2.20-2.22 (m, 3H),
0.89 (t, J=6.97 Hz, 3H).

A19

A20

A21

A22

A23

A24

(Z)-2-(5-Fluoro-2-methyl-1-(4-(quinolin-5-yloxy)ben-zylidene)-1H-inden-3-yl)acetic acid A22. $^1$H NMR (600 MHz, DMSO-d$_6$) δ 12.39 (br. s, 1H), 8.99 (dd, J=1.65, 4.22 Hz, 1H), 8.45-8.58 (m, 1H), 7.89 (d, J=8.44 Hz, 1H), 7.75-7.81 (m, 1H), 7.55-7.63 (m, 3H), 7.29-7.39 (m, 2H), 7.16-7.26 (m, 3H), 7.02 (dd, J=2.57, 9.17 Hz, 1H), 6.68-6.82 (m, 1H), 3.58 (s, 2H), 2.16 (s, 3H).

2-[(1Z)-5-Fluoro-1-[(4-phenoxyphenyl)methyl-idene]-1H-inden-3-yl]-N-hydroxyacetamide A23. $^1$H NMR (600 MHz, DMSO-d$_6$) δ 10.69 (d, J=1.28 Hz, 1H), 8.86 (d, J=1.65 Hz, 1H), 7.55 (d, J=8.44 Hz, 2H), 7.32 (dd, J=5.32, 8.25 Hz, 1H), 7.26-7.31 (m, 3H), 7.16-7.22 (m, 2H), 7.13 (dd, J=2.38, 9.35 Hz, 1H), 7.03-7.10 (m, 2H), 6.74 (dt, J=2.38, 8.89 Hz, 1H), 3.30 (s, 2H), 2.18 (s, 3H).

2-[(1Z)-5-Fluoro-1-{[4-(4-fluorophenoxy)phenyl]meth-ylidene}-2-methyl-1H-inden-3-yl]-N-hydroxyacetamide A24. $^1$H NMR (600 MHz, DMSO-d$_6$) δ10.69 (d, J=1.28 Hz, 1H), 8.86 (d, J=1.65 Hz, 1H), 7.55 (d, J=8.44 Hz, 2H), 7.32 (dd, J=5.32, 8.25 Hz, 1H), 7.26-7.31 (m, 3H), 7.16-7.22 (m, 2H), 7.13 (dd, J=2.38, 9.35 Hz, 1H), 7.03-7.10 (m, 2H), 6.74 (dt, J=2.38, 8.89 Hz, 1H), 3.30 (s, 2H), 2.18 (s, 3H).

2-[(1Z)-5-Fluoro-1-{[4-(4-fluorophenoxy)phenyl]meth-ylidene}-2-methyl-1H-inden-3-yl]acetamide A25. $^1$H NMR (600 MHz, CDCl$_3$) δ 7.38-7.45 (m, 2H), 7.34 (dd, J=5.14, 8.44 Hz, 1H), 7.12 (s, 1H), 6.98-7.05 (m, 4H), 6.92-6.97 (m, 2H), 6.81 (dd, J=2.29, 8.71 Hz, 1H), 6.56 (dt, J=2.38, 8.80 Hz, 1H), 5.52 (br. s., 1H), 5.38 (br. s., 1H), 3.47 (s, 2H), 2.15 (s, 3H).

2-[(1Z)-5-Fluoro-1-{[4-(4-fluorophenoxy)phenyl]meth-ylidene}-2-methyl-1H-inden-3-yl]-N-methylacetamide A26. $^1$H NMR (600 MHz, CDCl$_3$) δ 7.47-7.54 (m, 2H), 7.43 (dd, J=5.04, 8.34 Hz, 1H), 7.20 (s, 1H), 7.05-7.15 (m, 4H), 6.99-7.05 (m, 2H), 6.86 (dd, J=2.38, 8.80 Hz, 1H), 6.64 (dt, J=2.38, 8.71 Hz, 1H), 5.58 (br s, 1H), 3.54 (s, 2H), 2.78 (d, J=4.95 Hz, 3H), 2.21 (s, 3H).

2-[(1Z)-5-Fluoro-1-{[4-(4-fluorophenoxy)phenyl]meth-ylidene}-2-methyl-1H-inden-3-yl]-N-(2-hydroxyethyl)acet-amide A27. $^1$H NMR (600 MHz, CDCl$_3$) δ 7.47-7.53 (m, 2H), 7.42 (dd, J=5.14, 8.44 Hz, 1H), 7.27 (s, 1H), 7.20 (s, 1H), 7.06-7.13 (m, 4H), 7.00-7.06 (m, 2H), 6.87 (dd, J=2.38, 8.80 Hz, 1H), 6.64 (dt, J=2.38, 8.71 Hz, 1H), 6.05 (br. s., 1H), 3.68 (t, J=5.10 Hz, 2H), 3.56 (s, 2H), 3.40 (q, J=5.50 Hz, 2H), 2.22 (s, 3H).

(dd, J=2.38, 9.35 Hz, 1H), 6.86-6.90 (m, 2H), 6.74 (dt, J=2.38, 8.99 Hz, 1H), 5.05 (s, 2H), 3.54 (s, 2H), 2.12 (s, 3H).

A25

A26

A27

A28

A29

A30

(Z)-2-(5-Fluoro-2-methyl-1-(4-phenoxybenzylidene)-1H-inden-3-yl)-N-(1H-tetrazol-5-yl)acetamide A28. $^1$H NMR (600 MHz, DMSO-d$_6$) δ15.86 (br. s., 1H), 12.33 (br. s., 1H), 7.58 (d, J=7.15 Hz, 2H), 7.41-7.50 (m, 2H), 7.31-7.40 (m, 2H), 7.16-7.25 (m, 2H), 7.13 (d, J=6.97 Hz, 2H), 7.09 (d, J=7.15 Hz, 2H), 6.71-6.81 (m, 1H), 3.83 (s, 2H), 2.23 (s, 3H); $^{13}$C NMR (151 MHz, DMSO-d$_6$) δ169.2, 162.8 (d, J=244.29 Hz), 157.6, 156.4, 147.2 (d, J=8.80 Hz), 139.4, 139.3, 131.7, 131.6, 131.2, 131.2, 130.7, 130.0, 124.5, 123.5 (d, J=9.90 Hz), 119.8, 118.6, 110.8 (d, J=22.01 Hz), 106.6 (d, J=23.11 Hz), 32.6, 11.0.

2-[(1Z)-5-Fluoro-2-methyl-1-({4-[methyl(phenyl)amino]phenyl}methylidene)-1H-inden-3-yl]acetic acid A29. LC-MS (m/z, ESI) [M+H]$^+$=400, found: 400.

2-[(1Z)-1-({4-[Benzyl(4-fluorophenyl)amino]phenyl}methylidene)-5-fluoro-2-methyl-1H-inden-3-yl]acetic acid A30. $^1$H NMR (600 MHz, DMSO-d$_6$) δ12.31 (br. s., 1H), 7.54 (dd, J=5.32, 8.44 Hz, 1H), 7.42 (d, J=8.62 Hz, 2H), 7.36 (d, J=4.77 Hz, 1H), 7.34-7.35 (m, 2H), 7.32-7.34 (m, 3H), 7.23 (d, J=8.62 Hz, 2H), 7.18-7.23 (m, 2H), 6.99

2-[(1Z)-5-Fluoro-1-({4-[(4-fluorophenyl)(methyl)amino]phenyl}methylidene)-2-methyl-1H-inden-3-yl]acetic acid A31. LC-MS (m/z, ESI) [M+H]$^+$=418, found: 418.

2-[(1Z)-1-({4-[Ethyl(4-fluorophenyl)amino]phenyl}methylidene)-5-fluoro-2-methyl-1H-inden-3-yl]acetic acid A32. LC-MS (m/z, ESI) [M+H]$^+$=432, found: 432.

2-[(1Z)-5-Fluoro-1-({4-[(4-fluorophenyl)(propyl)amino]phenyl}methylidene)-2-methyl-1H-inden-3-yl]acetic acid A33. LC-MS (m/z, ESI) [M+H]$^+$=446, found: 446.

113                        114

A31

A32

A33

A34

A35

A36

2-[(1Z)-5-Fluoro-1-({4-[(4-fluorophenyl)(2-hydroxy-ethyl)amino]phenyl}-methylidene)-2-methyl-1H-inden-3-yl]acetic acid A34. HR-MS (m/z, ESI) [M+H]$^+$=448.1719, found: 448.1720.

2-[(1Z)-5-Fluoro-1-({4-[(4-fluorophenyl)(4-formylphe-nyl)amino]phenyl}-methylidene)-2-methyl-1H-inden-3-yl] acetic acid A35. $^1$H NMR (600 MHz, DMSO-d$_6$) δ12.41 (br. s., 1H), 9.82 (s, 1H), 7.79 (d, J=8.80 Hz, 2H), 7.59 (d, J=8.25 Hz, 2H), 7.44 (dd, J=5.32, 8.44 Hz, 1H), 7.28-7.34 (m, 5H), 7.24 (d, J=8.44 Hz, 2H), 6.96-7.04 (m, 3H), 6.78 (dt, J=2.57, 7.70 Hz, 1H), 3.57 (s, 2H), 2.15 (s, 3H).

2-[(1Z)-5-Fluoro-1-({4-[(4-formylphenyl)(phenyl) amino]phenyl}methylidene)-2-methyl-1H-inden-3-yl]acetic acid A36. LC-MS (m/z, ESI) [M+H]$^+$=490, found: 490.

2-[(1Z)-5-Fluoro-2-methyl-1-({4-[methyl(phenyl)amino] phenyl}methylidene)-1H-inden-3-yl]-N-hydroxyacetamide A37. LC-MS (m/z, ESI) [M+H]$^+$=415, found: 415.

2-[(1Z)-1-({4-[Benzyl(4-fluorophenyl)amino] phenyl}methylidene)-5-fluoro-2-methyl-1H-inden-3-yl]-N-hydroxyacetamide A38. $^1$H NMR (600 MHz, DMSO-d$_6$) δ 10.67 (s, 1H), 8.84 (s, 1H), 7.62-7.69 (m, 1H), 7.52 (dd, J=5.32, 8.44 Hz, 1H), 7.38-7.43 (m, 1H), 7.34-7.35 (m, 2H), 7.32-7.34 (m, 2H), 7.28-7.32 (m, 2H), 7.20-7.26 (m, 4H), 7.18 (s, 1H), 7.07-7.15 (m, 1H), 6.84-6.93 (m, 2H), 6.72 (dt, J=2.38, 8.89 Hz, 1H), 5.05 (s, 1H), 3.29 (s, 2H), 2.16 (s, 3H).

5-{[(1Z)-2-Methyl-1-[(3-phenoxyphenyl)methylidene]-1H-inden-3-yl]methyl}-1H-1,2,3,4-tetrazole A39. $^1$H NMR (600 MHz, DMSO-d$_6$) 97.51 (t, J=7.79 Hz, 1H), 7.40 (t, J=7.89 Hz, 2H), 7.34 (s, 1H), 7.28 (d, J=7.70 Hz, 1H), 7.30 (d, J=7.70 Hz, 1H), 7.15 (t, J=6.79 Hz, 1H), 7.07-7.14 (m, 6H), 6.91 (t, J=7.34 Hz, 1H), 4.24 (s, 2H), 2.19 (s, 3H); $^{13}$C NMR (151 MHz, DMSO-d$_6$) δ157.5, 156.8, 143.9, 141.3, 138.6, 136.6, 133.8, 133.3, 130.9, 130.8, 130.6, 128.4, 125.0, 124.7, 124.3, 122.6, 119.6, 119.1, 118.7, 20.1, 10.6.

A37

A38

A39

5-{[(1Z)-2-Methyl-1-[(4-phenoxyphenyl)methylidene]-1H-inden-3-yl]methyl}-1H-1,2,3,4-tetrazole A40. $^1$H NMR (600 MHz, DMSO-d$_6$) 97.58 (d, J=8.44 Hz, 2H), 7.45 (q, J=1.00 Hz, 2H), 7.41 (d, J=7.52 Hz, 1H), 7.36 (s, 1H), 7.21 (t, J=1.00 Hz, 1H), 7.14 (d, J=1.00 Hz, 3H), 7.11 (d, J=8.44 Hz, 1H), 7.09 (d, J=1.00 Hz, 2H), 6.94 (q, J=1.00 Hz, 1H), 4.25 (s, 2H), 2.23 (s, 3H); $^{13}$C NMR (151 MHz, DMSO-d$_6$)

δ157.5, 156.4, 143.8, 140.5, 136.7, 134.0, 132.8, 131.7, 131.4, 131.4, 130.7, 128.2, 125.0, 124.5, 122.4, 119.8, 118.6, 118.6, 20.2, 10.7.

5-{2-[(1Z)-2-Methyl-1-{[4-(4-methylphenoxy)phenyl]methylidene}-1H-inden-3-yl]ethyl}-1H-1,2,3,4-tetrazole A41. $^1$H NMR (600 MHz, DMSO-d$_6$) δ7.53 (d, J=8.44 Hz, 2H), 7.39 (d, J=7.70 Hz, 1H), 7.22-7.27 (m, 3H), 7.15-7.22 (m, 2H), 6.99-7.06 (m, 4H), 6.94 (dt, J=0.73, 7.52 Hz, 1H), 3.10 (t, J=7.34 Hz, 2H), 2.99 (t, J=7.70 Hz, 2H), 2.31 (s, 3H), 1.96 (s, 3H); $^{13}$C NMR (151 MHz, DMSO-d$_6$) δ158.0, 154.0, 144.2, 140.6, 137.0, 135.1, 134.3, 133.7, 131.6, 131.2, 131.0, 130.4, 128.3, 124.8, 122.4, 120.0, 118.3, 118.0, 23.9, 22.7, 20.8, 10.2.

5-{2-[(1Z)-1-{[4-(4-Bromophenoxy)phenyl]methylidene}-2-methyl-1H-inden-3-yl]ethyl}-1H-1,2,3,4-tetrazole A42. $^1$H NMR (600 MHz, DMSO-d$_6$) 57.61 (d, J=8.99 Hz, 2H), 7.57 (d, J=8.44 Hz, 2H), 7.40 (d, J=7.70 Hz, 1H), 7.26 (d, J=7.52 Hz, 1H), 7.23 (s, 1H), 7.20 (t, J=7.34 Hz, 1H), 7.12 (d, J=8.62 Hz, 2H), 7.09 (d, J=8.80 Hz, 2H), 6.95 (t, J=7.15 Hz, 1H), 3.13 (t, J=7.52 Hz, 2H), 3.00 (t, J=7.61 Hz, 2H), 1.98 (s, 3H); $^{13}$C NMR (151 MHz, DMSO-d$_6$) δ156.8, 156.0, 144.2, 140.8, 137.1, 135.1, 134.2, 133.4, 132.1, 131.8, 130.2, 128.3, 124.9 122.5, 121.7 (2 C), 118.9 (2 C), 118.3, 116.1, 23.9, 22.7, 10.2.

A40

A41

-continued

A42

A43

5-{2-[(1Z)-2-Methyl-1-({4-[4-(propan-2-yl)phenoxy] phenyl}methylidene)-1H-inden-3-yl]ethyl}-1H-1,2,3,4-tetrazole A43. ¹H NMR (600 MHz, DMSO-d₆) δ7.54 (d, J=8.44 Hz, 2H), 7.40 (d, J=7.70 Hz, 1H), 7.31 (d, J=8.44 Hz, 2H), 7.24 (d, J=7.52 Hz, 1H), 7.21 (s, 1H), 7.19 (t, J=7.00 Hz, 1H), 7.03-7.07 (m, 4H), 6.94 (dt, J=1.00, 7.70 Hz, 1H), 3.11 (t, J=7.52 Hz, 2H), 2.99 (t, J=7.61 Hz, 2H), 2.92 (quin, J=6.88 Hz, 1H), 1.97 (s, 3H), 1.22 (d, J=6.79 Hz, 6H); ¹³C NMR (151 MHz, DMSO-d₆) δ157.8, 154.2, 144.6, 144.2, 140.6, 137.0, 135.1, 134.2, 131.7 (2 C), 131.2, 130.4, 128.4 (2 C) 128.3, 124.9, 122.4, 119.8 (2 C), 118.3, 118.1 (2 C), 33.3, 24.5 (3 C), 23.9, 22.7, 10.2.

5-{2-[(1Z)-1-{[4-(4-Methoxyphenoxy)phenyl]methyl-idene}-2-methyl-1H-inden-3-yl]ethyl}-1H-1,2,3,4-tetrazole A44. ¹H NMR (600 MHz, DMSO-d₆) δ7.52 (d, J=8.62 Hz, 2H), 7.41 (d, J=7.52 Hz, 1H), 7.24 (d, J=7.34 Hz, 1H), 7.16-7.21 (m, 2H), 7.11 (d, J=8.99 Hz, 2H), 6.99 (d, J=8.62 Hz, 2H), 7.01 (d, J=9.17 Hz, 2H), 6.92-6.96 (m, 1H), 3.77 (s, 3H), 3.11 (t, J=7.52 Hz, 2H), 2.99 (t, J=7.43 Hz, 2H), 1.97 (s, 3H); ¹³C NMR (151 MHz, DMSO-d₆) δ158.3, 156.0, 148.7, 143.7, 140.0, 136.5, 134.6, 133.8, 131.2 (3 C), 130.3, 130.0, 127.8, 124.4, 122.0, 121.3 (2 C), 117.8, 116.8 (2 C), 115.2 (2 C), 55.4, 23.4, 22.2, 9.7.

5-{2-[(1Z)-2-Methyl-1-({4-[4-(trifluoromethyl)phenoxy] phenyl}methylidene)-1H-inden-3-yl]ethyl}-1H-1,2,3,4-tetrazole A45. ¹H NMR (600 MHz, DMSO-d₆) δ7.79 (d, J=8.44 Hz, 2H), 7.62 (d, J=8.25 Hz, 2H), 7.37 (d, J=7.52 Hz, 1H), 7.24-7.28 (m, 4H), 7.18-7.24 (m, 3H), 6.96 (t, J=7.43 Hz, 1H), 3.13 (t, J=7.52 Hz, 2H), 3.00 (t, J=7.52 Hz, 2H), 1.99 (s, 3H); ¹³C NMR (151 MHz, DMSO-d₆) δ159.9, 155.2, 143.8, 140.6, 136.8, 134.6, 133.7, 132.6, 131.4 (2 C), 129.5, 127.9, 127.6 (q, J=3.30 Hz), 124.5, 124.4 (d, J=228.88 Hz), 123.6 (d, J=73.73 Hz), 122.1, 119.6 (2 C), 118.6 (2 C), 117.9, 23.4, 22.2, 9.7.

A44

A45

5-{2-[(1Z)-2-Methyl-1-{[4-(3-methylphenoxy)phenyl] methylidene}-1H-inden-3-yl]ethyl}-1H-1,2,3,4-tetrazole A46. ¹H NMR (600 MHz, DMSO-d₆) δ7.53-7.56 (m, J=8.44 Hz, 2H), 7.39 (d, J=7.52 Hz, 1H), 7.32 (t, J=7.79 Hz, 1H), 7.24 (d, J=7.34 Hz, 1H), 7.22 (s, 1H), 7.19 (dt, J=1.00, 7.20 Hz, 1H), 7.05-7.09 (m, 2H), 7.02 (d, J=7.52 Hz, 1H), 6.93-6.97 (m, 2H), 6.91 (dd, J=2.20, 8.07 Hz, 1H), 3.12 (t, J=7.61 Hz, 2H), 3.00 (t, J=7.61 Hz, 2H), 2.32 (s, 3H), 1.97 (s, 3H); ¹³C NMR (151 MHz, DMSO-d₆) δ157.0, 156.0, 143.7, 140.2, 139.9, 136.6, 134.6, 133.8, 131.2 (2 C), 131.0, 129.9 (2 C), 129.7, 127.8, 124.7, 124.4, 122.0, 119.8, 118.0 (2 C), 117.8, 116.3, 23.4, 22.2, 20.9, 9.7.

3-(4-{[(1Z)-2-Methyl-3-[2-(1H-1,2,3,4-tetrazol-5-yl) ethyl]-1H-inden-1-ylidene]methyl}phenoxy)benzonitrile A47. $^1$H NMR (600 MHz, DMSO-d$_6$) δ7.61-7.66 (m, 3H), 7.59 (d, J=8.44 Hz, 2H), 7.44-7.47 (m, 1H), 7.37 (d, J=7.70 Hz, 1H), 7.25 (d, J=7.34 Hz, 1H), 7.23 (s, 1H), 7.17-7.21 (m, 1H), 7.16 (d, J=8.62 Hz, 2H), 6.94 (dt, J=0.70, 7.20 Hz, 1H), 3.12 (t, J=7.50 Hz, 2H), 3.00 (t, J=7.61 Hz, 2H), 1.98 (s, 3H); $^{13}$C NMR (151 MHz, DMSO-d$_6$) δ156.7, 155.7, 143.8, 140.6, 136.8, 134.6, 133.8, 132.3, 131.6, 131.4 (2 C), 129.6, 127.9, 127.6, 124.4, 123.9, 122.2 (2 C) 122.1, 118.9 (2 C), 118.2, 117.9, 112.9, 23.4, 22.2, 9.7.

5-{2-[(1Z)-1-{[4-(3-Methoxyphenoxy)phenyl]methyl-idene}-2-methyl-1H-inden-3-yl]ethyl}-1H-1,2,3,4-tetrazole A48. $^1$H NMR (600 MHz, DMSO-d$_6$) δ7.55 (d, J=8.44 Hz, 2H), 7.38 (d, J=7.70 Hz, 1H), 7.33 (t, J=8.25 Hz, 1H), 7.24 (d, J=7.52 Hz, 1H), 7.22 (s, 1H), 7.18 (t, J=7.34 Hz, 1H), 7.09 (d, J=8.62 Hz, 2H), 6.93 (qt, J=1.00, 7.70 Hz, 1H), 6.77 (dd, J=2.20, 8.07 Hz, 1H), 6.68 (t, J=2.29 Hz, 1H), 6.64-6.67 (m, 1H), 3.76 (s, 3H), 3.11 (t, J=7.50 Hz, 2H), 2.99 (t, J=7.61 Hz, 2H), 1.97 (s, 3H); $^{13}$C NMR (151 MHz, DMSO-d$_6$) δ160.8, 157.2, 156.7, 143.7, 140.3, 136.6, 134.6, 133.8, 131.3, 131.2 (2 C), 130.7 (2 C), 129.8, 127.8, 124.4, 122.0, 118.2 (2 C), 117.8, 111.1, 109.7, 105.2, 55.3, 23.4, 22.2, 9.7.

A46

A47

A48

5-{2-[(1Z)-1-{[4-(3-Bromophenoxy)phenyl]methyl-idene}-2-methyl-1H-inden-3-yl]ethyl}-1H-1,2,3,4-tetrazole A49. $^1$H NMR (600 MHz, DMSO-d$_6$) δ7.57 (d, J=8.25 Hz, 2H), 7.36 (s, 2H), 7.35 (d, J=7.70 Hz, 1H), 7.28-7.30 (m, 1H), 7.23-7.25 (m, 1H), 7.22 (s, 1H), 7.18 (dt, J=1.00, 7.70 Hz, 1H), 7.10-7.15 (m, 3H), 6.93 (dt, J=1.00, 7.20 Hz, 1H), 3.11 (t, J=7.61 Hz, 2H), 2.99 (t, J=7.61 Hz, 2H), 1.97 (s, 3H); $^{13}$C NMR (151 MHz, DMSO-d$_6$) δ157.4, 156.0, 143.7, 140.5, 136.8, 134.6, 133.8, 132.0, 131.9, 131.3 (2 C), 129.6, 127.9, 126.6, 124.4, 122.3, 122.0, 121.6 (2 C), 118.8 (2 C), 117.9, 117.9, 23.4, 22.2, 9.7.

5-{2-[(1Z)-2-Methyl-1-({4-[3-(trifluoromethyl)phenoxy]phenyl}methylidene)-1H-inden-3-yl]ethyl}-1H-1,2,3,4-tet-razole A50. $^1$H NMR (600 MHz, DMSO-d$_6$) δ7.66 (t, J=7.90 Hz, 1H), 7.59 (d, J=8.44 Hz, 2H), 7.53 (d, J=7.70 Hz, 1H), 7.38-7.44 (m, 2H), 7.35 (d, J=7.70 Hz, 1H), 7.23-7.26 (m, 2H), 7.18-7.21 (m, 1H), 7.17 (d, J=8.62 Hz, 2H), 6.92 (dt, J=1.00, 7.70 Hz, 1H), 3.13 (t, J=7.61 Hz, 2H), 3.00 (t, J=7.61 Hz, 2H), 1.98 (s, 3H); $^{13}$C NMR (151 MHz, DMSO-d$_6$) δ157.0, 155.7, 143.8, 140.6, 136.8, 134.6, 133.8, 132.3, 131.5, 131.4 (2 C), 130.9 (q, J=33.00 Hz), 129.6, 127.9, 124.4, 122.7, 122.0, 123.4 (q, J=272.90 Hz), 120.2 (q, J=4.40 Hz), 119.0 (2 C), 117.9, 115.2 (q, J=3.30 Hz), 23.4, 22.2, 9.7.

5-{2-[(1Z)-2-Methyl-1-{[4-(naphthalen-2-yloxy)phenyl]methylidene}-1H-inden-3-yl]ethyl}-1H-1,2,3,4-tetrazole A51. $^1$H NMR (600 MHz, DMSO-d$_6$) δ8.02 (d, J=8.80 Hz, 1H), 7.95 (d, J=8.07 Hz, 1H), 7.88 (d, J=8.07 Hz, 1H), 7.59 (d, J=8.62 Hz, 2H), 7.55 (d, J=2.20 Hz, 1H), 7.52 (dt, J=0.92, 7.90 Hz, 1H), 7.48 (dt, J=1.00, 7.00 Hz, 1H), 7.43 (d, J=7.52 Hz, 1H), 7.38 (dd, J=2.38, 8.99 Hz, 1H), 7.22-7.27 (m, 2H), 7.19 (t, J=7.34 Hz, 1H), 7.15 (d, J=8.80 Hz, 2H), 6.96 (t, J=7.34 Hz, 1H), 3.12 (t, J=7.52 Hz, 2H), 3.00 (t, J=7.52 Hz, 2H), 1.98 (s, 3H); $^{13}$C NMR (151 MHz, DMSO-d$_6$) δ156.9, 153.9, 143.8, 140.3, 136.6, 134.6, 134.0, 133.8, 131.4, 131.3 (2 C), 130.3, 130.1, 129.8, 127.8, 127.7, 127.2, 126.8, 125.1, 124.4, 122.0, 120.0, 118.4 (2 C), 117.8, 114.7 (2 C), 23.4, 22.2, 9.8.

A49

A50

A51

7.23-7.30 (m, 3H), 7.21 (q, J=1.00 Hz, 1H), 7.07-7.13 (m, 4H), 6.99 (s, 1H), 4.37 (s, 2H); $^{13}$C NMR (151 MHz, DMSO-d$_6$) δ157.5, 155.8, 141.5, 140.3, 138.0, 136.8, 132.0 (2 C), 131.4, 130.2 (3 C), 128.2, 127.2, 125.6, 124.1, 123.6, 119.4, 119.4 (2 C), 119.0, 118.5 (2 C), 22.2.

5-{[(1E)-1-[(3-Phenoxyphenyl)methylidene]-1H-inden-3-yl]methyl}-1H-1,2,3,4-tetrazole A54. $^1$H NMR (600 MHz, DMSO-d$_6$) δ7.82-7.86 (m, 1H), 7.67 (s, 1H), 7.50 (t, J=1.00 Hz, 1H), 7.40-7.45 (m, 3H), 7.23-7.29 (m, 4H), 7.18 (t, J=1.00 Hz, 1H), 7.06-7.09 (m, 2H), 7.04 (d, J=1.00 Hz, 1H), 6.87 (s, 1H), 4.36 (s, 2H); $^{13}$C NMR (151 MHz, DMSO-d$_6$) δ 157.2, 156.3, 140.5, 138.5, 138.3, 137.7, 130.6, 130.2 (3 C), 129.7, 128.0, 127.6, 125.8, 124.9, 123.8, 123.4, 119.7, 119.6, 119.1, 119.0 (2 C), 118.7, 22.2.

A52

A53

A54

(Z)-3-((2-Methyl-1-(4-phenoxybenzylidene)-1H-inden-3-yl)methyl)-1,2,4-oxadiazol-5(4H)-one A52. $^1$H NMR (600 MHz, DMSO-d$_6$) δ12.33 (br. s., 1H), 7.58 (d, J=8.25 Hz, 2H), 7.40-7.49 (m, 3H), 7.35 (s, 1H), 7.15-7.24 (m, 3H), 7.06-7.15 (m, 4H), 6.96 (t, J=7.24 Hz, 1H), 3.89 (s, 2H), 2.20 (s, 3H); $^{13}$C NMR (151 MHz, DMSO-d$_6$) δ160.3, 158.6, 157.6, 156.4, 143.8, 140.3, 137.8, 133.9, 131.7, 131.6, 131.4, 130.7, 130.4, 128.3, 125.1, 124.5, 122.4, 119.8, 118.6, 118.5, 22.0, 10.8.

5-{[(1E)-1-[(4-Phenoxyphenyl)methylidene]-1H-inden-3-yl]methyl}-1H-1,2,3,4-tetrazole A53. $^1$H NMR (600 MHz, DMSO-d$_6$) δ7.84 (dd, J=3.30, 5.14 Hz, 1H), 7.71 (d, J=8.62 Hz, 2H), 7.67 (s, 1H), 7.44 (q, J=1.00 Hz, 2H), 2-[(1Z)-5-Fluoro-2-methyl-1-{[4-(morpholin-4-yl)phenyl]methylidene}-1H-inden-3-yl]acetic acid A55. $^1$H NMR (600 MHz, DMSO-d$_6$) δ12.39 (br. s., 1H), 7.55 (dd, J=5.32, 8.44 Hz, 1H), 7.47 (d, J=8.80 Hz, 2H), 7.25 (s, 1H), 7.03 (d, J=8.80 Hz, 2H), 7.00 (dd, J=2.38, 9.35 Hz, 1H), 6.75 (d, J=2.20 Hz, 1H), 3.74-3.79 (m, 4H), 3.56 (s, 2H), 3.21-3.25 (m, 4H), 2.14 (s, 3H).

2-[(1Z)-5-Fluoro-2-methyl-1-{[4-(piperidin-1-yl)phenyl]methylidene}-1H-inden-3-yl]acetic acid A56.

2-[(1Z)-5-Fluoro-1-{[4-(1H-indol-1-yl)phenyl]methylidene}-2-methyl-1H-inden-3-yl]acetic acid A57.

123                                                          124

A55

A58

A56

A59

A57

A60

2-[(1Z)-1-{[4-(2-Amino-1H-imidazol-1-yl)phenyl]meth-ylidene}-5-fluoro-2-meth yl-1H-inden-3-yl]acetic acid A58.

2-[(1Z)-5-Fluoro-2-methyl-1-{[4-(pyrrolidin-1-yl)phe-nyl]methylidene}-1H-inden-3-yl]acetic acid A59. LC-MS (m/z, ESI) [M+H]⁺=364, found: 364.

2-[(1Z)-5-Fluoro-2-methyl-1-{[4-(1H-pyrrol-1-yl)phe-nyl]methylidene}-1H-inden-3-yl]acetic acid A60. $^1$H NMR (600 MHz, DMSO-d$_6$) δ12.43 (br. s., 1H), 7.73 (d, J=8.62 Hz, 2H), 7.63 (d, J=8.44 Hz, 2H), 7.50 (t, J=2.20 Hz, 2H), 7.31-7.39 (m, 2H), 7.02 (dd, J=2.38, 9.17 Hz, 1H), 6.74 (d, J=1.83 Hz, 1H), 6.31 (t, J=2.20 Hz, 2H), 3.58 (s, 2H), 2.16 (s, 3H).

(2E)-3-[(1Z)-5-Fluoro-1-{[4-(4-fluorophenoxy)phenyl] methylidene}-2-methyl-1H-inden-3-yl]prop-2-enoic    acid A61.

2-[(1Z)-5-Fluoro-1-{[4-(4-fluorobenzenesulfonyl)phe-nyl]methylidene}-2-methyl-1H-inden-3-yl]acetic acid A62.

2-[(1Z)-5-Fluoro-1-{[4-(4-fluorobenzenesulfinyl)phenyl] methylidene}-2-methyl-1H-inden-3-yl]acetic acid A63.

125
126

A61

A64

A62

A65

A63

(2E)-4-[(1Z)-5-Fluoro-1-{[4-(4-fluorophenoxy)phenyl]
methylidene}-2-methyl-1H-inden-3-yl]but-2-enoic acid
A67.

2-[(1Z)-4,5-Difluoro-1-{[4-(4-fluorophenoxy)phenyl]
50 methylidene}-2-methyl-1H-inden-3-yl]acetic acid A68. ¹H
NMR (600 MHz, DMSO-d₆) 97.55 (d, J=8.44 Hz, 2H), 7.34
(s, 1H), 7.25-7.31 (m, 2H), 7.21-7.25 (m, 1H), 7.20 (d,
J=4.40 Hz, 1H), 7.18 (d, J=4.40 Hz, 1H), 7.15 (dd, J=7.70,
11.37 Hz, 1H), 7.08 (d, J=8.44 Hz, 2H), 3.48 (s, 2H), 2.12
(s, 3H); LC-MS (m/z, ESI) [M+H]⁺=423, found: 423.

2-[(1Z)-5-Fluoro-1-{[4-(4-fluorophenoxy)phenyl]meth-
ylidene}-2,4-dimethyl-1H-inden-3-yl]acetic acid A69. ¹H
NMR (600 MHz, DMSO-d₆) 97.54 (d, J=8.44 Hz, 2H),
7.23-7.31 (m, 2H), 7.12-7.20 (m, 4H), 7.07 (d, J=8.62 Hz,
2H), 6.95 (d, J=10.09 Hz, 1H), 3.37 (s, 2H), 2.09 (s, 3H),
2.04 (s, 3H); ¹³C NMR (151 MHz, DMSO-d₆) δ172.6,
172.4, 161.4, 159.8, 159.3, 157.7, 157.2, 152.2 (d, J=2.20
Hz, 1 C), 145.4 (d, J=8.80 Hz, 1 C), 139.9, 135.4, 134.1,
131.2, 129.6, 128.7, 124.5 (d, J=5.50 Hz, 1 C), 121.1, 121.1, 118.3 (d, J=18.71 Hz, 1 C), 117.9, 116.8, 116.7, 105.8 (d,
J=24.21 Hz, 1 C), 33.5, 21.8, 10.3; LC-MS (m/z, ESI)
[M+H]⁺=419, found: 419.

A66

2-[(1Z)-5-Fluoro-1-({4-[(4-fluorophenyl)sulfanyl]
phenyl}methylidene)-2-methyl-1H-inden-3-yl]acetic acid
A64.

2-[(1Z)-5-Fluoro-1-{[6-(4-fluorophenoxy)pyridine-3-yl]
methylidene}-2-methyl-1H-inden-3-yl]acetic acid A65.

2-[(1Z)-5-Fluoro-1-{[6-(4-fluorophenoxy)-5-methylpyri-
din-3-yl]methylidene}-2-methyl-1H-inden-3-yl]acetic acid
A66.

A67

A70

A68

A71

A69

A72

2-[(1Z)-5-Fluoro-2-methyl-1-{[4-(morpholin-4-yl)phe-
nyl]methylidene}-1H-inden-3-yl]-N-hydroxyacetamide
A70.

2-[(1Z)-5-Fluoro-2-methyl-1-{[4-(piperidin-1-yl)phenyl]
methylidene}-1H-inden-3-yl]-N-hydroxyacetamide A71.

2-[(1Z)-5-Fluoro-1-{[4-(1H-indol-1-yl)phenyl]methyl-
idene}-2-methyl-1H-inden-3-yl]-N-hydroxyacetamide A72.

2-[(1Z)-1-{[4-(2-Amino-1H-imidazol-1-yl)phenyl]meth-
ylidene}-5-fluoro-2-methyl-1H-inden-3-yl]-N-hydroxyac-
etamide A73.

2-[(1Z)-5-Fluoro-2-methyl-1-{[4-(pyrrolidin-1-yl)phe-
nyl]methylidene}-1H-inden-3-yl]-N-hydroxyacetamide
A74.

2-[(1Z)-5-Fluoro-2-methyl-1-{[4-(1H-pyrrol-1-yl)phe-
nyl]methylidene}-1H-inden-3-yl]-N-hydroxyacetamide
A75.

A73

A76

A74

A77

A75

A78

(2E)-3-[(1Z)-5-Fluoro-1-{[4-(4-fluorophenoxy)phenyl]
methylidene}-2-methyl-1H-inden-3-yl]-N-hydroxyprop-2-
enamide A76.

2-[(1Z)-5-Fluoro-1-{[4-(4-fluorobenzenesulfonyl)phe-
nyl]methylidene}-2-methyl-1H-inden-3-yl]-N-hydroxyac-
etamide A77.

2-[(1Z)-5-Fluoro-1-{[4-(4-fluorobenzenesulfinyl)phenyl]
methylidene}-2-methyl-1H-inden-3-yl]-N-hydroxyacet-
amide A78.

2-[(1Z)-5-Fluoro-1-({4-[(4-fluorophenyl)sulfanyl]
phenyl}methylidene)-2-methyl-1H-inden-3-yl]-N-hydroxy-
acetamide A79.

2-[(1Z)-5-Fluoro-1-{[6-(4-fluorophenoxy)pyridine-3-yl]
methylidene}-2-methyl-1H-inden-3-yl]-N-hydroxyacet-
amide A80.

2-[(1Z)-5-Fluoro-1-{[6-(4-fluorophenoxy)-5-methylpyri-
din-3-yl]methylidene}-2-methyl-1H-inden-3-yl]-N-hy-
droxyacetamide A81.

131                                        132

A79

A82

A80

A83

A81

A84

2-[(1Z)-5-Fluoro-1-{[4-(4-fluorophenoxy)phenyl]meth-ylidene}-2,4-dimethyl-1H-inden-3-yl]-N-hydroxyacet-amide A84.

2-[(1Z)-5-Fluoro-1-({4-[(4-fluorophenyl)(2-hydroxy-ethyl)amino]phenyl}-methylidene)-2-methyl-1H-inden-3-yl]-N-hydroxyacetamide A85. HR-MS (m/z, ESI) [M+H]$^+$ =463.1828, found: 463.1825.

(2E)-4-[(1Z)-5-Fluoro-1-{[4-(4-fluorophenoxy)phenyl] methylidene}-2-methyl-1H-inden-3-yl]-N-hydroxybut-2-enamide A82.

2-[(1Z)-4,5-Difluoro-1-{[4-(4-fluorophenoxy)phenyl] methylidene}-2-methyl-1H-inden-3-yl]-N-hydroxyacet-amide A83.

A85

2-[(1Z)-5-Fluoro-2-methyl-1-[(4-phenoxyphenyl)methyl-idene]-1H-inden-3-yl]-N-hydroxy-N-methylacetamide C1. $^1$H NMR (600 MHz, DMSO-d$_6$) δ10.06 (br s, 1H), 7.56 (d, J=8.80 Hz, 2H), 7.45 (t, J=7.89 Hz, 2H), 7.33 (dd, J=5.23, 8.34 Hz, 1H), 7.28 (s, 1H), 7.20 (t, J=7.34 Hz, 1H), 7.13 (d, J=8.07 Hz, 2H), 7.09 (d, J=8.44 Hz, 2H), 7.00 (dd, J=2.38, 9.35 Hz, 1H), 6.73 (dt, J=2.38, 8.89 Hz, 1H), 3.67 (s, 2H), 3.12 (s, 3H), 2.14 (s, 3H).

2-[(1Z)-5-Fluoro-1-{[4-(4-fluorophenoxy)phenyl]meth-ylidene}-2-methyl-1H-inden-3-yl]-N-hydroxy-N-methylac-etamide C2. $^1$H NMR (600 MHz, DMSO-d$_6$) δ10.13 (s, 1H), 7.60 (d, J=8.25 Hz, 2H), 7.38 (dd, J=5.32, 8.25 Hz, 1H), 7.36-7.31 (m, 3H), 7.27-7.21 (m, 2H), 7.15-7.09 (m, 2H), 7.05 (dd, J=2.38, 9.17 Hz, 1H), 6.78 (dt, J=2.57, 8.80 Hz, 1H), 3.73 (s, 2H), 3.17 (s, 3H), 2.19 (s, H); $^{13}$C NMR (151 MHz, DMSO-d$_6$) 169.6, 163.1, 161.5, 159.4, 157.8, 157.4, 151.9, 147.3, 139.2, 137.9, 132.5, 131.2, 130.8, 129.8, 129.6, 122.9, 121.4, 117.7, 116.8, 116.7, 110.1, 106.1, 105.9, 36.1, 31.0, 10.4.

(Z)-2-(5-Fluoro-2-methyl-1-(3-phenoxybenzylidene)-1H-inden-3-yl)-N-hydroxy-N-methylacetamide C3. $^1$H NMR (600 MHz, DMSO-d$_6$) δ10.06 (br s, 1H), 7.51 (t, J=7.89 Hz, 1H), 7.45-7.37 (m, 2H), 7.31-7.25 (m, 2H), 7.20 (dd, J=5.32, 8.25 Hz, 1H), 7.17-7.13 (m, 1H), 7.12-7.07 (m, 3H), 7.04 (br. s, 1H), 6.98 (dd, J=2.20, 9.35 Hz, 1H), 6.70 (dt, J=2.38, 7.70 Hz, 1H), 3.65 (s, 2H), 3.11 (s, 3H), 2.10 (s, 3H).

C1

C2

C3

2-[(1Z)-5-Fluoro-2-methyl-1-({4-[4-(propan-2-yl)phe-noxy]phenyl}methylidene)-1H-inden-3-yl]-N-hydroxyacet-amide D1. $^1$H NMR (600 MHz, DMSO-d$_6$) δ10.75 (br s, 1H), 9.02 (br s, 1H), 7.54 (d, J=8.44 Hz, 2H), 7.33 (dd, J=5.32, 7.89 Hz, 1H), 7.32-7.26 (m, 3H), 7.13 (d, J=9.35 Hz, 1H), 7.07-7.01 (m, 4H), 6.73 (td, J=1.80, 9.40 Hz, 1H), 3.30 (s, 2H), 2.96-2.85 (m, 1H), 2.18 (s, 3H), 1.22 (d, J=6.79 Hz, 6H).

2-[(1Z)-5-Fluoro-2-methyl-1-({4-[4-(tert-butyl)phenoxy]phenyl}methylidene)-1H-inden-3-yl]acetic acid D2. $^1$H NMR (600 MHz, DMSO-d$_6$) δ7.55 (d, J=8.44 Hz, 2H), 7.36 (t, J=7.89 Hz, 1H), 7.31 (dd, J=5.32, 8.44 Hz, 1H), 7.29 (s, 1H), 7.22 (td, J=0.87, 7.79 Hz, 1H), 7.12 (t, J=2.11 Hz, 1H), 7.10-7.04 (m, 2H), 7.03-6.99 (m, 1H), 6.90 (ddd, J=0.73, 2.38, 8.25 Hz, 1H), 6.70 (dt, J=2.38, 8.89 Hz, 1H), 3.51 (s, 2H), 2.14 (s, 3H), 1.28 (s, 9H); $^{13}$C NMR (151 MHz, DMSO-d$_6$) δ171.9, 163.1, 161.5, 157.1, 155.8, 153.3, 147.2 (d, J=9.90 Hz, 1C), 144.0, 139.2, 137.5, 131.2 (2C), 130.8, 130.1, 129.7, 122.9 (d, J=9.90 Hz, 1C), 120.9, 118.1 (2C), 116.3, 116.1, 110.0 (d, J=23.11 Hz, 1C), 105.9 (d, J=24.21 Hz, 1C), 34.5, 31.0 (3C), 10.3.

2-[(1Z)-5-Fluoro-2-methyl-1-({4-[3-(tert-butyl)phenoxy]phenyl}methylidene)-1H-inden-3-yl]acetic acid D3. $^1$H NMR (600 MHz, DMSO-d$_6$) δ7.55 (d, J=8.44 Hz, 2H), 7.45 (d, J=8.62 Hz, 2H), 7.35 (dd, J=5.23, 8.34 Hz, 1H), 7.29 (s, 1H), 7.05 (dd, J=2.29, 8.71 Hz, 4H), 7.01 (d, J=7.52 Hz, 1H), 6.73 (dt, J=2.20, 9.90 Hz, 1H), 3.54 (br s, 2H), 2.14 (s, 3H), 1.30 (s, 9H); $^{13}$C NMR (151 MHz, DMSO-d$_6$) δ171.8, 163.1, 161.5, 157.4, 153.4, 147.0 (d, J=9.90 Hz, 1C), 146.4, 139.0, 137.8, 132.0, 131.2 (2C), 130.5, 130.3, 129.6, 126.9 (2C), 123.0 (d, J=8.80 Hz, 1C), 119.0 (2C), 117.8 (2C), 110.2 (d, J=23.11 Hz, 1C), 105.8 (d, J=23.11 Hz, 1C), 34.1, 31.2 (3C), 10.3.

D1

D2

D3

D4

D5

D6

2-[(1Z)-5-Fluoro-2-methyl-1-({4-[3-fluoro-4-methylphe-noxy]phenyl}-methylidene)-1H-inden-3-yl]acetic acid D4. $^1$H NMR (600 MHz, DMSO-d$_6$) δ12.41 (br s, 1H), 7.57 (d, J=8.62 Hz, 2H), 7.37-7.32 (m, 2H), 7.32-7.29 (m, 1H), 7.14-7.07 (m, 2H), 7.01 (dd, J=2.48, 9.26 Hz, 1H), 6.98 (dd, J=2.38, 10.82 Hz, 1H), 6.87 (dd, J=2.38, 8.25 Hz, 1H), 6.74 (dt, J=1.83, 8.99 Hz, 1H), 3.57 (s, 2H), 2.22 (d, J=1.47 Hz, 3H), 2.15 (s, 3H); $^{13}$C NMR (151 MHz, DMSO-d$_6$) δ 171.6, 162.1 (d, J=243.19 Hz, 1C), 160.9 (d, J=244.29 Hz, 1C), 156.8, 155.0 (d, J=11.01 Hz, 1C), 146.9 (d, J=8.80 Hz, 1C), 139.1, 138.0, 132.4 (d, J=6.60 Hz, 1C), 131.7 (d, J=2.20 Hz, 1C), 131.3 (2C), 130.7 (d, J=114.44 Hz, 1C), 129.5 (d, J=3.30 Hz, 1C), 123.0 (d, J=8.80 Hz, 1C), 119.8, 119.7, 118.2 (2C), 115.0 (d, J=3.30 Hz, 1C), 110.3 (d, J=23.11 Hz, 1C), 106.8 (d, J=25.31 Hz, 1C), 105.8 (d, J=23.11 Hz, 1C), 31.1, 13.6 (d, J=3.30 Hz, 1C), 10.3.

2-[(1Z)-5-Fluoro-2-methyl-1-({4-[3,4-difluorophenoxy]phenyl}methylidene)-1H-inden-3-yl]acetic acid D5. $^1$H NMR (600 MHz, DMSO-d$_6$) 97.57 (d, J=8.44 Hz, 2H), 7.50 (d, J=10.45 Hz, 1H), 7.36-7.32 (m, 1H), 7.32-7.29 (m, 1H), 7.27 (s, 1H), 7.16-7.07 (m, 2H), 7.01 (dd, J=2.48, 9.26 Hz, 1H), 7.00-6.92 (m, 1H), 6.72 (dt, J=2.38, 8.10 Hz, 1H), 3.50 (s, 2H), 2.13 (s, 3H); $^{13}$C NMR (151 MHz, DMSO-d$_6$) δ171.9, 163.1, 161.5, 156.6, 152.3 (dd, J=8.80, 3.30 Hz, 1C), 149.8 (dd, J=246.49, 14.30 Hz, 1C), 147.3 (d, J=8.80 Hz, 1C), 146.2 (dd, J=238.78, 13.20 Hz, 1C), 139.4, 137.3, 131.5, 131.3 (2C), 129.7, 129.6 (d, J=2.20 Hz, 1C), 122.9 (d, J=8.80 Hz, 1C), 118.3 (d, J=18.71 Hz, 1C), 118.2 (2C), 115.8 (dd, J=6.60, 3.30 Hz, 1C), 110.1 (d, J=22.01 Hz, 1C), 109.4 (d, J=19.81 Hz, 1C), 106.0 (d, J=24.21 Hz, 1C), 32.2, 10.3.

2-[(1Z)-5-Fluoro-2-methyl-1-({4-[3-nitrophenoxy]phenyl}methylidene)-1H-inden-3-yl]acetic acid D6. $^1$H NMR (600 MHz, DMSO-d$_6$) δ8.03 (ddd, J=0.83, 2.15, 8.21 Hz, 1H), 7.80 (t, J=2.29 Hz, 1H), 7.72 (t, J=8.25 Hz, 1H), 7.63-7.55 (m, 3H), 7.26-7.22 (m, 2H), 7.20 (s, 1H), 7.19 (dd, J=5.32, 7.89 Hz, 1H), 7.05 (dd, J=2.48, 9.44 Hz, 1H), 6.65 (dt, J=2.57, 8.99 Hz, 1H), 3.20 (s, 2H), 2.11 (s, 3H).

2-[(1Z)-5-Fluoro-2-methyl-1-({4-[4-(trifluoromethyl)phenoxy]phenyl}-methylidene)-1H-inden-3-yl]acetic acid D7. $^1$H NMR (600 MHz, DMSO-d$_6$) δ12.42 (br s, 1H), 7.79 (d, J=8.62 Hz, 2H), 7.62 (d, J=8.62 Hz, 2H), 7.35 (s, 1H), 7.32 (dd, J=5.23, 8.34 Hz, 1H), 7.26 (d, J=8.62 Hz, 2H), 7.23 (d, J=8.44 Hz, 2H), 7.02 (dd, J=2.38, 9.35 Hz, 1H), 6.76 (dt, J=2.38, 8.89 Hz, 1H), 3.58 (s, 2H), 2.16 (s, 3H); $^{13}$C NMR (151 MHz, DMSO-d$_6$) δ172.1, 160.2, 155.8, 147.4 (d, J=8.80 Hz, 1C), 139.9, 138.4, 132.8, 132.4 (2C), 131.9 (2C), 130.6, 129.9 (d, J=2.20 Hz, 1C), 128.1 (q, J=3.30 Hz, 1C), 125.6, 124.2 (d, J=31.91 Hz, 1C), 123.8, 123.6 (d, J=8.80

Hz, 1C), 120.2 (2C), 119.1 (2C), 110.7 (d, J=23.11 Hz, 1C), 106.4 (d, J=23.11 Hz, 1C), 31.6, 10.7.

2-[(1Z)-5-Fluoro-1-{[4-(4-fluorophenoxy)phenyl]methylidene}-2-(2-methylpropyl)-1H-inden-3-yl]acetic acid D8. $^1$H NMR (600 MHz, DMSO-d$_6$) δ12.40 (br s, 1H), 7.55 (d, J=8.62 Hz, 2H), 7.33 (dd, J=5.32, 8.44 Hz, 1H), 7.31-7.25 (m, 3H), 7.22-7.15 (m, 2H), 7.06 (d, J=8.62 Hz, 2H), 7.01 (dd, J=2.38, 9.35 Hz, 1H), 6.75 (dt, J=2.38, 8.89 Hz, 1H), 3.58 (s, 2H), 2.48 (d, J=7.34 Hz, 2H), 1.92-1.79 (m, 1H), 0.93 (d, J=6.60 Hz, 6H).

2-[(1Z)-5-Fluoro-2-benzyl-1-({4-[4-fluorophenoxy]phenyl}methylidene)-1H-inden-3-yl]acetic acid D9. $^1$H NMR (600 MHz, DMSO-d$_6$) δ12.48 (br s, 1H), 7.46 (d, J=8.62 Hz, 2H), 7.38 (dd, J=5.32, 8.44 Hz, 1H), 7.33-7.22 (m, 7H), 7.19-7.13 (m, 3H), 7.07 (dd, J=2.48, 9.26 Hz, 1H), 7.05-6.99 (m, 2H), 6.82-6.73 (m, 1H), 4.03 (s, 2H), 3.67 (s, 2H).

2-[(1Z)-5-Methoxy-2-methyl-1-[(4-phenoxyphenyl)methylidene]-1H-inden-3-yl]acetic acid D11. $^1$H NMR (600 MHz, DMSO-d$_6$) δ12.38 (br s, 1H), 7.56 (d, J=8.44 Hz, 2H), 7.45 (t, J=7.98 Hz, 2H), 7.30 (d, J=8.44 Hz, 1H), 7.23-7.17 (m, 1H), 7.15 (s, 1H), 7.14-7.10 (m, 2H), 7.10-7.05 (m, 2H), 6.76 (d, J=2.20 Hz, 1H), 6.50 (dd, J=2.38, 8.44 Hz, 1H), 3.73 (s, 3H), 3.53 (s, 2H), 2.12 (s, 3H).

2-[(1Z)-1-{[2-Trifluoromethyl-4-(4-fluorophenoxy)phenyl]methylidene}-5-fluoro-2-methyl-1H-inden-3-yl]acetic acid D12. $^1$H NMR (600 MHz, DMSO-d$_6$) 97.60 (d, J=8.44 Hz, 1H), 7.43 (d, J=2.38 Hz, 1H), 7.36-7.28 (m, 3H), 7.28-7.25 (m, 2H), 7.23 (br s, 1H), 7.02 (dd, J=2.11, 9.26 Hz, 1H), 6.67 (dt, J=2.38, 8.80 Hz, 1H), 6.65-6.58 (m, 1H), 3.50 (s, 2H), 2.11 (s, 3H).

D7

D8

D9

D10

D11

D12

2-[(1Z)-5-Methoxy-2-methyl-1-({4-[4-fluorophenoxy]phenyl}methylidene)-1H-inden-3-yl]acetic acid D10. $^1$H NMR (600 MHz, DMSO-d$_6$) δ12.37 (br s, 1H), 7.55 (d, J=8.62 Hz, 2H), 7.32-7.23 (m, 3H), 7.20-7.15 (m, 2H), 7.14 (s, 1H), 7.06 (d, J=8.62 Hz, 1H), 6.76 (d, J=2.38 Hz, 1H), 6.49 (dd, J=2.29, 8.34 Hz, 1H), 3.73 (s, 3H), 3.53 (s, 2H), 2.12 (s, 3H).

2-[(1Z)-1-{[3-Methyl-4-(4-fluorophenoxy)phenyl]methylidene}-5-fluoro-2-methyl-1H-inden-3-yl]acetic acid D13. $^1$H NMR (600 MHz, DMSO-d$_6$) δ12.45 (br. s, 1H), 7.49 (d, J=1.47 Hz, 1H), 7.38 (dd, J=1.93, 8.34 Hz, 1H), 7.35 (dd, J=5.23, 8.34 Hz, 1H), 7.29 (s, 1H), 7.27-7.21 (m, 2H), 7.10-7.04 (m, 2H), 7.01 (dd, J=2.48, 9.26 Hz, 1H), 6.89 (d, J=8.25 Hz, 1H), 6.75 (dt, J=2.38, 8.89 Hz, 1H), 3.57 (s, 2H), 2.25 (s, 3H), 2.14 (s, 3H).

2-[(1Z)-1-{[2-Methyl-4-(4-fluorophenoxy)phenyl]methylidene}-5-fluoro-2-methyl-1H-inden-3-yl]acetic acid D14.

¹H NMR (500 MHz, DMSO-d₆) δ 12.46 (s, 1H), 7.38 (d, J=8.4 Hz, 1H), 7.31-7.24 (m, 3H), 7.19-7.12 (m, 2H), 7.04-6.97 (m, 2H), 6.95 (dd, J=8.4, 5.3 Hz, 1H), 6.87 (dd, J=8.4, 2.7 Hz, 1H), 6.71 (td, J=9.1, 2.5 Hz, 1H), 3.57 (s, 2H), 2.25 (s, 3H), 2.16 (s, 3H).

2-[(1Z)-5,7-Difluoro-2-methyl-1-({4-[4-fluorophenoxy]phenyl}methylidene)-1H-inden-3-yl]acetic acid D15. ¹H NMR (500 MHz, DMSO-d₆) δ 12.48 (s, 1H), 7.47 (s, 1H), 7.38 (dd, J=8.8, 2.8 Hz, 2H), 7.30-7.26 (m, 2H), 7.16-7.12 (m, 2H), 7.02-6.97 (m, 3H), 6.83 (td, J=10.1, 2.2 Hz, 1H), 3.61 (s, 2H), 2.19 (s, 3H).

D13

D14

D15

2-[(1Z)-4,6-Difluoro-2-methyl-1-({4-[4-fluorophenoxy]phenyl}methylidene)-1H-inden-3-yl]acetic acid D16. ¹H NMR (500 MHz, DMSO-d₆) δ 12.38 (s, 1H), 7.57 (d, J=8.6 Hz, 2H), 7.46 (s, 1H), 7.33-7.25 (m, 2H), 7.23-7.18 (m, 2H), 7.11-7.08 (m, 2H), 7.02 (dq, J=8.1, 2.1 Hz, 1H), 6.97-6.91 (m, 1H), 3.63 (s, 2H), 2.11 (s, 3H).

2-[(1Z)-5-Tert-butyl-2-methyl-1-({4-[4-fluorophenoxy]phenyl}methylidene)-1H-inden-3-yl]acetic acid D17.

(Z)-2-(5-Fluoro-2-methyl-1-(3-phenoxybenzylidene)-1H-inden-3-yl)acetic acid D18. ¹H NMR (600 MHz, DMSO-d₆) δ 12.42 (br. s., 1H), 7.51 (t, J=7.89 Hz, 1H), 7.45-7.37 (m, 2H), 7.30 (s, 1H), 7.29 (d, J=8.07 Hz, 1H), 7.21 (dd, J=5.23, 8.34 Hz, 1H), 7.15 (t, J=7.43 Hz, 1H), 7.11

(d, J=2.38 Hz, 1H), 7.10-7.07 (m, 2H), 7.05 (s, 1H), 6.99 (dd, J=2.48, 9.26 Hz, 1H), 6.72 (d, J=1.65 Hz, 1H), 3.55 (s, 2H), 2.11 (s, 3H); ¹³C NMR (151 MHz, DMSO-d₆) δ171.6, 163.2, 161.6, 157.1, 156.2, 146.9, 139.8, 137.9, 132.2, 130.4, 130.2, 130.0, 129.3, 124.2, 123.9, 123.2, 119.2, 118.5, 110.3, 105.9, 31.1, 10.2.

D16

D17

D18

2-[(1Z)-5-Fluoro-1-(2-(phenoxy)benzylidene)-2-methyl-1H-inden-3-yl]-acetic acid D19. LC-MS (m/z, ESI) [M+H]⁺ =387, found: 387.

2-[(1Z)-5,7-Difluoro-1-(3-(phenoxy)benzylidene)-2-methyl-1H-inden-3-yl]-acetic acid D20. ¹H NMR (500 MHz, DMSO-d₆) δ 12.53 (s, 1H), 7.46 (s, 1H), 7.40 (dt, J=15.5, 7.9 Hz, 3H), 7.12 (t, J=7.6 Hz, 2H), 7.04 (t, J=7.8 Hz, 3H), 6.97 (d, J=8.5 Hz, 1H), 6.87 (s, 1H), 6.82 (t, J=10.1 Hz, 1H), 3.58 (s, 2H), 2.15 (s, 3H).

2-[(1Z)-4,6-Difluoro-1-(3-(phenoxy)benzylidene)-2-methyl-1H-inden-3-yl]-acetic acid D21. ¹H NMR (500 MHz, DMSO-d₆) δ 7.55 (t, J=7.9 Hz, 1H), 7.46 (s, 1H), 7.40 (t, J=7.8 Hz, 2H), 7.30 (d, J=7.6 Hz, 1H), 7.20-7.11 (m, 2H), 7.09 (d, J=8.0 Hz, 2H), 7.05 (d, J=13.6 Hz, 2H), 6.80 (d, J=9.2 Hz, 1H), 3.60 (s, 2H), 2.08 (s, 3H).

D19

D20

D21

D22

D23

D24

2-[(1Z)-5-Fluoro-2-methyl-1-({3-[4-methoxyphenoxy] phenyl}methylidene)-1H-inden-3-yl]acetic acid D22. $^1$H NMR (500 MHz, DMSO-d$_6$) δ 12.47 (s, 1H), 7.53-7.43 (m, 1H), 7.28 (s, 1H), 7.26-7.19 (m, 2H), 7.10-7.06 (m, 2H), 7.04 (dd, J=8.2, 2.5 Hz, 1H), 7.01-6.98 (m, 1H), 6.98-6.96 (m, 3H), 6.74 (ddd, J=9.4, 8.4, 2.5 Hz, 1H), 3.73 (s, 3H), 3.55 (s, 2H), 2.11 (s, 3H).

2-[(1Z)-5-Fluoro-1-(4-fluoro-3-(phenoxy)benzylidene)-2-methyl-1H-inden-3-yl]-acetic acid D23. $^1$H NMR (500 MHz, DMSO-d$_6$) δ 12.43 (s, 1H), 7.51 (ddq, J=15.2, 10.3, 4.5 Hz, 1H), 7.44-7.32 (m, 3H), 7.29-7.04 (m, 6H), 6.98 (ddd, J=7.9, 5.5, 2.5 Hz, 1H), 6.82-6.57 (m, 1H), 3.53 (s, 2H), 2.13 (s, 3H).

2-[(1Z)-5-Fluoro-2-methyl-1-({3-[4-cyanophenoxy] phenyl}methylidene)-1H-inden-3-yl]acetic acid D24. $^1$H NMR (500 MHz, DMSO-d$_6$) δ 12.50 (s, 1H), 7.87 (d, J=8.4 Hz, 2H), 7.58 (t, J=8.2 Hz, 1H), 7.42 (d, J=7.7 Hz, 1H), 7.32 (s, 1H), 7.27-7.14 (m, 5H), 7.10-6.96 (m, 1H), 6.73 (d, J=8.8, 3.2 Hz, 1H), 3.56 (s, 2H), 2.13 (s, 3H).

2-[(1Z)-5-Fluoro-2-methyl-1-({3-[4-chlorophenoxy] phenyl}methylidene)-1H-inden-3-yl]acetic acid D25. $^1$H NMR (500 MHz, DMSO-d$_6$) δ 12.47 (s, 1H), 7.53 (t, J=7.9 Hz, 1H), 7.50-7.41 (m, 2H), 7.38-7.29 (m, 2H), 7.21 (dd, J=8.4, 5.2 Hz, 1H), 7.18-7.05 (m, 4H), 7.00 (dd, J=9.3, 2.5 Hz, 1H), 6.73 (ddd, J=9.5, 8.3, 2.5 Hz, 1H), 3.56 (s, 2H), 2.12 (s, 3H).

2-[(1Z)-5-Fluoro-2-methyl-1-({3-[4-trifluoromethylphenoxy]phenyl}-methylidene)-1H-inden-3-yl]acetic acid D26. LC-MS (m/z, ESI) [M+H]$^+$=455, found: 455.

2-[(1Z)-5-Fluoro-2-methyl-1-({3-[3-trifluoromethylphenoxy]phenyl}-methylidene)-1H-inden-3-yl]acetic acid D27. LC-MS (m/z, ESI) [M+H]$^+$=455, found: 455.

-continued

D25

D26

D27

2-[(1Z)-4-Methoxy-1-(4-(phenoxy)benzylidene)-2-methyl-1H-inden-3-yl]-acetic acid D28.

2-[(1Z)-6-Methoxy-1-(4-(phenoxy)benzylidene)-2-methyl-1H-inden-3-yl]-acetic acid D29.

2-[(1Z)-6-Trifluoromethyl-2-methyl-1-({4-[4-fluorophenoxy]phenyl}-methylidene)-1H-inden-3-yl]acetic acid D30.

D28

D29

D30

2-[(1Z)-5-Trifluoromethyl-2-methyl-1-({4-[4-fluorophenoxy]phenyl}-methylidene)-1H-inden-3-yl]acetic acid D31.

2-[(1Z)-1-{[4-(4-Fluorophenoxy)phenyl]methylidene}-1H-inden-3-yl]acetic acid D32.

2-[(1Z)-5-Fluoro-1-{[4-(4-fluorophenoxy)phenyl]methylidene}-1H-inden-3-yl]acetic acid D33.

D31

D32

-continued

D33

2-[(1Z)-5-Trifluoromethyl-1-(3-(phenoxy)benzylidene)-2-methyl-1H-inden-3-yl]-acetic acid D34.

2-[(1Z)-6-Methoxy-1-(3-(phenoxy)benzylidene)-2-methyl-1H-inden-3-yl]-acetic acid D35.

2-[(1Z)-6-Trifluoromethyl-1-(3-(phenoxy)benzylidene)-2-methyl-1H-inden-3-yl]-acetic acid D36.

D34

D35

D36

2-[(1Z)-5-Fluoro-2-methyl-1-({3-[methyl(phenyl)amino]phenyl}methylidene)-1H-inden-3-yl]acetic acid D37.

2-[(1Z)-5-Fluoro-1-[(3-methoxy-5-phenoxyphenyl)methylidene]-2-methyl-1H-inden-3-yl]acetic acid D38.

D37

D38

2-[(1E)-5-Fluoro-2-methyl-1-({4-[3,4-difluorophenoxy]phenyl}methylidene)-1H-inden-3-yl]acetic acid E1. $^1$H NMR (600 MHz, DMSO-d$_6$) δ12.42 (br s, 1H), 7.79 (s, 1H), 7.73 (dd, J=5.14, 8.25 Hz, 1H), 7.53-7.48 (m, 1H), 7.48-7.44 (m, 2H), 7.29 (ddd, J=2.93, 6.79, 11.74 Hz, 1H), 7.11-7.07 (m, 2H), 7.06 (dd, J=2.38, 7.89 Hz, 1H), 6.98-6.95 (m, 1H), 6.95-6.91 (m, 1H), 3.56 (s, 2H), 1.85 (s, 3H); $^{13}$C NMR (151 MHz, DMSO-d$_6$) δ171.4, 162.4 (d, J=240.98 Hz, 1C), 156.5, 152.4 (d, J=8.80 Hz, 1C), 149.8 (dd, J=246.49, 14.31 Hz, 1C), 146.1 (dd, J=240.99, 12.10 Hz, 1C), 143.7 (d, J=9.90 Hz, 1C), 138.6, 136.3 (d, J=2.20 Hz, 1C), 134.5, 133.2, 131.6 (2C), 131.4, 129.3, 120.1 (d, J=8.80 Hz, 1C), 118.3 (d, J=18.71 Hz, 1C), 117.8 (2C), 115.6 (dd, J=5.50, 3.30 Hz, 1C), 110.6 (d, J=23.11 Hz, 1C), 109.2 (d, J=19.81 Hz, 1C), 105.5 (d, J=24.21 Hz, 1C), 31.2, 14.0.

2-[(1E)-5-Fluoro-2-methyl-1-({4-[4-fluorophenoxy]phenyl}methylidene)-1H-inden-3-yl]acetic acid E2. $^1$H NMR (600 MHz, DMSO-d$_6$) δ7.77 (s, 1H), 7.72 (dd, J=5.14, 8.25 Hz, 1H), 7.44 (d, J=8.44 Hz, 2H), 7.30-7.23 (m, 2H), 7.16-7.12 (m, 2H), 7.03 (dd, J=2.38, 9.17 Hz, 1H), 7.03-7.00 (m, 2H), 6.97-6.91 (m, 1H), 3.55 (s, 2H), 1.84 (s, 3H).

2-[(1E)-5-Fluoro-2-methyl-1-[(4-phenoxyphenyl)methylidene]-1H-inden-3-yl]acetic acid E3. $^1$H NMR (600 MHz, DMSO-d$_6$) δ12.42 (br. s., 1H), 7.78 (s, 1H), 7.72 (dd, J=4.95, 8.25 Hz, 1H), 7.46-7.44 (m, 2H), 7.44-7.41 (m, 2H), 7.19 (t, J=7.43 Hz, 1H), 7.10-7.07 (m, 2H), 7.06-7.05 (m, J=2.40 Hz, 1H), 7.05-7.04 (m, 1H), 7.04-7.02 (m, 1H), 6.95 (dt, J=2.40, 8.80 Hz, 1H), 3.56 (s, 2H), 1.85 (s, 3H); $^{13}$C NMR (151 MHz, DMSO-d$_6$) δ171.5, 162.4 (d, J=242.09 Hz, 1C), 156.9, 156.1, 143.7 (d, J=8.80 Hz, 1C), 138.4, 136.2 (d, J=2.20 Hz, 1C), 134.5, 133.2 (d, J=2.20 Hz, 1C), 131.6 (2C), 130.9, 130.2 (2C), 129.4, 123.9, 120.1 (d, J=9.90 Hz, 1C), 119.1 (2C), 117.8 (2C), 110.6 (d, J=24.21 Hz, 1C), 105.5 (d, J=24.21 Hz, 1C), 31.2, 14.0.

E1

E2

E3

2-[(1E)-5,7-Difluoro-2-methyl-1-({4-[4-fluorophenoxy]phenyl}methylidene)-1H-inden-3-yl]acetic acid E4. $^1$H NMR (500 MHz, DMSO-d$_6$) δ 12.49 (s, 1H), 7.87 (d, J=2.6 Hz, 1H), 7.48-7.41 (m, 2H), 7.33-7.23 (m, 2H), 7.20-7.11 (m, 2H), 7.06-6.96 (m, 4H), 3.58 (s, 2H), 1.80 (s, 3H).

5-{2-[(1E)-1-[(4-Phenoxyphenyl)methylidene]-1H-inden-3-yl]ethyl}-1H-1,2,3,4-tetrazole E5. $^1$H NMR (600 MHz, DMSO-d$_6$) δ7.81 (d, J=7.15 Hz, 1H), 7.71 (d, J=8.80 Hz, 2H), 7.56 (s, 1H), 7.43-7.49 (m, 2H), 7.38 (d, J=7.15 Hz, 1H), 7.29 (dt, J=1.01, 7.29 Hz, 1H), 7.25 (dt, J=1.10, 7.30 Hz, 1H), 7.20-7.24 (m, 1H), 7.10-7.15 (m, 2H), 7.08 (d, J=8.99 Hz, 2H), 6.91 (s, 1H), 3.35 (t, J=7.30 Hz, 2H), 3.11 (t, J=7.52 Hz, 2H). $^{13}$C NMR (151 MHz, DMSO-d$_6$) δ157.8, 156.3, 146.7, 141.4, 138.5, 137.6, 132.5, 132.0, 130.7, 127.7, 127.3, 125.9, 124.6, 121.9, 119.9, 119.8, 119.2, 118.8, 25.8, 22.1.

2-[(1E)-5,7-Difluoro-1-(3-(phenoxy)benzylidene)-2-methyl-1H-inden-3-yl]-acetic acid E6. $^1$H NMR (500 MHz, DMSO-d$_6$) δ 12.51 (s, 1H), 7.86 (d, J=2.6 Hz, 1H), 7.46 (t, J=7.9 Hz, 1H), 7.45-7.37 (m, 2H), 7.22-7.13 (m, 2H), 7.09-6.97 (m, 6H), 3.56 (s, 2H), 1.73 (s, 3H).

E4

-continued

E5

E6

Example B1

Inhibition of Alpha-Smooth Muscle Actin

The ability of a compound to inhibit the TGF-β induced expression of alpha-smooth muscle actin (α-SMA) was evaluated in CCL$_4$-treated fat storing (CFSC) cells. α-SMA is considered as a reliable marker of hepatic stellate cell activation and a key biomarker for liver fibrosis. See, e.g., Meng et al., *Nat. Rev. Nephrol.* 2016, 12, 325-38; Fabregat et al., *FEBS J.* 2016, 283, 2219-32.

CFSC cells maintained in a DMEM medium supplemented with 10% fetal bovine serum were seeded to 12-well culture dishes and grown to a confluence of 60-70% the next day. Culture was changed to a serum-free DMEM medium and treated with a compound at 10 μM in the presence of TGF-β (10 ng/mL). The cells were incubated for another 24 hours. All culture was maintained at 37° C. in 5% carbon dioxide.

A NP-40 lysate solution (50 mM Tris (pH 7.4), 150 mM NaCl, 1% NP-40) with EDTA free cocktail added was used to lyse the cells on ice for 30 min. The lysate was collected and centrifuged at 4° C. for 10 min at 12,000 rpm. The pellet was discarded and the supernatant was transferred to a new tube. Cell lysates were loaded with 5×loading buffer and boiled for 10 min, resolved by 10% SDS-polyacrylamide gel electrophoresis (SDS-PAGE), and transferred to PVDF membrane. The membrane was blocked with 5% skim milk in Tris-buffered saline and TWEEN® 20 (TBST; 10 mM Tris-HCl (pH 8.0), 150 mM NaCl, 0.1% TWEEN® 20) for 1 h at room temperature and then incubated with α-SMA and p-actin antibodies overnight at 4° C. After washing twice with TBST, the membrane was probed with a horseradish peroxidase-linked anti-immunoglobulin (1:5000 dilution) for 1 h at room temperature. After two subsequent rinses in TBST, immunoreactive products were reacted with ECL and visualized by a UVP CHEMSTUDIO™ imaging system. The western blotting bands are quantitated using an ImageJ software. The percentage of inhibition was obtained by calculating the percentage decrease in the band intensity compared to the one treated with TGF-β only.

The results are summarized in Table 1, wherein A represents a value no less of 90% inhibition, B represents a value less than 90% but no less than 80% inhibition, C represents a value less than 80% but no less than 70% inhibition, D represents a value less than 70% but no less than 50% inhibition, and E represents a value less than 50% with a compound at 10 μM.

TABLE 1

Inhibition of α-SMA

| Cmpd. | Activity |
| --- | --- |
| A1 | A |
| A2 | A |
| A3 | A |
| A4 | A |
| A5 | A |
| A6 | A |
| A7 | A |
| A9 | A |
| A10 | A |
| A11 | B |
| A12 | A |
| A13 | E |
| A14 | A |
| A15 | B |
| A16 | A |
| A17 | A |
| A18 | C |
| A19 | A |
| A20 | E |
| A21 | B |
| A22 | D |
| A23 | A |
| A24 | B |
| A25 | C |
| A26 | C |
| A27 | B |
| A29 | C |
| A30 | C |
| A31 | A |
| A32 | A |
| A33 | C |
| A34 | A |
| A35 | A |
| A36 | A |
| A38 | C |
| A39 | A |
| A40 | A |
| A42 | C |
| A43 | A |
| A45 | A |
| A46 | A |
| A47 | A |
| A48 | A |
| A51 | A |
| A54 | A |
| A55 | E |
| A60 | E |
| A68 | A |
| A69 | A |
| A85 | A |
| B9 | A |
| B10 | C |
| B30 | A |
| B34 | A |
| B35 | A |
| B36 | A |
| B37 | B |
| B39 | E |
| B42 | B |
| C1 | B |
| C2 | A |
| C3 | B |
| D1 | A |

TABLE 1-continued

Inhibition of α-SMA

| Cmpd. | Activity |
| --- | --- |
| D2 | A |
| D3 | A |
| D4 | E |
| D5 | A |
| D6 | E |
| D7 | A |
| D8 | A |
| D9 | E |
| D10 | A |
| D11 | A |
| D12 | E |
| D13 | E |
| D14 | A |
| D15 | A |
| D16 | E |
| D18 | A |
| D19 | E |
| D20 | A |
| D21 | A |
| D22 | A |
| D23 | A |
| D25 | A |
| D26 | A |
| D27 | A |
| E1 | A |
| E2 | A |
| E3 | A |
| E4 | A |
| E6 | A |

Example B2

Antifibrotic Activity

CCl$_4$-induced liver fibrosis was described previously. Henderson et al., *Proc. Nat'l. Acad. Sci. U.S.A.* 2006, 103, 5060-5; Henderson et al., *Nat. Med.* 2013, 19, 1617-24. Briefly, eight-week-old C57BL/6 mice were randomly divided into two groups: a control group and a CCl$_4$ administered group. Liver fibrosis was induced by intraperitoneal administration of 25% CCl$_4$ at 0.5 mL/kg body weight (diluted in corn oil) twice weekly for 6 weeks. Dosing was started during the last 2 weeks of CCl$_4$ administration. Malotilate (Mal) as a reference and compounds A11, A23, and B9 were each freshly prepared by dissolving in PEG 400 and orally administered in a dosing volume of 10 mL/kg. The mice were stratified (n=6-8 per group) based on their body weights and dosed once daily for 2 weeks with a vehicle, malotilate (60 mg/kg), compound A11 (50 mg/kg), compound A23 (50 mg/kg), or compound B9 (50 mg/kg). Their body weights were monitored daily during the intervention period. At the terminal of treatment, the mice were sacrificed and their liver samples were processed as below.

The mice liver samples were all taken at the same position of each large lobe, and then post-fixed in a 10% buffered formaldehyde for 48 h. The fixed livers were embedded in paraffin for microtome slicing into 5-μm-thick sections. The tissue sections were mounted onto MS-coated glass slides, deparaffinized, and stained with picric acid-Sirius red. Stained sections were photographed using a microscope with a digital camera. Images were taken at a full resolution with a single image dimension set at 1,360×1,024 pixels.

Figure 2:
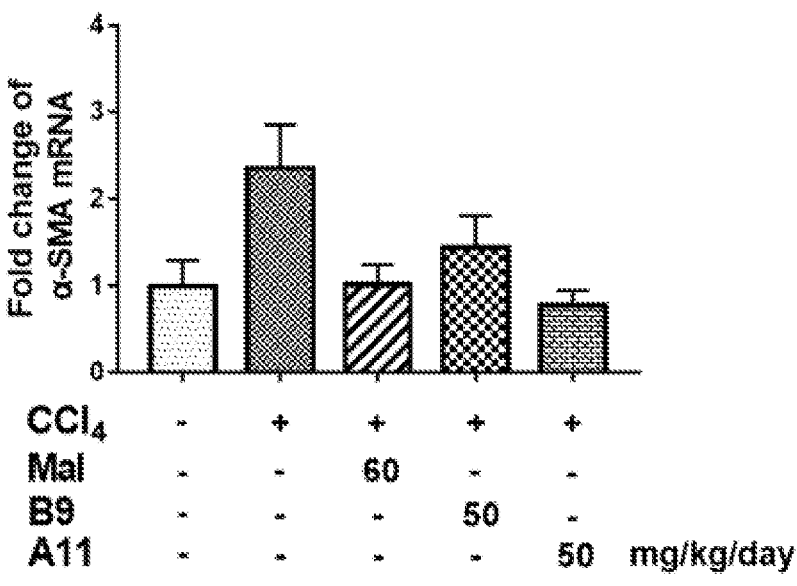
FIG. 2 shows the effect of Mal, and compounds A11 and B9 on the mRNA level of α-SMA in C57/BL6 mice.
Figures 3, 4:
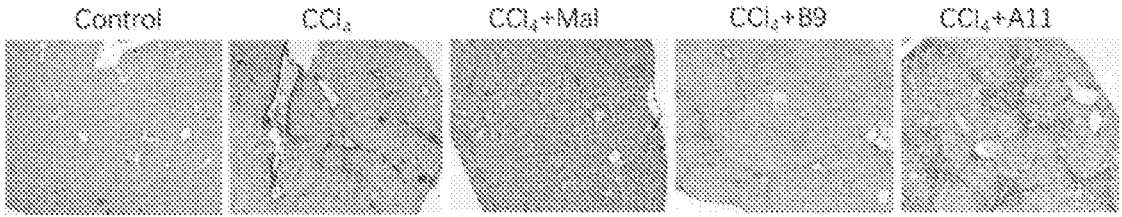
FIG. 3 shows the effect of Mal, and compounds A11 and B9 on the mRNA level of Col1a1 in C57/BL6 mice.
FIG. 4 shows Sirius red pathological staining images of the liver samples of C57/BL6 mice treated with Mal, or compound A11 or B9, indicating that each compound reversed the fibrosis induced by CCl$_4$.
Figure 5:
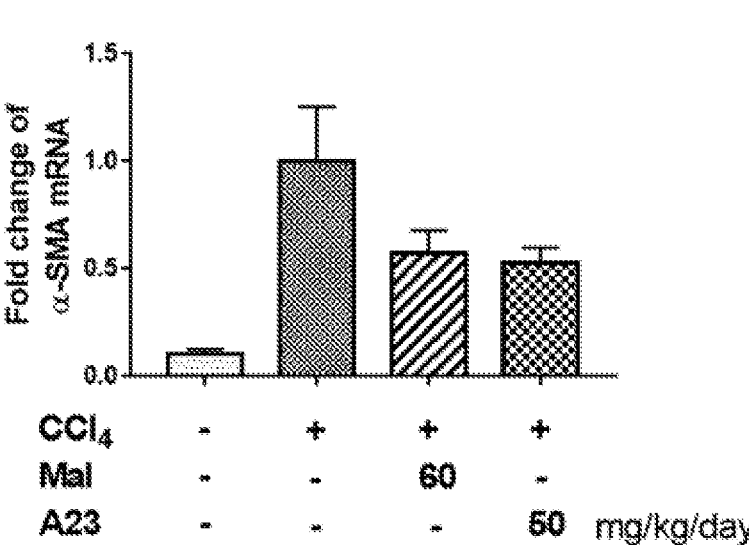
FIG. 5 shows the effect of Mal and compound A23 on the mRNA level of α-SMA in C57/BL6 mice.
Figure 6:
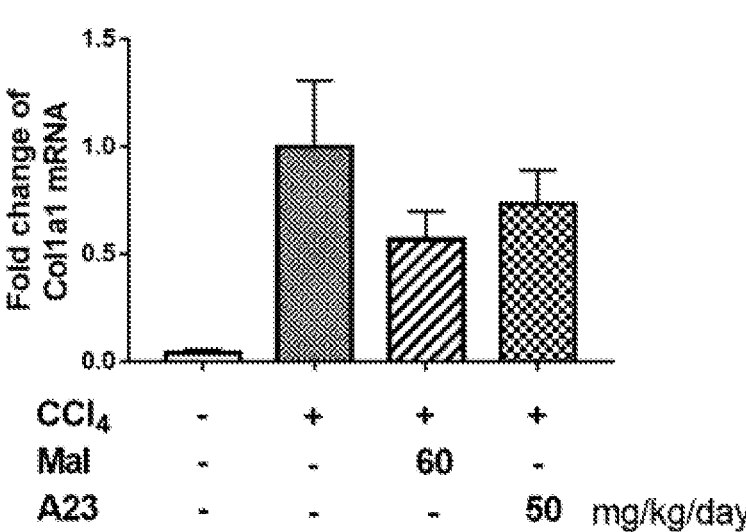
FIG. 6 shows the effect of Mal and compound A23 on the mRNA level of Col1a1 in C57/BL6 mice.

Total RNA was extracted from the liver using an MOL-PURE® TRIEASY™ Plus Total RNA Kit (Yeasen, Shanghai, China). Total RNA (5 μg) was reverse-transcribed using 1st strand cDNA Synthesis SuperMix for qPCR (gDNA digester plus) Kit (Yeasen, Shanghai, China). The following primer sets were used: α-SMA, 5'-GTTCAGTGGTGCCTCTGTCA-3' (sense) (SEQ ID NO: 1) and 5'-ACTGGGACGACATGGAAAAG-3' (antisense) (SEQ ID NO: 2); Col1a1, 5'-TAGGCCATTG-TGTATGCAGC-3' (sense) (SEQ ID NO: 3) and 5'-ACATGTT-CAGCTTTGTGGACC-3' (antisense) (SEQ ID NO: 4); HPRT, 5'-GTTAAGCAGTACAGC-CCCAAA-3' (sense) (SEQ ID NO: 5) and 5'-AGGGCATATC-CAACAACAAACTT-3' (antisense) (SEQ ID NO: 6). qRT-PCR was conducted using a STEPONE real-time PCR instrument and qPCR SYBR Green Master Mix (Low Rox Plus) Kit (Yeasen, Shanghai, China). The expression was normalized to that of HPRT RNA. The results are shown in FIGS. 1 to 6.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula (I):

(I)

or an enantiomer, a mixture of enantiomers, a diaste-reomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is (a) hydrogen, deuterium, cyano, halo, or nitro; or (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^2$ is —C(O)OR$^{2a}$, —C(O)NR$^{2b}$R$^{2c}$, —C(O)N(R$^{2b}$) OR$^{2c}$, or heteroaryl; wherein each R$^{2a}$, R$^{2b}$, and R$^{2c}$ is independently hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^3$, $R^4$, $R^5$, and $R^6$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C (NR$^{1d}$)NR$^{1b}$R$^{1c}$, —NR$^{1a}$S(O)R$^{1d}$, —NR$^{1a}$S(O)$_2$ R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^4$ is $C_{6-14}$ arylene or heteroarylene;

$R^B$ and X are (i), (ii), or (iii):

(i) X is —O—, —S—, —S(O)—, or —S(O)$_2$—; and $R^B$ is $C_{6-14}$ aryl or heteroaryl;

(ii) X is —N(R$^X$)—;
$R^B$ is $C_{6-14}$ aryl or heteroaryl; and
$R^X$ is hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) X is —N(R$^X$)—; and
$R^B$ and R$^X$ together with the N atom to which they are attached form heteroaryl;

L is $C_{1-6}$ alkylene, $C_{2-6}$ alkenylene, $C_{3-10}$ cycloal-kylene, or heterocyclylene; and each R$^{1a}$, R$^{1b}$, R$^{1c}$, and R$^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or Ria and R$^{1c}$ together with the C and N atoms to which they are attached form het-erocyclyl; or R$^{1b}$ and R$^{1c}$ together with the N atom to which they are attached form heterocyclyl;

wherein each alkyl, alkylene, alkenyl, alkenylene, alky-nyl, cycloalkyl, cycloalkylene, aryl, arylene, aralkyl, heteroaryl, heteroarylene, heterocyclyl, and hetero-cyclylene is optionally substituted with one or more substituents Q, wherein each Q is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more substituents Q$^a$; and (c) —C(O)R$^a$, —C(O)OR$^a$, —C(O)NR$^b$R$^c$, —C(O) SR$^a$, —C(NR$^a$)NR$^b$R$^c$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(NR$^a$)NR$^b$R$^c$, —OC(S)R$^a$, —OC(S)OR$^a$, —OC(S)NR$^b$R$^c$, —OS (O)R$^a$, —OS(O)$_2$R$^a$, —OS(O)NR$^b$R$^c$, —OS(O)$_2$ NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(NR$^d$) NR$^b$R$^c$, —NR$^a$C(S)R$^d$, —NR$^a$C(S)OR$^d$, —NR$^a$C(S) NR$^b$R$^c$, —NR$^a$S(O)R$^d$, —NR$^a$S(O)$_2$R$^d$, —NR$^a$S(O) NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$ NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aral-kyl, heteroaryl, or heterocyclyl, each of which is optionally substituted with one or more substituents Q$^a$; or (iii) R$^b$ and R$^c$ together with the N atom to which they are attached form heterocyclyl optionally substituted with one or more substituents Q$^a$;

wherein each Q$^a$ is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(O) SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(NR$^h$)NR$^f$R$^g$, —NR$^e$C(S)R$^h$, —NRC(S)OR$^f$, —NR$^e$C(S)NR$^f$R$^g$, —NR$^e$S(O)R$^h$, —NRS(O)$_2$R$^h$, —NRS(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

2. The compound of claim 1, having the structure of Formula (III):

(III)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

U$^1$, V$^1$, W$^1$, and X$^1$ are each independently (i) C or N; or (ii) —CR$^{7a}$=, —N=, —NR$^{7b}$—, —O—, or —S—;

Y$^1$ is (i) C or N; or (ii) a bond, —CR$^{7a}$=, —N=, —NR$^{7b}$—, —O—, or —S—;

Z$^1$ is C or N;

each R$^{7a}$ is independently (a) hydrogen, deuterium, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^a$C(O)OR$^{1d}$, —NR$^{1a}$C(O)NR$^{1b}$R$^{1c}$, —NR$^{1a}$C(NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; and each R$^{7b}$ is independently hydrogen, C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl;

wherein each alkyl, alkenyl, alkynyl, cycloalkyl, aryl, aralkyl, heteroaryl, and heterocyclyl is optionally substituted with one or more substituents Q.

3. The compound of claim 1, having the structure of Formula (IX):

(IX)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

each R$^7$ is independently (a) deuterium, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is optionally substituted with one or more substituents Q; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^d$, —NR$^{1a}$C(O)NR$^{1b}$R$^{1c}$, —NR$^{1a}$C(NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; and n is an integer of 0, 1, 2, 3, or 4.

4. The compound of claim 1, wherein X is —O— or —NR$^X$—, wherein R$^X$ is (i) hydrogen; or (ii) C$_{1-6}$ alkyl, C$_{6-14}$ aryl, or C$_{7-15}$ aralkyl, each of which is optionally substituted with one or more substituents Q.

5. The compound of claim 3, having the structure of Formula (XIV):

(XIV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^{2A}$ is —$OR^{2a}$, —$NR^{2b}R^{2c}$, or —$N(R^{2b})OR^{2c}$; wherein each $R^{2a}$, $R^{2b}$, and $R^{2c}$ is independently (i) hydrogen, or (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents Q; and p is an integer of 1, 2, or 3.

6. The compound of claim 5, having the structure of Formula (XV):

(XV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

7. The compound of claim 5, having the structure of Formula (XVI):

(XVI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

8. The compound of claim 5, having the structure of Formula (XVIII):

(XVIII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

9. The compound of claim 5, having the structure of Formula (XVII):

(XVII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

10. The compound of claim 1, wherein $R^B$ is monocyclic or bicyclic $C_{6-14}$ aryl, or monocyclic or bicyclic heteroaryl, each of which is optionally substituted with one or more substituents Q.

11. The compound of claim 3, having the structure of Formula (XIX):

(XIX)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^{2A}$ is —$OR^{2a}$, —$N^{2b}R^{2c}$, or —$N(R^{2b})OR^{2c}$; wherein each $R^{2a}$, $R^{2b}$, and $R^{2c}$ is independently (i) hydrogen, or (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents Q; and p is an integer of 1, 2, or 3.

12. The compound of claim 11, having the structure of Formula (XX):

(XX)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

13. The compound of claim 11, having the structure of Formula (XXI):

(XXI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

14. The compound of claim 11 having the structure of Formula (XXIII):

(XXIII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

15. The compound of claim 11, having the structure of Formula (XXII):

(XXII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^{7a}$ is (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents Q; or (c) —C(O)$R^{1a}$, —C(O)O$R^{1a}$, —C(O)N$R^{1b}R^{1c}$, —C(N$R^{1a}$)N$R^{1b}R^{c}$, —O$R^{1a}$, —OC(O)$R^{1a}$, —OC(O)O$R^{1a}$, —OC(O)N$R^{1b}R^{1c}$, —OC(N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$.

16. The compound of claim 5, wherein $R^{2A}$ is —O$R^{2a}$.

17. The compound of claim 16, wherein $R^{2A}$ is —OH.

18. The compound of claim 5, wherein $R^{2A}$ is —N$R^{2b}R^{2c}$.

19. The compound of claim 1, wherein $R^2$ is heteroaryl, optionally substituted with one or more substituents Q.

20. The compound of claim 3, having the structure of Formula (XXIV):

(XXIV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$U^2$ is —N═ or —O—;

$V^2$ is —N═ or —C(OH)═; and p is an integer of 1, 2, or 3.

21. The compound of claim 20, wherein the compound is a compound of Formula (XXV):

(XXV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

22. The compound of claim 20, wherein the compound is a compound of Formula (XXVI):

(XXVI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

23. The compound of claim 20, wherein the compound is a compound of Formula (XXVIII):

(XXVIII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

24. The compound of claim 20, wherein the compound is a compound of Formula (XXVII):

(XXVII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^{7a}$ is (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents Q; or (c) —C(O)$R^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O) NR$^{1b}$R$^{1c}$, —OC(NR$^{1a}$)NR$^{1b}$R$^{1c}$, —OS(O)R$^{1a}$, —OS (O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O) NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

25. The compound of claim 3, having the structure of Formula (XXIX):

(XXIX)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$U^2$ is —N= or —O—;

$V^2$ is —N= or —C(OH)=; and p is an integer of 1, 2, or 3.

26. The compound of claim 25, having the structure of Formula (XXX):

(XXX)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

27. The compound of claim 25, having the structure of Formula (XXXI):

(XXXI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

28. The compound of claim 25, having the structure of Formula (XXXIII):

(XXXIII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

29. The compound of claim 25, having the structure of Formula (XXXII):

(XXXII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^{7a}$ is (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each optionally substituted with one or more substituents Q; or (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$, or $-S(O)_2NR^{1b}R^{1c}$.

30. A compound of:

2-[(1Z)-5-fluoro-2-methyl-1-[(4-phenoxyphenyl)methylidene]-1H-inden-3-yl]acetic acid A1;

2-[(1Z)-5-fluoro-1-{[4-(4-methoxyphenoxy)phenyl]methylidene}-2-methyl-1H-inden-3-yl]acetic acid A2;

2-[(1Z)-1-({2-chloro-4-[3-(trifluoromethyl)phenoxy]phenyl}methylidene)-5-fluoro-2-methyl-1H-inden-3-yl]acetic acid A3;

2-[(1Z)-5-fluoro-2-methyl-1-{[4-(4-methylphenoxy)phenyl]methylidene}-1H-inden-3-yl]acetic acid A4;

2-[(1Z)-5-fluoro-2-methyl-1-({4-[4-(propan-2-yl)phenoxy]phenyl}methylidene)-1H-inden-3-yl]acetic acid A5;

2-[(1Z)-1-{[4-(4-bromophenoxy)phenyl]methylidene}-5-fluoro-2-methyl-1H-inden-3-yl]acetic acid A6;

2-[(1Z)-5-fluoro-2-methyl-1-{[4-(3-methylphenoxy)phenyl]methylidene}-1H-inden-3-yl]acetic acid A7;

2-[(1Z)-1-{[4-(3-cyanophenoxy)phenyl]methylidene}-5-fluoro-2-methyl-1H-inden-3-yl]acetic acid A8;

(Z)-2-(5-fluoro-2-methyl-1-(4-(3-(trifluoromethyl)phenoxy)benzylidene)-1H-inden-3-yl)acetic acid A9;

2-[(1Z)-1-{[4-(4-ethylphenoxy)phenyl]methylidene}-5-fluoro-2-methyl-1H-inden-3-yl]acetic acid A10;

2-[(1Z)-5-fluoro-1-{[4-(4-fluorophenoxy)phenyl]methylidene}-2-methyl-1H-inden-3-yl]acetic acid A11;

2-[(1Z)-1-{[2-chloro-4-(4-methoxyphenoxy)phenyl]methylidene}-5-fluoro-2-methyl-1H-inden-3-yl]acetic acid A12;

2-[(1Z)-5-fluoro-1-({2-methoxy-4-[4-(propan-2-yl)phe-noxy]phenyl}-methylidene)-2-methyl-1H-inden-3-yl] acetic acid A13;

2-[(1Z)-5-fluoro-2-methyl-1-{[4-(naphthalen-2-yloxy) phenyl]methylidene}-1H-inden-3-yl]acetic acid A14;

2-[(1Z)-1-({2-chloro-4-[4-(propan-2-yl)phenoxy] phenyl}methylidene)-5-fluoro-2-methyl-1H-inden-3-yl]acetic acid A15;

2-[(1Z)-1-{[4-(2,4-difluorophenoxy)phenyl]methyl-idene}-5-fluoro-2-methyl-1H-inden-3-yl]acetic acid A16;

2-[(1Z)-1-{[4-(2-bromo-4-fluorophenoxy)phenyl]meth-ylidene}-5-fluoro-2-methyl-1H-inden-3-yl]acetic acid A17;

2-[(1Z)-5-fluoro-2-methyl-1-{[4-(2,4,5-trifluorophe-noxy)phenyl]methylidene}-1H-inden-3-yl]acetic acid A18;

3-[(1Z)-1-{[4-(4-fluorophenoxy)phenyl]methylidene}-2-methyl-1H-inden-3-yl]propanoic acid A19;

2-[(1Z)-5-fluoro-1-({4-[(6-fluoropyridin-3-yl)oxy] phenyl}methylidene)-2-methyl-1H-inden-3-yl]acetic acid A20;

2-[(1Z)-5-fluoro-1-({4-[(6-fluoro-5-methylpyridin-3-yl) oxy]phenyl}-methylidene)-2-methyl-1H-inden-3-yl] acetic acid A21;

(Z)-2-(5-fluoro-2-methyl-1-(4-(quinolin-5-yloxy)ben-zylidene)-1H-inden-3-yl)acetic acid A22;

2-[(1Z)-5-fluoro-2-methyl-1-[(4-phenoxyphenyl)methyl-idene]-1H-inden-3-yl]-N-hydroxyacetamide A23;

2-[(1Z)-5-fluoro-1-{[4-(4-fluorophenoxy)phenyl]methyl-idene}-2-methyl-1H-inden-3-yl]-N-hydroxyacetamide A24;

2-[(1Z)-5-fluoro-1-{[4-(4-fluorophenoxy)phenyl]methyl-idene}-2-methyl-1H-inden-3-yl]acetamide A25;

2-[(1Z)-5-fluoro-1-{[4-(4-fluorophenoxy)phenyl]methyl-idene}-2-methyl-1H-inden-3-yl]-N-methylacetamid A26;

2-[(1Z)-5-fluoro-1-{[4-(4-fluorophenoxy)phenyl]methyl-idene}-2-methyl-1H-inden-3-yl]-N-(2-hydroxyethyl) acetamide A27;

(Z)-2-(5-fluoro-2-methyl-1-(4-phenoxybenzylidene)-1H-inden-3-yl)-N-(1H-tetrazol-5-yl)acetamide A28;

2-[(1Z)-5-fluoro-2-methyl-1-({4-[methyl(phenyl)amino] phenyl}methylidene)-1H-inden-3-yl]acetic acid A29;

2-[(1Z)-1-({4-[benzyl(4-fluorophenyl)amino] phenyl}methylidene)-5-fluoro-2-methyl-1H-inden-3-yl]acetic acid A30;

2-[(1Z)-5-fluoro-1-({4-[(4-fluorophenyl)(methyl)amino] phenyl}methylidene)-2-methyl-1H-inden-3-yl]acetic acid A31;

2-[(1Z)-1-({4-[ethyl(4-fluorophenyl)amino] phenyl}methylidene)-5-fluoro-2-methyl-1H-inden-3-yl]acetic acid A32;

2-[(1Z)-5-fluoro-1-({4-[(4-fluorophenyl)(propyl)amino] phenyl}methylidene)-2-methyl-1H-inden-3-yl]acetic acid A33;

(Z)-2-(5-fluoro-1-(4-((4-fluorophenyl)(2-hydroxyethyl) amino)benzylidene)-2-methyl-1H-inden-3-yl)acetic acid A34;

2-[(1Z)-5-fluoro-1-({4-[(4-fluorophenyl)(4-formylphe-nyl)amino]phenyl}-methylidene)-2-methyl-1H-inden-3-yl]acetic acid A35;

2-[(1Z)-5-fluoro-1-({4-[(4-formylphenyl)(phenyl)amino] phenyl}methylidene)-2-methyl-1H-inden-3-yl]acetic acid A36;

2-[(1Z)-5-fluoro-2-methyl-1-({4-[methyl(phenyl)amino] phenyl}methylidene)-1H-inden-3-yl]-N-hydroxyacet-amide A37;

2-[(1Z)-1-({4-[benzyl(4-fluorophenyl)amino] phenyl}methylidene)-5-fluoro-2-methyl-1H-inden-3-yl]-N-hydroxyacetamide A38;

5-{[(1Z)-2-methyl-1-[(3-phenoxyphenyl)methylidene]-1H-inden-3-yl]methyl}-1H-1,2,3,4-tetrazole A39;

5-{[(1Z)-2-methyl-1-[(4-phenoxyphenyl)methylidene]-1H-inden-3-yl]methyl}-1H-1,2,3,4-tetrazole A40;

5-{2-[(1Z)-2-methyl-1-{[4-(4-methylphenoxy)phenyl] methylidene}-1H-inden-3-yl]ethyl}-1H-1,2,3,4-tetra-zole A41;

5-{2-[(1Z)-1-{[4-(4-bromophenoxy)phenyl]methyl-idene}-2-methyl-1H-inden-3-yl]ethyl}-1H-1,2,3,4-tet-razole A42;

5-{2-[(1Z)-2-methyl-1-({4-[4-(propan-2-yl)phenoxy] phenyl}methylidene)-1H-inden-3-yl]ethyl}-1H-1,2,3, 4-tetrazole A43;

5-{2-[(1Z)-1-{[4-(4-methoxyphenoxy)phenyl]methyl-idene}-2-methyl-1H-inden-3-yl]ethyl}-1H-1,2,3,4-tet-razole A44;

5-{2-[(1Z)-2-methyl-1-({4-[4-(trifluoromethyl)phenoxy] phenyl}methylidene)-1H-inden-3-yl]ethyl}-1H-1,2,3, 4-tetrazole A45;

5-{2-[(1Z)-2-methyl-1-{[4-(3-methylphenoxy)phenyl] methylidene}-1H-inden-3-yl]ethyl}-1H-1,2,3,4-tetra-zole A46;

3-(4-{[(1Z)-2-methyl-3-[2-(1H-1,2,3,4-tetrazol-5-yl) ethyl]-1H-inden-1-ylidene]methyl}phenoxy)benzoni-trile A47;

5-{2-[(1Z)-1-{[4-(3-methoxyphenoxy)phenyl]methyl-idene}-2-methyl-1H-inden-3-yl]ethyl}-1H-1,2,3,4-tet-razole A48;

5-{2-[(1Z)-1-{[4-(3-bromophenoxy)phenyl]methyl-idene}-2-methyl-1H-inden-3-yl]ethyl}-1H-1,2,3,4-tet-razole A49;

5-{2-[(1Z)-2-methyl-1-({4-[3-(trifluoromethyl)phenoxy] phenyl}methylidene)-1H-inden-3-yl]ethyl}-1H-1,2,3, 4-tetrazole A50;

5-{2-[(1Z)-2-methyl-1-{[4-(naphthalen-2-yloxy)phenyl] methylidene}-1H-inden-3-yl]ethyl}-1H-1,2,3,4-tetra-zole A51;

(Z)-3-((2-methyl-1-(4-phenoxybenzylidene)-1H-inden-3-yl)methyl)-1,2,4-oxadiazol-5(4H)-one A52;

5-{[(1E)-1-[(4-phenoxyphenyl)methylidene]-1H-inden-3-yl]methyl}-1H-1,2,3,4-tetrazole A53;

5-{[(1E)-1-[(3-phenoxyphenyl)methylidene]-1H-inden-3-yl]methyl}-1H-1,2,3,4-tetrazole A54;

2-[(1Z)-5-fluoro-2-methyl--{[4-(morpholin-4-yl)phenyl] methylidene}-1H-inden-3-yl]acetic acid A55;

2-[(1Z)-5-fluoro-2-methyl-1-{[4-(piperidin-1-yl)phenyl] methylidene}-1H-inden-3-yl]acetic acid A56;

2-[(1Z)-5-fluoro-1-{[4-(1H-indol-1-yl)phenyl]methyl-idene}-2-methyl-1H-inden-3-yl]acetic acid A57;

2-[(1Z)-1-{[4-(2-amino-1H-imidazol-1-yl)phenyl]meth-ylidene}-5-fluoro-2-methyl-1H-inden-3-yl]acetic acid A58;

2-[(1Z)-5-fluoro-2-methyl--{[4-(pyrrolidin-1-yl)phenyl] methylidene}-1H-inden-3-yl]acetic acid A59;

2-[(1Z)-5-fluoro-2-methyl-1-{[4-(1H-pyrrol-1-yl)phenyl] methylidene}-1H-inden-3-yl]acetic acid A60;

(2E)-3-[(1Z)-5-fluoro-1-{[4-(4-fluorophenoxy)phenyl] methylidene}-2-methyl-1H-inden-3-yl]prop-2-enoic acid A61;

2-[(1Z)-5-fluoro-1-{[4-(4-fluorobenzenesulfonyl)phenyl] methylidene}-2-methyl-1H-inden-3-yl]acetic acid A62;

2-[(1Z)-5-fluoro-1-{[4-(4-fluorobenzenesulfinyl)phenyl] methylidene}-2-methyl-1H-inden-3-yl]acetic acid A63;

2-[(1Z)-5-fluoro-1-({4-[(4-fluorophenyl)sulfanyl] phenyl}methylidene)-2-methyl-1H-inden-3-yl]acetic acid A64;

2-[(1Z)-5-fluoro-1-{[6-(4-fluorophenoxy)pyridine-3-yl] methylidene}-2-methyl-1H-inden-3-yl]acetic acid A65;

2-[(1Z)-5-fluoro-1-{[6-(4-fluorophenoxy)-5-methylpyridin-3-yl]methylidene}-2-methyl-1H-inden-3-yl]acetic acid A66;

(2E)-4-[(1Z)-5-fluoro-1-{[4-(4-fluorophenoxy)phenyl] methylidene}-2-methyl-1H-inden-3-yl]but-2-enoic acid A67;

2-[(1Z)-4,5-difluoro-1-{[4-(4-fluorophenoxy)phenyl] methylidene}-2-methyl-1H-inden-3-yl]acetic acid A68;

2-[(1Z)-5-fluoro-1-{[4-(4-fluorophenoxy)phenyl]methylidene}-2,4-dimethyl-1H-inden-3-yl]acetic acid A69;

2-[(1Z)-5-fluoro-2-methyl-1-{[4-(morpholin-4-yl)phenyl]methylidene}-1H-inden-3-yl]-N-hydroxyacetamide A70;

2-[(1Z)-5-fluoro-2-methyl-1-{[4-(piperidin-1-yl)phenyl] methylidene}-1H-inden-3-yl]-N-hydroxyacetamide A71;

2-[(1Z)-5-fluoro-1-{[4-(1H-indol-1-yl)phenyl]methylidene}-2-methyl-1H-inden-3-yl]-N-hydroxyacetamide A72;

2-[(1Z)-1-{[4-(2-amino-1H-imidazol-1-yl)phenyl]methylidene}-5-fluoro-2-methyl-1H-inden-3-yl]-N-hydroxyacetamide A73;

2-[(1Z)-5-fluoro-2-methyl-1-{[4-(pyrrolidin-1-yl)phenyl] methylidene}-1H-inden-3-yl]-N-hydroxyacetamide A74;

2-[(1Z)-5-fluoro-2-methyl-1-{[4-(1H-pyrrol-1-yl)phenyl] methylidene}-1H-inden-3-yl]-N-hydroxyacetamide A75;

(2E)-3-[(1Z)-5-fluoro-1-{[4-(4-fluorophenoxy)phenyl] methylidene}-2-methyl-1H-inden-3-yl]-N-hydroxyprop-2-enamide A76;

2-[(1Z)-5-fluoro-1-{[4-(4-fluorobenzenesulfonyl)phenyl] methylidene}-2-methyl-1H-inden-3-yl]-N-hydroxyacetamide A77;

2-[(1Z)-5-fluoro-1-{[4-(4-fluorobenzenesulfinyl)phenyl] methylidene}-2-methyl-1H-inden-3-yl]-N-hydroxyacetamide A78;

2-[(1Z)-5-fluoro-1-({4-[(4-fluorophenyl)sulfanyl] phenyl}methylidene)-2-methyl-1H-inden-3-yl]-N-hydroxyacetamide A79;

2-[(1Z)-5-fluoro-1-{[6-(4-fluorophenoxy)pyridine-3-yl] methylidene}-2-methyl-1H-inden-3-yl]-N-hydroxyacetamide A80;

2-[(1Z)-5-fluoro-1-{[6-(4-fluorophenoxy)-5-methylpyridin-3-yl]methylidene}-2-methyl-1H-inden-3-yl]-N-hydroxyacetamide A81;

(2E)-4-[(1Z)-5-fluoro-1-{[4-(4-fluorophenoxy)phenyl] methylidene}-2-methyl-1H-inden-3-yl]-N-hydroxybut-2-enamide A82;

2-[(1Z)-4,5-difluoro-1-{[4-(4-fluorophenoxy)phenyl] methylidene}-2-methyl-1H-inden-3-yl]-N-hydroxyacetamide A83;

2-[(1Z)-5-fluoro-1-{[4-(4-fluorophenoxy)phenyl]methylidene}-2,4-dimethyl-1H-inden-3-yl]-N-hydroxyacetamide A84; or 2-[(1Z)-5-Fluoro-1-({4-[(4-fluorophenyl)(2-hydroxyethyl)amino]phenyl}-methylidene)-2-methyl-1H-inden-3-yl]-N-hydroxyacetamide A85;

2-[(1Z)-5-fluoro-2-methyl-1-[(4-phenoxyphenyl)methylidene]-1H-inden-3-yl]-N-hydroxy-N-methylacetamide C1;

2-[(1Z)-5-fluoro-1-{[4-(4-fluorophenoxy)phenyl]methylidene}-2-methyl-1H-inden-3-yl]-N-hydroxy-N-methylacetamide C2;

(Z)-2-(5-fluoro-2-methyl-1-(3-phenoxybenzylidene)-1H-inden-3-yl)-N-hydroxy-N-methylacetamide C3;

2-[(1Z)-5-fluoro-2-methyl-1-({4-[4-(propan-2-yl)phenoxy]phenyl}methylidene)-1H-inden-3-yl]-N-hydroxyacetamide D1;

2-[(1Z)-5-fluoro-2-methyl-1-({4-[4-(tert-butyl)phenoxy] phenyl}methylidene)-1H-inden-3-yl]acetic acid D2;

2-[(1Z)-5-fluoro-2-methyl-1-({4-[3-(tert-butyl)phenoxy] phenyl}methylidene)-1H-inden-3-yl]acetic acid D3;

2-[(1Z)-5-fluoro-2-methyl-1-({4-[3-fluoro-4-methylphenoxy]phenyl}-methylidene)-1H-inden-3-yl]acetic acid D4;

2-[(1Z)-5-fluoro-2-methyl-1-({4-[3,4-difluorophenoxy] phenyl}methylidene)-1H-inden-3-yl]acetic acid D5;

2-[(1Z)-5-fluoro-2-methyl-1-({4-[3-nitrophenoxy] phenyl}methylidene)-1H-inden-3-yl]acetic acid D6;

2-[(1Z)-5-fluoro-2-methyl-1-({4-[4-(trifluoromethyl) phenoxy]phenyl}-methylidene)-1H-inden-3-yl]acetic acid D7;

2-[(1Z)-5-fluoro-1-{[4-(4-fluorophenoxy)phenyl]methylidene}-2-(2-methyl-propyl)-1H-inden-3-yl]acetic acid D8;

2-[(1Z)-5-fluoro-2-benzyl-1-({4-[4-fluorophenoxy] phenyl}methylidene)-1H-inden-3-yl]acetic acid D9;

2-[(1Z)-5-methoxy-2-methyl-1-({4-[4-fluorophenoxy] phenyl}methylidene)-1H-inden-3-yl]acetic acid D10;

2-[(1Z)-5-methoxy-2-methyl-1-[(4-phenoxyphenyl) methylidene]-1H-inden-3-yl]acetic acid D11;

2-[(1Z)-1-{[2-trifluoromethyl-4-(4-fluorophenoxy)phenyl]methylidene}-5-fluoro-2-methyl-1H-inden-3-yl] acetic acid D12;

2-[(1Z)-1-{[3-methyl-4-(4-fluorophenoxy)phenyl]methylidene}-5-fluoro-2-methyl-1H-inden-3-yl]acetic acid D13;

2-[(1Z)-1-{[2-methyl-4-(4-fluorophenoxy)phenyl]methylidene}-5-fluoro-2-methyl-1H-inden-3-yl]acetic acid D14;

2-[(1Z)-5,7-difluoro-2-methyl-1-({4-[4-fluorophenoxy] phenyl}methylidene)-1H-inden-3-yl]acetic acid D15;

2-[(1Z)-4,6-difluoro-2-methyl-1-({4-[4-fluorophenoxy] phenyl}methylidene)-1H-inden-3-yl]acetic acid D16;

2-[(1Z)-5-tert-butyl-2-methyl-1-({4-[4-fluorophenoxy] phenyl}methylidene)-1H-inden-3-yl]acetic acid D17;

(Z)-2-(5-fluoro-2-methyl-1-(3-phenoxybenzylidene)-1H-inden-3-yl)acetic acid D18;

2-[(1Z)-5-fluoro-1-(2-(phenoxy)benzylidene)-2-methyl-1H-inden-3-yl]-acetic acid D19;

2-[(1Z)-5,7-difluoro-1-(3-(phenoxy)benzylidene)-2-methyl-1H-inden-3-yl]-acetic acid D20;

2-[(1Z)-4,6-difluoro-1-(3-(phenoxy)benzylidene)-2-methyl-1H-inden-3-yl]-acetic acid D21;

2-[(1Z)-5-fluoro-2-methyl-1-({3-[4-methoxyphenoxy] phenyl}methylidene)-1H-inden-3-yl]acetic acid D22;

2-[(1Z)-5-fluoro-1-(4-fluoro-3-(phenoxy)benzylidene)-2-methyl-1H-inden-3-yl]-acetic acid D23;

2-[(1Z)-5-fluoro-2-methyl-1-({3-[4-cyanophenoxy]
phenyl}methylidene)-1H-inden-3-yl]acetic acid D24;

2-[(1Z)-5-fluoro-2-methyl-1-({3-[4-chlorophenoxy]
phenyl}methylidene)-1H-inden-3-yl]acetic acid D25;

2-[(1Z)-5-fluoro-2-methyl-1-({3-[4-trifluoromethylphe-
noxy]phenyl}-methylidene)-1H-inden-3-yl]acetic acid
D26;

2-[(1Z)-5-fluoro-2-methyl-1-({3-[3-trifluoromethylphe-
noxy]phenyl}-methylidene)-1H-inden-3-yl]acetic acid
D27;

2-[(1Z)-4-methoxy-1-(4-(phenoxy)benzylidene)-2-
methyl-1H-inden-3-yl]-acetic acid D28;

2-[(1Z)-6-methoxy-1-(4-(phenoxy)benzylidene)-2-
methyl-1H-inden-3-yl]-acetic acid D29;

2-[(1Z)-6-trifluoromethyl-2-methyl-1-({4-[4-fluorophe-
noxy]phenyl}-methylidene)-1H-inden-3-yl]acetic acid
D30;

2-[(1Z)-5-trifluoromethyl-2-methyl-1-({4-[4-fluorophe-
noxy]phenyl}-methylidene)-1H-inden-3-yl]acetic acid
D31;

2-[(1Z)-1-{[4-(4-fluorophenoxy)phenyl]methylidene}-
1H-inden-3-yl]acetic acid D32;

2-[(1Z)-5-fluoro-1-{[4-(4-fluorophenoxy)phenyl]methyl-
idene}-1H-inden-3-yl]acetic acid D33;

2-[(1Z)-5-trifluoromethyl-1-(3-(phenoxy)benzylidene)-2-
methyl-1H-inden-3-yl]-acetic acid D34;

2-[(1Z)-6-methoxy-1-(3-(phenoxy)benzylidene)-2-
methyl-1H-inden-3-yl]-acetic acid D35;

2-[(1Z)-6-trifluoromethyl-1-(3-(phenoxy)benzylidene)-2-
methyl-1H-inden-3-yl]-acetic acid D36;

2-[(1Z)-5-fluoro-2-methyl-1-({3-[methyl(phenyl)amino]
phenyl}methylidene)-1H-inden-3-yl]acetic acid D37;

2-[(1Z)-5-fluoro-1-[(3-methoxy-5-phenoxyphenyl)meth-
ylidene]-2-methyl-1H-inden-3-yl]acetic acid D38;

2-[(1E)-5-fluoro-2-methyl-1-({4-[3,4-difluorophenoxy]
phenyl}methylidene)-1H-inden-3-yl]acetic acid E1;

2-[(1E)-5-fluoro-2-methyl-1-({4-[4-fluorophenoxy]
phenyl}methylidene)-1H-inden-3-yl]acetic acid E2;

2-[(1E)-5-fluoro-2-methyl-1-[(4-phenoxyphenyl)methyl-
idene]-1H-inden-3-yl]acetic acid E3;

2-[(1E)-5,7-difluoro-2-methyl-1-({4-[4-fluorophenoxy]
phenyl}methylidene)-1H-inden-3-yl]acetic acid E4;

5-{2-[(1E)-1-[(4-phenoxyphenyl)methylidene]-1H-in-
den-3-yl]ethyl}-1H-1,2,3,4-tetrazole E5; and 2-[(1E)-5,7-difluoro-1-(3-(phenoxy)benzylidene)-2-
methyl-1H-inden-3-yl]-acetic acid E6;

or a tautomer, a mixture of two or more tautomers, or an isotopic variant thereof; or a pharmaceutically acceptable salt, solvate, hydrate, or prodrug thereof.

31. A pharmaceutical composition comprising the compound of claim 1, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof, and a pharmaceutically acceptable excipient.

32. A method of treating, preventing, or ameliorating one or more symptoms of a fibrotic disease in a subject, comprising administering to the subject in need thereof a therapeutically effective amount of the compound of claim 1.

33. A method of treating, preventing, or ameliorating one or more symptoms of a proliferative disease in a subject, comprising administering to the subject a therapeutically effective amount of the compound of claim 1.

34. The compound of claim 1, wherein the compound is 2-[(1Z)-1-{[4-(4-bromophenoxy)phenyl]methylidene}-5-fluoro-2-methyl-1H-inden-3-yl]acetic acid A6; or a pharmaceutically acceptable salt thereof.

35. The compound of claim 1, wherein the compound is 2-[(1Z)-5-fluoro-2-methyl-1-{[4-(3-methylphenoxy)phe-nyl]methylidene}-1H-inden-3-yl]acetic acid A7; or a pharmaceutically acceptable salt thereof.

36. The compound of claim 1, wherein the compound is (Z)-2-(5-fluoro-2-methyl-1-(4-(3-(trifluoromethyl)phe-noxy)benzylidene)-1H-inden-3-yl)acetic acid A9; or a pharmaceutically acceptable salt thereof.

37. The compound of claim 1, wherein the compound is 2-[(1Z)-1-{[4-(4-ethylphenoxy)phenyl]methylidene}-5-fluoro-2-methyl-1H-inden-3-yl]acetic acid A10; or a pharmaceutically acceptable salt thereof.

38. The compound of claim 1, wherein the compound is 2-[(1Z)-5-fluoro-1-{[4-(4-fluorophenoxy)phenyl]methyl-idene}-2-methyl-1H-inden-3-yl]acetic acid A11; or a pharmaceutically acceptable salt thereof.

39. The compound of claim 1, wherein the compound is 2-[(1Z)-1-{[2-chloro-4-(4-methoxyphenoxy)phenyl]meth-ylidene}-5-fluoro-2-methyl-1H-inden-3-yl]acetic acid A12; or a pharmaceutically acceptable salt thereof.

40. The compound of claim 1, wherein the compound is 2-[(1Z)-5-fluoro-2-methyl-1-{[4-(naphthalen-2-yloxy)phe-nyl]methylidene}-1H-inden-3-yl]acetic acid A14; or a pharmaceutically acceptable salt thereof.

41. The compound of claim 1, wherein the compound is 2-[(1Z)-1-({2-chloro-4-[4-(propan-2-yl)phenoxy] phenyl}methylidene)-5-fluoro-2-methyl-1H-inden-3-yl] acetic acid A15; or a pharmaceutically acceptable salt thereof.

42. The compound of claim 1, wherein the compound is 2-[(1Z)-1-{[4-(2,4-difluorophenoxy)phenyl]methylidene}-5-fluoro-2-methyl-1H-inden-3-yl]acetic acid A16; or a pharmaceutically acceptable salt thereof.

43. The compound of claim 1, wherein the compound is 2-[(1Z)-1-{[4-(2-bromo-4-fluorophenoxy)phenyl]methyl-idene}-5-fluoro-2-methyl-1H-inden-3-yl]acetic acid A17; or a pharmaceutically acceptable salt thereof.

44. The compound of claim 1, wherein the compound is 2-[(1Z)-5-methoxy-2-methyl-1-[(4-phenoxyphenyl)methyl-idene]-1H-inden-3-yl]acetic acid D11; or a pharmaceuti-cally acceptable salt thereof.

45. The compound of claim 1, wherein the compound is 2-[(1Z)-1-{[2-methyl-4-(4-fluorophenoxy)phenyl]methyl-idene}-5-fluoro-2-methyl-1H-inden-3-yl]acetic acid D14; or a pharmaceutically acceptable salt thereof.

46. The compound of claim 1, wherein the compound is 2-[(1Z)-5,7-difluoro-2-methyl-1-({4-[4-fluorophenoxy] phenyl}methylidene)-1H-inden-3-yl]acetic acid D15; or a pharmaceutically acceptable salt thereof.

47. The compound of claim 1, wherein the compound is (Z)-2-(5-fluoro-2-methyl-1-(3-phenoxybenzylidene)-1H-in-den-3-yl)acetic acid D18; or a pharmaceutically acceptable salt thereof.

48. The compound of claim 1, wherein the compound is 2-[(1Z)-5,7-difluoro-1-(3-(phenoxy)benzylidene)-2-methyl-1H-inden-3-yl]-acetic acid D20; or a pharmaceutically acceptable salt thereof.

49. The compound of claim 1, wherein the compound is 2-[(1Z)-4,6-difluoro-1-(3-(phenoxy)benzylidene)-2-methyl-1H-inden-3-yl]-acetic acid D21; or a pharmaceutically acceptable salt thereof.

50. The compound of claim 1, wherein the compound is 2-[(1Z)-5-fluoro-2-methyl-1-({3-[4-methoxyphenoxy] phenyl}methylidene)-1H-inden-3-yl]acetic acid D22; or a pharmaceutically acceptable salt thereof.

51. The compound of claim 1, wherein the compound is 2-[(1Z)-5-fluoro-1-(4-fluoro-3-(phenoxy)benzylidene)-2-methyl-1H-inden-3-yl]-acetic acid D23; or a pharmaceutically acceptable salt thereof.

52. The compound of claim 1, wherein the compound is 2-[(1Z)-5-fluoro-2-methyl-1-({3-[4-cyanophenoxy]phenyl}methylidene)-1H-inden-3-yl]acetic acid D24; or a pharmaceutically acceptable salt thereof.

53. The compound of claim 1, wherein the compound is 2-[(1Z)-5-fluoro-2-methyl-1-({3-[4-chlorophenoxy]phenyl}methylidene)-1H-inden-3-yl]acetic acid D25; or a pharmaceutically acceptable salt thereof.

\*   \*   \*   \*   \*